(12) United States Patent
Inoue et al.

(10) Patent No.: US 9,065,061 B2
(45) Date of Patent: Jun. 23, 2015

(54) ORGANOMETALLIC COMPLEX, LIGHT-EMITTING ELEMENT, DISPLAY DEVICE, ELECTRONIC DEVICE, AND LIGHTING DEVICE

(75) Inventors: Hideko Inoue, Kanagawa (JP); Tomoka Nakagawa, Kanagawa (JP); Nobuharu Ohsawa, Kanagawa (JP); Satoshi Seo, Kanagawa (JP); Yui Yamada, Kanagawa (JP)

(73) Assignee: Semiconductor Energy Laboratory Co., Ltd. (JP)

(*) Notice: Subject to any disclaimer, the term of this patent is extended or adjusted under 35 U.S.C. 154(b) by 271 days.

(21) Appl. No.: 12/914,216

(22) Filed: Oct. 28, 2010

(65) Prior Publication Data

US 2011/0101854 A1 May 5, 2011

(30) Foreign Application Priority Data

Nov. 2, 2009 (JP) .................................. 2009-252168
Jul. 28, 2010 (JP) .................................. 2010-169870

(51) Int. Cl.
*H01L 51/54* (2006.01)
*C09K 11/06* (2006.01)
*H01L 51/00* (2006.01)
*C07F 15/00* (2006.01)
*C09B 57/10* (2006.01)
*H05B 33/14* (2006.01)
*H01L 51/50* (2006.01)

(52) U.S. Cl.
CPC ........ *H01L 51/0085* (2013.01); *C07F 15/0033* (2013.01); *C07F 15/0086* (2013.01); *C09B 57/10* (2013.01); *C09K 11/06* (2013.01); *C09K 2211/1059* (2013.01); *C09K 2211/185* (2013.01); *H01L 51/0059* (2013.01); *H01L 51/0072* (2013.01); *H01L 51/0074* (2013.01); *H01L 51/5016* (2013.01); *H01L 51/5036* (2013.01); *H05B 33/14* (2013.01)

(58) Field of Classification Search
None
See application file for complete search history.

(56) References Cited

U.S. PATENT DOCUMENTS

| 7,807,839 | B2 | 10/2010 | Inoue et al. | |
|---|---|---|---|---|
| 7,915,415 | B2 | 3/2011 | Knowles et al. | |
| 8,142,909 | B2 | 3/2012 | Beers et al. | |
| 2004/0124766 | A1* | 7/2004 | Nakagawa et al. | 313/504 |
| 2007/0085073 | A1 | 4/2007 | Inoue et al. | |
| 2007/0190359 | A1 | 8/2007 | Knowles et al. | |
| 2011/0057560 | A1 | 3/2011 | Inoue et al. | |
| 2011/0073849 | A1 | 3/2011 | Knowles et al. | |

FOREIGN PATENT DOCUMENTS

| CN | 001951947 A | 4/2007 |
|---|---|---|
| EP | 1 777 229 A1 | 4/2007 |
| EP | 2 243 785 A1 | 10/2010 |
| EP | 2 275 428 A2 | 1/2011 |
| EP | 2 399 922 A1 | 12/2011 |
| JP | 2007-137872 | 6/2007 |
| JP | 2007-208102 | 8/2007 |
| JP | 2008-69221 | 3/2008 |
| JP | 2008-74921 | 4/2008 |
| JP | 2009-001742 A | 1/2009 |
| WO | WO 2007/095118 A2 | 8/2007 |
| WO | WO 2008/156879 A1 | 12/2008 |
| WO | WO 2009/107497 A1 | 9/2009 |

OTHER PUBLICATIONS

English language machine translation of JP 2008-069221 A, 2008.*
International Search Report re application No. PCT/JP2010/068796, dated Nov. 30, 2010.
Written Opinion re application No. PCT/JP2010/068796, dated Nov. 30, 2010.
Chinese Office Action re Application No. CN 201080047397.X, dated Mar. 21, 2014.
Search Report re European application No. EP 10826648.7, dated Apr. 26, 2013.

* cited by examiner

*Primary Examiner* — Michael H Wilson
(74) *Attorney, Agent, or Firm* — Husch Blackwell LLP

(57) ABSTRACT

Provided are organometallic complexes that can exhibit phosphorescence. One of the novel organometallic complexes is represented by General Formula (G1). In General Formula (G1), $R^1$ represents any of an alkyl group having 1 to 6 carbon atoms, a cycloalkyl group having 5 to 8 carbon atoms which may have a substituent, and an aralkyl group having 7 to 10 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an arylene group having 6 to 13 carbon atoms which may have a substituent. Further, M represents a Group 9 element or a Group 10 element.

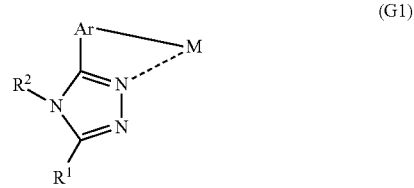

(G1)

26 Claims, 55 Drawing Sheets

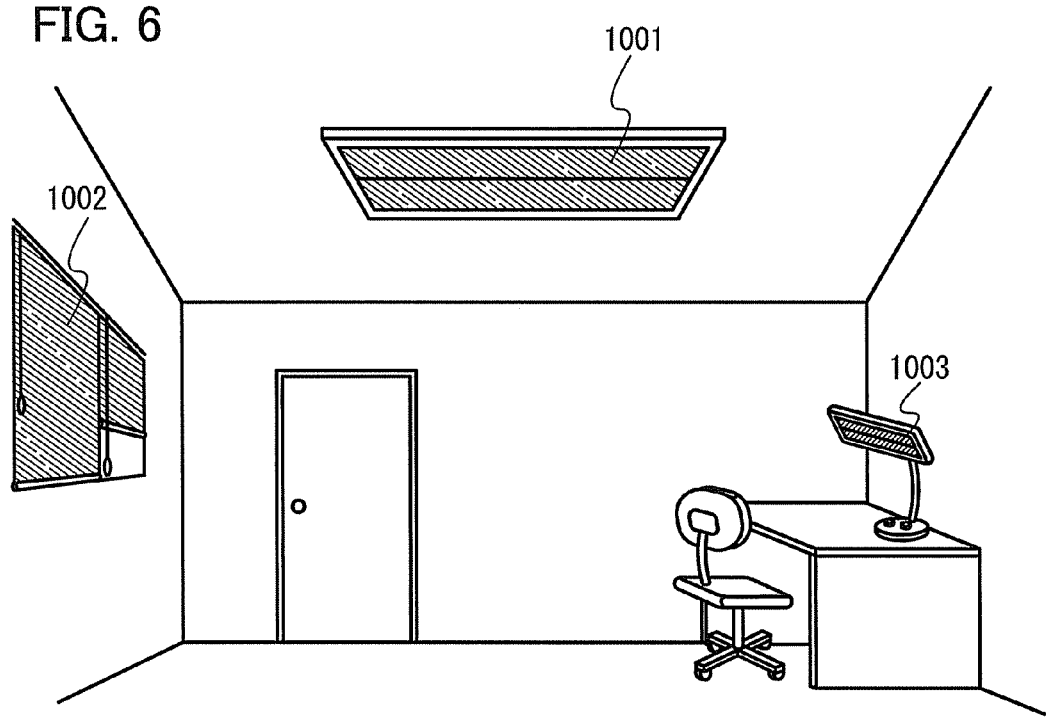

ORGANOMETALLIC COMPLEX, LIGHT-EMITTING ELEMENT, DISPLAY DEVICE, ELECTRONIC DEVICE, AND LIGHTING DEVICE

TECHNICAL FIELD

The invention disclosed in this specification relates to substances that can emit light by current excitation. In particular, the invention relates to substances that can emit light from a triplet excited state. In addition, the invention relates to light-emitting elements, display devices, electronic devices, light-emitting devices, and lighting devices in each of which any of the substances is used.

BACKGROUND ART

A light-emitting element includes a layer containing a light-emitting material (a light-emitting layer) between a pair of electrodes (an anode and a cathode). It has been reported that a variety of organic compounds can be used as the light-emitting material.

It is said that light emission mechanism of a light-emitting element is as follows: when voltage is applied between a pair of electrodes with a light-emitting layer interposed therebetween, electrons injected from a cathode and holes injected from an anode are recombined in the light emission center of the light-emitting layer to form molecular excitons, and energy is released to emit light when the molecular excitons relax to a ground state. A singlet excited state and a triplet excited state are known as excited states, and it is thought that light emission can be obtained through either of the excited states.

In such a light-emitting element, since more excitons are generated in a triplet excited state than in a singlet excited state, emission efficiency of the light-emitting element can be increased by using a material that can emit light from a triplet excited state (a phosphorescent material). Therefore, a phosphorescent material has been attempted to be used as a light-emitting material a large number of times.

A metal complex where iridium (Ir) is the central metal (hereinafter, referred to as an Ir complex) is a typical phosphorescent material which emits green to blue light (for example, see Patent Document 1). Disclosed in Patent Document 1 is an Ir complex where a triazole derivative is a ligand.

REFERENCE

Patent Document

[Patent Document 1] Japanese Published Patent Application No. 2007-137872

DISCLOSURE OF INVENTION

As reported in Patent Document 1, although phosphorescent materials emitting green light or blue light have been developed, further development is required for obtaining phosphorescent materials that are excellent in reliability, light-emitting characteristics, cost, or the like.

In view of the above problems, an object of one embodiment of the present invention is to provide a novel substance that can exhibit phosphorescence. Another object is to provide a novel substance with high emission efficiency. Another object is to provide a novel substance that exhibits phosphorescence having a wavelength band of green to blue. Another object is to provide a light-emitting element, a light-emitting device, a lighting device, or an electronic device in which the novel substance that can exhibit phosphorescence is used. Another object is to provide a light-emitting element, a light-emitting device, a lighting device, or an electronic device with high emission efficiency. Another object is to provide a light-emitting element, a light-emitting device, a lighting device, or an electronic device in which a novel substance that exhibits phosphorescence having a wavelength band of green to blue is used. Another object is to provide a light-emitting element, a light-emitting device, a lighting device, or an electronic device with high reliability. Furthermore, another object is to provide a light-emitting element, a light-emitting device, a lighting device, or an electronic device having low power consumption.

The inventors found that an ortho-metalated complex where a 3-aryl-4H-1,2,4-triazole derivative is a ligand exhibits phosphorescence having a wavelength band of green to blue.

One embodiment of the present invention is an organometallic complex having a structure represented by General Formula (G1).

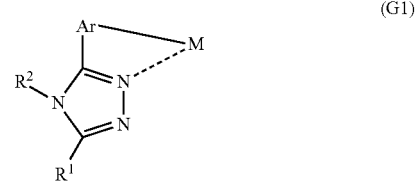

(G1)

Another embodiment of the present invention is an organometallic complex represented by General Formula (G2).

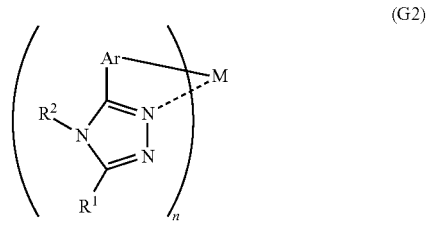

(G2)

In General Formulas (G1) and (G2), $R^1$ represents any of an alkyl group having 1 to 6 carbon atoms, a cycloalkyl group having 5 to 8 carbon atoms which may have a substituent, and an aralkyl group having 7 to 10 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an arylene group having 6 to 13 carbon atoms which may have a substituent. Further, M represents a Group 9 element or a Group 10 element.

In General Formula (G2), when M is a Group 9 element, n=3, and when M is a Group 10 element, n=2.

Note that specific examples of the alkyl group having 1 to 6 carbon atoms in $R^1$ include a methyl group, an ethyl group, a propyl group, an isopropyl group, a butyl group, a sec-butyl group, an isobutyl group, a tert-butyl group, and a hexyl group. In addition, specific examples of the cycloalkyl group having 5 to 8 carbon atoms which may have a substituent in $R^1$ include a cyclopentyl group, a cyclohexyl group, a cycloheptyl group, a cyclooctyl group, a 1-methylcyclohexyl group, and a 2,6-dimethylcyclohexyl group. Further, specific examples of the aralkyl group having 7 to 10 carbon atoms which may have a substituent in $R^1$ include a benzyl group, a phenylethyl group, a 3-phenylpropyl group, a 2,6-dimethylbenzyl group, and a 1-phenylethyl group.

Note that the alkyl group in $R^1$ preferably has more than or equal to 2 and less than or equal to 6 carbon atoms, particularly more than or equal to 3 and less than or equal to 6 carbon atoms. An allyl group having more than or equal to 2 and less than or equal to 6 carbon atoms suppresses interaction between molecules, so that the sublimation temperature can be reduced despite a high molecular weight. As a result, the evaporativity of the organometallic complex can be increased.

In addition, a branched allyl group is preferably used as the alkyl group in $R^1$. The branched alkyl group suppresses the level of polarity of the organometallic complex, so that yield in purification by column chromatography can be increased. Further, by using the branched alkyl group, the driving voltage of a light-emitting element fabricated including the organometallic complex can be reduced.

Therefore, it is more preferable to use an isopropyl group, an isobutyl group, a tert-butyl group, or a neopentyl group as the alkyl group in $R^1$.

Specific examples of $R^2$ include a methyl group, an ethyl group, a propyl group, an isopropyl group, a tert-butyl group, a hexyl group, a cyclohexyl group, a cyclohexyl group substituted by one or more methyl groups, a phenyl group, a biphenyl group, a phenyl group substituted by one or more methyl groups, a phenyl group substituted by one or more ethyl groups, a phenyl group substituted by one or more isopropyl groups, a phenyl group substituted by a tert-butyl group, a phenyl group substituted by a fluoro group, and a phenyl group substituted by a trifluoromethyl group.

Specific examples of Ar include a phenylene group, a phenylene group substituted by one or more alkyl groups, a phenylene group substituted by a cycloalkyl group, a phenylene group substituted by an alkoxy group, a phenylene group substituted by an aryloxy group, a phenylene group substituted by an alkylthio group, a phenylene group substituted by an arylthio group, a phenylene group substituted by a monoalkylamino group or a dialkylanimo group, a phenylene group substituted by a monoarylamino group or a diarylamino group, a phenylene group substituted by an aryl group, a phenylene group substituted by one or more halogen groups, a phenylene group substituted by one or more haloalkyl group, a biphenyl-diyl group, a naphthalene-diyl group, a fluorene-diyl group, a 9,9-dialkylfluorene-diyl group, and a 9,9-diarylfluorene-diyl group. Note that among these specific examples, when a substituent in which conjugation is extended from a benzene ring included in Ar is used as Ar (specifically, when a substituent having more than or equal to 10 carbon atoms is used as Ar) such as the biphenyl-diyl group, the naphthalene-diyl group, the fluorene-diyl group, the 9,9-dialkylfluorene-diyl group, or the 9,9-diarylfluorene-diyl group, an emission spectrum of the organometallic complex can be narrowed. In the case where Ar is a phenylene group, electron spin in an excited state enters between Ar and a triazole ring, whereby stretching vibration of carbon-carbon bonds of Ar and the triazole ring causes a local change when light is emitted. This is considered to be the reason why a second peak which originates from the stretching vibration from the short wavelength side in a spectrum is large. In contrast, when conjugation in Ar is extended from the benzene ring, the electron spin in an excited state enters Ar more easily. Thus, stretching vibration of carbon-carbon bonds of Ar and the triazole ring does not cause a local change, whereby the second peak becomes smaller. Therefore, a first peak on the shortest wavelength side in the emission spectrum becomes large. As a result, the emission wavelength of the organometallic complex can be shorter. In addition, the emission spectrum of the organometallic complex can be narrower.

Iridium and platinum are preferably used as the Group 9 element and the Group 10 element, respectively. In terms of a heavy atom effect, a heavy metal is preferably used as the central metal of the organometallic complex in order to more efficiently exhibit phosphorescence.

Another embodiment of the present invention is an organometallic complex having a structure represented by General Formula (G3).

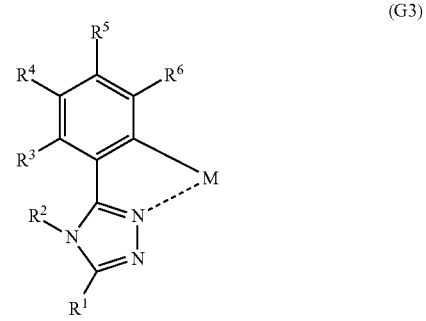

(G3)

Another embodiment of the present invention is an organometallic complex represented by General Formula (G4).

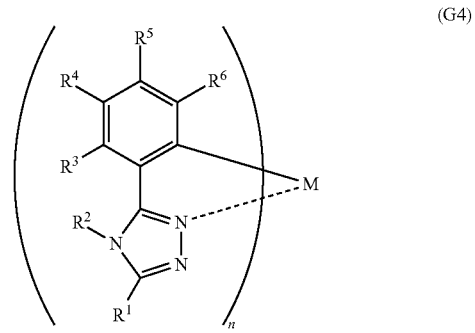

(G4)

In General Formulas (G3) and (G4), $R^1$ represents any of an alkyl group having 1 to 6 carbon atoms, a cycloallyl group having 5 to 8 carbon atoms which may have a substituent, and an aralkyl group having 7 to 10 carbon atoms which may have a substituent. In addition, $R^2$ represents any of an allyl group having 1 to 6 carbon atoms, a cycloallyl group having 5 to 8 carbon atoms which may have a substituent, and an aryl group having 6 to 12 carbon atoms which may have a substituent. Further, $R^3$ to $R^6$ individually represent any of hydrogen, an alkyl group having 1 to 6 carbon atoms, a cycloalkyl group having 5 to 8 carbon atoms, an alkoxy group having 1 to 4 carbon atoms, an aryloxy group having 6 to 12 carbon atoms, an alkylthio group having 1 to 4 carbon atoms, an arylthio group having 6 to 12 carbon atoms, an alkylamino group having 1 to 4 carbon atoms, a monoarylamino or diarylamino group having 6 to 24 carbon atoms, a cyano group, a halogen group, a haloalkyl group having 1 to 4 carbon atoms, and an aryl group having 6 to 12 carbon atoms. Note that substituents that are adjacent to each other in $R^3$ to $R^6$ may be directly bonded to each other form a ring structure. Further, M represents a Group 9 element or a Group 10 element.

In General Formula (G4), when M is a Group 9 element, n=3, and when M is a Group 10 element, n=2.

Note that specific examples of $R^1$ and $R^2$ can be the same as those in General Formulas (G1) and (G2).

Specific examples of $R^3$ to $R^6$ include, individually, hydrogen, a methyl group, an ethyl group, an isopropyl group, a tert-butyl group, a hexyl group, a cyclohexyl group, a methoxy group, an ethoxy group, a propoxy group, an isopropoxy group, a phenoxy group, a methylthio group, a phenylthio group, a dimethylamino group, diphenylamino group, a fluoro group, a fluoromethyl group, a difluoromethyl group, a trifluoromethyl group, a chloromethyl group, a dichloromethyl group, a bromomethyl group, a 2,2,2-trifluoroethyl group, a 3,3,3-trifluoropropyl group, a 1,1,1,3,3,3-hexafluoroisopropyl group, a phenyl group, a phenyl group substituted by a fluoro group, and a phenyl group substituted by a trifluoromethyl group. Note that at least one of $R^3$ to $R^6$ is preferably an electron-withdrawing group. Specific examples of the electron-withdrawing group include a cyano group, a fluoro group, a trifluoromethyl group, a phenyl group substituted by a fluoro group, a phenyl group substituted by a trifluoromethyl group. Since at least one of $R^3$ to $R^6$ is an electron-withdrawing group, the HOMO level of an organometallic complex is decreased, and an energy gap is increased accordingly; thus, the energy of the organometallic complex is stabilized. As a result, an emission wavelength of the organometallic complex can be shorter. For that reason, an organometallic complex having an electron-withdrawing group is especially preferable as a material that exhibits phosphorescence having a blue wavelength band.

It is preferable that hydrogen or an electron-withdrawing group be used individually in $R^3$ to $R^6$ in the organometallic complex having a structure represented by General Formula (G3) above because quantum yield is increased. That is, another embodiment of the present invention is an organometallic complex having a structure represented by General Formula (G5).

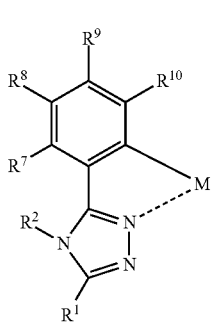

(G5)

It is preferable that hydrogen or an electron-withdrawing group be used individually in $R^3$ to $R^6$ in the organometallic complex represented by General Formula (G4) above because quantum yield is increased. That is, another embodiment of the present invention is an organometallic complex represented by General Formula (G6).

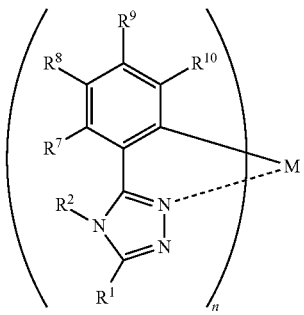

(G6)

In General Formulas (G5) and (G6), $R^1$ represents any of an alkyl group having 1 to 6 carbon atoms, a cycloalkyl group having 5 to 8 carbon atoms which may have a substituent, and an aralkyl group having 7 to 10 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, $R^7$ to $R^{10}$ individually represent hydrogen or an electron-withdrawing group. Further, M represents a Group 9 element or a Group 10 element.

In General Formula (G6), when M is a Group 9 element, n=3, and when M is a Group 10 element, n=2.

Note that at least one of $R^7$ to $R^{10}$ is preferably an electron-withdrawing group. Since at least one of $R^7$ to $R^{10}$ is an electron-withdrawing group, the HOMO level of an organometallic complex is decreased, and an energy gap is increased accordingly; thus, the energy of the organometallic complex is stabilized. As a result, the emission wavelength of the organometallic complex can be shorter.

Note that specific examples of $R^1$ and $R^2$ in General Formulas (G5) and (G6) can be the same as those in General Formulas (G1) and (G2).

A phenyl group is preferably used in $R^2$ in the organometallic complex having a structure represented by General Formula (G5) above because synthesis is easy. That is, another embodiment of the present invention is an organometallic complex having a structure represented by General Formula (G7).

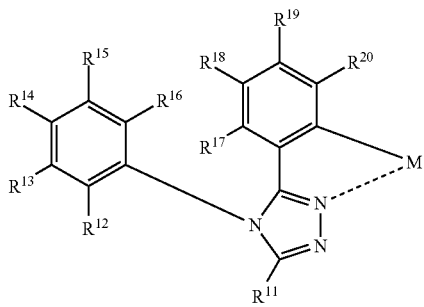

(G7)

A phenyl group is preferably used in $R^2$ in the organometallic complex represented by General Formula (G6) above because synthesis is easy. That is, another embodiment of the present invention is an organometallic complex represented by General Formula (G8).

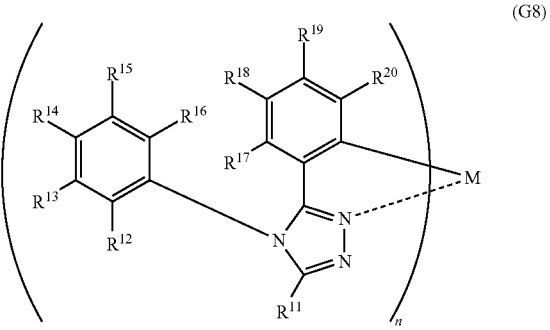

(G8)

In General Formulas (G7) and (G8), $R^{11}$ represents an alkyl group having 1 to 6 carbon atoms or a cycloalkyl group having 5 to 8 carbon atoms. Further, $R^{12}$ to $R^{16}$ individually represent any of hydrogen, an alkyl group having 1 to 6 carbon atoms, a cycloalkyl group having 5 to 8 carbon atoms, and a phenyl group. Further, $R^{17}$ to $R^{20}$ individually represent hydrogen or an electron-withdrawing group. Further, M represents a Group 9 element or a Group 10 element.

In General Formula (G8), when M is a Group 9 element, n=3, and when M is a Group 10 element, n=2.

Note that it is preferable that either $R^{12}$ or $R^{16}$, or both $R^{12}$ and $R^{16}$ have a substituent other than hydrogen, in which case a triazole ring and a phenyl group do not become flat due to steric hindrance of the substituent, so that the emission wavelength of the organometallic complex can be shorter. Alternatively, at least one of $R^{17}$ to $R^{20}$ is preferably an electron-withdrawing group. Since at least one of $R^{17}$ to $R^{20}$ is an electron-withdrawing group, the HOMO level of an organometallic complex is decreased, and an energy gap is increased accordingly; thus, the energy of the organometallic complex is stabilized. As a result, the emission wavelength of the organometallic complex can be shorter.

Note that specific examples of $R^{11}$ in General Formulas (G7) and (G8) can be the same as those in General Formulas (G1) and (G2). In addition, specific examples of $R^{12}$ to $R^{16}$ include hydrogen, a methyl group, an ethyl group, an isopropyl group, a tert-butyl group, a hexyl group, a cyclohexyl group, a phenyl group, and the like.

In the organometallic complex having a structure represented by General Formula (G7) where each of $R^{12}$ to $R^{16}$ is hydrogen, an organometallic complex where $R^{11}$ is an alkyl group having 1 to 6 carbon atoms or a cycloallyl group having 5 to 8 carbon atoms is preferable as compared with an organometallic complex where $R^{11}$ is hydrogen because yield in synthesis is drastically increased. That is, another embodiment of the present invention is an organometallic complex having a structure represented by General Formula (G9).

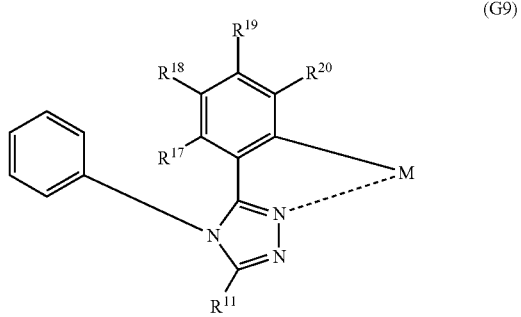

(G9)

In the organometallic complex represented by General Formula (G8) where each of $R^{12}$ to $R^{16}$ is hydrogen, an organometallic complex where $R^{11}$ is an alkyl group having 1 to 6 carbon atoms or a cycloalkyl group having 5 to 8 carbon atoms is preferable as compared with an organometallic complex where $R^{11}$ is hydrogen because yield in synthesis is drastically increased. That is, another embodiment of the present invention is an organometallic complex represented by General Formula (G10).

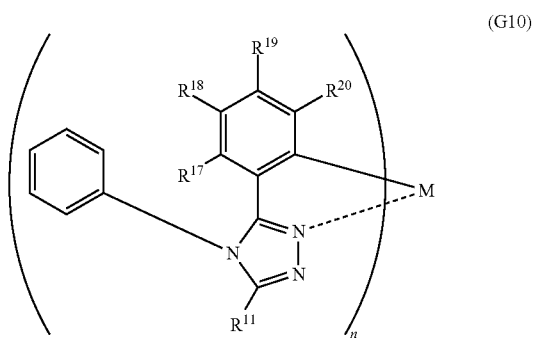

(G10)

In General Formulas (G9) and (G10), $R^{11}$ represents an alkyl group having 1 to 6 carbon atoms or a cycloalkyl group having 5 to 8 carbon atoms. Further, $R^{17}$ to $R^{20}$ individually represent hydrogen or an electron-withdrawing group. Further, M represents a Group 9 element or a Group 10 element.

In General Formula (G10), when M is a Group 9 element, n=3, and when M is a Group 10 element, n=2.

Note that at least one of $R^{17}$ to $R^{20}$ is preferably an electron-withdrawing group. Since at least one of $R^{17}$ to $R^{20}$ is an electron-withdrawing group, the HOMO level of an organometallic complex is decreased, and an energy gap is increased accordingly; thus, the energy of the organometallic complex is stabilized. As a result, the emission wavelength of the organometallic complex can be shorter.

Note that specific examples of $R^{11}$ in General Formulas (G9) and (G10) can be the same as those of $R^1$ in General Formulas (G1) and (G2).

In General Formulas (G5) to (G10), examples of the electron-withdrawing group include a halogen group, a haloalkyl group, a phenyl group substituted by a halogen group, and a phenyl group substituted by a haloalkyl group. More specific examples include a cyano group, a fluoro group, a trifluoromethyl group, a phenyl group substituted by a fluoro group, a phenyl group substituted by a trifluoromethyl group; in particular, a fluoro group and a trifluoromethyl group are preferable. In the case where $R^7$ and/or $R^9$ in General Formulas (G5) and (G6), and $R^{17}$ and/or $R^{19}$ in General Formulas (G7) to (G10) are substituted by an alkoxy group such as a methoxy group, an ethoxy group, a propoxy group, or an isopropoxy group, the alkoxy group can function as the electron-withdrawing group.

Another embodiment of the present invention is a light-emitting element including a layer containing any of the organometallic complexes between a pair of electrodes. The layer containing the organometallic complex may be a light-emitting layer.

Another embodiment of the present invention is a light-emitting element including, between a pair of electrodes, a first light-emitting unit containing any of the organometallic complexes and a second light-emitting unit containing a light-emitting material that emits light with a longer wavelength than the organometallic complex.

Another embodiment of the present invention is a light-emitting element including, between a pair of electrodes, a first light-emitting unit containing any of the organometallic complexes, a second light-emitting unit containing a first light-emitting material that emits light with a longer wavelength than the organometallic complex, and a third light-emitting unit containing a second light-emitting material that emits light with a longer wavelength than the organometallic complex and a shorter wavelength than the first light-emitting material.

Another embodiment of the present invention is a display device including any of the light-emitting elements in a pixel portion.

Another embodiment of the present invention is an electronic device including the display device in a display portion.

Another embodiment of the present invention is a lighting device including any of the above-described light-emitting elements as a light source.

In one embodiment of the present invention, a cycloalkyl group having 5 to 8 carbon atoms, an aralkyl group having 7 to 10 carbon atoms, an aryl group having 6 to 12 carbon atoms, and an arylene group having 6 to 13 carbon atoms each may have a substituent or may not have a substituent. When a substituent is included, carbon atoms contained in the substituent is not counted as the carbon atoms described above. For example, a cycloalkyl group having a substituent has more than or equal to 5 and less than or equal to 8 carbon atoms except for carbon contained in the substituent.

In this specification, "a light-emitting device" means general devices each having a light-emitting element; specifically, it includes in its category a backlight used in a display device such as a television or a mobile phone, a traffic light, a lighting application such as a streetlight or illuminations on the street, a lighting device, lighting for breeding that can be used in a plastic greenhouse, and the like.

In this specification, the expression "A and B are connected to each other" includes a case where A and B are electrically connected to each other (i.e., a case where A and B are connected to each other with another element or another circuit interposed therebetween), a case where A and B are functionally connected to each other (i.e., a case where A and B are functionally connected with another circuit interposed therebetween), and a case where A and B are directly connected to each other (i.e., a case where A and B are connected to each other without another element or another circuit interposed therebetween).

With one embodiment of the present invention, it is possible to provide a novel substance that can exhibit phosphorescence or a novel substance with high emission efficiency. It is also possible to provide a light-emitting element, a light-emitting device, a lighting device, and an electronic device using the novel substance. It is also possible to provide a light-emitting element, a light-emitting device, a lighting device, or an electronic device with high emission efficiency. It is also possible to provide a light-emitting element, a light-emitting device, a lighting device, or an electronic device with excellent reliability. It is also possible to provide a light-emitting element, a light-emitting device, a lighting device, or an electronic device with low power consumption.

BRIEF DESCRIPTION OF DRAWINGS

FIG. 6 illustrates examples of lighting devices according to one embodiment of the present invention.

BEST MODE FOR CARRYING OUT THE INVENTION

Figure 1A:
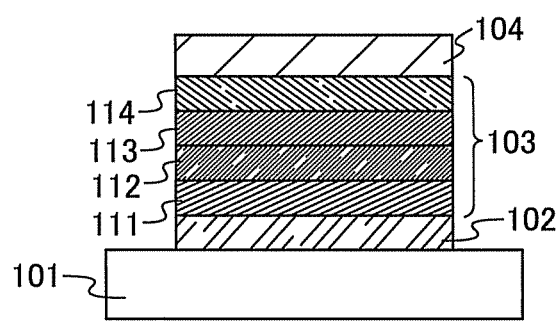
FIGS. 1A and 1B are conceptual diagrams of light-emitting elements according to embodiments of the present invention.

Embodiments and Examples of the present invention will be described in detail with reference to the accompanying drawings. Note that the present invention is not defined to description below, and it is easily understood by those skilled in the art that modes and details can be modified in various ways without departing from the purpose and the scope of the present invention. Therefore, in Embodiments and Examples of the present invention which will be described below, the same portions are commonly denoted by the same reference numerals in different drawings.

In addition, each of Embodiments and Examples described below can be implemented in combination with any of the other Embodiments and Examples which are described in this specification unless otherwise mentioned.

Embodiment 1

One embodiment of the present invention is an organometallic complex having a structure represented by General Formula (G1).

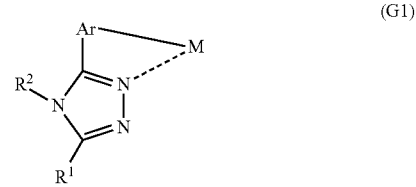

(G1)

In General Formula (G1), $R^1$ represents any of an alkyl group having 1 to 6 carbon atoms, a cycloallyl group having 5 to 8 carbon atoms which may have a substituent, and an aralkyl group having 7 to 10 carbon atoms which may have a substituent. In addition, $R^2$ represents any of an alkyl group having 1 to 6 carbon atoms, a cycloallyl group having 5 to 8 carbon atoms which may have a substituent, and an aryl group having 6 to 12 carbon atoms which may have a substituent. Further, Ar represents an arylene group having 6 to 13 carbon atoms which may have a substituent. Further, M represents a Group 9 element or a Group 10 element.

Specific examples of organometallic complexes containing the structure represented by General Formula (G1) can be organometallic complexes represented by Structural Formulas (100) to (150). Note that the present invention is not limited to the organometallic complexes represented by these structural formulas.

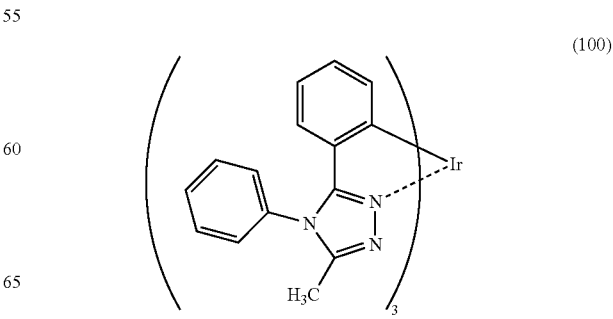

(100)

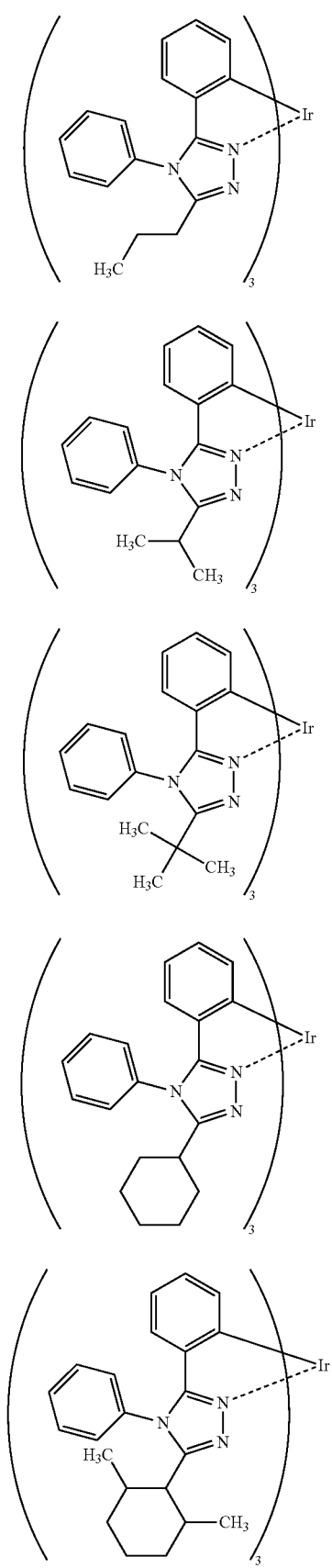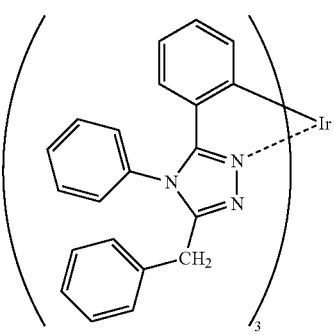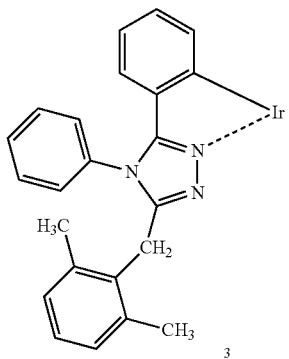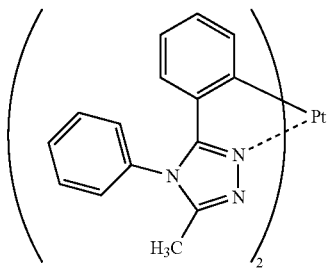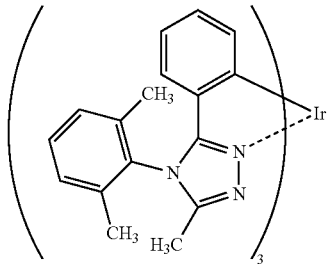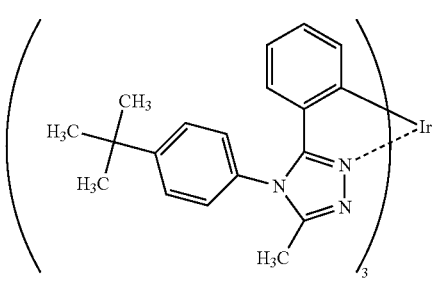

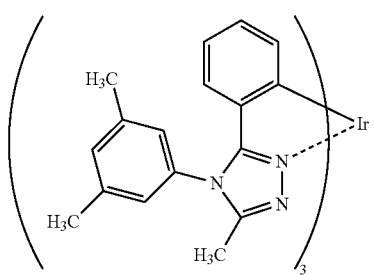 (111)
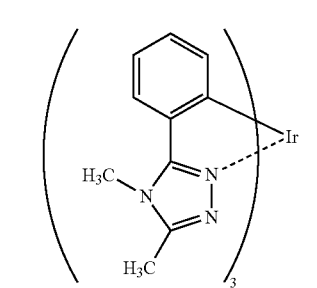 (112)
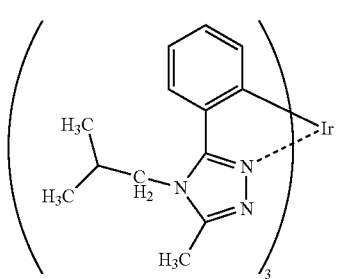 (113)
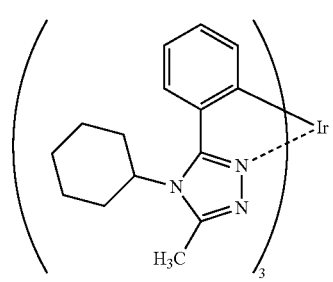 (114)
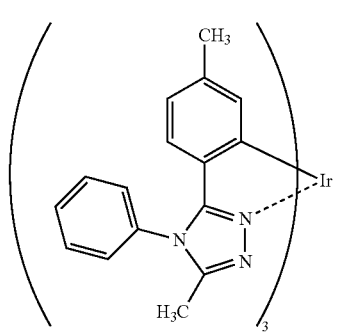 (115)
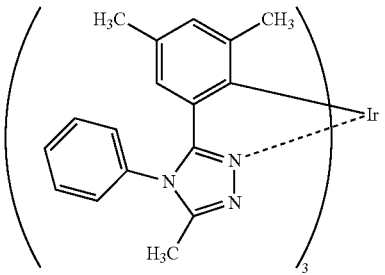 (116)
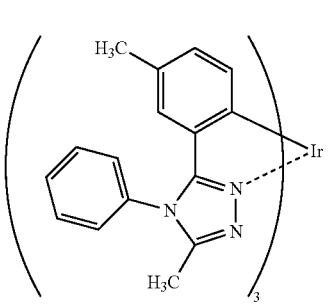 (117)
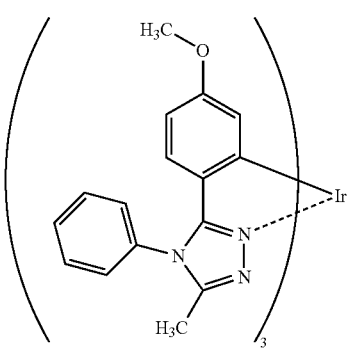 (118)
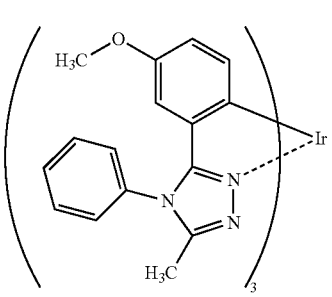 (119)
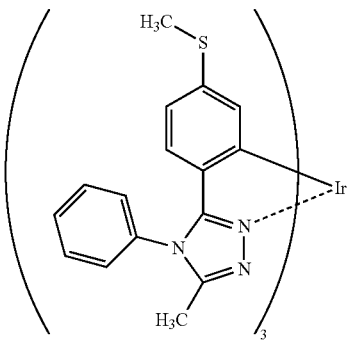 (120)

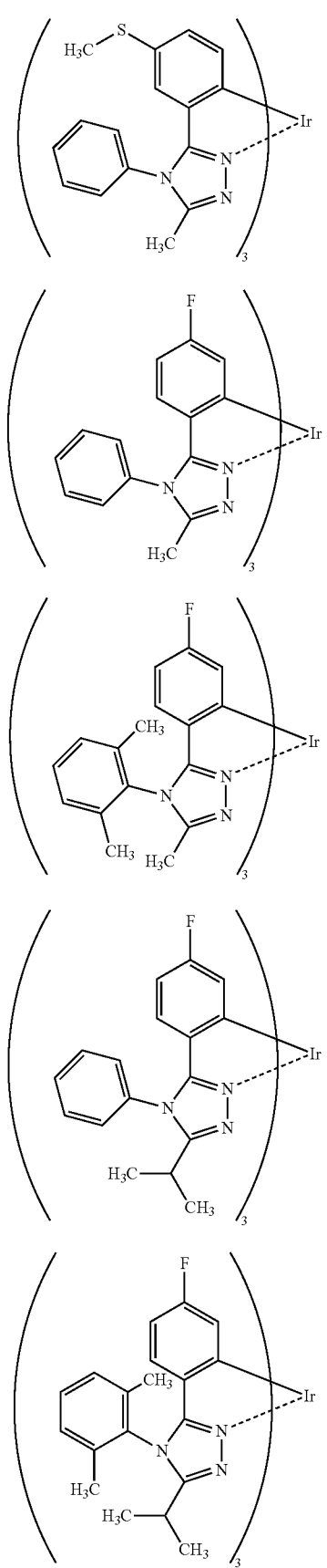
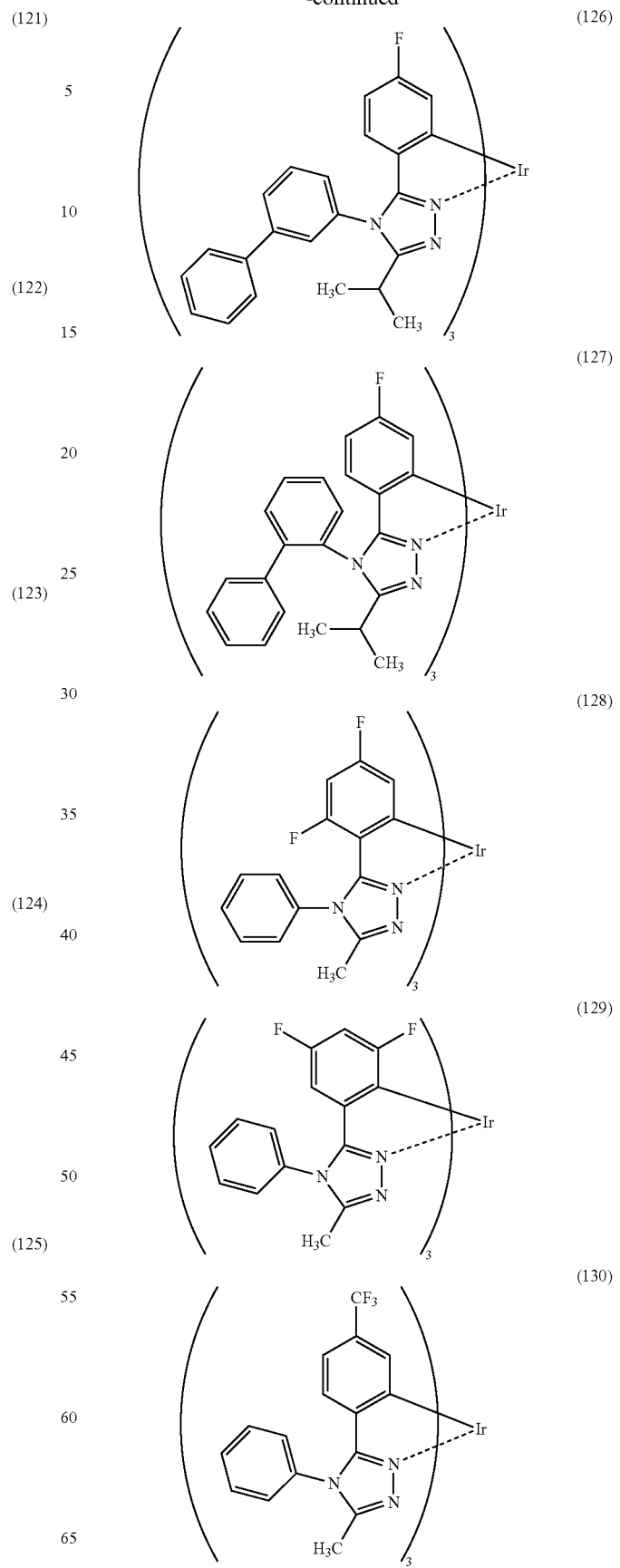

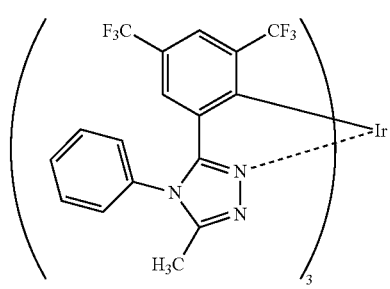
(131)
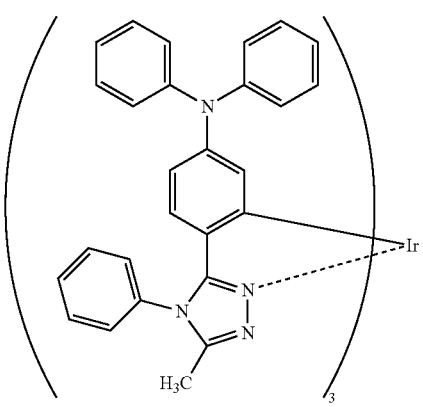
(132)
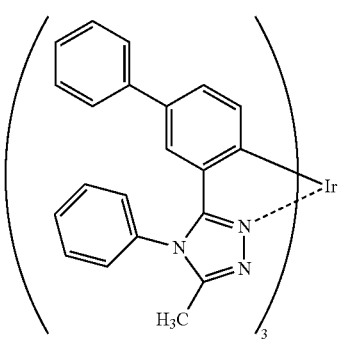
(135)
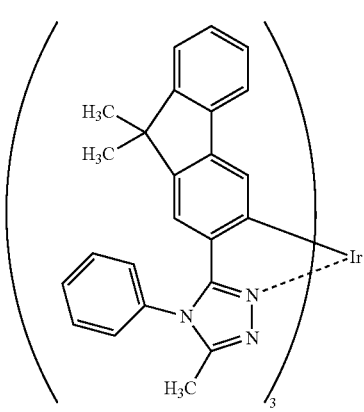
(136)
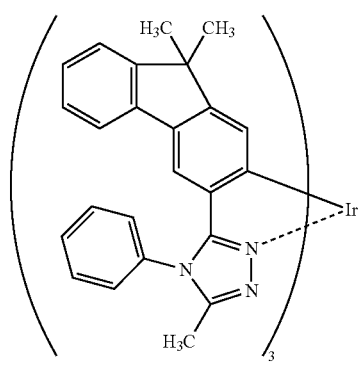
(137)
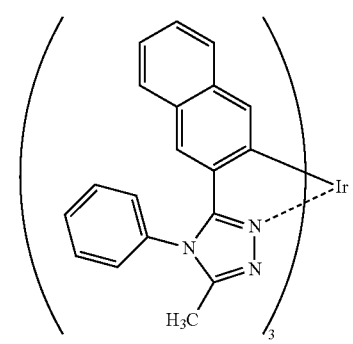
(138)
(133)
(134)

(139) 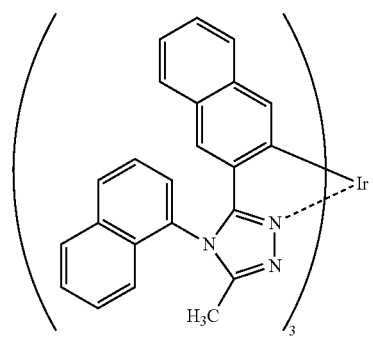
(140) 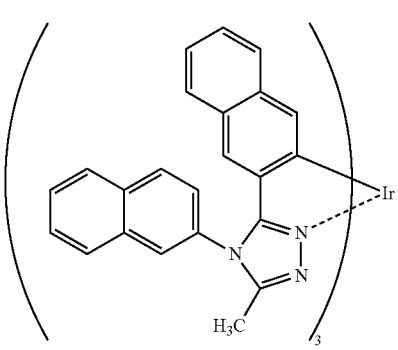
(141) 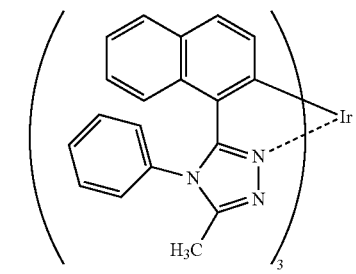
(142) 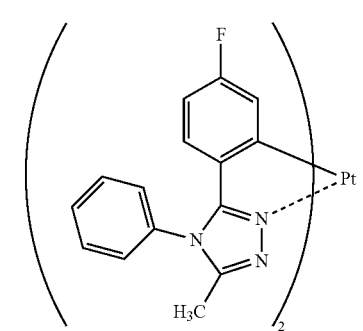
(143) 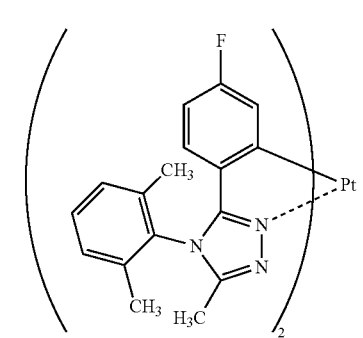
(144) 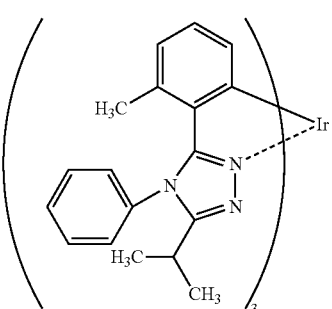
(145) 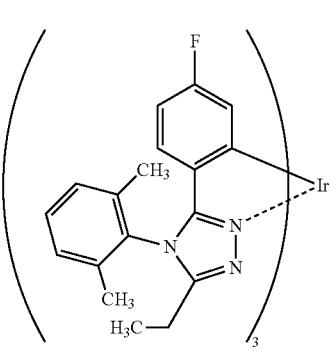
(146) 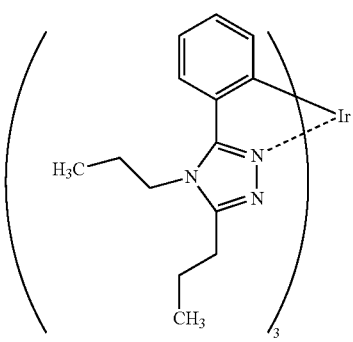
(147) 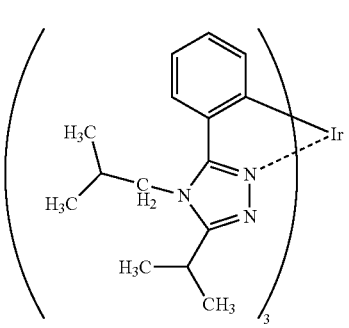

(148)
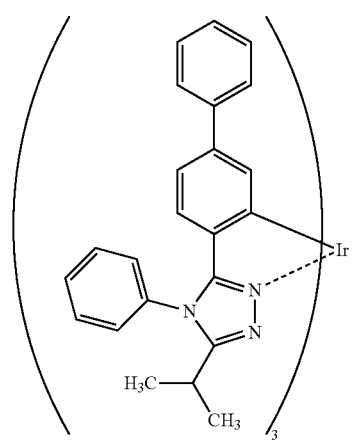

(149)
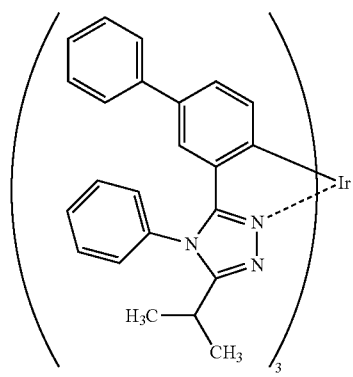

(150)
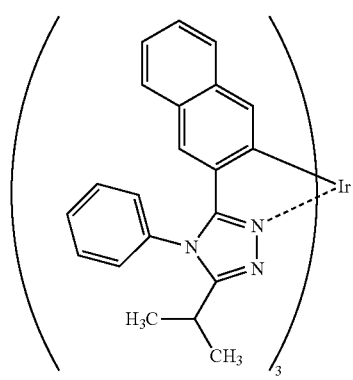

(151)
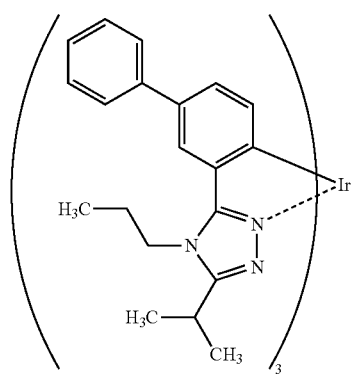

(152)
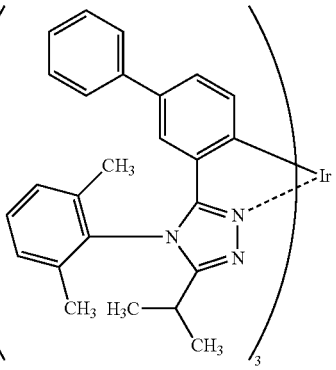

The above-described organometallic complexes each of which is one embodiment of the present invention are novel substances that can exhibit phosphorescence.

Next, an example of a synthesis method of an organometallic complex having the structure represented by General Formula (G1) is described.

Step 1: Synthesis Method of 3-aryl-4H-1,2,4-triazole Derivative

First, since a 3-aryl-4H-1,2,4-triazole derivative which is represented by General Formula (G0) below is a novel substance, an example of a synthesis method thereof is described. In General Formula (G0), $R^1$ represents any of an alkyl group having 1 to 6 carbon atoms, a cycloalkyl group having 5 to 8 carbon atoms which may have a substituent, and an aralkyl group having 7 to 10 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an aryl group having 6 to 13 carbon atoms which may have a substituent.

(G0)
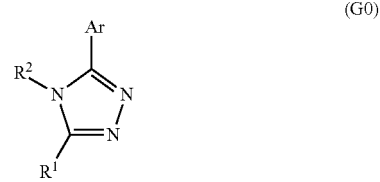

Note that specific examples of the alkyl group having 1 to 6 carbon atoms in $R^1$ include a methyl group, an ethyl group, a propyl group, an isopropyl group, a butyl group, a sec-butyl group, an isobutyl group, a tert-butyl group, and a hexyl group. In addition, specific examples of the cycloalkyl group having 5 to 8 carbon atoms which may have a substituent in $R^1$ include a cyclopentyl group, a cyclohexyl group, a cycloheptyl group, a cyclooctyl group, a 1-methylcyclohexyl group, and a 2,6-dimethylcyclohexyl group. Further, specific examples of the aralkyl group having 7 to 10 carbon atoms which may have a substituent in $R^1$ include a benzyl group, a phenylethyl group, a 3-phenylpropyl group, a 2,6-dimethylbenzyl group, and a 1-phenylethyl group.

Specific examples of $R^2$ include a methyl group, an ethyl group, a propyl group, an isopropyl group, a tert-butyl group, a hexyl group, a cyclohexyl group, a cyclohexyl group substituted by one or more methyl groups, a phenyl group, a biphenyl group, a phenyl group substituted by one or more methyl groups, a phenyl group substituted by one or more ethyl groups, a phenyl group substituted by one or more isopropyl groups, a phenyl group substituted by a tert-butyl group, a phenyl group substituted by a fluoro group, and a phenyl group substituted by a trifluoromethyl group.

Specific examples of Ar include a phenylene group, a phenylene group substituted by one or more alkyl groups, a phenylene group substituted by a cycloalkyl group, a phenylene group substituted by an alkoxy group, a phenylene group substituted by an aryloxy group, a phenylene group substituted by an alkylthio group, a phenylene group substituted by an arylthio group, a phenylene group substituted by a monoalkylamino group or a dialkylanimo group, a phenylene group substituted by a monoarylamino group or a diarylamino group, a phenylene group substituted by an aryl group, a phenylene group substituted by one or more halogen groups, a phenylene group substituted by one or more haloalkyl group, a biphenyl-diyl group, a naphthalene-diyl group, a fluorene-diyl group, a 9,9-dialkylfluorene-diyl group, and a 9,9-diarylfluorene-diyl group.

As shown in Scheme (a) below, by reacting a thioether compound containing Ar or an N-substituted thioamide compound containing Ar (A1) with an alkyl hydrazide compound (A2), a 3-aryl-4H-1,2,4-triazole derivative can be prepared. Note that in Scheme (a), $R^1$ represents any of an alkyl group having 1 to 6 carbon atoms, a cycloalkyl group having 5 to 8 carbon atoms which may have a substituent, and an aralkyl group having 7 to 10 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an arylene group having 6 to 13 carbon atoms which may have a substituent.

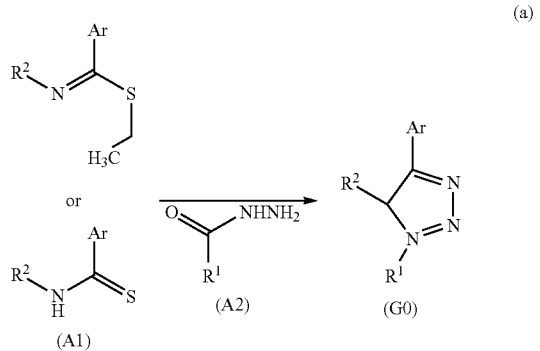

Note that the synthesis method for the 3-aryl-4H-1,2,4-triazole derivative is not limited to Scheme (a). For example, there is another example of a synthesis method in which a thioether compound containing $R^1$ and $R^2$ or an N-substituted thioamide compound containing $R^1$ and $R^2$ is reacted with an aryl hydrazide compound. As shown in Scheme (a') below, there is also a method in which a dihydrazide compound (A1') and a primary amine compound (A2') are reacted. Note that in Scheme (a'), $R^1$ represents any of an alkyl group having 1 to 6 carbon atoms, a cycloalkyl group having 5 to 8 carbon atoms which may have a substituent, and an aralkyl group having 7 to 10 carbon atoms which may have a substituent. In addition, $R^2$ represents any of an alkyl group having 1 to 6 carbon atoms, a cycloallyl group having 5 to 8 carbon atoms which may have a substituent, and an aryl group having 6 to 12 carbon atoms which may have a substituent. Further, Ar represents an arylene group having 6 to 13 carbon atoms which may have a substituent.

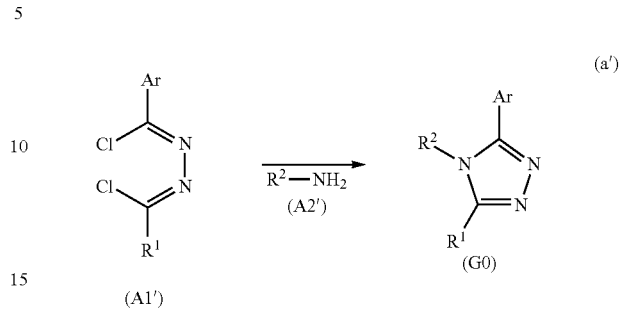

In the above-described manner, the 3-aryl-4H-1,2,4-triazole derivative can be synthesized by a simple synthetic scheme.

Step 2: Synthesis Method of Orthometalated Complex Having 3-aryl-4H-1,2,4-triazole Derivative as Ligand As shown in Synthetic scheme (b) below, by mixing the 3-aryl-4H-1,2,4-triazole derivative that can be prepared in accordance with Step 1 and a Group 9 or Group 10 metal compound containing a halogen (e.g., rhodium chloride hydrate, palladium chloride, iridium chloride hydrate, ammonium hexachloroiridate, or potassium tetrachloroplatinate) or a Group 9 or Group 10 organometallic complex compound (e.g., an acetylacetonate complex or a diethylsulfide complex), and then by heating the mixture, an organometallic complex having the structure represented by General Formula (G1) can be prepared. This heating process can be performed after the 3-aryl-4H-1,2,4-triazole derivative, which can be prepared in accordance with Step 1, and a Group 9 or Group 10 metal compound containing a halogen or a Group 9 or Group 10 organometallic complex compound are dissolved in an alcohol-based solvent (e.g., glycerol, ethylene glycol, 2-metoxyethanol, or 2-ethoxyethanol). Note that in Synthetic scheme (b), M represents a Group 9 or Group 10 element. When M is a Group 9 element, n=3, and when M is a Group 10 element, n=2.

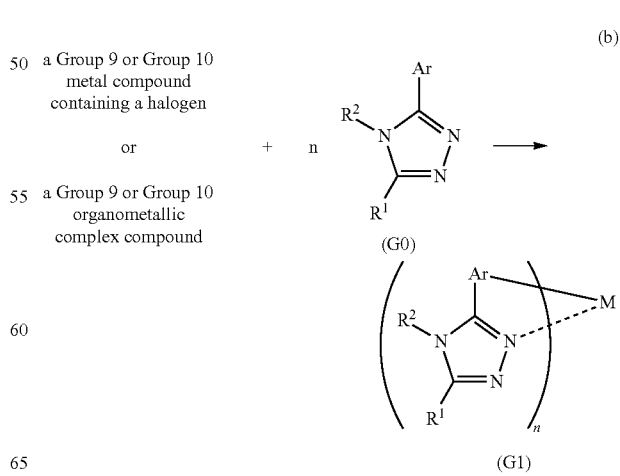

Since various kinds of the above-described compounds (A1), (A2), (A1'), and (A2') are commercially available or can be synthesized, many kinds of 3-aryl-4H-1,2,4-triazole derivatives represented by General Formula (G0) can be synthesized. Accordingly, an organometallic complex which is one embodiment of the present invention has a feature of wide variations of a ligand. By using such an organometallic complex having wide variations of a ligand in manufacture of a light-emitting element, fine adjustment of element characteristics required for the light-emitting element can be performed easily.

Embodiment 2

One embodiment of a light-emitting element using the organometallic complex described in Embodiment 1 is described with reference to FIG. 1A.

The light-emitting element includes a pair of electrodes (a first electrode 102 and a second electrode 104) and an EL layer 103 interposed between the pair of electrodes. The light-emitting element described in this embodiment is provided over a substrate 101.

The substrate 101 is used as a support of the light-emitting element. As the substrate 101, a glass substrate, a plastic substrate, or the like can be used. As the substrate 101, a substrate having flexibility (a flexible substrate) or a substrate having a curved surface can also be used. A substrate other than the above substrates can also be used as the substrate 101 as long as it functions as a support of the light-emitting element.

One of the first electrode 102 and the second electrode 104 serves as an anode and the other serves as a cathode. In this embodiment, the first electrode 102 is used as the anode and the second electrode 104 is used as the cathode; however, the present invention is not limited to this structure.

It is preferable to use a metal, an alloy, or a conductive compound, a mixture thereof, or the like having a high work function (specifically, more than or equal to 4.0 eV) as a material for the anode. Specifically, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like can be given.

It is preferable to use a metal, an alloy, or a conductive compound, a mixture thereof, or the like having a low work function (specifically, less than or equal to 3.8 eV) as a material for the cathode. Specifically, an element belonging to Group 1 or Group 2 of the periodic table, that is, an alkali metal such as lithium (Li) and cesium (Cs), and an alkaline earth metal such as magnesium (Mg), calcium (Ca), and strontium (Sr) can be given. An alloy containing an alkali metal or an alkaline earth metal (e.g., MgAg or AlLi) can also be used. Moreover, a rare earth metal such as europium (Eu) or ytterbium (Yb), or an alloy containing a rare earth metal can also be used. In the case where an electron-injection layer in contact with the second electrode 104 is provided as part of the EL layer 103, the second electrode 104 can be formed using a variety of conductive materials such as Al, Ag or ITO, regardless of their work functions. These conductive materials can be deposited by a sputtering method, an inkjet method, a spin-coating method, or the like.

Although the EL layer 103 can be formed to have a single-layer structure, it is normally formed to have a stacked-layer structure. There is no particular limitation on the stacked-layer structure of the EL layer 103. It is possible to combine, as appropriate, a layer containing a substance having a high electron-transport property (an electron-transport layer) or a layer containing a substance having a high hole-transport property (a hole-transport layer), a layer containing a substance having a high electron-injection property (an electron-injection layer), a layer containing a substance having a high hole-injection property (a hole-injection layer), a layer containing a bipolar substance (a substance having high electron- and hole-transport properties), a layer containing a light-emitting material (a light-emitting layer), and the like. For example, it is possible to combine, as appropriate, a hole-injection layer, a hole-transport layer, a light-emitting layer, an electron-transport layer, an electron-injection layer, and the like. FIG. 1A illustrates as the EL layer 103 formed over the first electrode 102, a structure in which a hole-injection layer 111, a hole-transport layer 112, a light-emitting layer 113, and an electron-transport layer 114 are sequentially stacked.

A light-emitting element emits light when current flows due to a potential difference generated between the first electrode 102 and the second electrode 104, and holes and electrons are recombined in the light-emitting layer 113 containing a substance having a high light-emitting property. That is, a light-emitting region is formed in the light-emitting layer 113.

The emitted light is extracted out through one or both of the first electrode 102 and the second electrode 104. Therefore, one or both of the first electrode 102 and the second electrode 104 are light-transmitting electrodes. When only the first electrode 102 is a light-transmitting electrode, light emission is extracted from a substrate side through the first electrode 102. Meanwhile, when only the second electrode 104 is a light-transmitting electrode, light emission is extracted from the side opposite to the substrate side through the second electrode 104. When both the first electrode 102 and the second electrode 104 are light-transmitting electrodes, light emission is extracted from both the substrate side and the side opposite to the substrate through the first electrode 102 and the second electrode 104.

An organometallic complex represented by General Formula (G1) which is one embodiment of the present invention can be used for the light-emitting layer 113, for example. In this case, the light-emitting layer 113 may be formed with a thin film containing the organometallic complex represented by General Formula (G1), or may be formed with a thin film in which a host material is doped with the organometallic complex represented by General Formula (G1). When the light-emitting layer 113 is formed with the thin film in which a host material is doped with the organometallic complex, an alkyl group in $R^1$ in General Formula (G1) is preferably a branched alkyl group. The branched alkyl group suppresses the entry of carriers into the organometallic complex due to steric hindrance, and thus has an effect of decreasing the carrier trapping property of the organometallic complex and reducing the driving voltage of the element as a result. Therefore, an alkyl group in $R^1$ is more preferably an isopropyl group, an isobutyl group, a tert-butyl group, or a neopentyl group.

In order to suppress energy transfer from an exciton which is generated in the light-emitting layer 113, the hole-transport layer 112 or the electron-transport layer 114 which is in contact with the light-emitting layer 113, particularly a carrier- (electron- or hole-) transport layer in contact with a side closer to a light-emitting region in the light-emitting layer 113, is preferably formed using a substance having an energy gap larger than an energy gap of a light-emitting material contained in the light-emitting layer or an energy gap of an emission center substance contained in the light-emitting layer.

The hole-injection layer 111 contains a substance having a high hole-injection property, and has a function of helping injection of holes from the first electrode 102 to the hole-transport layer 112. By providing the hole-injection layer 111, a difference between the ionization potential of the first electrode 102 and the hole-transport layer 112 is relieved, so that holes are easily injected. The hole-injection layer 111 is preferably formed using a substance having smaller ionization potential than a substance contained in the hole-transport layer 112 and having larger ionization potential than a substance contained in the first electrode 102, or a substance in which an energy band is bent when the substance being provided as a thin film with a thickness of 1 to 2 nm between the hole-transport layer 112 and the first electrode 102. That is, a material for the hole-injection layer 111 is preferably selected so that the ionization potential of the hole-injection layer 111 is relatively smaller than that of the hole-transport layer 112. Specific examples of substances having a high hole-injection property include phthalocyanine (abbreviation: $H_2Pc$), a phthalocyanine-based compound such as copper phthalocyanine (abbreviation: CuPc), a high molecular compound such as poly(ethylenedioxythiophene)/poly(styrenesulfonate) aqueous solution (PEDOT/PSS), and the like.

The hole-transport layer 112 contains a substance having a high hole-transport property. Note that a substance having a high hole-transport property refers to a material having higher mobility of holes than that of electrons and having a ratio value of hole mobility to electron mobility (=hole mobility/electron mobility) of more than 100. A substance having a hole mobility of more than or equal to $1\times10^{-6}$ $cm^2/Vs$ is preferably used as a substance having a high hole-transport property. Specific examples of substances having a high hole-transport property include 4,4'-bis[N-(1-naphthyl)-N-phenylamino]biphenyl (abbreviation: NPB), 4,4'-bis[N-(3-methylphenyl)-N-phenylamino]biphenyl (abbreviation: PD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis{N-[4-(N,N-di-m-tolylamino)phenyl]-N-phenylamino}biphenyl (abbreviation: DNTPD), 1,3,5-tris[N,N-di(m-tolyl)amino]benzene (abbreviation: m-MTDAB), 4,4',4"-tris(N-carbazolyl)triphenylamine (abbreviation: TCTA), phthalocyanine (abbreviation: $H_2Pc$), copper phthalocyanine (abbreviation: CuPc), vanadyl phthalocyanine (abbreviation: VOPc), and the like. Note that the hole-transport layer 112 may have a single-layer structure or a stacked-layer structure.

The electron-transport layer 114 contains a substance having a high electron-transport property. Note that a substance having a high electron-transport property refers to a material having higher mobility of electrons than that of holes and having a ratio value of electron mobility to hole mobility (=electron mobility/hole mobility) of more than 100. A substance having an electron mobility of more than or equal to $1\times10^{-6}$ $cm^2/Vs$ is preferably used as a substance having a high electron-transport property. Specific examples of the substances having a high electron-transport property include a metal complex having a quinoline skeleton, a metal complex having a benzoquinoline skeleton, a metal complex having an oxazole-based ligand, and a metal complex having a thiazole-based ligand. Specific examples of metal complexes having a quinoline skeleton include tris(8-quinolinolate)aluminum (abbreviation: Alq), tris(4-methyl-8-quinolinolato) aluminum (abbreviation: $Almq_3$), and bis(2-methyl-8-quino-linolato)(4-phenylphenolate)aluminum (abbreviation: BAlq). A specific example of a metal complex having a benzoquinoline skeleton is bis(10-hydroxybenzo[h]quinolinato) beryllium (abbreviation: $BeBq_2$). A specific example of a metal complex having an oxazole-based ligand is bis[2-(2-hydroxyphenyl)benzoxazolato]zinc (abbreviation: $Zn(BOX)_2$). A specific example of a metal complex having a thiazole-based ligand is bis[2-(2-hydroxyphenyl)benzothiazolato]zinc (abbreviation: $Zn(BTZ)_2$). In addition to the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-buthylphenyl)-1,2,4-triazole (abbreviation: TAZ 01), bathophenanthroline (abbreviation: BPhen), bathocuproine (BCP), or the like can be used. The substances specifically listed above are mainly substances having an electron mobility of more than or equal to $10^{-6}$ $cm^2/Vs$. Note that any substance other than the above substances may be used for the electron-transport layer 114 as long as the electron-transport property is higher than the hole-transport property. Further, the electron-transport layer 114 may have a single-layer structure or a stacked-layer structure.

Further, a layer for controlling transport of electron carriers may be provided between the light-emitting layer 113 and the electron-transport layer 114. Note that the layer for controlling transport of electron carriers is a layer obtained by adding a small amount of substance having a high electron-trapping property to the above-described material having a high electron-transport property. By providing the layer for controlling transport of electron carriers, it is possible to suppress transfer of electron carriers, and to adjust carrier balance. Such a structure is very effective in suppressing a problem (such as a short life of an element) caused when electrons pass through the light-emitting layer.

In addition, an electron-injection layer may be provided between the electron-transport layer 114 and the second electrode 104, in contact with the second electrode 104. As the electron-injection layer, a layer which contains a substance having an electron-transport property and an alkali metal, an alkaline earth metal, or a compound thereof such as lithium fluoride (LiF), cesium fluoride (CsF), or calcium fluoride ($CaF_2$) may be used. Specifically, a layer containing Alq and magnesium (Mg) can be used. By providing the electron-injection layer, electrons can be injected efficiently from the second electrode 104.

Various methods can be used for forming the EL layer 103, regardless of a dry method or a wet method. For example, a vacuum evaporation method, an inkjet method, a spin-coating method, or the like can be used. When the EL layer 103 has a stacked-layer structure, deposition methods of the layers may be different or the same.

The first electrode 102 and the second electrode 104 may be formed by a wet method using a sol-gel method, or a wet method using a paste of a metal material. Further, the electrodes may be formed by a dry method such as sputtering or vacuum evaporation.

Embodiment 3

In this embodiment, an embodiment of a light-emitting element in which a plurality of light-emitting units are stacked (hereinafter this light-emitting element is referred to as a "tandem light-emitting element") is described with reference to FIG. 1B. The tandem light-emitting element is a light-emitting element having a plurality of light-emitting units between a first electrode and a second electrode. The light-emitting units can be formed using a structure similar to that of the EL layer 103 described in Embodiment 2. That is, the light-emitting element described in Embodiment 2 has a single light-emitting unit, and the light-emitting element described in this embodiment has a plurality of light-emitting units.

Figure 1B:
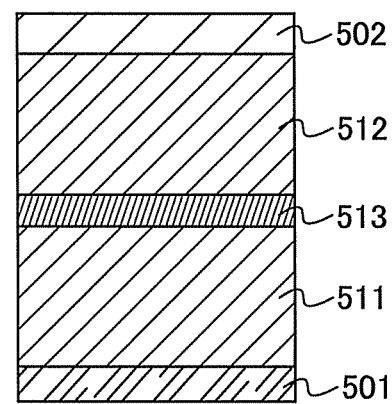

In FIG. 1B, a first light-emitting unit 511 and a second light-emitting unit 512 are stacked between a first electrode 501 and a second electrode 502. Electrodes similar to those described in Embodiment 2 can be used as the first electrode 501 and the second electrode 502. Alternatively, the structures of the first light-emitting unit 511 and the second light-emitting unit 512 may be the same or different from each other, and each of the structures can be similar to the structure described in Embodiment 2.

A charge-generating layer 513 is provided between the first light-emitting unit 511 and the second light-emitting unit 512. The charge-generating layer 513 contains a composite material of an organic compound and a metal oxide and has a function of injecting electrons to one side of the light-emitting unit, and holes to the other side of the light-emitting unit, when voltage is applied between the first electrode 501 and the second electrode 502. The composite material of the organic compound and the metal oxide can achieve low-voltage driving and low-current driving because it has a superior carrier-injection property and carrier-transport property.

It is preferable to use an organic compound which has a hole-transport property and has a hole mobility of more than or equal to $10^{-6}$ cm$^2$/Vs as the organic compound. Specific examples of the organic compound include an aromatic amine compound, a carbazole compound, aromatic hydrocarbon, and a high molecular compound (an oligomer, a dendrimer, a polymer, or the like). It is possible to use oxide of a metal belonging to Group 4 to Group 8 in the periodic table as the metal oxide; specifically, it is preferable to use any of vanadium oxide, niobium oxide, tantalum oxide, chromium oxide, molybdenum oxide, tungsten oxide, manganese oxide, and rhenium oxide because their electron-accepting property is high. In particular, molybdenum oxide is especially preferable because it is stable in the air, its hygroscopic property is low, and it can be easily handled.

The charge-generating layer 513 may have a single-layer structure or a stacked-layer structure. For example, it is possible to have a stacked-layer structure of a layer containing a composite material of an organic compound and a metal oxide, and a layer containing one compound selected from electron-donating substances and a compound having a high electron-transport property; or a stacked-layer structure of a layer containing a composite material of an organic compound and a metal oxide, and a transparent conductive film.

In this embodiment, the light-emitting element having two light-emitting units is described; however, the present invention is not limited to this structure. That is, a tandem light-emitting element may be a light-emitting element having three or more light-emitting units. Note that the light-emitting elements having three or more light-emitting units include a charge-generating layer between the light-emitting units. For example, it is possible to form a light-emitting element having a first unit formed using an organometallic complex of one embodiment of the present invention, and a second unit formed using a light-emitting material which emits light with a longer wavelength than the organometallic complex (e.g., red light). In addition, it is also possible to form a light-emitting element having a first unit formed using an organometallic complex of one embodiment of the present invention, a second unit formed using a first light-emitting material which emits light with a longer wavelength than the organometallic complex (e.g., red light), and a third unit formed using a second light-emitting material which emits light with a longer wavelength than the organometallic complex and a shorter wavelength than the first light-emitting material (e.g., green light). By using these light-emitting elements, a white light-emitting device can be realized. In particular, an emission spectrum of the organometallic complex of one embodiment of the present invention has a feature of a broad peak. Thus, by using the organometallic complex of one embodiment of the present invention in at least one light-emitting unit in a tandem light-emitting element, a light-emitting device with excellent white reproducibility (color rendering properties) can be easily provided.

By arranging a plurality of light-emitting units that are partitioned by a charge-generating layer between a pair of electrodes, the tandem light-emitting element of this embodiment can be an element having the long life in a high luminance region while keeping a current density low.

Embodiment 4

In this embodiment, described are a passive-matrix light-emitting device and an active-matrix light-emitting device which are examples of a light-emitting device manufactured with the use of the light-emitting element described in the above embodiments.

FIGS. 2A to 2D and FIG. 3 illustrate an example of the passive-matrix light-emitting device.

In a passive-matrix (also called simple-matrix) light-emitting device, a plurality of anodes arranged in stripes (in stripe form) are provided to be perpendicular to a plurality of cathodes arranged in stripes. A light-emitting layer is interposed at each intersection. Therefore, a pixel at an intersection of an anode selected (to which voltage is applied) and a cathode selected emits light.

Figure 2A:
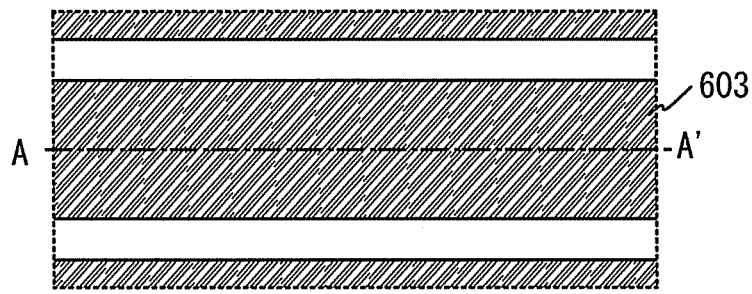
FIGS. 2A to 2D illustrate an example of a light-emitting device according to one embodiment of the present invention.
Figure 2B:
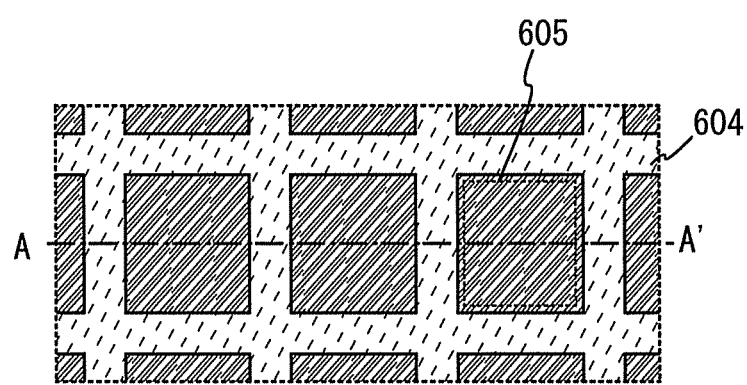
Figure 2C:
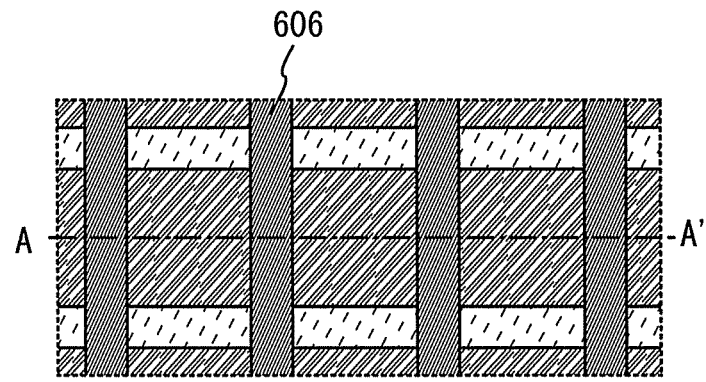
Figure 2D:
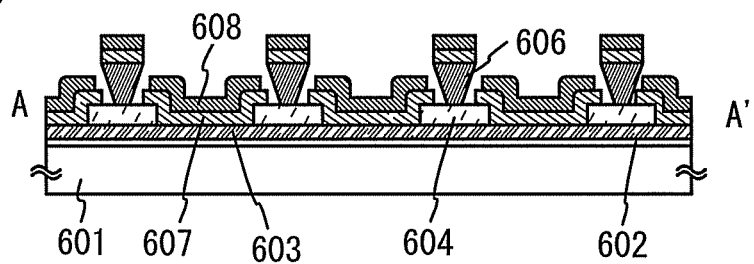

FIGS. 2A to 2C are top views of a pixel portion before sealing. FIG. 2D is a cross-sectional view taken along chain line A-A' in FIGS. 2A to 2C.

Over a substrate 601, an insulating layer 602 is formed as a base insulating layer. Note that the insulating layer 602 may be omitted when unnecessary. Over the insulating layer 602, a plurality of first electrodes 603 are arranged in stripes at regular intervals (FIG. 2A). Note that each of the first electrodes 603 in this embodiment corresponds to the first electrode 102 in Embodiment 3.

In addition, a partition 604 having openings 605 corresponding to pixels is provided over the first electrodes 603. The partition 604 is formed using an insulating material. For example, polyimide, acrylic, polyamide, polyimide amide, a resist, a photosensitive or non-photosensitive organic material such as benzocyclobutene, or an SOG film such as an SiO$_x$ film that contains an alkyl group can be used as the insulating material. Note that the openings 605 corresponding to pixels serve as light-emitting regions (FIG. 2B).

Over the partition 604 having openings, a plurality of partitions 606 are provided to intersect with the first electrodes 603 (FIG. 2C). The plurality of partitions 606 are formed in parallel to each other, and are inversely tapered.

Over each of the first electrodes 603 and the partition 604, an EL layer 607 and a second electrode 608 are sequentially stacked (FIG. 2D). Note that the EL layer 607 in this embodiment corresponds to the EL layer 103 in Embodiment 3, and the second electrode 608 in this embodiment corresponds to the second electrode 104 in Embodiment 3. The total height of the partition 604 and the partition 606 is larger than the total thickness of the EL layer 607 and the second electrode 608; therefore, the EL layer 607 and the second electrode 608 are divided into a plurality of regions as illustrated in FIG. 2D. Note that the plurality of divided regions are electrically isolated from one another.

The second electrodes 608 are formed in stripes and extend in the direction in which they intersect with the first electrodes 603. Note that part of a layer forming the EL layer 607 and part of a conductive layer forming the second electrodes 608 are formed over the inversely tapered partitions 606; however, they are separated from the EL layer 607 and the second electrodes 608.

In addition, when necessary, a sealing material such as a sealing can or a glass substrate may be attached to the substrate 601 by an adhesive agent for sealing so that the light-emitting element can be disposed in the sealed space. Thus, deterioration of the light-emitting element can be prevented. The sealed space may be filled with filler or a dry inert gas. Further, a desiccant or the like is preferably put between the substrate and the sealing material to prevent deterioration of the light-emitting element due to moisture or the like. The desiccant removes a minute amount of moisture, thereby achieving sufficient desiccation. As the desiccant, oxide of an alkaline earth metal such as calcium oxide or barium oxide, zeolite, or silicagel can be used. Oxide of an alkaline earth metal absorbs moisture by chemical adsorption, and zeolite and silicagel adsorb moisture by physical adsorption.

Figure 3:
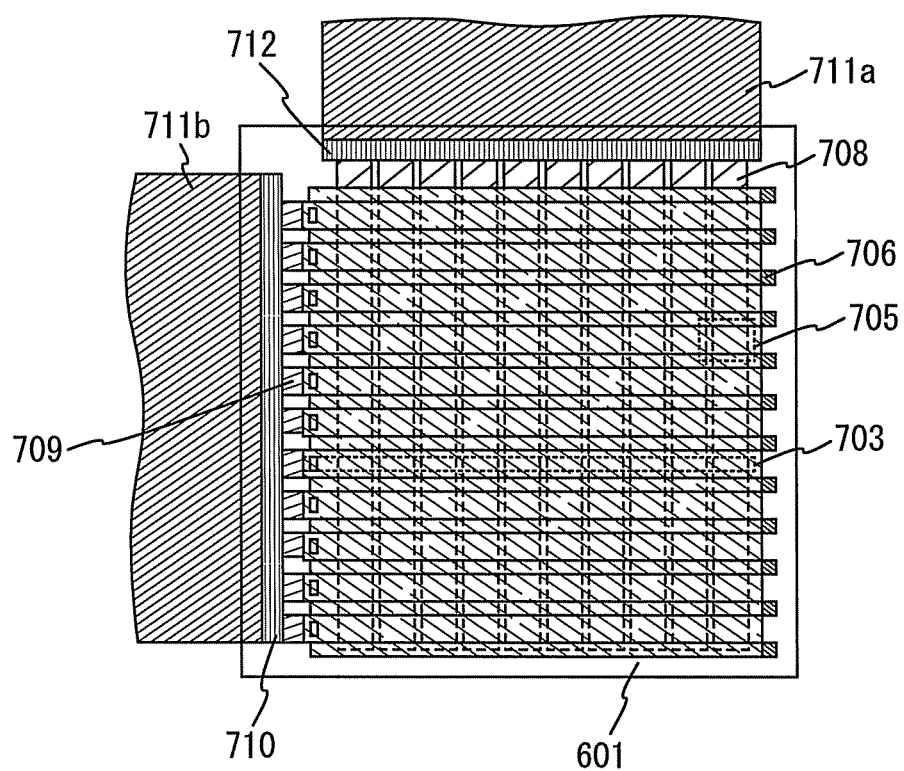
FIG. 3 illustrates an example of a light-emitting device according to one embodiment of the present invention.

FIG. 3 is a top view of the passive-matrix light-emitting device illustrated in FIGS. 2A to 2D that is provided with a flexible printed circuit (an FPC) or the like.

As illustrated in FIG. 3, in a pixel portion forming an image display, scanning lines and data lines are arranged to intersect with each other so that the scanning lines and the data lines are perpendicular to each other.

The first electrodes 603 in FIGS. 2A to 2D correspond to scan lines 703 in FIG. 3; the second electrodes 608 in FIGS. 2A to 2D correspond to data lines 708 in FIG. 3; and the inversely-tapered partitions 606 correspond to partitions 706. The EL layer 607 illustrated in FIG. 2D are interposed between the data lines 708 and the scanning lines 703, and an intersection indicated by a region 705 corresponds to one pixel.

The scanning lines 703 are electrically connected at their ends to connection wirings 709, and the connection wirings 709 are connected to an FPC 711b via an input terminal 710. In addition, the data lines 708 are connected to an FPC 711a via an input terminal 712.

An optical film such as a polarizing plate, a circularly polarizing plate (including an elliptically polarizing plate), a retardation plate (a quarter-wave plate or a half-wave plate), or a color filter may be provided as needed. Further, an anti-reflection film may be provided in addition to the polarizing plate or the circularly polarizing plate. By providing the anti-reflection film, anti-glare treatment may be carried out by which reflected light can be scattered by roughness of a surface so as to reduce reflection.

Although FIG. 3 illustrates the example in which a driver circuit is not provided over the substrate, an IC chip including a driver circuit may be mounted on the substrate.

When the IC chip is mounted, a data line side IC and a scanning line side IC, in each of which the driver circuit for transmitting a signal to a pixel portion is formed, are mounted on the periphery of (outside) the pixel portion. As a method for mounting an IC chip, a COG method, TCP, a wire bonding method, or the like can be used. The TCP is a TAB tape mounted with the IC, and the TAB tape is connected to a wiring over an element formation substrate to mount the IC. The data line side IC and the scanning line side IC may be formed over a silicon substrate, a silicon on insulator (SOI) substrate, a glass substrate, a quartz substrate, or a plastic substrate.

Figure 4A:
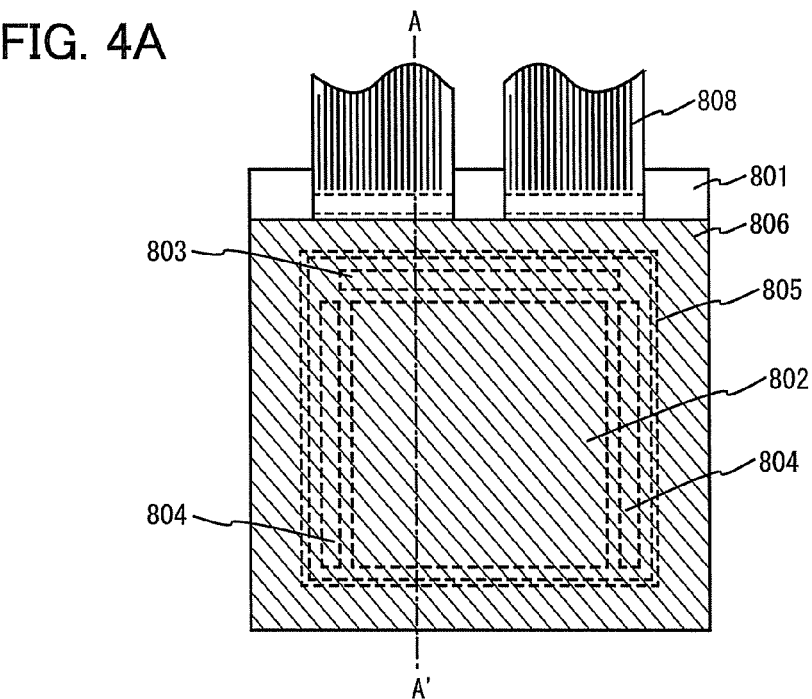
FIGS. 4A and 4B illustrate an example of a light-emitting device according to one embodiment of the present invention.
Figure 4B:
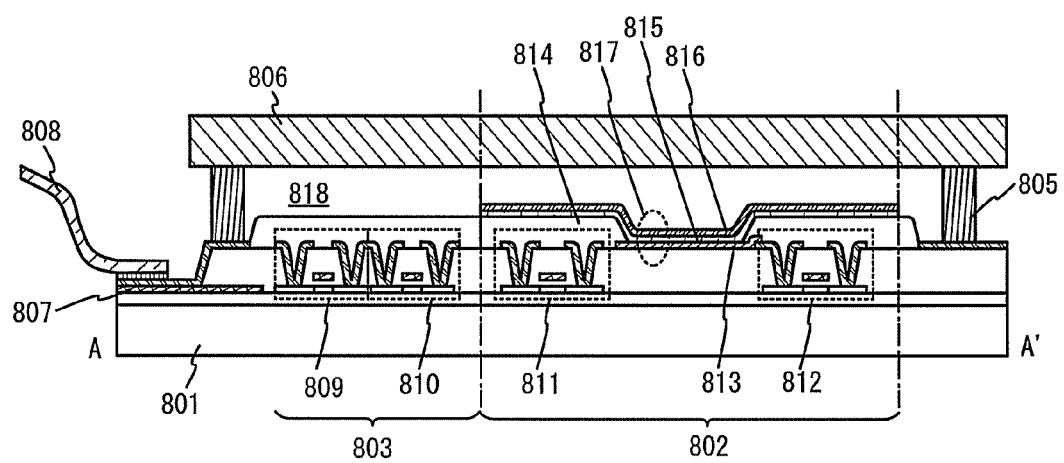

Next, an example of the active-matrix light-emitting device is described with reference to FIGS. 4A and 4B. FIG. 4A is a top view illustrating a light-emitting device and FIG. 4B is a cross-sectional view taken along dashed line A-A' in FIG. 4A. The active-matrix light-emitting device of this embodiment includes a pixel portion 802 provided over an element substrate 801, a driver circuit portion (a source-side driver circuit) 803, and a driver circuit portion (a gate-side driver circuit) 804. The pixel portion 802, the driver circuit portion 803 and the driver circuit portion 804 are sealed between the element substrate 801 and the sealing substrate 806 by the sealing material 805.

Over the element substrate 801, a lead wiring 807 for connecting an external input terminal through which a signal (e.g., a video signal, a clock signal, a start signal, a reset signal, or the like) or electric potential from the outside is transmitted to the driver circuit portion 803 and the driver circuit portion 804 is provided. Here, an example is described in which a FPC 808 is provided as the external input terminal. Note that although only an FPC is illustrated here, a printed wiring board (PWB) may be attached thereto. In this specification, the light-emitting device includes in its category the light-emitting device itself and the light-emitting device on which the FPC or the PWB is mounted.

Next, a cross-sectional structure of the active-matrix light-emitting device is described with reference to FIG. 4B. Although the driver circuit portion 803, the driver circuit portion 804, and the pixel portion 802 are formed over the element substrate 801, the pixel portion 802 and the driver circuit portion 803 which is the source side driver circuit are illustrated in FIG. 4B.

In the driver circuit portion 803, an example including a CMOS circuit which is a combination of an n-channel TFT 809 and a p-channel TFT 810 is illustrated. Note that a circuit included in the driver circuit portion can be formed using various types of circuits such as a CMOS circuit, a PMOS circuit, or an NMOS circuit. In this embodiment, a driver-integrated type in which a driver circuit and the pixel portion are formed over the same substrate is shown; however, the present invention is not limited to this structure, and a driver circuit can be formed over a substrate that is different from the substrate over which a pixel portion is formed.

The pixel portion 802 has a plurality of pixels, each including a switching TFT 811, a current-controlling TFT 812, and an anode 813 electrically connected to a wiring (a source electrode or a drain electrode) of the current-controlling TFT 812. An insulator 814 is formed so as to cover an end portion of the anode 813. In this embodiment, the insulator 814 is formed using a positive photosensitive acrylic resin. Note that there is no particular limitation on structures of the TFTs such as the switching TFT 811 and the current-controlling TFT 812. For example, a staggered TFT or an inverted-staggered TFT may be used. A top-gate TFT or a bottom-gate TFT may also be used. There is no particular limitation also on materials of a semiconductor used for the TFTs, and silicon or an oxide semiconductor such as oxide including indium, gallium, and zinc may be used. In addition, there is no particular limitation also on crystallinity of a semiconductor used for the TFTs, and an amorphous semiconductor or a crystalline semiconductor may be used.

A light-emitting element 817 includes an anode 813, an EL layer 815, and a cathode 816. Since the structure and materials for the light-emitting element is described in Embodiment 2, a detailed description is omitted in this embodiment. Note that the anode 813, the EL layer 815, and the cathode 816 in FIGS. 4A and 4B correspond to the first electrode 102, the EL layer 103, and the second electrode 104 in Embodiment 2, respectively. Although not illustrated, the cathode 816 is electrically connected to the FPC 808 which is an external input terminal.

The insulator 814 is provided at an end portion of the anode 813. In addition, in order that the cathode 816 that is formed over the insulator 814 at least favorably covers the insulator 814, the insulator 814 is preferably formed so as to have a curved surface with curvature at an upper end portion or a lower end portion. For example, it is preferable that the upper end portion or the lower end portion of the insulator 814 have a curved surface with a radius of curvature (0.2 μm to 3 μm). The insulator 814 can be formed using an organic compound such as a negative photosensitive resin which becomes insoluble in an etchant by light or a positive photosensitive resin which becomes soluble in an etchant by light, or an inorganic compound such as silicon oxide or silicon oxynitride can be used.

Although the cross-sectional view of FIG. 4B illustrates only one light-emitting element 817, a plurality of light-emitting elements are arranged in matrix in the pixel portion 802. For example, light-emitting elements that emit light of three kinds of colors (R, G, and B) are formed in the pixel portion 802, so that a light-emitting device capable of full color display can be obtained. Alternatively, a light-emitting device which is capable of full color display may be manufactured by a combination with color filters.

The light-emitting element 817 is formed in a space 818 that is surrounded by the element substrate 801, the sealing substrate 806, and the sealing material 805. The space 818 may be filled with a rare gas, a nitrogen gas, or the sealing material 805.

It is preferable to use as the sealing material 805, a material that transmits as little moisture and oxygen as possible, such as an epoxy-based resin. As the sealing substrate 806, a glass substrate, a quartz substrate, a plastic substrate formed of FRP (fiberglass-reinforced plastics), PVF (polyvinyl fluoride), polyester, acrylic, or the like can be used.

In the above-described manner, an active-matrix light-emitting device can be obtained.

Embodiment 5

In this embodiment, specific examples of electronic devices and lighting devices each of which is manufactured using a light-emitting device described in any of the above embodiments are described with reference to FIGS. 5A to 5E and FIG. 6.

Examples of electronic devices that can be applied to the present invention include a television set (also referred to as a television or a television receiver), a monitor of a computer, a digital camera, a digital video camera, a digital photo frame, a mobile phone, a portable game machine, a portable information terminal, an audio reproducing device, a game machine (e.g., a pachinko machine or a slot machine), a housing of a game machine, and the like. Some specific examples of these electronic devices and lighting devices are illustrated in FIGS. 5A to 5E and FIG. 6.

Figure 5A:
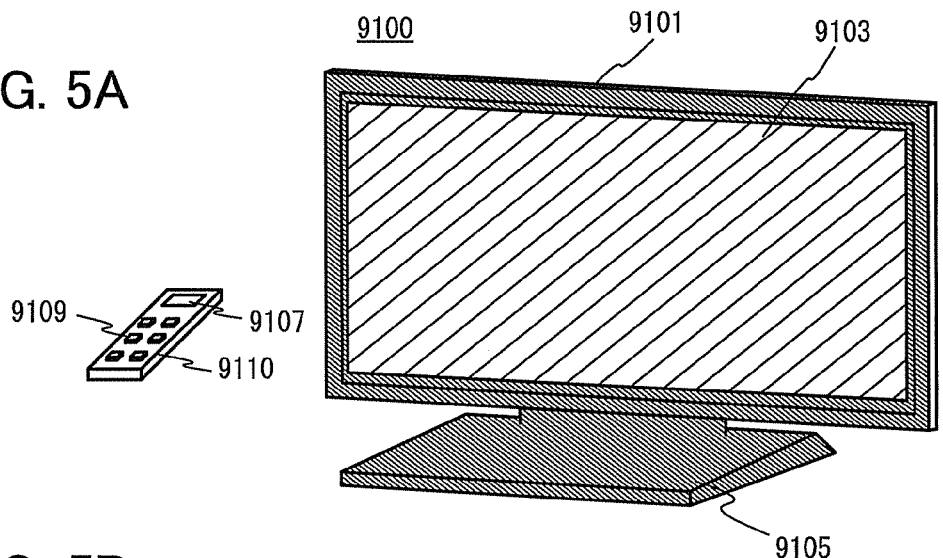
FIGS. 5A to 5E illustrate examples of electronic devices and lighting devices according to one embodiment of the present invention.

FIG. 5A illustrates a television set 9100. In the television set 9100, a display portion 9103 is incorporated in a housing 9101. A light-emitting device manufactured using one embodiment of the present invention can be used in the display portion 9103, so that an image can be displayed on the display portion 9103. Note that the housing 9101 is supported by a stand 9105 here.

The television set 9100 can be operated with an operation switch of the housing 9101 or a separate remote controller 9110. Channels and volume can be controlled with operation keys 9109 of the remote controller 9110 so that an image displayed on the display portion 9103 can be controlled. Furthermore, the remote controller 9110 may be provided with a display portion 9107 for displaying data output from the remote controller 9110.

The television set 9100 illustrated in FIG. 5A is provided with a receiver, a modem, and the like. With the receiver, the television set 9100 can receive a general television broadcast. Further, when the television set 9100 is connected to a communication network by wired or wireless connection via the modem, one-way (from a transmitter to a receiver) or two-way (between a transmitter and a receiver or between receivers) data communication can be performed.

Since a light-emitting device manufactured using one embodiment has a favorable chromaticity, the display portion 9103 including the light-emitting device in the television set can display an image with improved image quality as compared with conventional images.

Figure 5B:
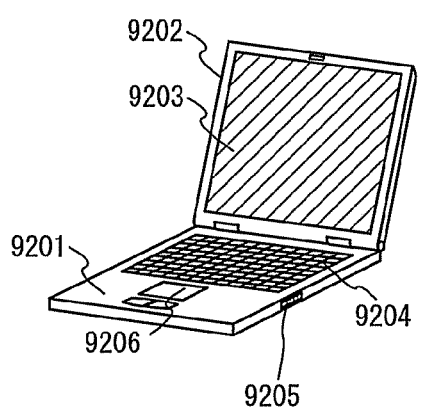

FIG. 5B illustrates a computer including a main body 9201, a housing 9202, a display portion 9203, a keyboard 9204, an external connection port 9205, a pointing device 9206, and the like. The computer is manufactured using a light-emitting device manufactured using one embodiment of the present invention for the display portion 9203.

Since a light-emitting device manufactured using one embodiment has a favorable chromaticity, the display portion 9203 including the light-emitting device in the computer can display an image with improved image quality as compared with conventional images.

Figure 5C:
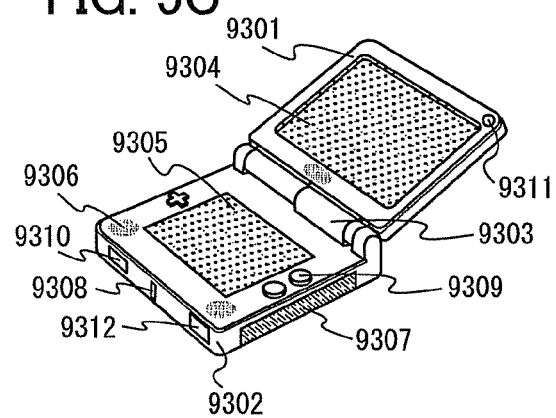

FIG. 5C illustrates a portable game machine including two housings, a housing 9301 and a housing 9302 which are jointed with a connector 9303 so as to be opened and closed. A display portion 9304 is incorporated in the housing 9301, and a display portion 9305 is incorporated in the housing 9302. In addition, the portable game machine illustrated in FIG. 5C includes an input means such as operation keys 9309, a connection terminal 9310, a sensor 9311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 9312. The portable game machine may further be provided with a speaker portion 9306, a recording medium insertion portion 9307, an LED lamp 9308, and the like. Needless to say, the structure of the portable game machine is not limited to the above, and it is acceptable as long as the light-emitting device manufactured using any of the above embodiments is used for one or both of the display portion 9304 and the display portion 9305.

The portable game machine illustrated in FIG. 5C has a function of reading a program or data stored in a recording medium to display it on the display portion, and a function of sharing information with another portable game machine by wireless communication. Note that a function of the portable game machine illustrated in FIG. 5C is not limited to the above, and the portable game machine can have a variety of functions.

Since a light-emitting device manufactured using one embodiment has a favorable chromaticity, the display portions (9304 and 9305) including the light-emitting device in the portable game machine can display an image with improved image quality as compared with conventional images.

Figure 5D:
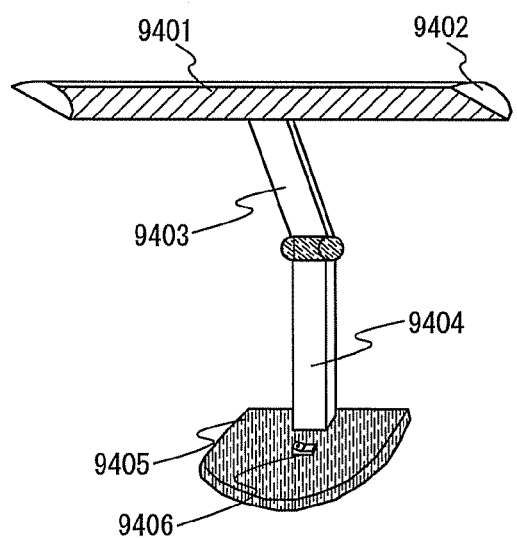
Figure 5E:
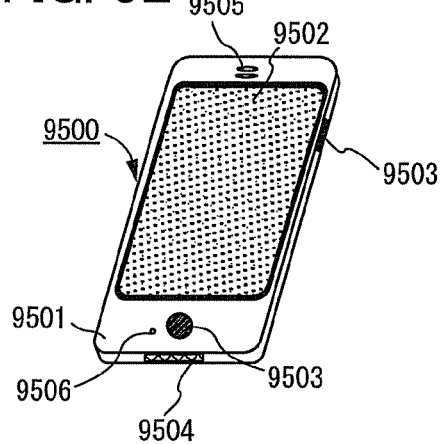

FIG. 5E illustrates an example of a mobile phone. A mobile phone 9500 is provided with a display portion 9502 incorporated in a housing 9501, operation buttons 9503, an external connection port 9504, a speaker 9505, a microphone 9506, and the like. Note that the mobile phone 9500 is manufactured using a light-emitting device manufactured using one embodiment of the present invention for the display portion 9502.

Users can input data, make a call, or text messaging by touching the display portion 9502 of the mobile phone 9500 illustrated in FIG. 5E with their fingers or the like.

There are mainly three screen modes for the display portion 9502. The first mode is a display mode mainly for displaying images. The second mode is an input mode mainly for inputting data such as text. The third mode is a display-and-input mode in which two modes of the display mode and the input mode are combined.

For example, in the case of making a call or text messaging, a text input mode mainly for inputting text is selected for the display portion 9502 so that characters displayed on a screen can be input. In this case, it is preferable to display a keyboard or number buttons on almost the entire screen of the display portion 9502.

By providing a detection device which includes a sensor for detecting inclination, such as a gyroscope or an acceleration sensor, inside the mobile phone 9500, the direction of the mobile phone 9500 (whether the mobile phone 9500 is placed horizontally or vertically for a landscape mode or a portrait mode) is determined so that display on the screen of the display portion 9502 can be automatically switched.

In addition, the screen mode is switched by touching the display portion 9502 or operating the operation buttons 9503 of the housing 9501. Alternatively, the screen mode can be switched depending on kinds of images displayed on the display portion 9502. For example, when a signal of an image displayed on the display portion is a signal of moving image data, the screen mode is switched to the display mode. When the signal is a signal of text data, the screen mode is switched to the input mode.

Furthermore, in the input mode, when input by touching the display portion 9502 is not performed for a certain period while a signal is detected by the optical sensor in the display portion 9502, the screen mode may be controlled so as to be switched from the input mode to the display mode.

The display portion 9502 can also function as an image sensor. For example, an image of a palm print, a fingerprint, or the like is taken by touching the display portion 9502 with the palm or the finger, whereby personal authentication can be performed. Further, by providing a backlight or a sensing light source which emits a near-infrared light in the display portion, an image of a finger vein, a palm vein, or the like can be taken.

Since a light-emitting device manufactured using one embodiment has a favorable chromaticity, the display portion 9502 including the light-emitting device in the mobile phone can display an image with improved image quality as compared with conventional images.

FIG. 5D illustrates a tabletop lighting device including a lighting portion 9401, a shade 9402, an adjustable arm 9403, a support 9404, a base 9405, and a power supply switch 9406. The tabletop lighting device is manufactured using a light-emitting device manufactured using one embodiment of the present invention for the lighting portion 9401. Note that the modes of the lighting device is not limited to tabletop lighting devices, but include ceiling-fixed lighting devices, wall-hanging lighting devices, portable lighting devices, and the like.

FIG. 6 illustrates an example in which the light-emitting device manufactured using one embodiment of the present invention is used for an indoor lighting device 1001. Since the light-emitting device manufactured using one embodiment of the present invention can have a large area, the light-emitting device can be used as a lighting apparatus having a large area. In addition, the light-emitting device described in any of the above embodiments can be made thin, and thus can be used as a roll-up type lighting device 1002. As illustrated in FIG. 6, a tabletop lighting device 1003 illustrated in FIG. 5D may be used in a room provided with the indoor lighting device 1001.

In the above-described manner, electronic devices and lighting devices can be provided using a light-emitting device manufactured using one embodiment of the present invention. The scope of application of the light-emitting device manufactured using one embodiment of the present invention is so wide that it can be applied to a variety of fields of electronic devices.

EXAMPLE 1

Synthesis Example 1

In Example 1, a synthesis example of the organometallic complex tris(5-methyl-3,4-diphenyl-4H-1,2,4-triazolato)iridium(III) (abbreviation: [Ir(Mptz)$_3$]) which is one embodiment of the present invention represented by Structural Formula (100) in Embodiment 1 is specifically described.

Step 1: Synthesis of
3-methyl-4,5-diphenyl-4H-1,2,4-triazole
(abbreviation: HMptz)

First, 5.04 g of thioacetanilide, 5.44 g of benzoylhydrazine, and 50 mL of 1-butanol were put in a round-bottomed flask provided with a reflux pipe, and the air in the flask was replaced with argon. This reaction container was subjected to irradiation with a microwave (2.45 GHz, 100 W) for 2 hours and 45 minutes to be heated. Then, water was added to this solution and an organic layer was extracted from dichloromethane. The organic layer was washed with water and dried with magnesium sulfate. After the drying, the solution was filtrated. The solvent of this solution was distilled off, and the resulting residue was purified by silica gel column chromatography which uses ethyl acetate as a developing solvent, so that 3-methyl-4,5-diphenyl-4H-1,2,4-triazole (abbreviation: HMptz) was prepared (light yellow powder, yield: 18%). The synthetic scheme of Step 1 is shown by (a-1).

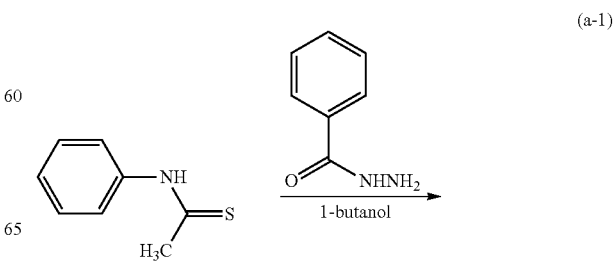

(a-1)

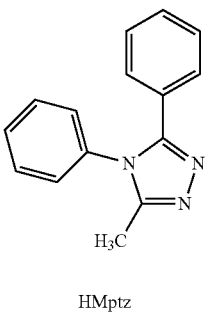

HMptz

Step 2: Synthesis of tris(5-methyl-3,4-diphenyl-4H-1,2,4-triazolato)iridium(III) (abbreviation: [Ir(Mptz)₃])

Next, 1.40 g of the ligand HMptz that was prepared in Step 1 described above, and 0.58 g of tris(acetylacetonate)iridium (II) were put in a reaction container provided with a three-way cock, and the air in the reaction container was replaced with argon. Then, the mixture was heated at 250° C. for 17 hours and 30 minutes to be reacted. The reactant was dissolved in dichloromethane, and the solution was filtrated. The solvent of the resulting filtrate was distilled off and purification was conducted by silica gel column chromatography which uses ethyl acetate as a developing solvent. Further, recrystallization was carried out with a mixed solvent of dichloromethane and hexane, so that the organometallic complex [Ir(Mptz)₃] which is one embodiment of the present invention was prepared (yellow powder, yield: 22%). The synthetic scheme of Step 2 is shown by (b-1).

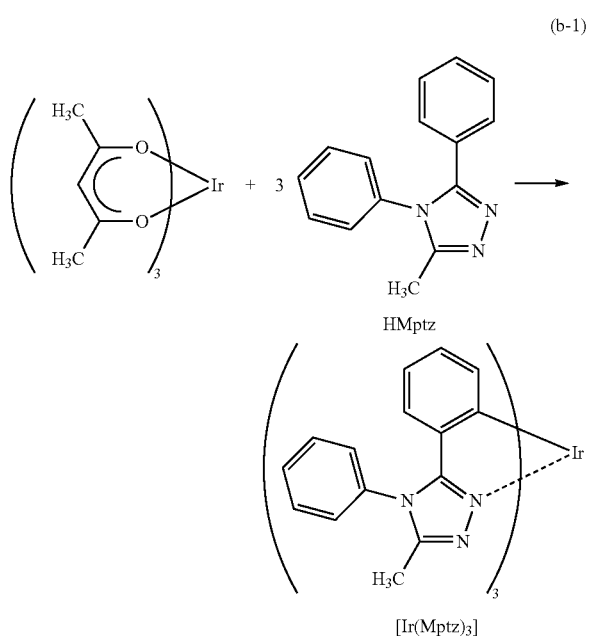

(b-1)

HMptz

[Ir(Mptz)₃]

Figure 7:
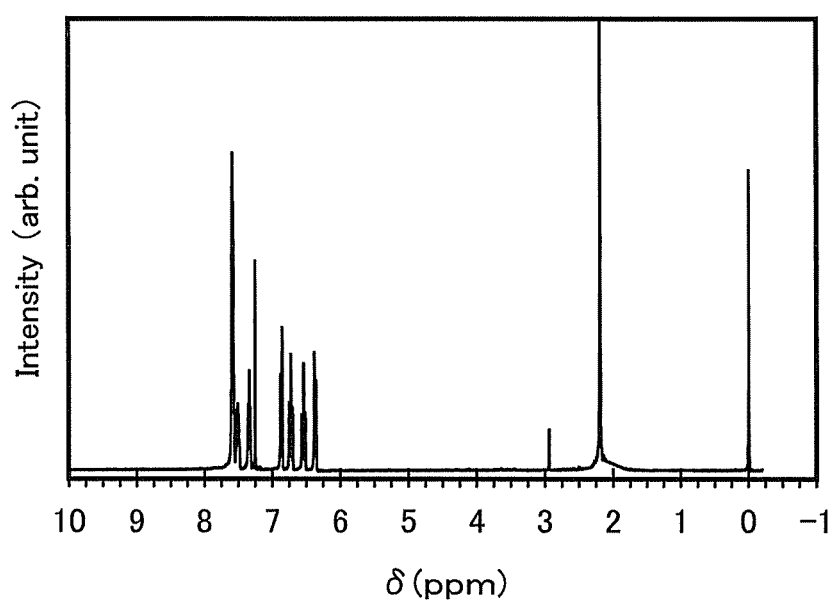
FIG. 7 shows a $^1$H-NMR chart of [Ir(Mptz)$_3$].

An analysis result by nuclear magnetic resonance spectroscopy (¹H-NMR) of the yellow powder prepared in Step 2 described above is shown below. The ¹H-NMR chart is shown in FIG. 7. From the results, it is found that the organometallic complex [Ir(Mptz)₃] which is one embodiment of the present invention represented by Structural Formula (100) was prepared in Synthesis Example 1.

¹H-NMR. δ(CDCl₃): 2.17 (s, 9H), 6.38 (d, 3H), 6.54 (t, 3H), 6.72 (dt, 3H), 6.87 (dd, 3H), 7.34 (m, 3H), 7.51 (brm, 3H), 7.57 (m, 9H).

Figure 8:
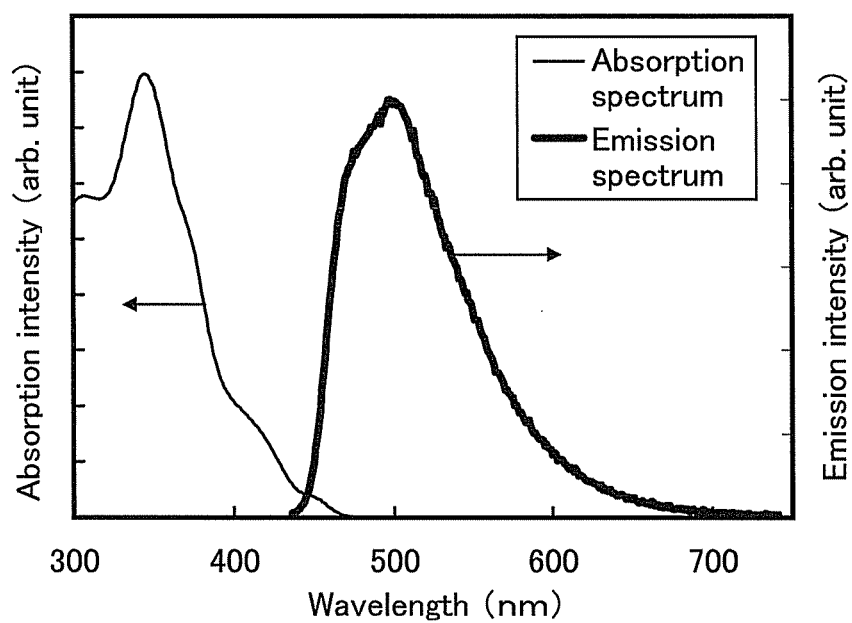
FIG. 8 shows an absorption spectrum and an emission spectrum of [Ir(Mptz)$_3$] in a dichloromethane solution.

Next, an ultraviolet-visible absorption spectrum (hereinafter, simply referred to as an absorption spectrum) and an emission spectrum of [Ir(Mptz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.106 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.106 mmol/L) was put in a quartz cell at room temperature. FIG. 8 shows measurement results of the absorption spectrum and emission spectrum. The horizontal axis represents wavelength, and the vertical axis represents absorption intensity and emission intensity. In FIG. 8, two solid lines are shown; a thin line represents the absorption spectrum, and a thick line represents the emission spectrum. Note that the absorption spectrum in FIG. 8 is a result obtained by subtraction of the absorption spectrum of only dichloromethane that was put in a quartz cell from the measured absorption spectrum of the dichloromethane solution (0.106 mmol/L) in a quartz cell.

As shown in FIG. 8, the organometallic complex [Ir(Mptz)₃] which is one embodiment of the present invention has a peak of emission at 498 nm, and green light was observed from the dichloromethane solution.

The sublimation temperature of the prepared organometallic complex [Ir(Mptz)₃] which is one embodiment of the present invention was measured with a high vacuum differential type differential thermal balance (TG-DTA2410SA manufactured by Bruker AXS K.K.). The degree of vacuum was 1×10³ Pa and the temperature increase rate was 10° C./min, and the temperature of a sample containing [Ir(Mptz)₃] was increased, whereby reduction in weight by 5% was observed at 311° C. From the results, it is found that [Ir(Mptz)₃] has a favorable sublimation property.

EXAMPLE 2

Synthesis Example 2

In Example 2, a synthesis example of the organometallic complex tris[3-(4-fluorophenyl)-5-methyl-4-phenyl-4H-1,2,4-triazolato]iridium(III) (abbreviation: [Ir(MFptz)₃]) which is one embodiment of the present invention represented by Structural Formula (122) in Embodiment 1 is specifically described.

Step 1: Synthesis of 4-fluorobenzoylhydrazine

First, 10 g of 4-fluoroethyl benzoate and 30 mL of ethanol were put in a 100 mL three-neck flask, and stirred. Then, 10 mL of hydrazine monohydrate was added to this mixed solution, and heated and stirred at 80° C. for 4 hours to be reacted. The reaction mixture was added to 100 mL of water, and a solid was precipitated. This solid was subjected to suction filtration and washed with a mixed solvent of ethanol and hexane, so that 4-fluorobenzoylhydrazine was prepared (a white solid, yield: 83%). The synthetic scheme of Step 1 is shown by (a-2).

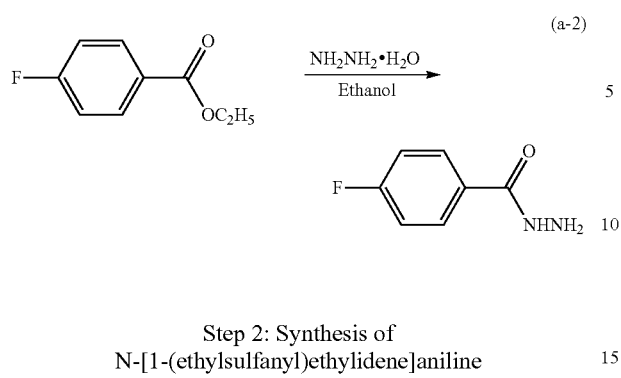

(a-2)

Step 2: Synthesis of
N-[1-(ethylsulfanyl)ethylidene]aniline

Next, 4.5 g of sodium ethoxide, 9.8 g of thioacetanilide, and 50 mL of ethanol were put in a 100 mL three-neck flask, and stirred at room temperature for 1 hour. Then, 5.3 mL of iodoethane was added to this mixture, and heated and stirred at 60° C. for 5 hours to be reacted. After the reaction, ethanol was distilled off under a reduced pressure to give a brown oily substance. This oily substance was dissolved in dichloromethane, and washed with water and then a saturated aqueous solution of sodium hydrogen carbonate. Anhydrous magnesium sulfate was added to the resulting organic layer for drying. After the drying, the solution was subjected to gravity filtration. The resulting filtrate was concentrated, so that N-[1-(ethylsulfanyl)ethylidene]aniline was prepared (a brown solid, yield: 73%). The synthetic scheme of Step 2 is shown by (b-2).

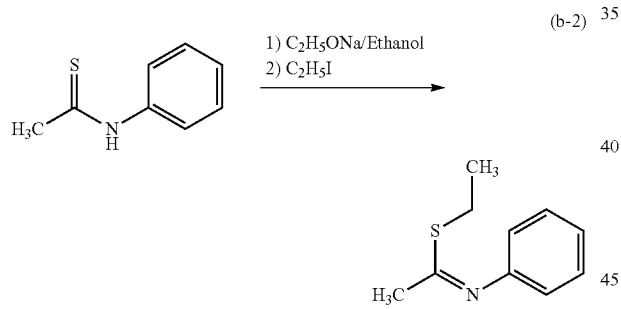

(b-2)

Step 3: Synthesis of 3-(4-fluorophenyl)-5-methyl-4-phenyl-4H-1,2,4-triazole (abbreviation: HMFptz)

Next, 5.8 g of 4-fluorobenzoylhydrazine that was prepared in Step 1 described above, 8.5 g of N-[1-(ethylsulfanyl)ethylidene]aniline that was prepared in Step 2 described above, and 40 mL of 1-butanol were put in a 100 mL three-neck flask, and heated and refluxed for 11 hours at 120° C. to be reacted. The reaction mixture was concentrated to give a brown solid. This solid was purified by silica gel column chromatography. Ethyl acetate was used as a developing solvent. The resulting fraction was concentrated to give a solid. The given solid was washed with ethyl acetate, so that 3-(4-fluorophenyl)-5-methyl-4-phenyl-4H-1,2,4-triazole (abbreviation: HMFptz) was prepared (a white solid, yield: 56%). The synthetic scheme of Step 3 is shown by (c-2).

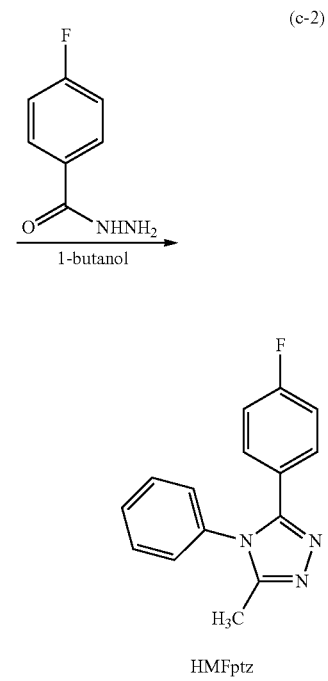

(c-2)

Step 4: Synthesis of tris[3-(4-fluorophenyl)-5-methyl-4-phenyl-4H-1,2,4-triazolato]iridium(III) (abbreviation: [Ir(MFptz)₃])

Next, 1.92 g of the ligand HMFptz that was prepared in Step 3 described above, and 0.74 g of tris(acetylacetonate)iridium(III) were put in a reaction container provided with a three-way cock, and the air in the reaction container was replaced with argon. Then, the mixture was heated at 250° C. for 30 hours to be reacted. The reactant was dissolved in dichloromethane, and the solution was filtrated. The solvent of the resulting filtrate was distilled off and purification was conducted by silica gel column chromatography which uses ethyl acetate as a developing solvent. Further, recrystallization was carried out with a methanol solvent, so that the organometallic complex [Ir(MFptz)₃] which is one embodiment of the present invention was prepared (light yellow powder, yield: 27%). The synthetic scheme of Step 4 is shown by (d-2).

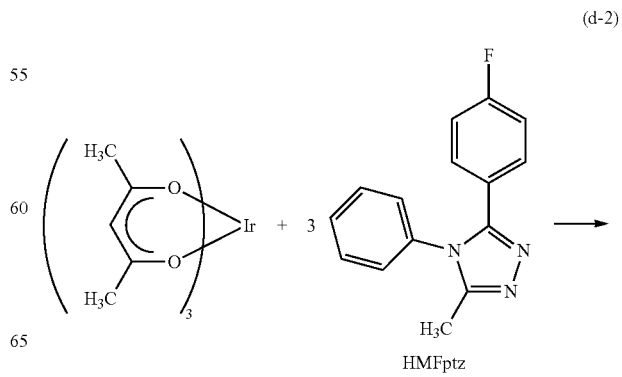

(d-2)

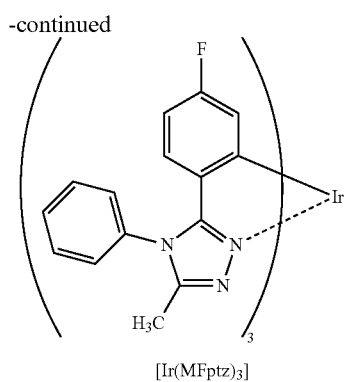

[Ir(MFptz)₃]

Figure 9:
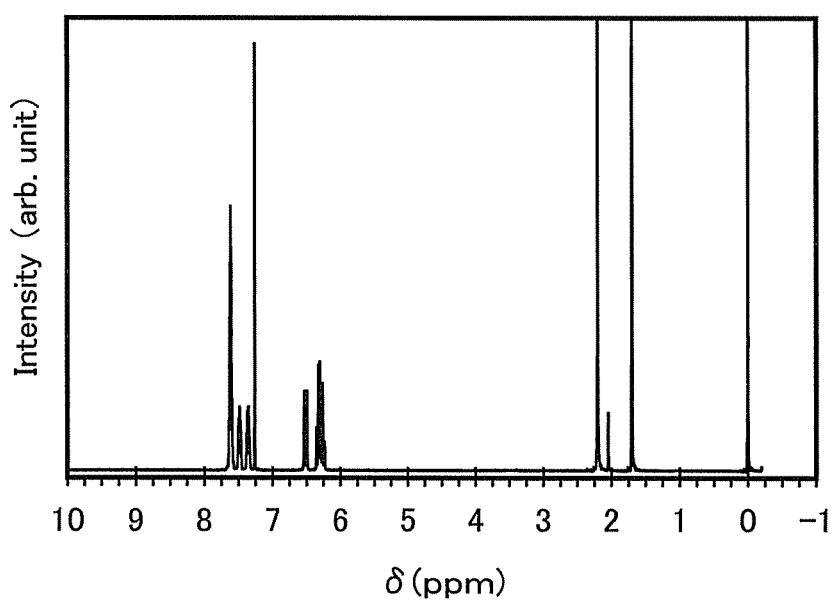
FIG. 9 shows a $^1$H-NMR chart of [Ir(MFptz)$_3$].

An analysis result by nuclear magnetic resonance spectroscopy (¹H-NMR) of the light yellow powder prepared in Step 4 described above is shown below. The ¹H-NMR chart is shown in FIG. 9. From the results, it is found that the organometallic complex [Ir(MFptz)₃] which is one embodiment of the present invention represented by Structural Formula (122) was prepared in Synthesis Example 2. ¹H-NMR. δ(CDCl₃): 2.10 (s, 9H), 6.30 (m, 6H), 6.51 (dd, 3H), 7.35 (m, 3H), 7.48 (m, 3H), 7.62 (m, 9H).

Figure 10:
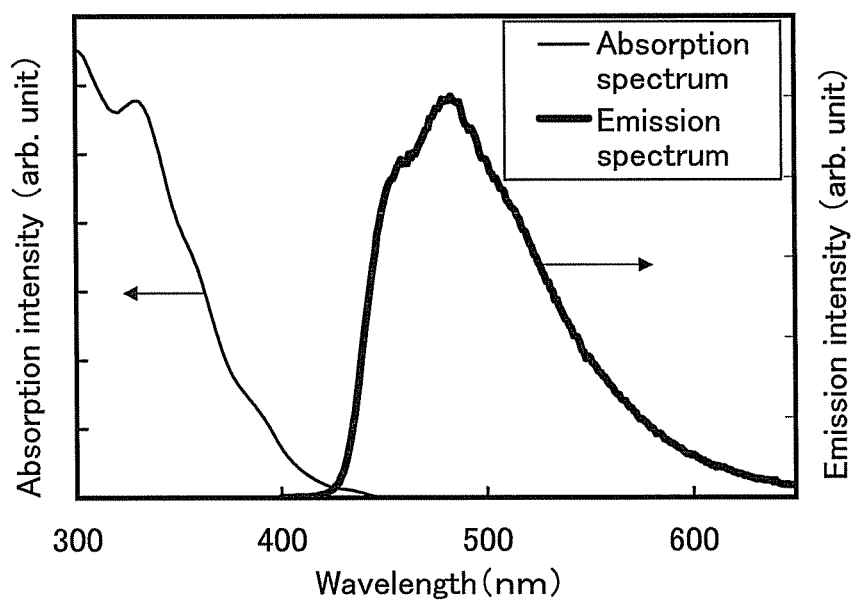
FIG. 10 shows an absorption spectrum and an emission spectrum of [Ir(MFptz)$_3$] in a dichloromethane solution.

Next, an ultraviolet-visible absorption spectrum (an absorption spectrum) and an emission spectrum of [Ir(MFptz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.038 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.23 mmol/L) was put in a quartz cell at room temperature. FIG. 10 shows measurement results of the absorption spectrum and emission spectrum. The horizontal axis represents wavelength, and the vertical axis represents absorption intensity and emission intensity. In FIG. 10, two solid lines are shown; a thin line represents the absorption spectrum, and a thick line represents the emission spectrum. Note that the absorption spectrum in FIG. 10 is a result obtained by subtraction of the absorption spectrum of only dichloromethane that was put in a quartz cell from the measured absorption spectrum of the dichloromethane solution (0.038 mmol/L) in a quartz cell.

As shown in FIG. 10, the organometallic complex [Ir(MFptz)₃] which is one embodiment of the present invention has peaks of emission at 460 nm and 483 nm, and light-blue light was observed from the dichloromethane solution.

In [Ir(MFptz)₃] described in Example 2, a fluoro group is substituted for hydrogen at the fourth position of a phenyl group bonded to the third position of a triazole ring in [Ir(Mptz)₃] described in Example 1. The measurement results of the emission spectra described in Example 1 and Example 2 indicate that the wavelengths of both of the emission peaks of [Ir(MFptz)₃] are shorter than the wavelength of the emission peak of [Ir(Mptz)₃]. As described above, an organometallic complex having at least one electron-withdrawing group for a phenyl group bonded to the third position of a triazole ring (a fluoro group in Example 2) has an emission peak at a short wavelength side as compared with an organometallic complex that does not have an electron-withdrawing group.

EXAMPLE 3

Synthesis Example 3

In Example 3, a synthesis example of the organometallic complex tris(5-cyclohexyl-3,4-diphenyl-4H-1,2,4-triazolato)iridium(III) (abbreviation: [Ir(chptz)₃]) which is one embodiment of the present invention represented by Structural Formula (104) in Embodiment 1 is specifically described.

Step 1: Synthesis of cyclohexanohydrazide

First, 5.0 g of methyl cyclohexanecarboxylate and 50 mL of ethanol were put in a 100 mL three-neck flask, and stirred. Then, 5 mL of hydrazine monohydrate was added to this mixed solution, and heated and stirred at 80° C. for 9 hours to be reacted. The reaction mixture was added to 100 mL of water, and a white solid was precipitated. Ethyl acetate was added to this suspension, whereby an organic layer and an aqueous layer were separated. The resulting organic layer was washed with saturated saline, and then anhydrous magnesium sulfate was added to the organic layer for drying. The resulting mixture was subjected to gravity filtration, and the filtrate was concentrated, so that cyclohexanohydrazide was prepared (a white solid, yield: 58%). The synthetic scheme of Step 1 is shown by (a-3).

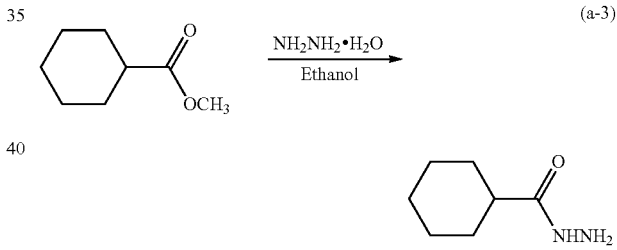

(a-3)

Step 2: Synthesis of N-[(ethylsulfanyl)phenylmethylidene]aniline

Next, 3.2 g of sodium ethoxide, 10 g of N-phenylthiobenzamide, and 60 mL of ethanol were put in a 300 mL three-neck flask, and stirred at room temperature for 1 hour. Then, 3.7 mL of iodoethane was added to this mixture, and heated and stirred at 60° C. for 6 hours to be reacted. After the reaction, ethanol was distilled off under a reduced pressure to give an oily substance. This oily substance was dissolved in dichloromethane, and washed with water and then a saturated aqueous solution of sodium hydrogen carbonate. Anhydrous magnesium sulfate was added to the resulting organic layer for drying. The resulting mixture was subjected to gravity filtration, and the filtrate was concentrated, so that N-[(ethylsulfanyl)phenylmethylidene]aniline was prepared (a brown oily substance, crude yield: 110%). The synthetic scheme of Step 2 is shown by (b-3).

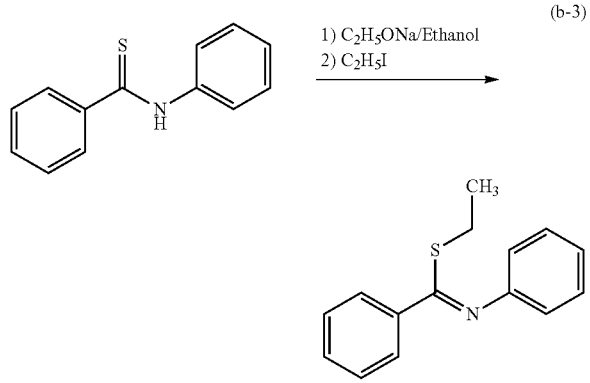

(b-3)

Step 3: Synthesis of 3-cyclohexyl-4,5-diphenyl-4H-1,2,4-triazole (abbreviation Hchptz)

Next, 1.9 g of cyclohexanohydrazide that was prepared in Step 1 described above, 3.5 g of N-[(ethylsulfanyl)phenylmethylidene]aniline that was prepared in Step 2 described above, and 40 mL of 1-butanol were put in a reaction container, and heated and refluxed for 8 hours to be reacted. After the reaction, 1-butanol was distilled off under a reduced pressure to give a solid. This solid was washed with hexane. The resulting solid was purified by silica gel column chromatography. Ethyl acetate was used as a developing solvent. The resulting fraction was concentrated to give a white solid. The given solid was recrystallized from a mixed solvent of chloroform and hexane, so that 3-cyclohexyl-4,5-diphenyl-4H-1,2,4-triazole (abbreviation: Hchptz) was prepared (a white solid, yield: 57%). The synthetic scheme of Step 3 is shown by (c-3).

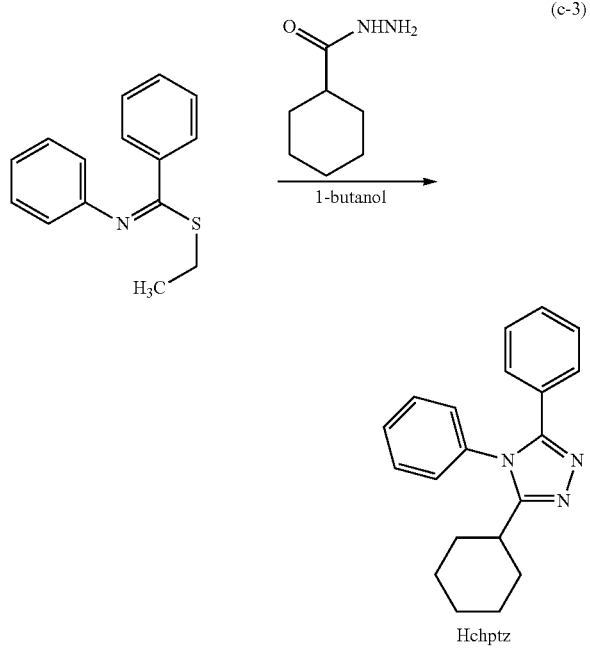

Step 4: Synthesis of tris(5-cyclohexyl-3,4-diphenyl-4H-1,2,4-triazolato)iridium(III) (abbreviation: [Ir(chptz)₃])

Next, 0.95 g of the ligand Hchptz that was prepared in Step 3 described above, and 0.31 g of tris(acetylacetonate)iridium (III) were put in a reaction container provided with a three-way cock, and the air in the reaction container was replaced with argon. Then, the mixture was heated at 250° C. for 48 hours to be reacted. The reactant was dissolved in dichloromethane, and the solution was filtrated. The solvent of the resulting filtrate was distilled off and purification was conducted by silica gel column chromatography which uses ethyl acetate as a developing solvent. Further, recrystallization was carried out with an ethanol solvent, so that the organometallic complex [Ir(chptz)₃] which is one embodiment of the present invention was prepared (light yellow powder, yield: 10%). The synthetic scheme of Step 4 is shown by (d-3).

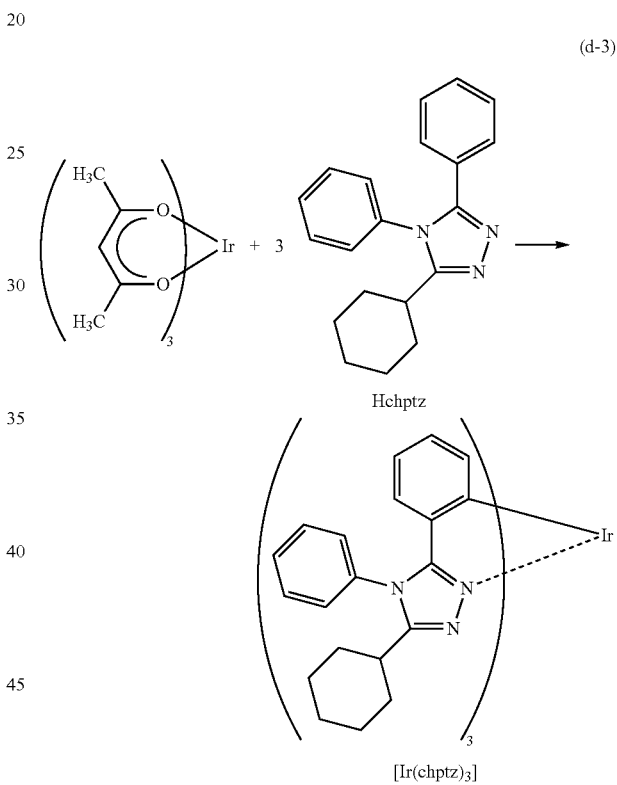

Figure 11:
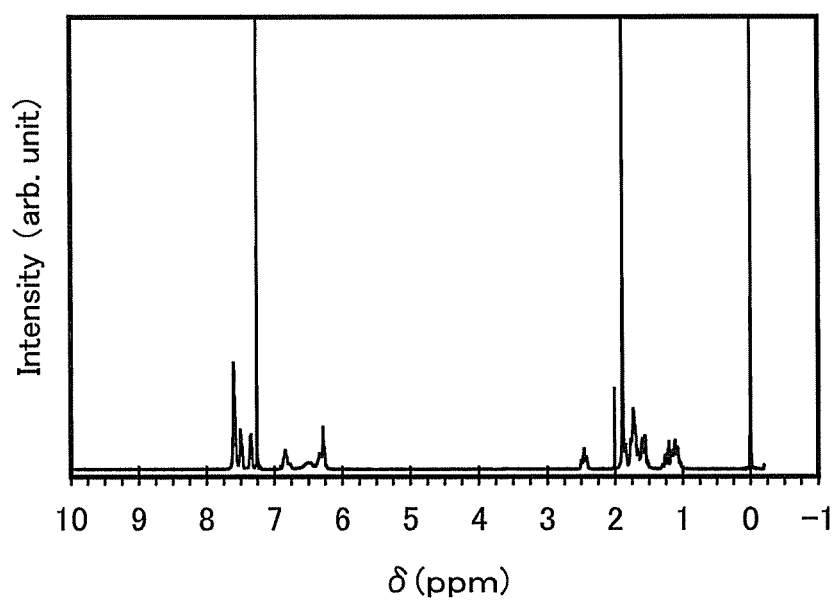
FIG. 11 shows a $^1$H-NMR chart of [Ir(chptz)$_3$].

An analysis result by nuclear magnetic resonance spectroscopy ($^1$H-NMR) of the light yellow powder prepared in Step 4 described above is shown below. The $^1$H-NMR chart is shown in FIG. 11. From the results, it is found that the organometallic complex [Ir(chptz)₃] which is one embodiment of the present invention represented by Structural Formula (104) was prepared in Synthesis Example 3.

$^1$H-NMR. δ(CDCl₃): 1.04-1.30 (m, 9H), 1.52-1.77 (m, 18H), 6.29 (m, 6H), 6.51 (brs, 3H), 6.84 (m, 3H), 7.34 (m, 3H), 7.50 (m, 3H), 7.61 (m, 9H).

Figure 12:
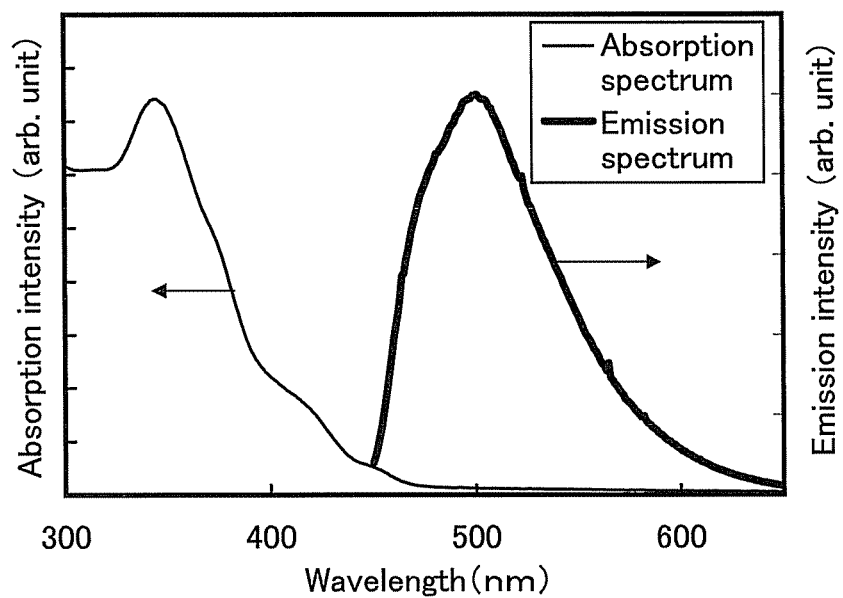
FIG. 12 shows an absorption spectrum and an emission spectrum of [Ir(chptz)$_3$] in a dichloromethane solution.

Next, an absorption spectrum and an emission spectrum of [Ir(chptz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.10 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.62 mmol/L) was put in a quartz cell at room temperature. FIG. 12 shows measurement results of the absorption spectrum and emission spectrum. The horizontal axis represents wavelength, and the vertical axis represents absorption intensity and emission intensity. In FIG. 12, two solid lines are shown; a thin line represents the absorption spectrum, and a thick line represents the emission spectrum. Note that the absorption spectrum in FIG. 12 is a result obtained by subtraction of the absorption spectrum of only dichloromethane that was put in a quartz cell from the measured absorption spectrum of the dichloromethane solution (0.10 mmol/L) in a quartz cell.

As shown in FIG. 12, the organometallic complex [Ir(chptz)$_3$] which is one embodiment of the present invention has a peak of emission at 502 nm, and green light was observed from the dichloromethane solution.

EXAMPLE 4

Synthesis Example 4

In Example 4, a synthesis example of the organometallic complex tris[4-(2,6-dimethyl-phenyl)-3-(4-fluorophenyl)-5-methyl-4H-1,2,4-triazolato]iridium(III) (abbreviation: [Ir(MFptz-dmp)$_3$]) which is one embodiment of the present invention represented by Structural Formula (123) in Embodiment 1 is specifically described.

Step 1: Synthesis of N-[1-(ethylsulfanyl)ethylidene]-2,6-dimethylaniline

First, 8.1 g of 2,6-dimethylacetanilide and 100 mL of toluene were put in a 200 mL three-neck flask, and stirred to be mixed. Then, 10 g of 2,4-bis(4-methoxyphenyl)-1,3,2,4-dithiadiphosphetane-2,4-disulfide (Lawesson's reagent) was added to this mixture, and heated and stirred at 120° C. for 2 hours to be reacted. The reaction solution was concentrated to give an oily substance. This oily substance was purified by silica gel column chromatography. As a developing solvent, hexane:ethyl acetate=5:1 was used. The resulting fraction was concentrated, so that N-(2,6-dimethylphenyl)thioacetanilide was prepared as a brown oily substance. The prepared oily substance, 3.4 g of sodium ethoxide, and 40 mL of ethanol were put in a 100 mL three-neck flask, and stirred at room temperature for 1 hour. Then, 4.0 mL of iodoethane was added to this mixture, and heated and stirred at 60° C. for 5 hours to be reacted. After the reaction, ethanol was distilled off under a reduced pressure to give a brown oily substance. This oily substance was dissolved in dichloromethane, and washed with water and then a saturated aqueous solution of sodium hydrogen carbonate. After the washing, anhydrous magnesium sulfate was added to the resulting organic layer for drying. The resulting mixture was subjected to gravity filtration, and the filtrate was concentrated, so that N-[1-(ethylsulfanyl)ethylidene]-2,6-dimethylaniline was prepared (a brown solid, crude yield: 76%). The synthetic scheme of Step 1 is shown by (a-4).

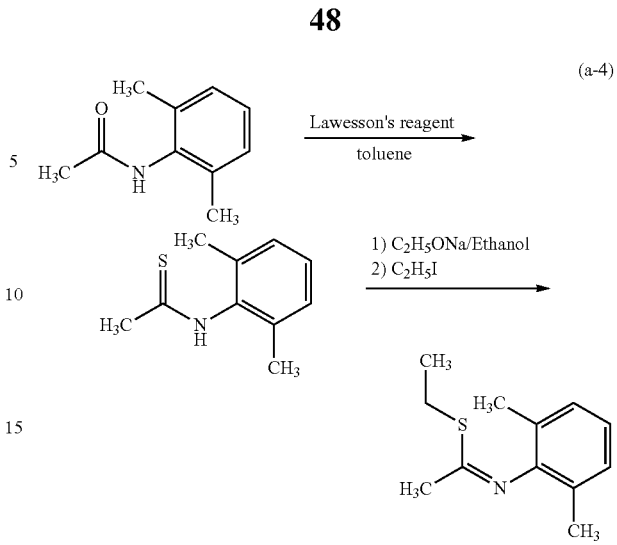

Step 2: Synthesis of 4-(2,6-dimethylphenyl)-5-(4-fluorophenyl)-3-methyl-4H-1,2,4-triazole (abbreviation: HMFptz-dmp)

Next, 13.2 g of N-[1-(ethylsulfanyl)ethylidene]-2,6-dimethylaniline that was prepared in Step 1 described above, 20 mL of 1-butanol, and 5.8 g of 4-fluorobenzoylhydrazine were put in a 100 mL three-neck flask, and heated and stirred at 130° C. for 17 hours. The reaction solution was concentrated under a reduced pressure to give a brown oily substance. Ethyl acetate was added to this oily substance, whereby a solid was precipitated. The resulting suspension was subjected to suction filtration. The resulting filtrate was recrystallized from a mixed solvent of ethyl acetate and hexane, so that 4-(2,6-dimethylphenyl)-5-(4-fluorophenyl)-3-methyl-4H-1,2,4-triazole (abbreviation: HMFptz-dmp) was prepared (a white solid, yield: 15%). The synthetic scheme of Step 2 is shown by (b-4).

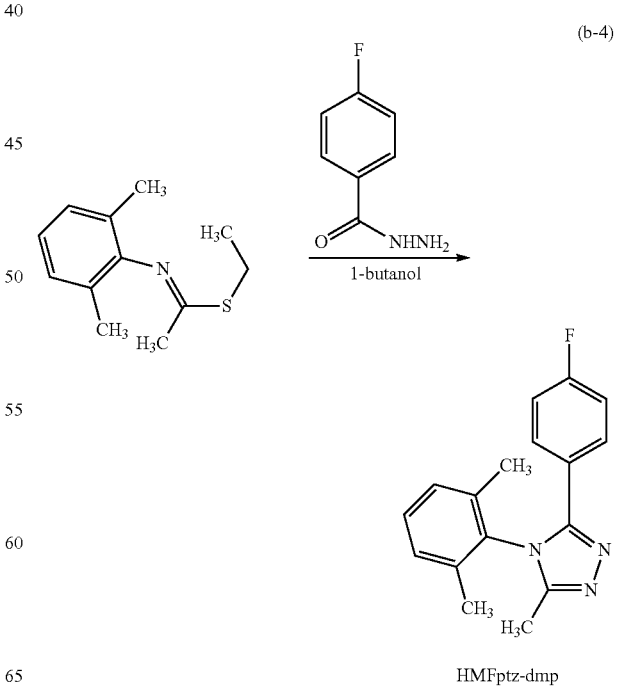

Step 3: Synthesis of tris[4-(2,6-dimethylphenyl)-3-(4-fluorophenyl)-5-methyl-4H-1,2,4-triazolato]iridium(III) (abbreviation: [Ir(MFptz-dmp)₃])

Next, 1.63 g of the ligand HMFptz-dmp that was prepared in Step 2 described above, and 0.57 g of tris(acetylacetonate)iridium(III) were put in a reaction container provided with a three-way cock, and the air in the reaction container was replaced with argon. Then, the mixture was heated at 245° C. for 45 hours to be reacted. The reactant was dissolved in dichloromethane, and the solution was filtrated. The solvent of the resulting filtrate was distilled off and purification was conducted twice by silica gel column chromatography which uses ethyl acetate as a developing solvent. Further, recrystallization was carried out with an ethyl acetate solvent, so that the organometallic complex [Ir(MFptz-dmp)₃] which is one embodiment of the present invention was prepared (light yellow powder, yield: 13%). The synthetic scheme of Step 3 is shown by (c-4).

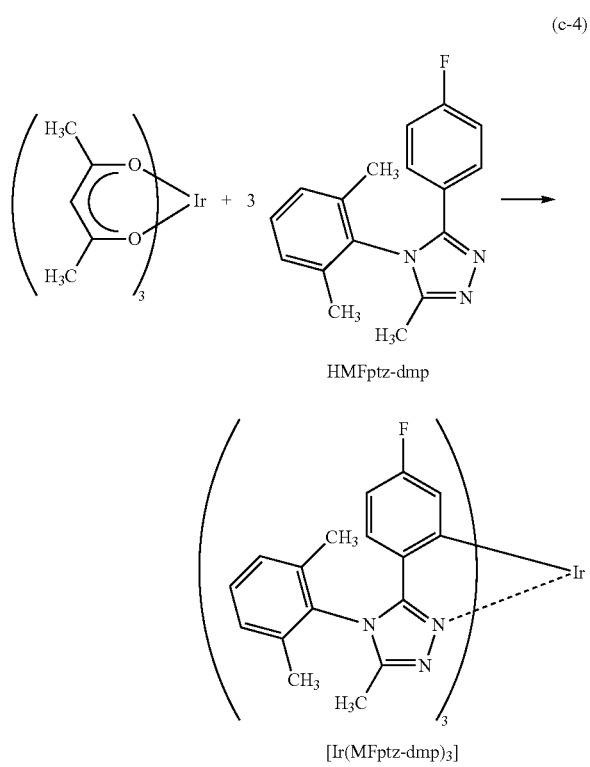

(c-4)

Figure 13:
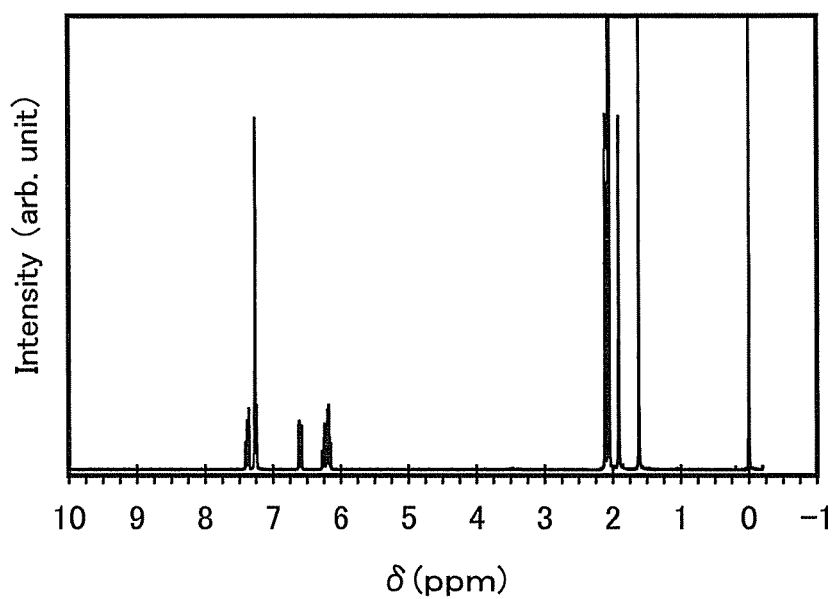
FIG. 13 shows a $^1$H-NMR chart of [Ir(MFptz-dmp)$_3$].

An analysis result by nuclear magnetic resonance spectroscopy (¹H-NMR) of the light yellow powder prepared in Step 3 described above is shown below. The ¹H-NMR chart is shown in FIG. 13. From the results, it is found that the organometallic complex [Ir(MFptz-dmp)₃] which is one embodiment of the present invention represented by Structural Formula (123) was prepared in Synthesis Example 4.

¹H-NMR. δ(CDCl₃): 1.94 (s, 9H), 2.09 (s, 9H), 2.14 (s, 9H), 6.33 (m, 6H), 6.69 (dd, 3H), 6.94 (m, 6H), 7.43 (t, 3H).

Figure 14:
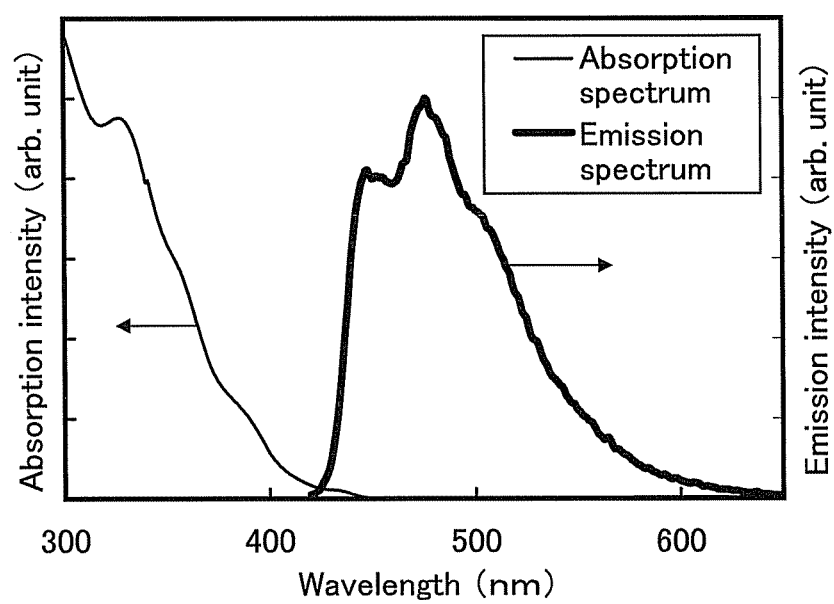
FIG. 14 shows an absorption spectrum and an emission spectrum of [Ir(MFptz-dmp)$_3$] in a dichloromethane solution.

Next, an absorption spectrum and an emission spectrum of [Ir(MFptz-dmp)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.0568 mmol/L) was put in a quartz cell at room temperature. The emission spectrum was measured with the use of a fluorescence spectrophotometer (F5920 manufactured by Hamamatsu Photonics Corporation) in the state where the degassed dichloromethane solution (0.341 mmol/L) was put in a quartz cell at room temperature. FIG. 14 shows measurement results of the absorption spectrum and emission spectrum. The horizontal axis represents wavelength, and the vertical axis represents absorption intensity and emission intensity. In FIG. 14, two solid lines are shown; a thin line represents the absorption spectrum, and a thick line represents the emission spectrum. Note that the absorption spectrum in FIG. 14 is a result obtained by subtraction of the absorption spectrum of only dichloromethane that was put in a quartz cell from the measured absorption spectrum of the dichloromethane solution (0.0568 mmol/L) in a quartz cell.

As shown in FIG. 14, the organometallic complex [Ir(MFptz-dmp)₃] which is one embodiment of the present invention has peaks of emission at 448 nm and 476 nm, and blue light was observed from the dichloromethane solution.

Comparative Example 1

In Comparative Example 1, a synthesis example of tris(3,4-diphenyl-4H-1,2,4-triazolato)iridium(III) (abbreviation: [Ir(ptz)₃]) represented by the following structural formula is specifically described.

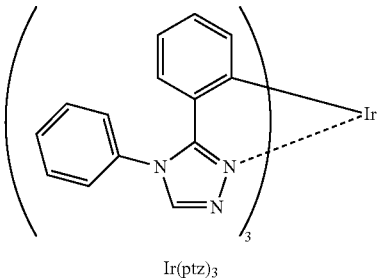

Ir(ptz)₃

Step 1: Synthesis of N-[(ethylsulfanyl)phenylmethylidene]aniline

First, 3.2 g of sodium ethoxide, 10 g of N-phenylthiobenzamide, and 60 mL of ethanol were put in a 300 mL three-neck flask, and this mixed solution was stirred at room temperature for 1 hour. Then, 3.7 mL of iodoethane was added to this mixed solution, and heated and stirred at 60° C. for 6 hours to be reacted. After the reaction, ethanol was distilled off under a reduced pressure to give a brown oily substance. This oily substance was dissolved in dichloromethane, and washed with water and then a saturated aqueous solution of sodium hydrogen carbonate. After the washing, anhydrous magnesium sulfate was added to the resulting organic layer for drying. The resulting mixture was subjected to gravity filtration, and the filtrate was concentrated, so that N-[(ethylsulfanyl)phenylmethylidene]aniline was prepared (a brown oily substance, crude yield: 110%). The synthetic scheme of Step 1 is shown by (a-5).

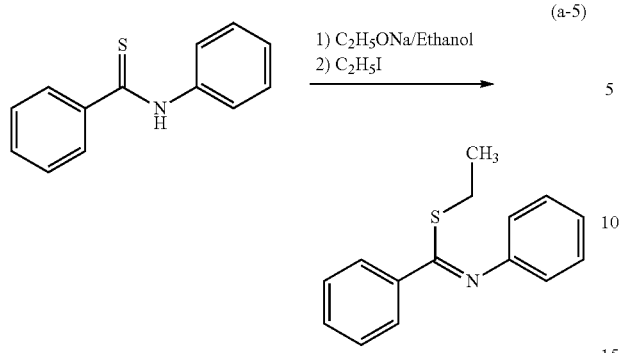

(a-5)

1) C₂H₅ONa/Ethanol
2) C₂H₅I

Step 2: Synthesis of 3,4-diphenyl-4H-1,2,4-triazole (abbreviation: Hptz)

Next, 13 g of N-[(ethylsulfanyl)phenylmethylidene]aniline that was prepared in Step 1 described above, 3.1 g of formylhydrazine, and 60 mL of 1-butanol were put in a 200 mL three-neck flask, and this mixed solution was heated and stirred at 120° C. for 5 hours to be reacted. Then, the reacted precipitate was removed by suction filtration, and the resulting filtrate was concentrated to give a brown solid. This solid was purified by silica gel column chromatography. As developing solvents, first, toluene was used, and then a mixed solvent of toluene:ethyl acetate=1:1 was used. The resulting fraction was concentrated to give a white solid. Further, the solid was recrystallized from a mixed solvent of ethanol and hexane, so that 3,4-diphenyl-4H-1,2,4-triazole (abbreviation: Hptz) was prepared (a white solid, yield: 19%). The synthetic scheme of Step 2 is shown by (b-5).

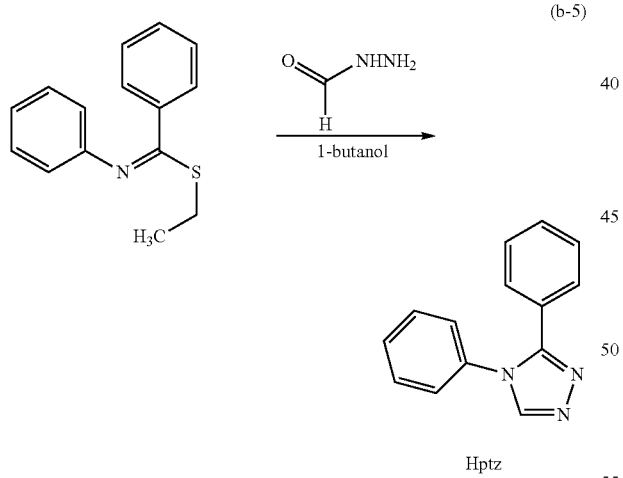

(b-5)

Step 3: Synthesis of tris(3,4-diphenyl-4H-1,2,4-triazolato)iridium(III) (abbreviation [Ir(ptz)₃])

Next, 2.10 g of the ligand Hptz that was prepared in Step 2 described above, and 0.93 g of tris(acetylacetonate)iridium (III) were put in a reaction container provided with a three-way cock, and the air in the reaction container was replaced with argon. Then, the mixture was heated at 250° C. for 44 hours to be reacted. The reactant was dissolved in dichloromethane, and the solution was filtrated. Although purification of the resulting filtrate was attempted, the objective iridium complex was not prepared. The synthetic scheme of Step 3 is shown by (c-5).

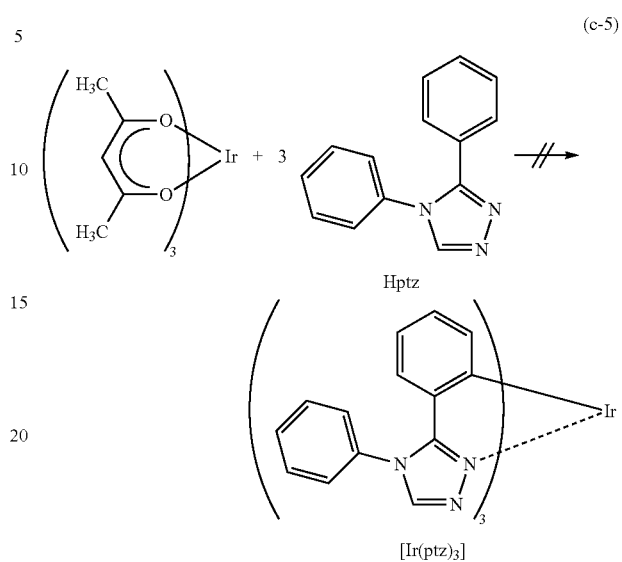

(c-5)

As described in Comparative Example 1, the synthesis of [Ir(ptz)₃] was difficult. Thus, it is found that as compared with the organometallic complexes which are described in Examples 1 to 4 and each of which is one embodiment of the present invention, a substance where a substituent bonded to the fifth position of a triazole ring is hydrogen has an extremely low yield or cannot be synthesized. That is, in the case of an organometallic complex which is one embodiment of the present invention, it is possible to suppress decomposition reaction in the synthesis of the complex; therefore, the yield of the synthesis is drastically improved as compared with [Ir(ptz)₃].

Comparative Example 2

In Comparative Example 2, a synthesis example of tris[4-(4-tert-butylphenyl)-3,5-diphenyl-4H-1,2,4-triazolato]iridium(III) (abbreviation: [Ir(m/z-tBuP)₃]) represented by the following structural formula is specifically described.

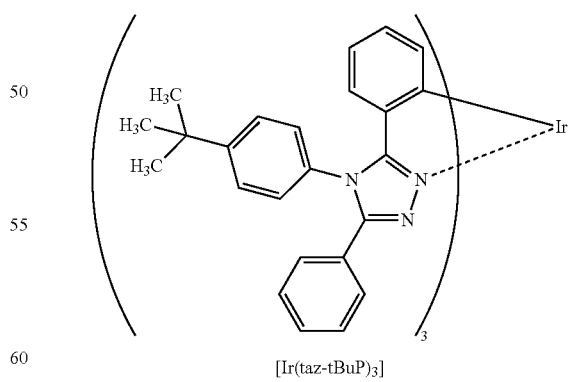

[Ir(taz-tBuP)₃]

Step 1: Synthesis of N,N'-dibenzoylhydrazine

First, 6.6 g of benzoylhydrazine and 50 mL of N-methyl-2-pyrrolidone (NMP) were put in a 200 mL three-neck flask, and mixed. Then, a mixed solution of 5 mL of benzoyl chloride and 10 mL of NMP was dripped to the above mixed solution through a 50 mL dropping funnel, and stirred at room temperature for 1 hour to be reacted. The reacted mixed solution was added to 250 mL of water, and a white solid was precipitated. The precipitated solid was washed with 1M hydrochloric acid and subjected to suction filtration to give a white solid. The given solid was washed with methanol, so that N,N'-dibenzoylhydrazine was prepared (a white solid, yield: 65%). The synthetic scheme of Step 1 is shown by (a-6).

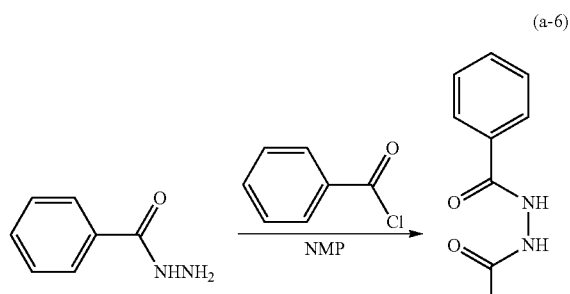

(a-6)

Step 2: Synthesis of 1,2-bis[chloro(phenyl)methylidene]hydrazine

Next, 7.5 g of N,N'-dibenzoylhydrazine that was prepared in Step 1 described above and 100 mL of toluene were put in a 300 mL three-neck flask, and mixed. Then, 13 g of phosphorus pentachloride was added to this mixed solution, and heated and stirred at 110° C. for 4 hours to be reacted. The reaction solution was added to 250 mL of water and stirred for 1 hour. After the stirring, an organic layer and an aqueous layer were separated, and the organic layer was washed with water and then a saturated aqueous solution of sodium hydrogen carbonate. After the washing, anhydrous magnesium sulfate was added to the organic layer for drying. The resulting mixture was subjected to gravity filtration, and the filtrate was concentrated to give a solid. This solid was washed with methanol, so that 1,2-bis[chloro(phenyl)methylidene]hydrazine was prepared (a yellow solid, yield: 82%). The synthetic scheme of Step 2 is shown by (b-6).

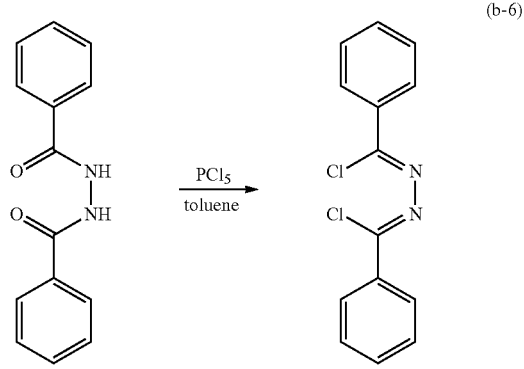 [SMILES: O=C(NNC(=O)c1ccccc1)c1ccccc1 ; "PCl5" ; Cl/C(=N\N=C(/Cl)c1ccccc1)c1ccccc1]

(b-6)

Step 3: Synthesis of 4-(4-tert-butylphenyl)-3,5-diphenyl-4H-1,2,4-triazole (abbreviation: Htaz-tBuP)

Next, 7.0 g of 1,2-bis[chloro(phenyl)methylidene]hydrazine that was prepared in Step 2 described above, 3.8 g of 4-tert-butylaniline, and 100 mL of N,N-dimethylaniline were put in a 200 mL three-neck flask, and heated and stirred at 120° C. for 6 hours to be reacted. The reaction solution was added to 1 M hydrochloric acid and stirred for 30 minutes, and a solid was precipitated to give a suspension. Toluene was added to this suspension, and an organic layer was extracted. The extracted organic layer was washed with water and then a saturated sodium carbonate solution. Anhydrate magnesium sulfate was added to the organic layer for drying, and this mixture was subjected to gravity filtration. The resulting filtrate was concentrated to give a yellow solid. This solid was recrystallized from a mixed solvent of hexane and ethanol, so that 4-(4-tert-butylphenyl)-3,5-diphenyl-4H-1,2,4-triazole (abbreviation: Htaz-tBuP) was prepared (a white solid, yield: 54%). The synthetic scheme of Step 3 is shown by (c-6).

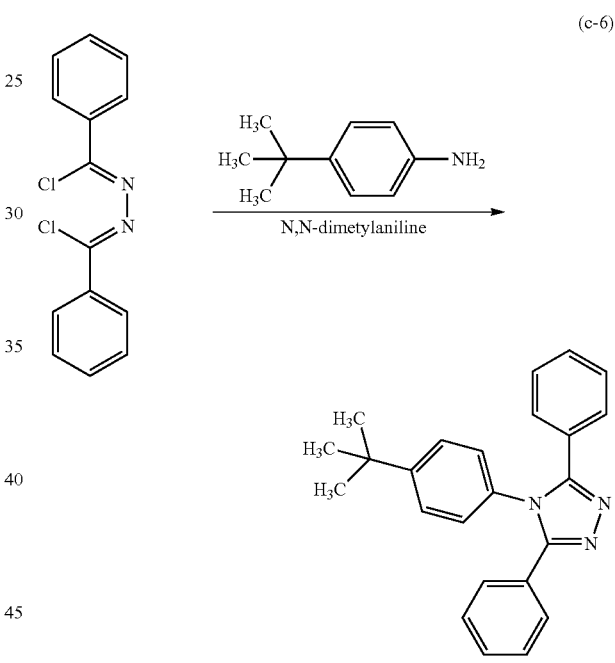

(c-6)

Htaz-tBuP

Step 4: Synthesis of tris[4-4-tert-butylphenyl)-3,5-diphenyl-4H-1,2,4-triazolato]iridium(III) (abbreviation: [Ir(m/z-tBuP)₃])

Next, 1.33 g of the ligand Htaz-tBuP that was prepared in Step 3 described above, and 0.37 g of tris(acetylacetonate)iridium(III) were put in a reaction container provided with a three-way cock, and the air in the reaction container was replaced with argon. Then, the mixture was heated at 250° C. for 43 hours to be reacted. The reactant was dissolved in dichloromethane, and the solution was filtrated. The solvent of the resulting filtrate was distilled off and purification was conducted by silica gel column chromatography which uses dichloromethane as a developing solvent. Further, recrystallization was carried out with an ethyl acetate solvent, so that the organometallic complex [Ir(m/z-tBuP)₃] which is a comparative example of the present invention was prepared (yellow powder, yield: 31%). The synthetic scheme of Step 4 is shown by (d-6).

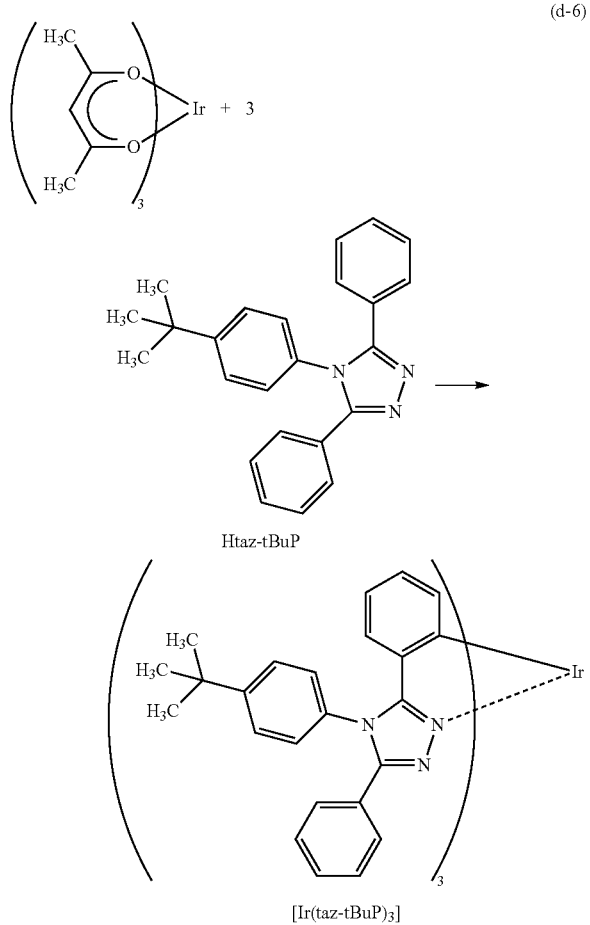

Figure 27:
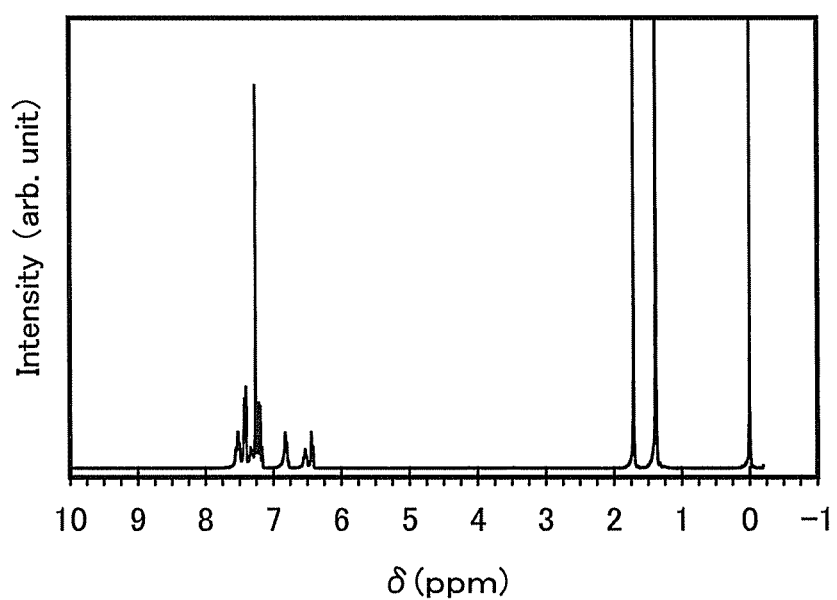
FIG. 27 shows a $^1$H-NMR chart of [Ir(m/z-tBuP)$_3$] which is a comparative example.

An analysis result by nuclear magnetic resonance spectroscopy ($^1$H-NMR) of the yellow powder prepared in Step 4 described above is shown below. The $^1$H-NMR chart is shown in FIG. 27. From the results, it is found that [Ir(m/z-tBuP)$_3$] was prepared by the synthesis method shown in Comparative Example 2.

$^1$H-NMR. δ(CDCl$_3$): 1.38 (s, 27H), 6.43 (d, 3H), 6.53 (t, 3H), 6.81 (d, 6H), 7.16-7.24 (m, 9H), 7.32 (d, 3H), 7.41 (m, 9H), 7.52 (t, 6H).

Figure 28:
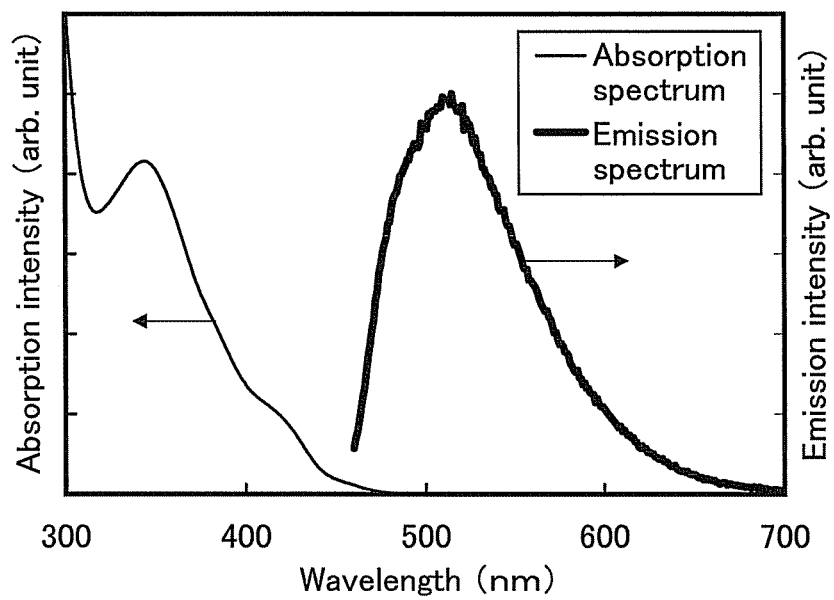
FIG. 28 shows an absorption spectrum and an emission spectrum of [Ir(m/z-tBuP)$_3$] which is a comparative example in a dichloromethane solution.

Next, an absorption spectrum and an emission spectrum of [Ir(m/z-tBuP)$_3$] in a dichloromethane solution were measured. The absorption spectrum was measured with the use of an ultraviolet-visible light spectrophotometer (V550 type manufactured by Japan Spectroscopy Corporation) in the state where the dichloromethane solution (0.097 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.58 mmol/L) was put in a quartz cell at room temperature. FIG. 28 shows measurement results of the absorption spectrum and emission spectrum. The horizontal axis represents wavelength, and the vertical axis represents absorption intensity and emission intensity. In FIG. 28, two solid lines are shown; a thin line represents the absorption spectrum, and a thick line represents the emission spectrum. Note that the absorption spectrum in FIG. 28 is a result obtained by subtraction of the absorption spectrum of only dichloromethane that was put in a quartz cell from the measured absorption spectrum of the dichloromethane solution (0.58 mmol/L) in a quartz cell.

As shown in FIG. 28, the organometallic complex [Ir(m/z-tBuP)$_3$] which is a comparative example of the present invention has a peak of emission at 511 nm, and green light was observed from the dichloromethane solution.

The wavelength of the peak of emission of [Ir(m/z-tBuP)$_3$] described in Comparative Example 2 is longer than that of [Ir(Mptz)$_3$] described in Example 1 and that of [Ir(chptz)$_3$] described in Example 3. Thus, the emission spectrum of a substance where a substituent bonded to the fifth position of a triazole ring is a phenyl group shifts to a long wavelength side as compared with a substance where the substituent bonded to the fifth position of a triazole ring is a methyl group or a cyclohexyl group. That is, an organometallic complex which is one embodiment of the present invention where a substituent bonded to the fifth position of a triazole ring is an allyl group having 1 to 6 carbon atoms, a cycloalkyl group having 5 to 8 carbon atoms which may have a substituent, and an aralkyl group having 7 to 10 carbon atoms which may have a substituent has a peak of emission on a short wavelength side as compared with an organometallic complex in which the substituent bonded to the fifth position of a triazole ring is a phenyl group. Therefore, the organometallic complex which is one embodiment of the present invention is advantageous in manufacture of a material that exhibits phosphorescence having a wavelength band of blue as compared with [Ir(m/z-tBuP)$_3$].

EXAMPLE 5

In Example 5, a light-emitting element using the organometallic complex tris(5-methyl-3,4-diphenyl-4H-1,2,4-triazolato)iridium(B1) (abbreviation: [Ir(Mptz)$_3$]), which is represented by Structural Formula (100) of Embodiment 1, is described (the light-emitting element is referred to as Light-emitting element 1 below). Structural formulas of part of materials used in Example 5 are shown below.

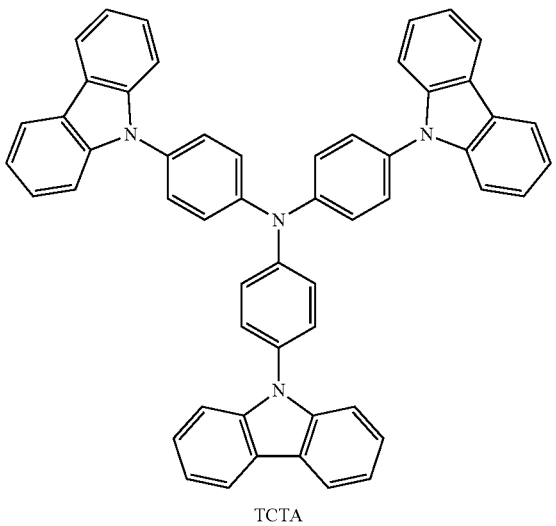

TCTA

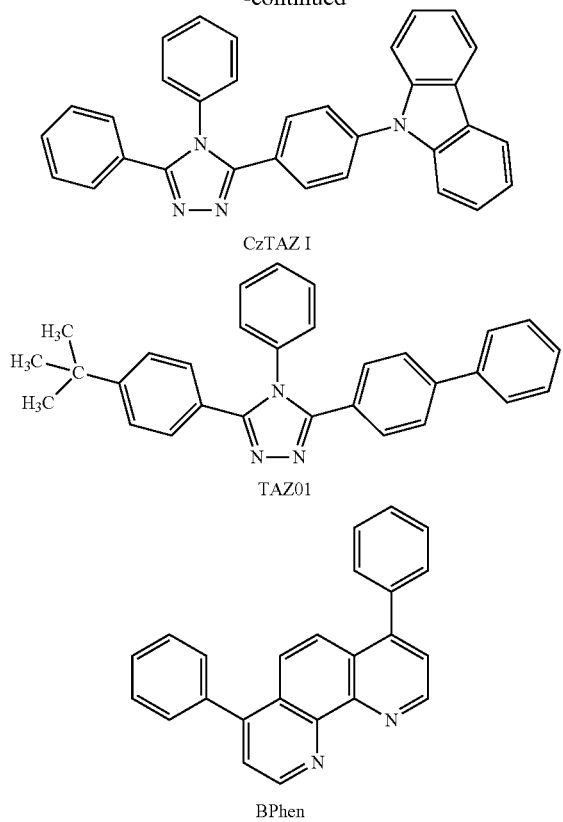

CzTAZ I

TAZ01

BPhen (Light-Emitting Element 1)

First, over a glass substrate, indium tin oxide containing silicon oxide (abbreviation: ITSO) was deposited by a sputtering method, so that a first electrode which functions as an anode was formed. The thickness of the first electrode was 110 nm and the electrode area was 2 mm×2 mm.

Next, the glass substrate over which the first electrode was formed was fixed to a substrate holder provided in a vacuum evaporation apparatus such that the side on which the first electrode was formed faced downward, and the pressure was reduced to approximately $10^{-4}$ Pa. After that, over the first electrode, a layer containing a composite material of an organic compound and an inorganic compound was formed by co-evaporation of 4,4',4"-tris(N-carbazolyl)triphenylamine (abbreviation: TCTA) and molybdenum(VI) oxide. The thickness of the layer containing a composite material was 50 nm, and the weight ratio of TCTA and molybdenum oxide was adjusted to 2:1 (=TCTA:molybdenum oxide). Note that the co-evaporation method refers to an evaporation method in which evaporation of a plurality of materials is performed using a plurality of evaporation sources at the same time in one treatment chamber.

Next, a 10-nm-thick TCTA layer was formed over the layer containing a composite material by an evaporation method using resistance heating, so that a hole-transport layer was formed.

Further, a 30-nm-thick light-emitting layer was formed over the hole-transport layer by co-evaporation of 9-[4-(4,5-diphenyl-4H-1,2,4-triazol-3-yl)phenyl]-9H-carbazole (abbreviation: CzTAZ I) and [Ir(Mptz)$_3$], which is the organometallic complex represented by Structural Formula (100) of Embodiment 1. Here, the weight ratio of CzTAZ I and [Ir(Mptz)$_3$] was adjusted to 1:0.06 (=CzTAZ I:[Ir(Mptz)$_3$]).

After that, over the light-emitting layer, a 10-nm-thick 3-(4-biphenylyl)-4-phenyl-5-(4-tert-buthylphenyl)-1,2,4-triazole (abbreviation: TAZ 01) layer was formed by an evaporation method using resistance heating, and then a 20-nm-thick bathophenanthroline (abbreviation: BPhen) layer was formed by an evaporation method using resistance heating. In such a manner, an electron-transport layer in which a layer formed using TAZ 01 and a layer formed using BPhen are stacked was formed over the light-emitting layer.

Furthermore, a 1-nm-thick lithium fluoride layer was formed over the electron-transport layer, so that an electron-injection layer was formed.

Lastly, a 200-nm-thick aluminum layer was formed over the electron-injection layer by an evaporation method using resistance heating, so that a second electrode which functions as a cathode was formed. Through the above-described process, Light-emitting element 1 was fabricated.

Figure 15:
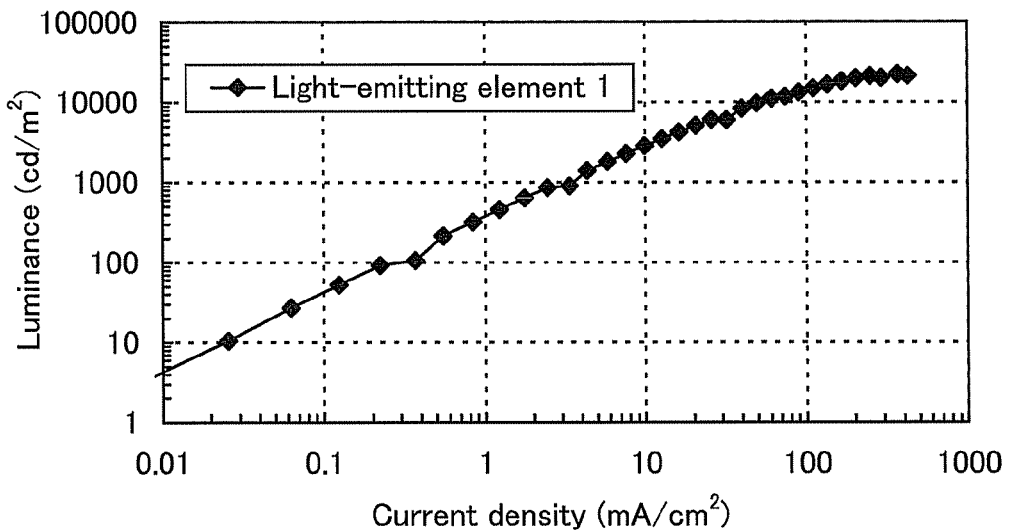
FIG. 15 shows current density vs. luminance characteristics of Light-emitting element 1.
Figure 16:
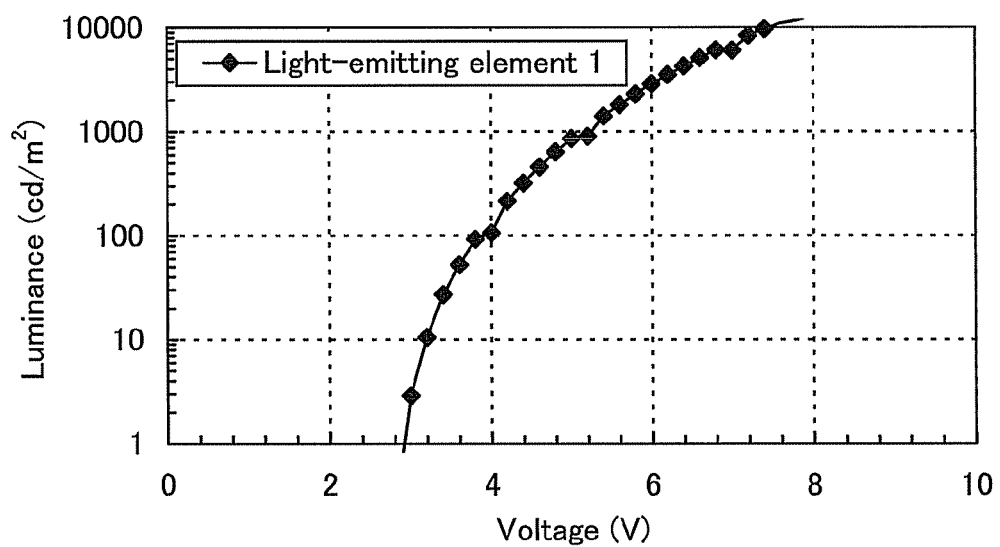
FIG. 16 shows voltage vs. luminance characteristics of Light-emitting element 1.
Figure 17:
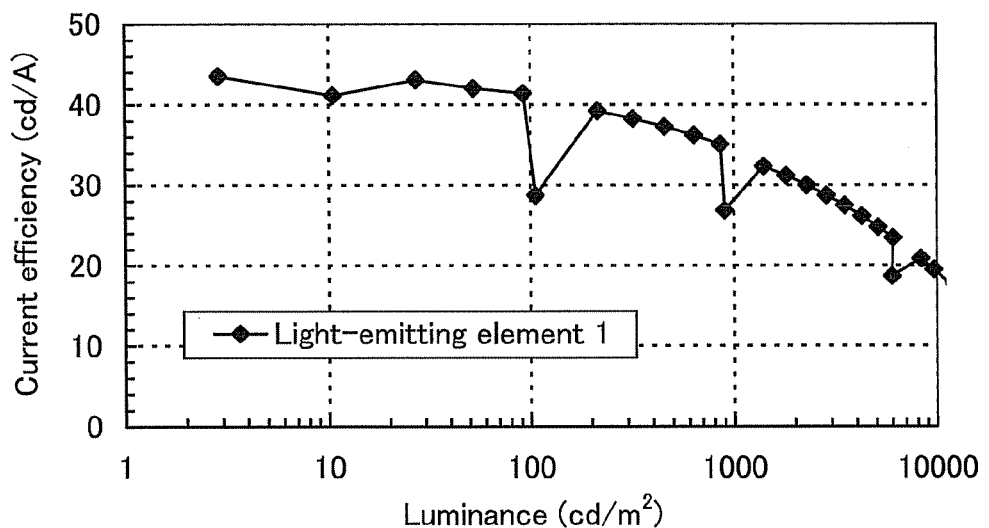
FIG. 17 shows luminance vs. current efficiency characteristics of Light-emitting element 1.
Figure 18:
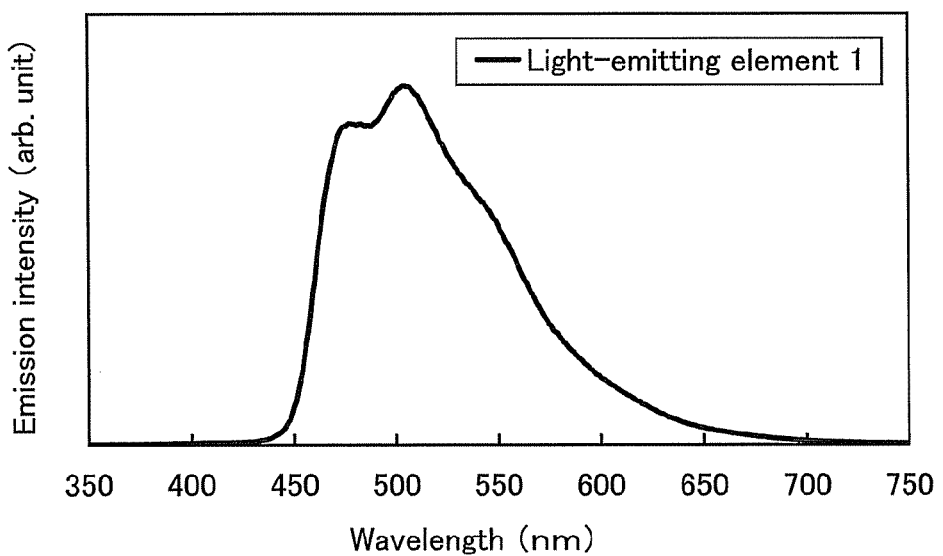
FIG. 18 shows an emission spectrum of Light-emitting element 1.

FIG. 15 shows current density vs. luminance characteristics of Light-emitting element 1. FIG. 16 shows voltage vs. luminance characteristics thereof. FIG. 17 shows luminance vs. current efficiency characteristics thereof. Further, FIG. 18 shows the emission spectrum thereof at a current of 0.5 MA. From FIG. 18, it is found that the light emission from Light-emitting element 1 originates from [Ir(Mptz)$_3$]. The CIE chromaticity coordinates of Light-emitting element 1 at a luminance of 859 cd/m$^2$ are (x, y)=(0.24, 0.44), and blue-green light was emitted. From FIG. 17, it is found that the current efficiency of Light-emitting element 1 at a luminance of 859 cd/m$^2$ is 35.1 cd/A, which is an extremely high current efficiency. From FIG. 16, it is found that the driving voltage at 859 cd/m$^2$ is 5.0 V, and that the power efficiency is 22.0 lm/W. These results indicate that Light-emitting element 1 needs a low voltage for obtaining a certain luminance, has low power consumption, and has an extremely high current efficiency and power efficiency.

EXAMPLE 6

In Example 6, a light-emitting element using the organometallic complex tris[3-(4-fluorophenyl)-5-methyl-4-phenyl-4H-1,2,4-triazolato]iridium(III) (abbreviation: [Ir(MFptz)$_3$]), which is represented by Structural Formula (122) of Embodiment 1, is described (the light-emitting element is referred to as Light-emitting element 2 below).

(Light Emitting Element 2)

The element structure of Light-emitting element 2 was the same as that of Light-emitting element 1 except for a light-emitting layer. In addition, Light-emitting element 2 was fabricated in accordance with the method for fabricating Light-emitting element 1. That is, over a glass substrate, an indium tin oxide layer containing silicon oxide (a first electrode), a layer containing a composite material formed by co-evaporation of TCTA and molybdenum oxide, a TCTA layer (a hole-transport layer), a light-emitting layer, a stack of TAZ 01 and BPhen (an electron-transport layer), a lithium fluoride layer (an electron-injection layer), and an aluminum layer (a second electrode) were formed.

The light-emitting layer of Light-emitting element 2 was formed with a thickness of 30 nm by co-evaporation of CzTAZ I and [Ir(MFptz)$_3$], which is the organometallic complex represented by Structural Formula (122) of Embodiment 1. Here, the weight ratio of CzTAZ I and [Ir(MFptz)$_3$] was adjusted to 1:0.06 (=CzTAZ I:[Ir(MFptz)$_3$]).

Figure 19:
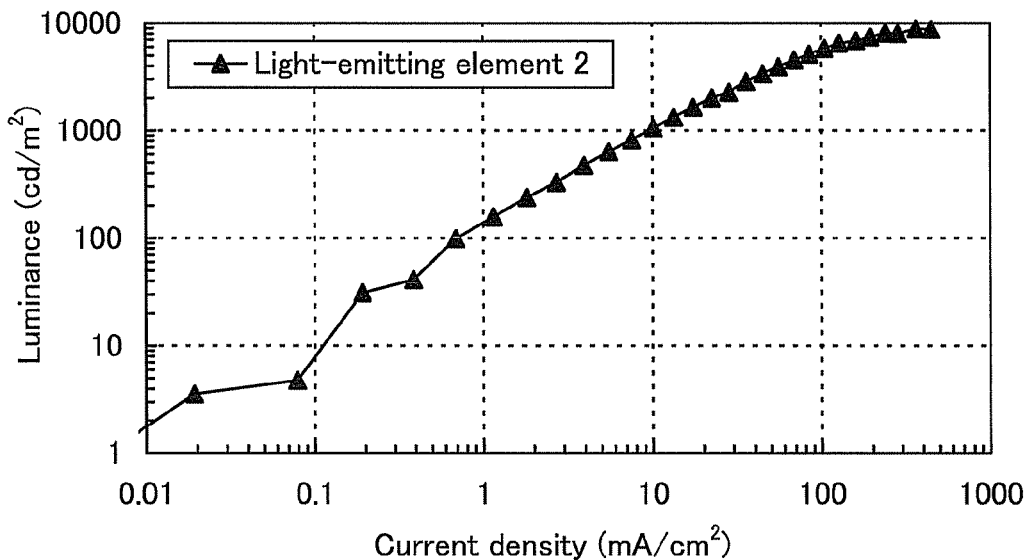
FIG. 19 shows current density vs. luminance characteristics of Light-emitting element 2.
Figure 20:
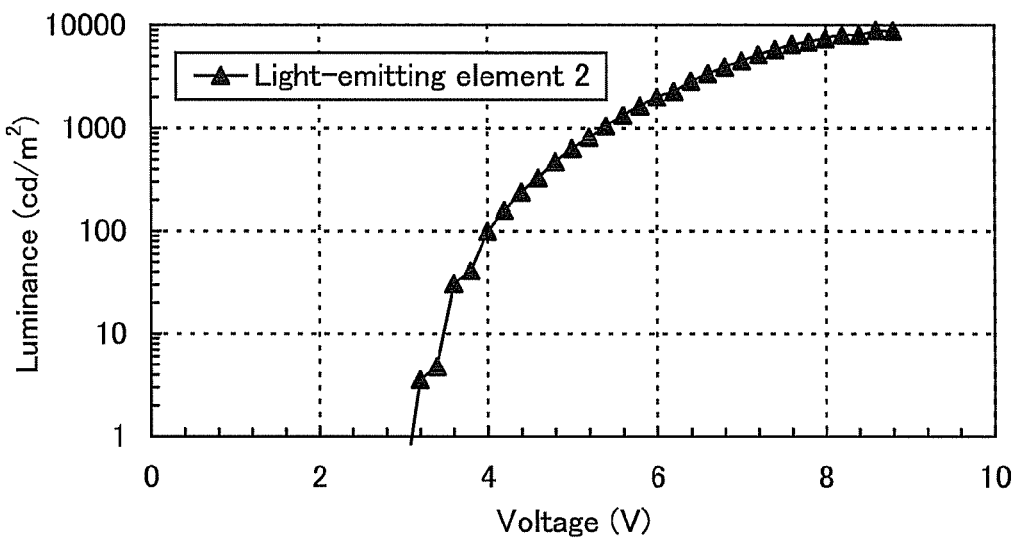
FIG. 20 shows voltage vs. luminance characteristics of Light-emitting element 2.
Figure 21:
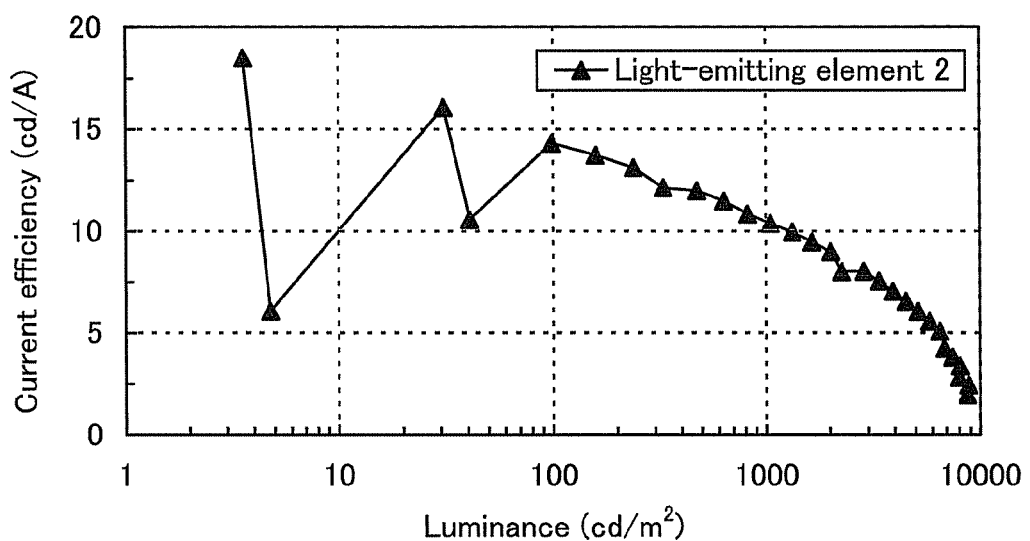
FIG. 21 shows luminance vs. current efficiency characteristics of Light-emitting element 2.
Figure 22:
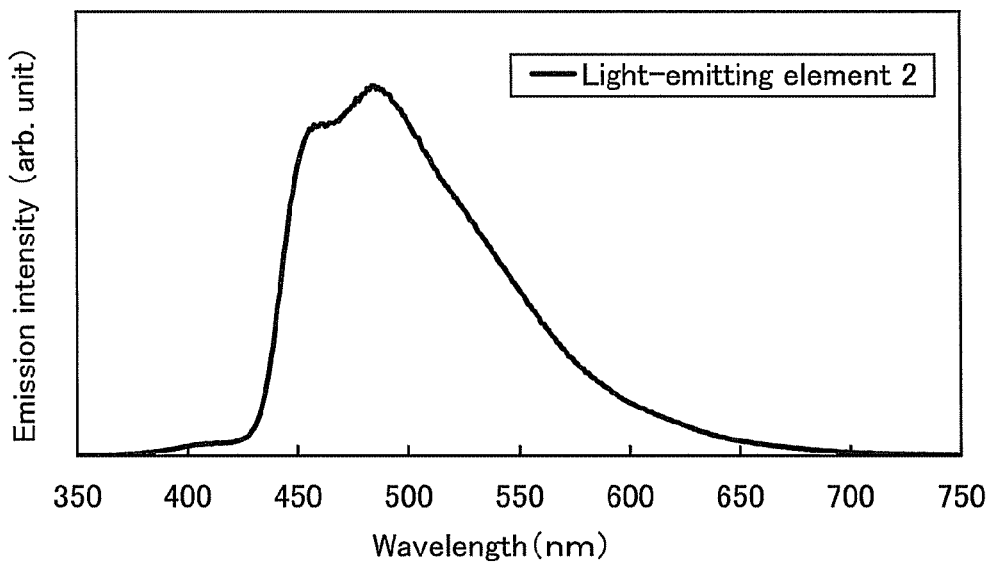
FIG. 22 shows an emission spectrum of Light-emitting element 2.

FIG. 19 shows current density vs. luminance characteristics of Light-emitting element 2. FIG. 20 shows voltage vs. luminance characteristics thereof FIG. 21 shows luminance vs. current efficiency characteristics thereof. Further, FIG. 22 shows the emission spectrum thereof at a current of 0.5 mA. From FIG. 22, it is found that the light emission from Light-emitting element 2 originates from [Ir(MFptz)$_3$]. The CIE chromaticity coordinates of Light-emitting element 2 at a luminance of 1050 cd/m$^2$ are (x, y)=(0.20, 0.31), and light-blue light was emitted. From FIG. 21, it is found that the current efficiency of Light-emitting element 2 at a luminance of 1050 cd/m$^2$ is 10.4 cd/A, which is a high current efficiency. From FIG. 20, it is found that the driving voltage at 1050 cd/m$^2$ is 5.4 V, and that the power efficiency is 6.0 lm/W. These results indicate that Light-emitting element 2 needs a low voltage for obtaining a certain luminance, has low power consumption, and has high current efficiency.

EXAMPLE 7

In Example 7, a light-emitting element using the organometallic complex tris(5-cyclohexyl-3,4-diphenyl-4H-1,2,4-triazolatoiridium(III) (abbreviation: [Ir(chptz)$_3$]), which is represented by Structural Formula (104) of Embodiment 1, is described (the light-emitting element is referred to as Light-emitting element 3 below). Structural formulas of part of materials used in Example 7 are shown below.

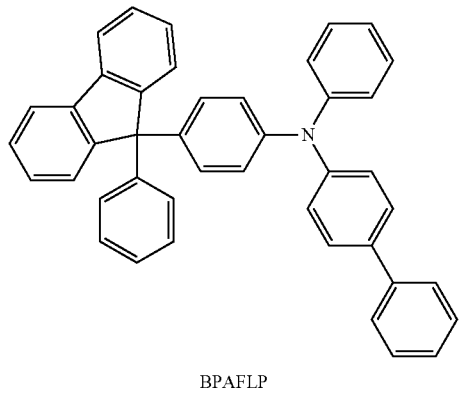 [SMILES: c1ccc(-c2ccc(N(c3ccccc3)c3ccc(C4(c5ccccc5)c5ccccc5-c5ccccc54)cc3)cc2)cc1]

BPAFLP (Light-Emitting Element 3)

First, over a glass substrate, indium tin oxide containing silicon oxide was deposited by a sputtering method, so that a first electrode which functions as an anode was formed. The thickness of the first electrode was 110 nm and the electrode area was 2 mm×2 mm.

Next, the glass substrate over which the first electrode was formed was fixed to a substrate holder provided in a vacuum evaporation apparatus such that the side on which the first electrode was formed faced downward, and the pressure was reduced to approximately 10$^{-4}$ Pa. After that, over the first electrode, a layer containing a composite material of an organic compound and an inorganic compound was formed by co-evaporation of 4-phenyl-4'-(9-phenylfluoren-9-yl) triphenylamine (abbreviation: BPAFLP) and molybdenum (VI) oxide. The thickness of the layer containing a composite material was 50 nm, and the weight ratio of BPAFLP and molybdenum oxide was adjusted to 2:1 (=BPAFLP:molybdenum oxide). Note that the co-evaporation method refers to an evaporation method in which evaporation of a plurality of materials is performed using a plurality of evaporation sources at the same time in one treatment chamber.

Next, a 10-nm-thick BPAFLP layer was formed over the layer containing a composite material by an evaporation method using resistance heating, so that a hole-transport layer was formed.

Further, a 30-nm-thick light-emitting layer was formed over the hole-transport layer by co-evaporation of CzTAZ I and [Ir(chptz)$_3$], which is the organometallic complex represented by Structural Formula (104) of Embodiment 1. Here, the weight ratio of CzTAZ I and [Ir(chptz)$_3$] was adjusted to 1:0.06 (=CzTAZ I:[Ir(chptz)$_3$]).

After that, over the light-emitting layer, a 10-nm-thick CzTAZ I layer was formed by an evaporation method using resistance heating, and then a 20-nm-thick BPhen layer was formed over the CzTAZ I layer by an evaporation method using resistance heating. In such a manner, an electron-transport layer in which a layer formed using CzTAZ I and a layer formed using BPhen are stacked was formed over the light-emitting layer.

Furthermore, a 1-nm-thick lithium fluoride layer was formed over the electron-transport layer, so that an electron-injection layer was formed.

Lastly, a 200-nm-thick aluminum layer was formed over the electron-injection layer by an evaporation method using resistance heating, so that a second electrode which functions as a cathode was formed. Through the above-described process, Light-emitting element 3 was fabricated.

Figure 23:
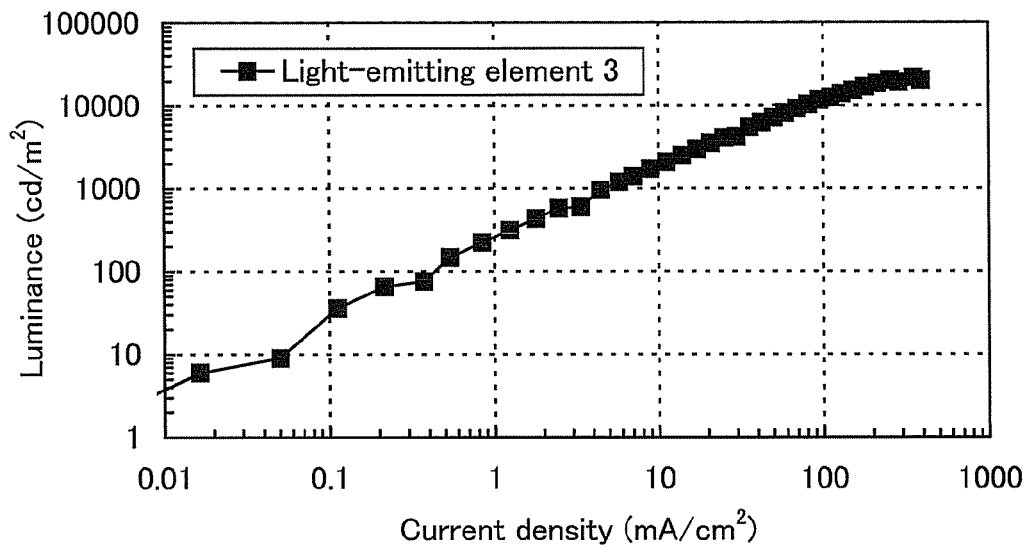
FIG. 23 shows current density vs. luminance characteristics of Light-emitting element 3.
Figure 24:
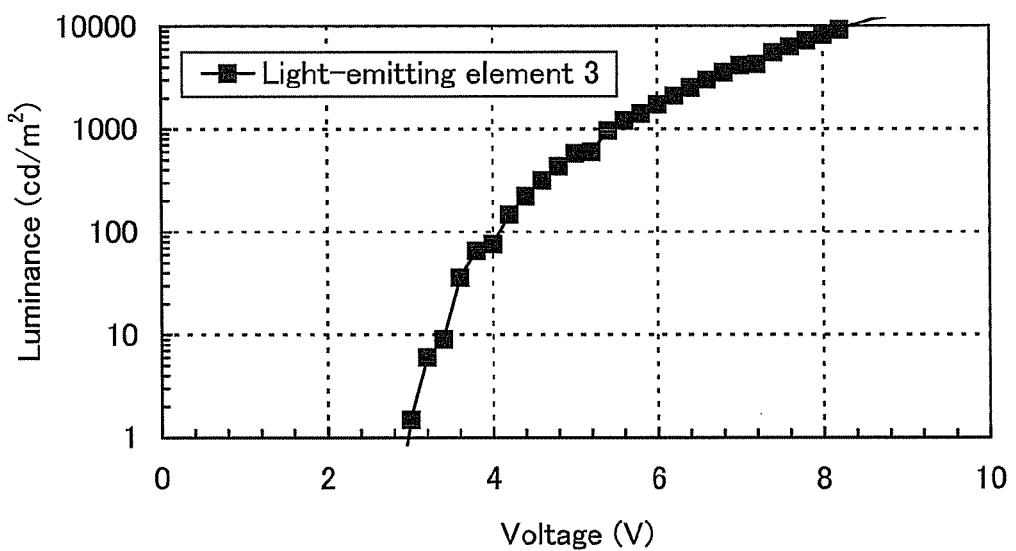
FIG. 24 shows voltage vs. luminance characteristics of Light-emitting element 3.
Figure 25:
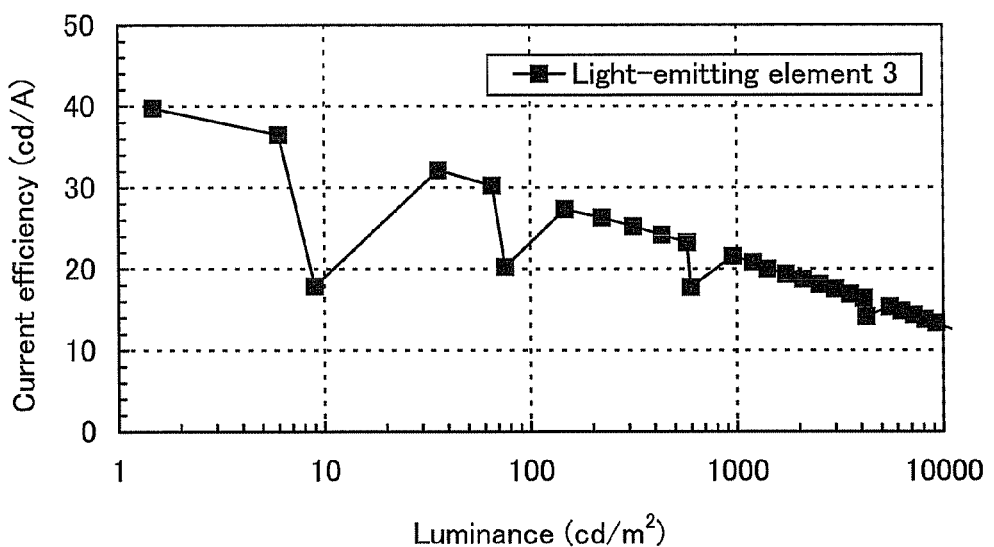
FIG. 25 shows luminance vs. current efficiency characteristics of Light-emitting element 3.
Figure 26:
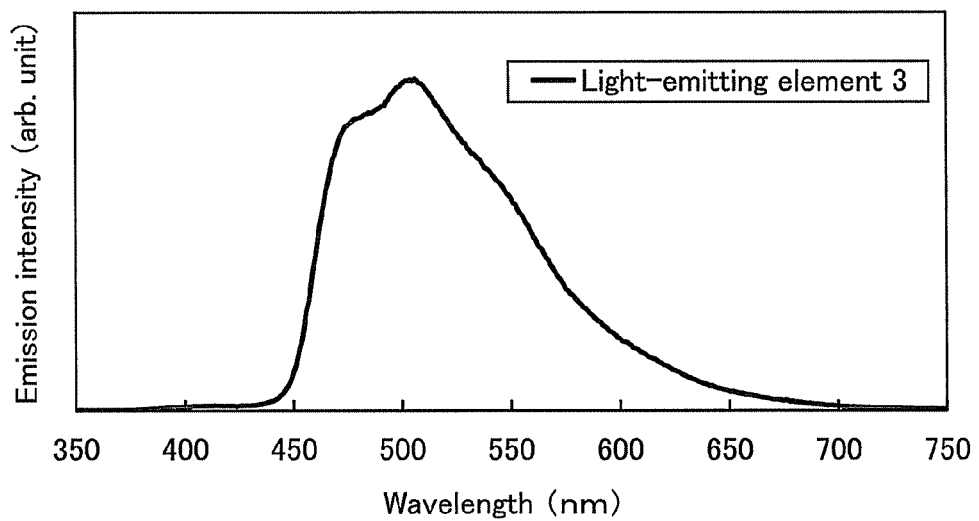
FIG. 26 shows an emission spectrum of Light-emitting element 3.

FIG. 23 shows current density vs. luminance characteristics of Light-emitting element 3. FIG. 24 shows voltage vs. luminance characteristics thereof. FIG. 25 shows luminance vs. current efficiency characteristics thereof. Further, FIG. 26 shows the emission spectrum thereof at a current of 0.1 mA. From FIG. 26, it is found that the light emission from Light-emitting element 3 originates from [Ir(chptz)$_3$]. The CIE chromaticity coordinates of Light-emitting element 3 at a luminance of 956 cd/m$^2$ are (x, y)=(0.25, 0.44), and blue-green light was emitted. From FIG. 25, it is found that the current efficiency of Light-emitting element 3 at a luminance of 956 cd/m$^2$ is 21.5 cd/A, which is an extremely high current efficiency. From FIG. 24, it is found that the driving voltage at 956 cd/m$^2$ is 5.4 V, and that the power efficiency is 12.5 lm/W. These results indicate that Light-emitting element 3 needs a low voltage for obtaining a certain luminance, has low power consumption, and has an extremely high current efficiency and power efficiency.

Note that detailed structures of the light-emitting elements fabricated using organometallic complexes of embodiments of the present invention in Examples 5 to 7 are shown in Table 1.

TABLE 1

| | First Electrode | Hole-injection Layer | Hole-transport Layer | Light-emitting Layer |
|---|---|---|---|---|
| Light-emitting Element 1 | ITSO | TCTA:MoOx (=2:1) | TCTA | CzTAZ I: [Ir(Mptz)$_3$] (=1:0.06) |
| | 110 nm | 50 nm | 10 nm | 30 nm |
| Light-emitting Element 2 | ITSO | TCTA:MoOx (=2:1) | TCTA | CzTAZ I: [Ir(MFptz)$_3$] (=1:0.06) |
| | 110 nm | 50 nm | 10 nm | 30 nm |
| Light-emitting Element 3 | ITSO | BPAFLP:MoOx (=2:1) | BPAFLP | CzTAZ I: [Ir(chptz)$_3$] (=1:0.06) |
| | 110 nm | 50 nm | 10 nm | 30 nm |

| | Electron-transport Layer | Electron-injection Layer | Second Electrode |
|---|---|---|---|
| Light-emitting Element 1 | TAZ 01 10 nm | BPhen 20 nm | LiF 1 nm | Al 200 nm |

TABLE 1-continued

| | | | | |
|---|---|---|---|---|
| Light-emitting Element 2 | TAZ 01 10 nm | BPhen 20 nm | LiF 1 nm | Al 200 nm |
| Light-emitting Element 3 | CzTAZ I 10 nm | BPhen 20 nm | LiF 1 nm | Al 200 nm |

EXAMPLE 8

Synthesis Example 5

In Example 8, a synthesis example of the organometallic complex tris(3,4-diphenyl-5-propyl-4H-1,2,4-triazolato)iridium(III) (abbreviation: [Ir(Prptz)$_3$]) which is one embodiment of the present invention represented by Structural Formula (101) in Embodiment 1 is specifically described.

Step 1: Synthesis of N-phenylbutyramide

First, 16 g of aniline, 200 mL of tetrahydrofuran (THF), 26 g of triethylamine (Et$_3$N) were put in a 500 mL three-neck flask, and stirred under cooling in ice. Then, a mixed solution of 18 g of btyryl chloride and 50 mL of THF was dripped to the above mixed solution through a 100 mL dropping funnel. After the dripping, the mixture was stirred for 2 hours while the temperature was increased to room temperature. After the stirring, the reaction mixture was added to 200 mL of water, and stirred at room temperature. This mixed solution was separated to an organic layer and an aqueous layer, and the aqueous layer was extracted with chloroform. The extract and the previously resulting organic layer were combined, and washed with saturated saline. After the washing, anhydrate magnesium sulfate was added to the organic layer for drying. The mixture after the drying was subjected to gravity filtration, and the filtrate was concentrated to give a solid. This solid was washed with a mixed solvent of chloroform and hexane, so that N-phenylbutyramide was prepared (a white solid, yield: 92%). The synthetic scheme of Step 1 is shown by (a-7).

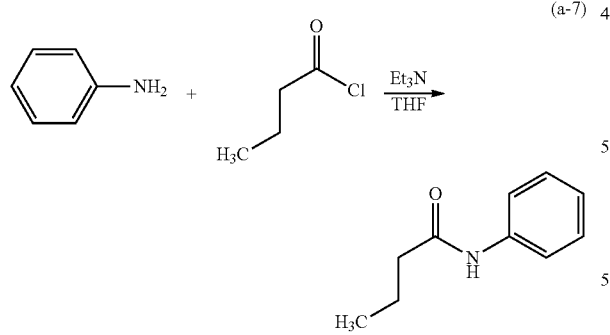

(a-7)

Step 2: Synthesis of N-phenylthiobutyramide

Next, 15.0 g of N-phenylbutyramide that was prepared in Step 1 described above and 120 mL of toluene were put in a 300 mL three-neck flask, and mixed. Then, 18.5 g of 2,4-bis (4-methoxyphenyl)-1,3,2,4-dithiadiphosphetane-2,4-disulfide (Lawesson's reagent) was added to this mixture, and heated and stirred at 110° C. for 2 hours. After the stirring, the reaction solution was concentrated under a reduced pressure to give a solid. The given solid was purified by silica gel column chromatography. Toluene was used as a developing solvent. The resulting fraction was concentrated, so that N-phenylthiobutyramide was prepared (an orange oily substance, yield: 89%). The synthetic scheme of Step 2 is shown by (b-7).

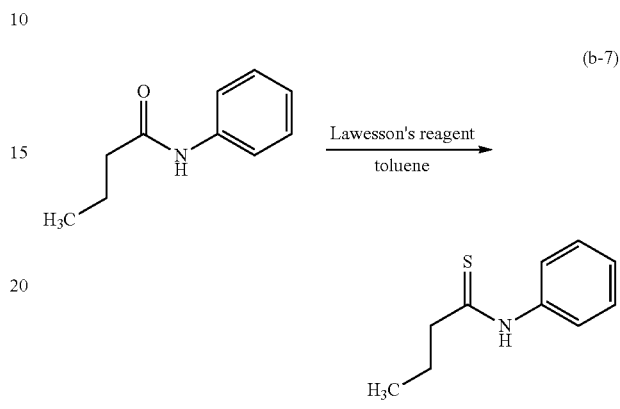

(b-7)

Step 3: Synthesis of N-[1-(ethylsulfanyl)butylidene]aniline

Next, 14.3 g of N-phenylthiobutyramide prepared in Step 2 described above and 100 mL of ethanol were put in a 200 mL three-neck flask. Then, 5.57 g of sodium ethoxide was added to this mixed solution, and stirred at room temperature for 1 hour to be reacted. Then, approximately 7 mL of iodoethane was added to this reaction mixture, and heated and stirred at 60° C. for 9 hours. After the stirring, ethanol was distilled off under a reduced pressure to give an oily substance. The given oily substance was dissolved in dichloromethane, and washed with water and then a saturated aqueous solution of sodium hydrogen carbonate. After the washing, anhydrous magnesium sulfate was added to the resulting organic layer for drying. After the drying, the mixture was subjected to gravity filtration, so that N-[1-(ethylsulfanyl)butylidene]aniline was prepared (a brown oily substance, yield: 64%) %). The synthetic scheme of Step 3 is shown by (c-7).

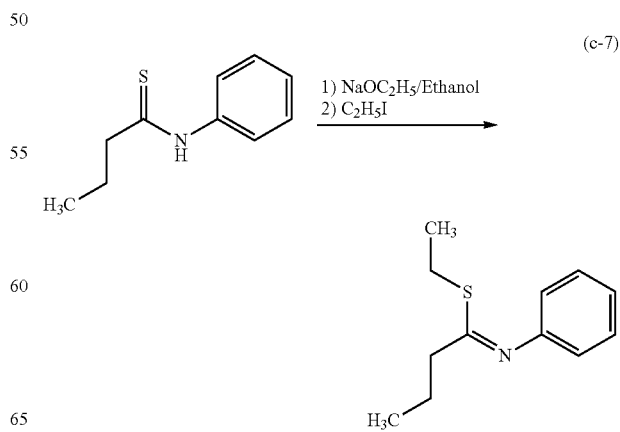

(c-7)

Step 4: Synthesis of 3,4-diphenyl-5-propyl-4H-1,2,4-triazole (abbreviation: HPrptz)

Next, 5.40 g of N-[1-(ethylsulfanyl)butylidene]aniline, 3.19 g of benzoylhydrazine, and 30 mL of 1-butanol were put in a 100 mL three-neck flask and heated and stirred at 130° C. for 12 hours. After the stirring, butanol was distilled off under a reduced pressure to give a brown solid. This solid was washed with ethyl acetate, and subjected to suction filtration to give a solid. The given solid was purified by silica gel column chromatography. As developing solvents, first, hexane:ethyl acetate=1:9 was used, and then ethyl acetate was used. The resulting fraction was concentrated to give a solid. This solid was recrystallized from a mixed solvent of hexane and ethyl acetate, so that 3,4-diphenyl-5-propyl-4H-1,2,4-triazole (abbreviation: HPrptz) was prepared (a white solid, yield: 28%). The synthetic scheme of Step 4 is shown by (d-7).

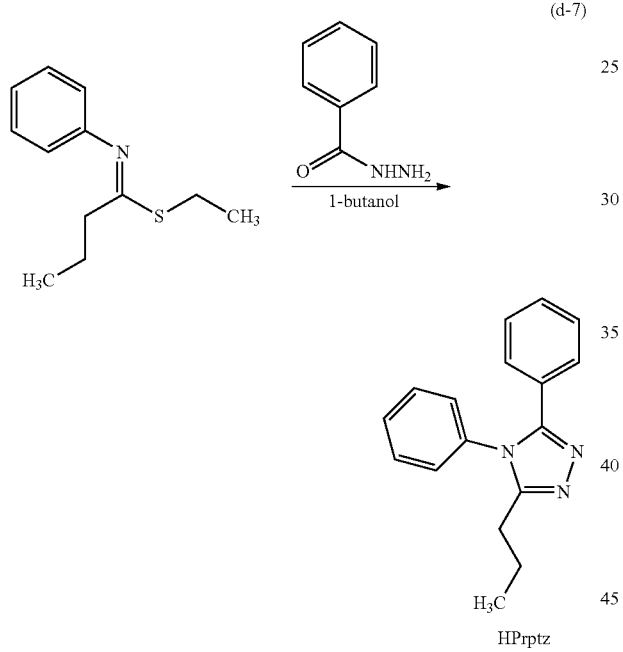

Step 5: Synthesis of tris(3,4-diphenyl-5-propyl-4H-1,2,4-triazolato)iridium(III) (abbreviation: [Ir(Prptz)₃])

Next, 1.93 g of the ligand HPrptz that was prepared in Step 4 described above, and 0.72 g of tris(acetylacetonate)iridium (III) were put in a reaction container provided with a three-way cock, and the air in the reaction container was replaced with argon. Then, the mixture was heated at 220° C. to 240° C. for 71 hours to be reacted. The reactant was purified by silica gel column chromatography which uses ethyl acetate as a developing solvent. The solvent of the resulting fraction was distilled off, the residue was dissolved in ethyl acetate, and then subjected to suction filtration through Celite (a product of Wako Pure Chemical Industries, Ltd., Catalog No. 531-16855) and silica gel. The resulting filtrate was concentrated to give a solid. Further, this solid was recrystallized from a mixed solvent of ethyl acetate and hexane, so that the organometallic complex [Ir(Prptz)₃] which is one embodiment of the present invention was prepared (light yellow powder, yield: 15%). The synthetic scheme of Step 5 is shown by (e-7).

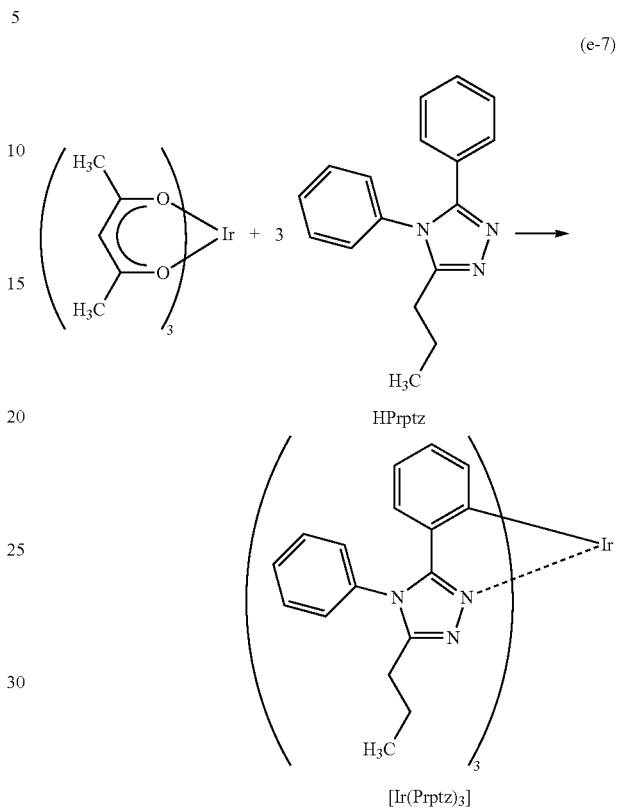

Figure 29:
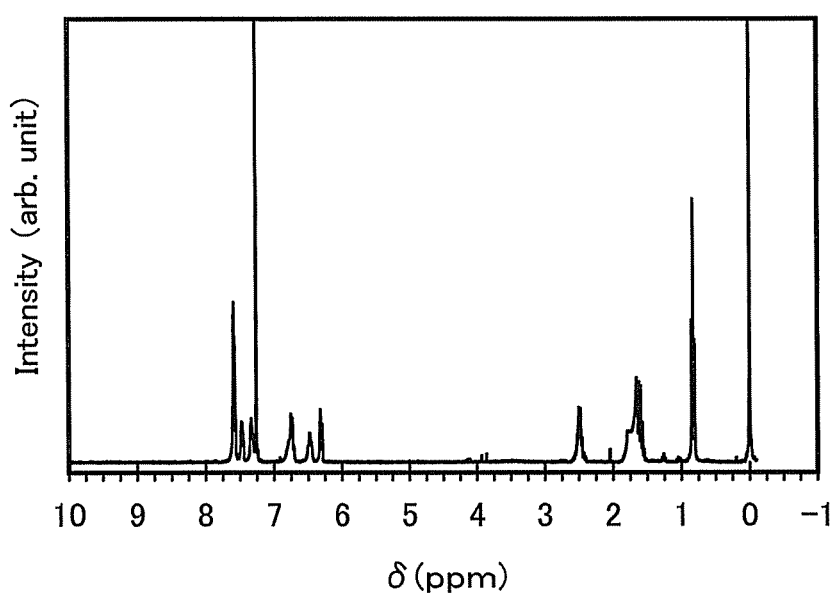
FIG. 29 shows a $^1$H-NMR chart of [Ir(Prptz)$_3$].

An analysis result by nuclear magnetic resonance spectroscopy ($^1$H-NMR) of the light yellow powder prepared in Step 5 described above is shown below. The $^1$H-NMR chart is shown in FIG. 29. From the results, it is found that the organometallic complex [Ir(Prptz)₃] which is one embodiment of the present invention represented by Structural Formula (101) was prepared in Synthesis Example 5.

$^1$H-NMR. δ(CDCl₃): 0.80-0.85 (t, 9H), 1.54-1.65 (m, 6H), 2.42-2.52 (m, 6H), 6.30 (d, 3H), 6.45-6.49 (m, 3H), 6.70-6.75 (m, 6H), 7.30-7.34 (m, 3H), 7.45-7.48 (m, 3H), 7.56-7.60 (m, 9H).

The sublimation temperature of the prepared organometallic complex [Ir(Prptz)₃] which is one embodiment of the present invention was measured with a high vacuum differential type differential thermal balance (TG-DTA2410SA manufactured by Bruker AXS K.K.). The degree of vacuum was $1 \times 10^{-3}$ Pa and the temperature increase rate was 10° C./min, and the temperature of a sample containing [Ir(Prptz)₃] was increased, whereby reduction in weight by 5% was observed at 278° C. From the results, it is found that [Ir(Prptz)₃] has a favorable sublimation property.

Figure 30:
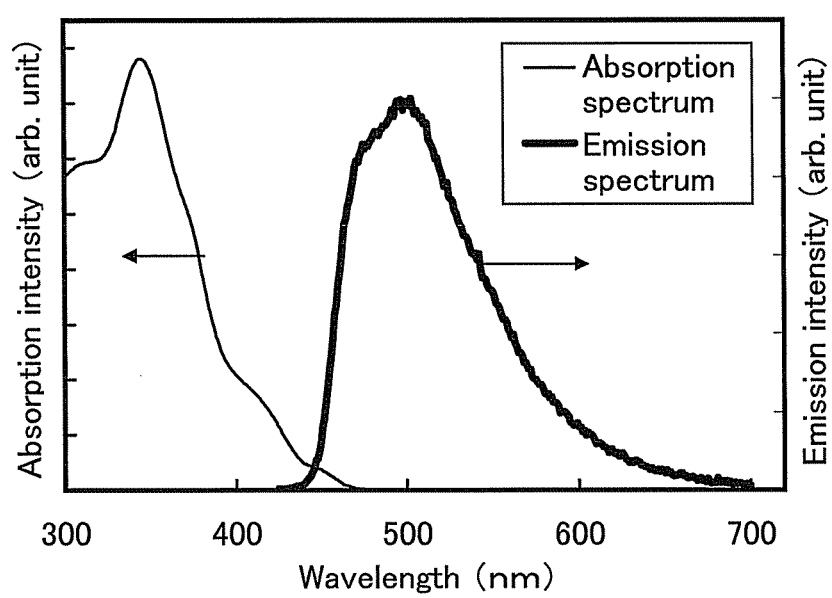
FIG. 30 shows an absorption spectrum and an emission spectrum of [Ir(Prptz)$_3$] in a dichloromethane solution.

Next, an ultraviolet-visible absorption spectrum (hereinafter, simply referred to as an absorption spectrum) and an emission spectrum of [Ir(Prptz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.078 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.078 mmol/L) was put in a quartz cell at room temperature. FIG. 30 shows measurement results of the absorption spectrum and emission spectrum. The horizontal axis represents wavelength, and the vertical axis represents absorption intensity and emission intensity. In FIG. 30, two solid lines are shown; a thin line represents the absorption spectrum, and a thick line represents the emission spectrum. Note that the absorption spectrum in FIG. 30 is a result obtained by subtraction of the absorption spectrum of only dichloromethane that was put in a quartz cell from the measured absorption spectrum of the dichloromethane solution (0.078 mmol/L) in a quartz cell.

As shown in FIG. 30, the organometallic complex [Ir(Prptz)$_3$] which is one embodiment of the present invention has a peak of emission at 500 nm, and green light was observed from the dichloromethane solution.

EXAMPLE 9

Synthesis Example 6

In Example 9, a synthesis example of the organometallic complex tris(5-isopropyl-3,4-diphenyl-4H-1,2,4-triazolato)iridium(III) (abbreviation: [Ir(iPrptz)$_3$]) which is one embodiment of the present invention represented by Structural Formula (102) in Embodiment 1 is specifically described.

Step 1: Synthesis of 3-isopropyl-4,5-diphenyl-4H-1,2,4-triazole (abbreviation HiPrptz)

First, 6.1 g of N-[1-(ethylsulfanyl)isobutylidene]aniline, 3.4 g of benzoylhydrazine, and 30 mL of 1-butanol were put in a 200 mL recovery flask, and heated and stirred at 130° C. for 7 hours to be reacted. After the reaction, 1-butanol was distilled off under a reduced pressure to give an oily substance. This oily substance was purified by silica gel column chromatography. As developing solvents, first, dichloromethane was used, and then ethyl acetate was used. The resulting fraction was concentrated to give a white solid. The given solid was recrystallized from a mixed solvent of ethanol and hexane, so that 1.6 g of 3-isopropyl-4,5-diphenyl-4H-1,2,4-triazole was prepared as a white solid with a yield of 24%. The synthetic scheme of Step 1 is shown by (a-8).

(a-8)

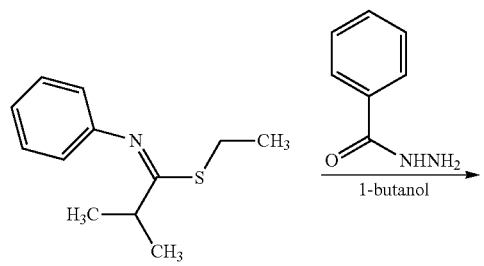

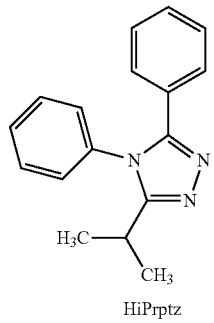

HiPrptz

Step 2: Synthesis of tris(5-isopropyl-3,4-diphenyl-4H-1,2,4-triazolato)iridium(III) (abbreviation: [Ir(iPrptz)$_3$])

Next, 1.56 g of the ligand HiPrptz that was prepared in Step 1 described above, and 0.58 g of tris(acetylacetonate)iridium(III) were put in a reaction container provided with a three-way cock, and the air in the reaction container was replaced with argon. Then, the mixture was heated at 220° C. for 45 hours to be reacted. The reactant was dissolved in dichloromethane, and the solution was filtrated. The solvent of the resulting filtrate was distilled off and purification was conducted by silica gel column chromatography which uses ethyl acetate as a developing solvent. Further, the solvent of the resulting fraction was distilled off and recrystallization was carried out with a mixed solvent of dichloromethane and ethanol, so that the organometallic complex [Ir(iPrptz)$_3$] which is one embodiment of the present invention was prepared (yellow powder, yield: 41%). The synthetic scheme of Step 2 is shown by (b-8). As described above, the objective compound of Example 9 has a favorable yield.

(b-8)

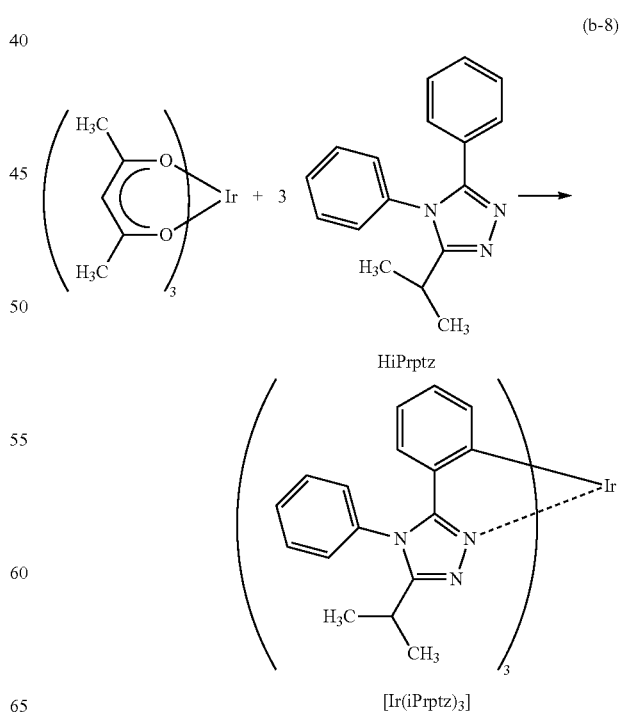

Figure 31:
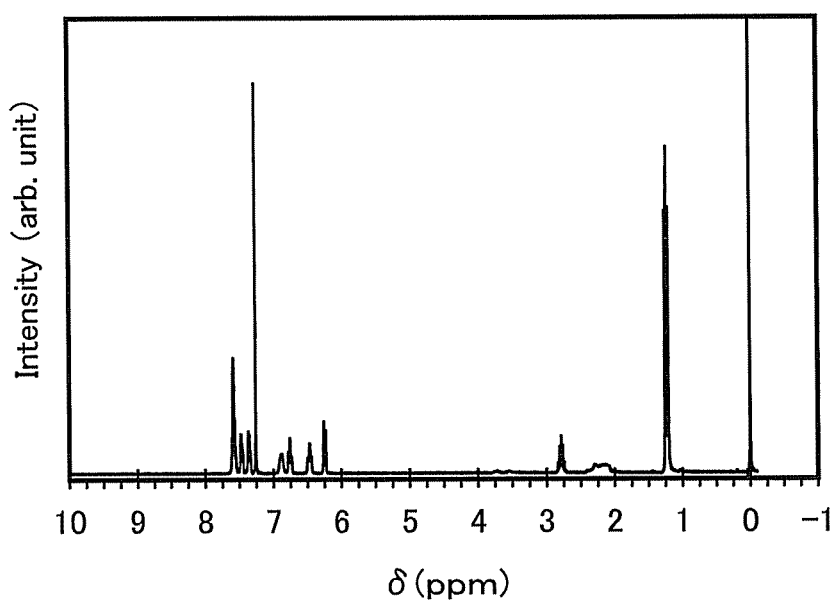
FIG. 31 shows a $^1$H-NMR. chart of [Ir(iPrptz)$_3$].

An analysis result by nuclear magnetic resonance spectroscopy ($^1$H-NMR) of the yellow powder prepared in Step 2 described above is shown below. The $^1$H-NMR chart is shown in FIG. 31. From the results, it is found that the organometallic complex [Ir(iPrptz)$_3$] which is one embodiment of the present invention represented by Structural Formula (102) was prepared in Synthesis Example 6.

$^1$H-NMR. δ(CDCl$_3$): 1.23 (dt, 24H), 2.74-2.83 (m, 3H), 6.25 (d, 3H), 6.47 (t, 3H), 6.78 (t, 3H), 6.87 (br, 3H), 7.34-7.37 (m, 3H), 7.44-7.48 (m, 3H), 7.54-7.61 (m, 9H).

The sublimation temperature of the prepared organometallic complex [Ir(iPrptz)$_3$] which is one embodiment of the present invention was measured with a high vacuum differential type differential thermal balance (TG-DTA2410SA manufactured by Bruker AXS K.K.). The degree of vacuum was $1 \times 10^{-3}$ Pa and the temperature increase rate was 10° C./min, and the temperature of a sample containing [Ir(iPrptz)$_3$] was increased, whereby reduction in weight by 5% was observed at 287° C. From the results, it is found that [Ir(iPrptz)$_3$] has a favorable sublimation property.

Figure 32:
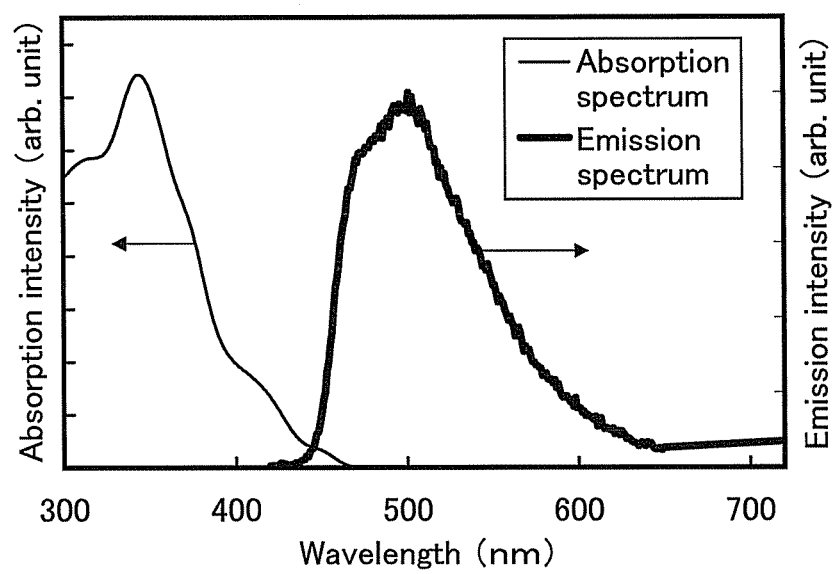
FIG. 32 shows an absorption spectrum and an emission spectrum of [Ir(iPrptz)$_3$] in a dichloromethane solution.

Next, an ultraviolet-visible absorption spectrum (hereinafter, simply referred to as an absorption spectrum) and an emission spectrum of [Ir(iPrptz)$_3$] in a dichloromethane solution were measured. The absorption spectrum was measured with the use of an ultraviolet-visible light spectrophotometer (V550 type manufactured by Japan Spectroscopy Corporation) in the state where the dichloromethane solution (0.097 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.097 mmol/L) was put in a quartz cell at room temperature. FIG. 32 shows measurement results of the absorption spectrum and emission spectrum. The horizontal axis represents wavelength, and the vertical axis represents absorption intensity and emission intensity. In FIG. 32, two solid lines are shown; a thin line represents the absorption spectrum, and a thick line represents the emission spectrum. Note that the absorption spectrum in FIG. 32 is a result obtained by subtraction of the absorption spectrum of only dichloromethane that was put in a quartz cell from the measured absorption spectrum of the dichloromethane solution (0.097 mmol/L) in a quartz cell.

As shown in FIG. 32, the organometallic complex [Ir(iPrptz)$_3$] which is one embodiment of the present invention has a peak of emission at 498 nm, and green light was observed from the dichloromethane solution.

EXAMPLE 10

Synthesis Example 7

In Example 10, a synthesis example of the organometallic complex tris[4-(2,6-dimethylphenyl)-5-ethyl-3-(4-fluorophenyl)-4H-1,2,4-triazolato]iridium(III) (abbreviation: [Ir(EFptz-dmp)$_3$]) which is one embodiment of the present invention represented by Structural Formula (145) in Embodiment 1 is specifically described.

Step 1: Synthesis of 4-(2,6-dimethylphenyl)-3-ethyl-5-(4-fluorophenyl)-4H-1,2,4-triazole (abbreviation: HEFptz-dmp)

First, 1.80 g of ethyl propionate, 10 mL of 1-butanol, and 0.88 g of hydrazine monohydrate (NH$_2$NH$_2$.H$_2$O) were put in a 100 mL three-neck flask, and heated and stirred at 80° C. for 5 hours to be reacted. Then, 5.0 g of N-[(ethylsulfanyl)(4-fluorophenyl)methylidene]-2,6-dimethylaniline was added to this mixed solution, and heated and stirred at 130° C. for 22 hours to be reacted. Further, a solution obtained by heating and stirring 0.90 g of ethyl propionate, 5 mL of 1-butanol, and 0.44 g of hydrazine monohydrate at 80° C. for 3 hours to be reacted was added to the above mixed solution, and the mixed solution was heated and stirred at 130° C. for 8 hours to be reacted. After the reaction, 1-butanol was distilled off under a reduced pressure. The resulting residue was purified by silica gel column chromatography. Ethyl acetate was used as a developing solvent. The resulting fraction was concentrated to give a solid. This solid was recrystallized from a mixed solvent of toluene and hexane, so that 4-(2,6-dimethylphenyl)-3-ethyl-5-(4-fluorophenyl)-4H-1,2,4-triazole (abbreviation: HEFptz-dmp) was prepared (a white solid, yield: 11%). The synthetic scheme of Step 1 is shown by (a-9).

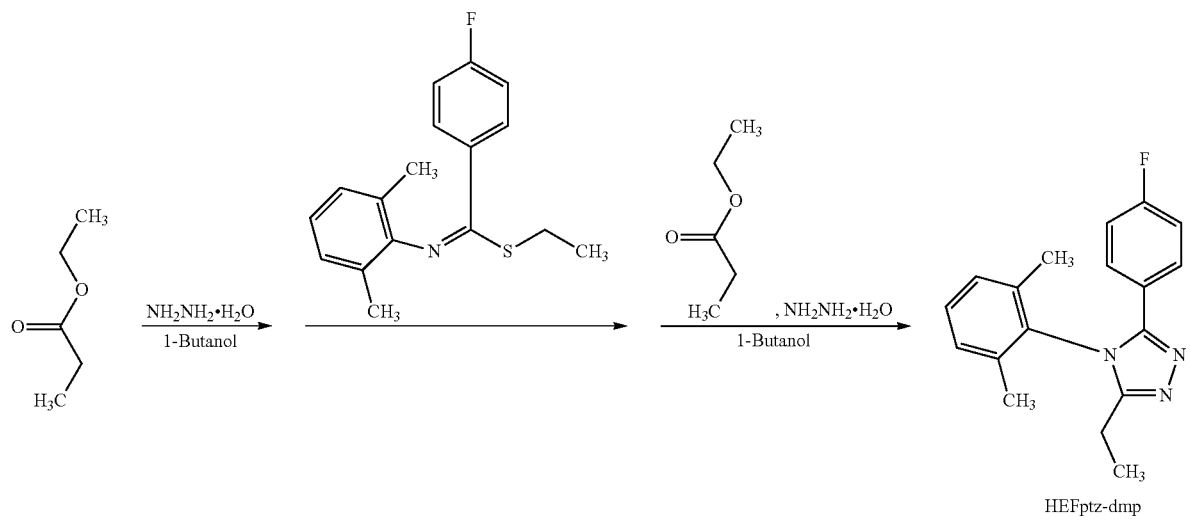

Step 2: Synthesis of tris[4-(2,6-dimethyl-phenyl)-5-ethyl-3-(4-fluorophenyl)-4H-1,2,4-triazolato]iridium (III) (abbreviation: [Ir(EFptz-dmp)$_3$])

Next, 1.35 g of the ligand HEFptz-dmp that was prepared in Step 1 described above, and 0.43 g of tris(acetylacetonate)iridium(III) were put in a reaction container provided with a three-way cock, and the air in the reaction container was replaced with argon. Then, the mixture was heated at 250° C. for 41 hours to be reacted. The reactant was dissolved in dichloromethane, and the solution was filtrated. The solvent of the resulting filtrate was distilled off and purification was conducted by silica gel column chromatography which uses ethyl acetate as a developing solvent. The solvent of the resulting fraction was distilled off, and the residue was dissolved in ethyl acetate, and then subjected to suction filtration through Celite and alumina. The resulting filtrate was concentrated to give a solid. Further, this solid was recrystallized from ethyl acetate, so that the organometallic complex [Ir(EFptz-dmp)$_3$] which is one embodiment of the present invention was prepared (light yellow powder, yield: 5%). The synthetic scheme of Step 2 is shown by (b-9).

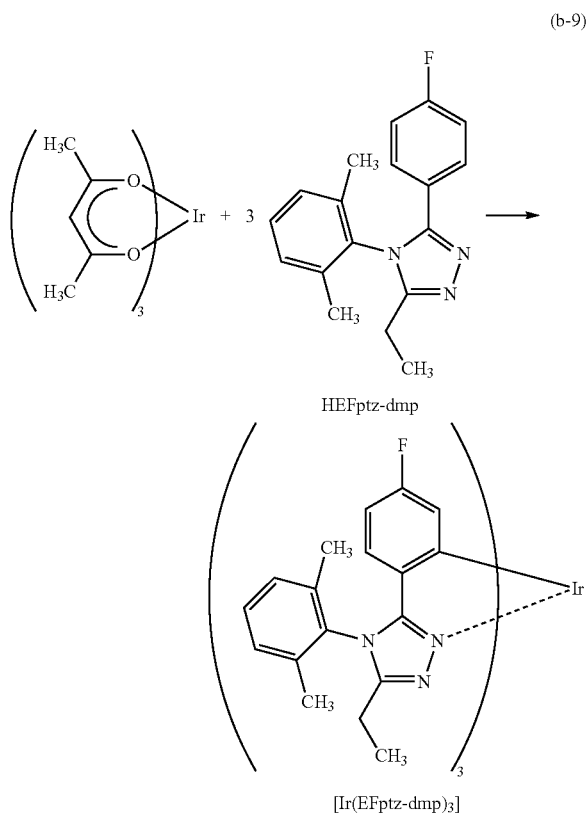

(b-9)

HEFptz-dmp

[Ir(EFptz-dmp)$_3$]

Figure 33:
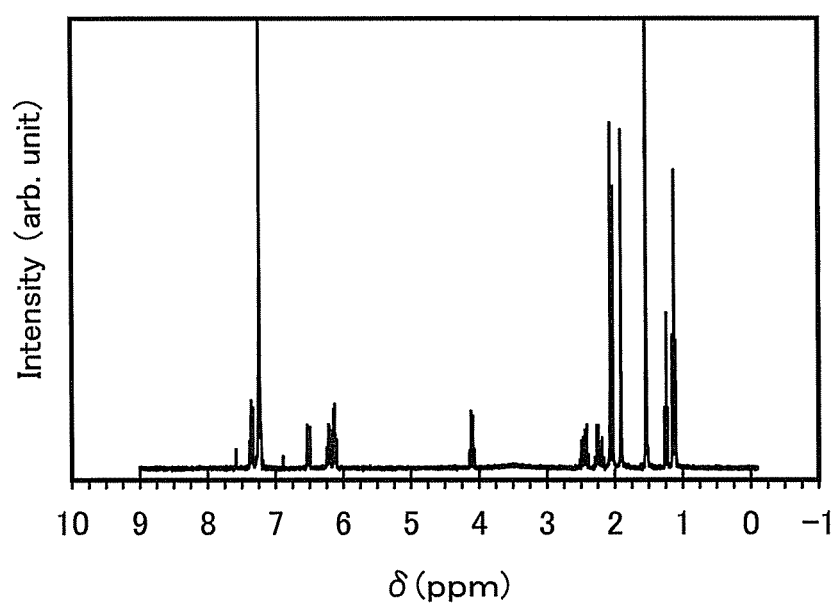
FIG. 33 shows a $^1$H-NMR chart of [Ir(EFptz-dmp)$_3$].

An analysis result by nuclear magnetic resonance spectroscopy ($^1$H-NMR) of the light yellow powder prepared in Step 2 described above is shown below. The $^1$H-NMR chart is shown in FIG. 33. From the results, it is found that the organometallic complex [Ir(EFptz-dmp)$_3$] which is one embodiment of the present invention represented by Structural Formula (145) was prepared in Synthesis Example 7.

$^1$H-NMR. δ(CDCl$_3$): 1.17 (t, 9H), 1.90 (s, 9H), 2.11 (s, 9H), 2.24-2.49 (m, 6H), 6.18-6.28 (m, 6H), 6.46 (dd, 3H), 7.28-7.30 (m, 6H), 7.39-7.44 (m, 3H).

Figure 34:
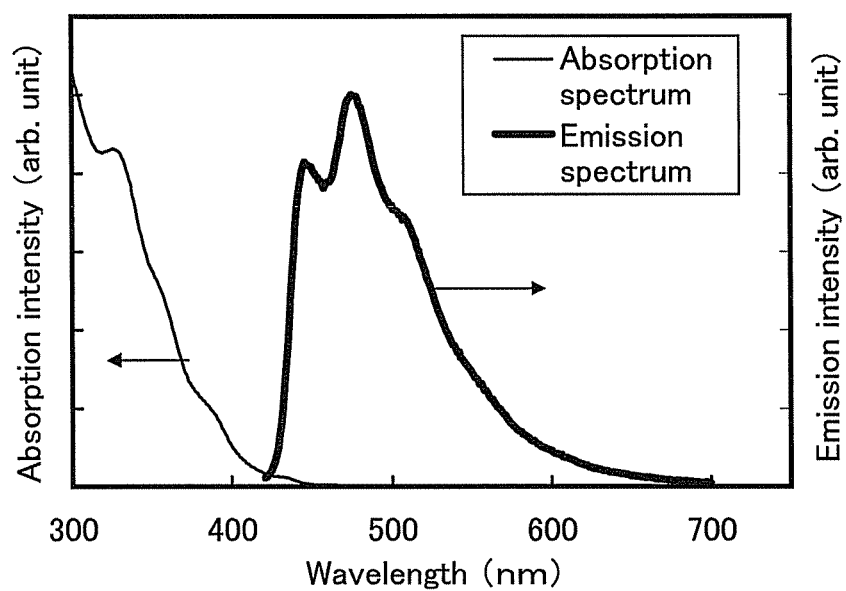
FIG. 34 shows an absorption spectrum and an emission spectrum of [Ir(EFptz-dmp)$_3$] in a dichloromethane solution.

Next, an ultraviolet-visible absorption spectrum (hereinafter, simply referred to as an absorption spectrum) and an emission spectrum of [Ir(EFptz-dmp)$_3$] in a dichloromethane solution were measured. The absorption spectrum was measured with the use of an ultraviolet-visible light spectrophotometer (V550 type manufactured by Japan Spectroscopy Corporation) in the state where the dichloromethane solution (0.0791 mmol/L) was put in a quartz cell at room temperature. The emission spectrum was measured with the use of a fluorescence spectrophotometer (F5920 manufactured by Hamamatsu Photonics Corporation) in the state where the degassed dichloromethane solution (0.0791 mmol/L) was put in a quartz cell at room temperature. FIG. 34 shows measurement results of the absorption spectrum and emission spectrum. The horizontal axis represents wavelength, and the vertical axis represents absorption intensity and emission intensity. In FIG. 34, two solid lines are shown; a thin line represents the absorption spectrum, and a thick line represents the emission spectrum. Note that the absorption spectrum in FIG. 34 is a result obtained by subtraction of the absorption spectrum of only dichloromethane that was put in a quartz cell from the measured absorption spectrum of the dichloromethane solution (0.0791 mmol/L) in a quartz cell.

As shown in FIG. 34, the organometallic complex [Ir(EFptz-dmp)$_3$] which is one embodiment of the present invention has peaks of emission at 446 nm and 476 nm, and blue light was observed from the dichloromethane solution.

EXAMPLE 11

Synthesis Example 8

In Example 11, a synthesis example of the organometallic complex tris[3-(4-fluorophenyl)-5-isopropyl-4-phenyl-4H-1,2,4-triazolato]iridium(III) (abbreviation: [Ir(iPrEptz)$_3$]) which is one embodiment of the present invention represented by Structural Formula (124) in Embodiment 1 is specifically described.

Step 1: Synthesis of N-phenylisobutyramide

First, 26.2 g of aniline, 100 mL of tetrahydrofuran (THF), and 56.9 g of triethylamine (Et$_3$N) were put in a 500 mL three-neck flask, and mixed. Then, under cooling in ice, a mixed solution of 30 g of isobutyryl chloride and 100 mL of THF was dripped through a 50 mL dropping funnel to the above mixed solution, and then the temperature was increased to room temperature and the solution was stirred for 19 hours to be reacted. After the reaction, this mixture was subjected to suction filtration to give a filtrate. The resulting filtrate was washed with water, and then saturated saline, and anhydrate magnesium sulfate was added for drying. After the drying, the mixture was subjected to gravity filtration, and the filtrate was concentrated, so that N-phenylisobutyramide was prepared (a white solid, yield: 91%). The synthetic scheme of Step 1 is shown by (a-10).

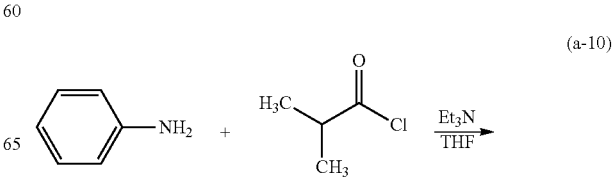

(a-10)

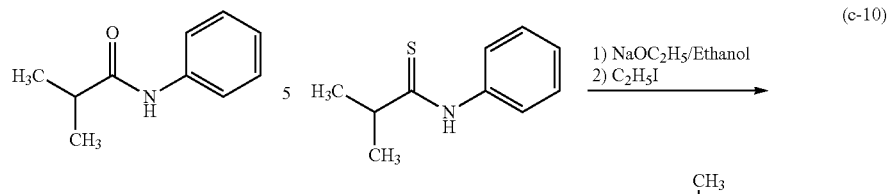

Step 2: Synthesis of N-phenylisobutyrthioamide

Next, 15.0 g of N-phenylisobutyramide that was prepared in Step 1 described above and 120 mL of toluene were put in a 500 mL three-neck flask, 18.6 g of 2,4-bis(4-methoxyphenyl)-1,3,2,4-dithiadiphosphetane-2,4-disulfide (Lawesson's reagent) was added to this mixture, and the mixture was heated at 120° C. for 10 hours to be reacted. After the reaction, the solution was concentrated to give an oily substance. This oily substance was purified by silica gel column chromatography. Toluene was used as a developing solvent. The resulting fraction was concentrated to give an oily substance. Ethanol was added to this oily substance, whereby a solid was precipitated. The resulting mixture was subjected to suction filtration and the filtrate was concentrated, so that N-phenylisobutyrthioamide was prepared (a yellow oily substance, yield: 99%). The synthetic scheme of Step 2 is shown by (b-10).

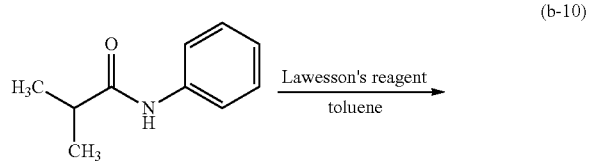

Step 3: Synthesis of N-[1-(ethylsulfanyl)isobutylidene]aniline

Next, 6.19 g of sodium ethoxide and 16.3 g of N-phenylisobutyrthioamide that was prepared in Step 2 described above were put in a 200 mL three-neck flask, 50 mL of ethanol was added, and the mixture was stirred at room temperature for 1 hour to be reacted. After the reaction, 7.2 mL of iodoethane was added to this mixture, and heated and stirred at 60° C. for 4 hours to be further reacted. After the reaction, ethanol was distilled off under a reduced pressure to give a brown oily substance. This oily substance was dissolved in dichloromethane, and washed with water and then a saturated aqueous solution of sodium hydrogen carbonate. After the washing, anhydrate magnesium sulfate was added into the resulting organic layer for drying. This mixture was subjected to gravity filtration, and the resulting filtrate was concentrated, so that N-[1-(ethylsulfanyl)isobutylidene]aniline was prepared (a brown oily substance, yield: 88%). The synthetic scheme of Step 3 is shown by (c-10).

Step 4: Synthesis of 3-(4-fluorophenyl)-5-isopropyl-4-phenyl-4H-1,2,4-triazole (abbreviation: HiPrFptz)

Next, 10.0 g of N-[1-(ethylsulfanyl)isobutylidene]aniline that was prepared in Step 3 described above, 5.0 g of 4-fluorobenzoylhydrazine, and 20 mL of 1-butanol were put in a 100 mL three-neck flask, and heated and stirred at 130° C. for 6 hours to be reacted. After the reaction, the solution was concentrated to give a solid. This solid was purified by silica gel column chromatography. A mixed solvent of toluene:ethyl acetate=3:2 was used as a developing solvent. The resulting fraction was concentrated to give a solid. This solid was recrystallized from a mixed solvent of toluene and hexane, so that 3-(4-fluorophenyl)-5-isopropyl-4-phenyl-4H-1,2,4-triazole (abbreviation: HiPrFptz) was prepared (a white solid, yield: 32%). The synthetic scheme of Step 4 is shown by (d-10).

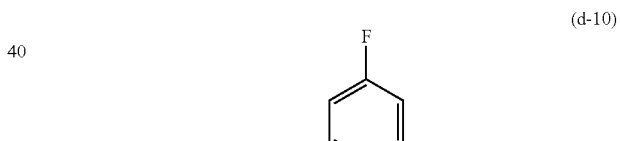

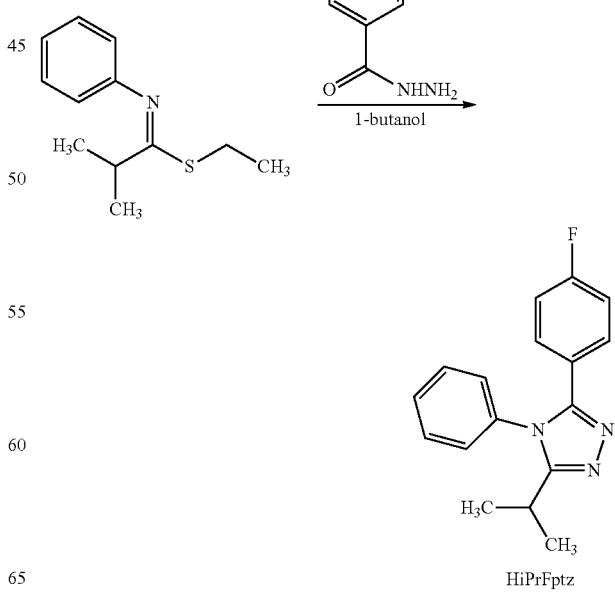

Step 5: Synthesis of tris[3-(4-fluorophenyl)-5-isopropyl-4-phenyl-4H-1,2,4-triazolato]iridium(III) (abbreviation: [Ir(iPrFptz)₃])

Next, 4.35 g of the ligand HiPrFptz that was prepared in Step 4 described above, and 1.52 g of tris(acetylacetonate)iridium(III) were put in a reaction container provided with a three-way cock, and the air in the reaction container was replaced with argon. Then, the mixture was heated at 250° C. for 44 hours to be reacted. The reactant was dissolved in dichloromethane, and the solution was filtrated. The solvent of the resulting filtrate was distilled off and purification was conducted by silica gel column chromatography which uses ethyl acetate as a developing solvent. Further, the solvent of the resulting fraction was distilled off and the residue was washed with methanol and then hexane, so that the organometallic complex [Ir(iPrFptz)₃] which is one embodiment of the present invention was prepared (light yellow powder, yield: 63%). The synthetic scheme of Step 5 is shown by (e-10). As described above, the objective compound of Example 11 has a favorable yield.

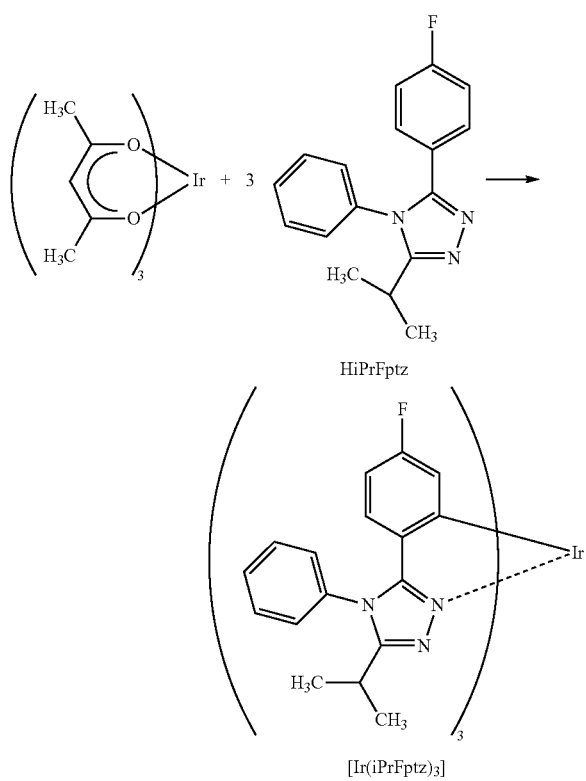

(e-10)

Figure 35:
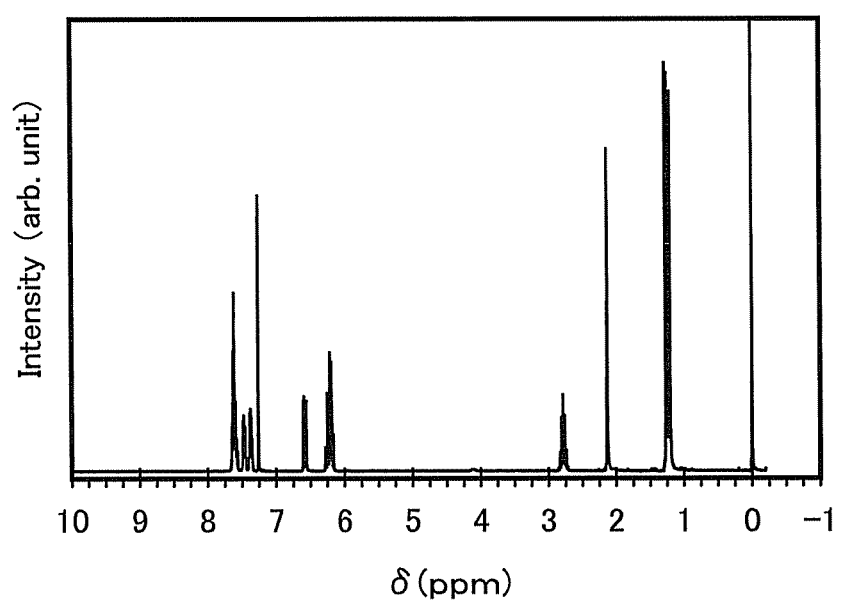
FIG. 35 shows a $^1$H-NMR chart of [Ir(iPrFptz)$_3$].

An analysis result by nuclear magnetic resonance spectroscopy (¹H-NMR) of the light yellow powder prepared in Step 5 described above is shown below. The ¹H-NMR chart is shown in FIG. 35. From the results, it is found that the organometallic complex [Ir(iPrFptz)₃] which is one embodiment of the present invention represented by Structural Formula (124) was prepared in Synthesis Example 8.

¹H-NMR. δ(CDCl₃): 1.21 (d, 9H), 1.25 (d, 9H), 2.78 (sep, 3H), 6.16-6.28 (m, 4H), 6.58 (dd, 3H), 7.38 (m, 3H), 7.47 (m, 3H), 7.56-7.65 (m, 9H).

Figure 36:
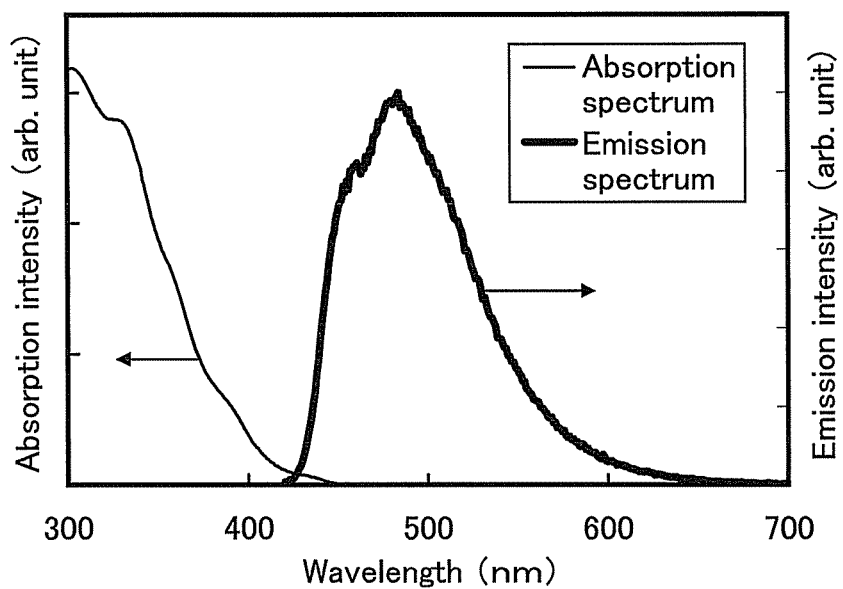
FIG. 36 shows an absorption spectrum and an emission spectrum of [Ir(iPrFptz)$_3$] in a dichloromethane solution.

Next, an ultraviolet-visible absorption spectrum (hereinafter, simply referred to as an absorption spectrum) and an emission spectrum of [Ir(iPrFptz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.0513 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.308 mmol/L) was put in a quartz cell at room temperature. FIG. 36 shows measurement results of the absorption spectrum and emission spectrum. The horizontal axis represents wavelength, and the vertical axis represents absorption intensity and emission intensity. In FIG. 36, two solid lines are shown; a thin line represents the absorption spectrum, and a thick line represents the emission spectrum. Note that the absorption spectrum in FIG. 36 is a result obtained by subtraction of the absorption spectrum of only dichloromethane that was put in a quartz cell from the measured absorption spectrum of the dichloromethane solution (0.0513 mmol/L) in a quartz cell.

As shown in FIG. 36, the organometallic complex [Ir(iPrFptz)₃] which is one embodiment of the present invention has a peak of emission at 485 nm, and light-blue light was observed from the dichloromethane solution.

EXAMPLE 12

Synthesis Example 9

In Example 12, a synthesis example of the organometallic complex tris[4-(2,6-dimethylphenyl)-3-(4-fluorophenyl)-5-isopropyl-4H-1,2,4-triazolato]iridium(III) (abbreviation: [Ir(iPrFptz-dmp)₃]) which is one embodiment of the present invention represented by Structural Formula (125) in Embodiment 1 is specifically described.

Step 1: Synthesis of 4-(2,6-dimethylphenyl)-3-(4-fluorophenyl)-5-isopropyl-4H-1,2,4-triazole (abbreviation: HiPrFptz-dmp)

First, 2.40 g of ethyl isobutyrate, 10 mL of 1-butanol, and 1.05 g of hydrazine monohydrate (NH₂NH₂.H₂O) were put in a 100 nil, three-neck flask, and heated and stirred at 80° C. for 5 hours to be reacted. Then, 5.0 g of N-[(ethylsulfanyl)(4-fluorophenyl)methylidene]-2,6-dimethylaniline was added to this mixed solution, and heated and stirred at 130° C. for 22 hours to be reacted. Further, 0.96 g of isobutyric acid hydrazide was added to this mixed solution, and heated and stirred at 130° C. for 15 hours to be reacted. After the reaction, 1-butanol was distilled off under a reduced pressure. The resulting residue was purified by silica gel column chromatography. Ethyl acetate was used as a developing solvent. The resulting fraction was concentrated to give a solid. This solid was recrystallized from a mixed solvent of toluene and hexane, so that 4-(2,6-dimethyl-phenyl)-3-(4-fluorophenyl)-5-isopropyl-4H-1,2,4-triazole (abbreviation: HiPrFptz-dmp) was prepared (a white solid, yield: 11%). The synthetic scheme of Step 1 is shown by (a-11).

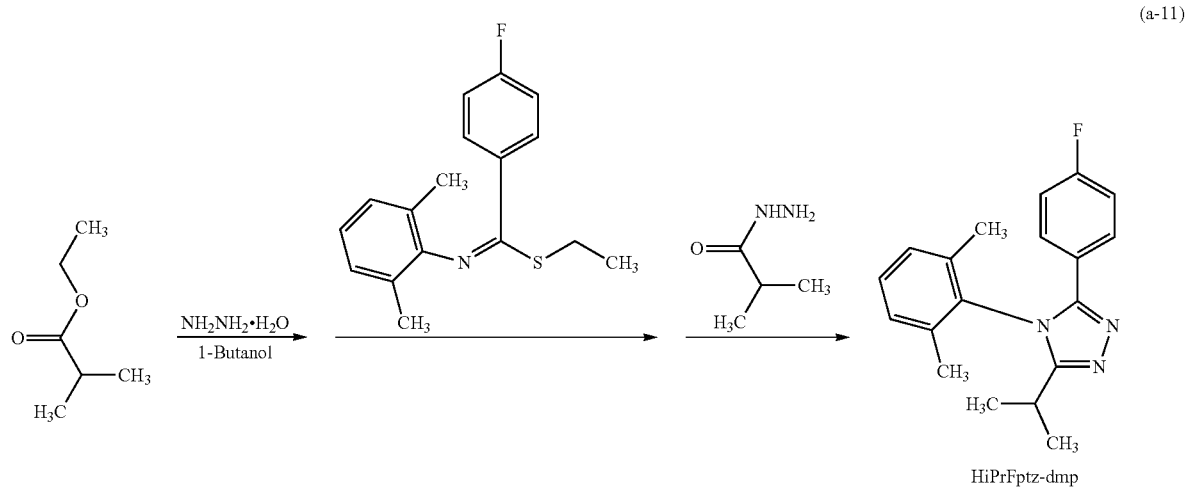

(a-11)

Step 2: Synthesis of tris[4-(2,6-dimethylphenyl)-3-(4-fluorophenyl)-5-isopropyl-4H-1,2,4-triazolato]iridium(III) (abbreviation: [Ir(iPrFptz-dmp)$_3$])

Next, 1.35 g of the ligand HiPrFptz-dmp that was prepared in Step 1 described above, and 0.43 g of tris(acetylacetonate) iridium(III) were put in a reaction container provided with a three-way cock, and the air in the reaction container was replaced with argon. Then, the mixture was heated at 250° C. for 44 hours to be reacted. The reactant was dissolved in dichloromethane, and the solution was filtrated. The solvent of the resulting filtrate was distilled off and purification was conducted by silica gel column chromatography which uses dichloromethane as a developing solvent. Further, the solvent of the resulting fraction was distilled off and the residue was recrystallized from ethyl acetate, so that the organometallic complex [Ir(iPrFptz-dmp)$_3$] which is one embodiment of the present invention was prepared (light yellow powder, yield: 39%). The synthetic scheme of Step 2 is shown by (b-11). As described above, the objective compound of Example 12 has a favorable yield.

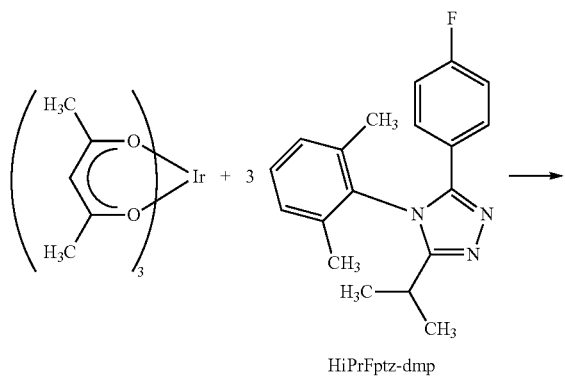

(b-11)

HiPrFptz-dmp

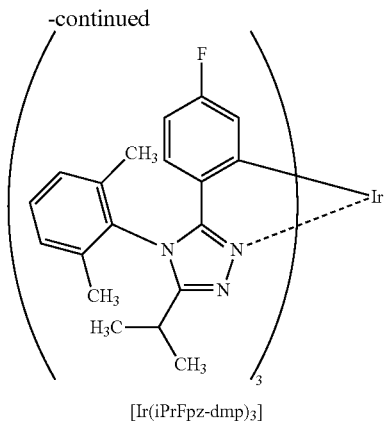

[Ir(iPrFpz-dmp)$_3$]

Figure 37:
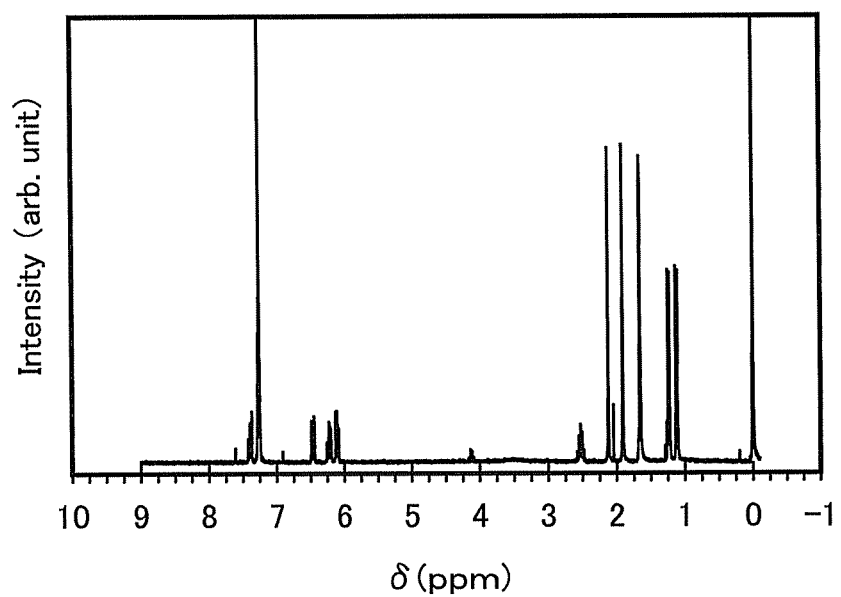
FIG. 37 shows a $^1$H-NMR chart of [Ir(iPrFptz-dmp)$_3$].

An analysis result by nuclear magnetic resonance spectroscopy ($^1$H-NMR) of the light yellow powder prepared in Step 2 described above is shown below. The $^1$H-NMR chart is shown in FIG. 37. From the results, it is found that the organometallic complex [Ir(iPrFptz-dmp)$_3$] which is one embodiment of the present invention represented by Structural Formula (125) was prepared in Synthesis Example 9.

$^1$H-NMR. δ(CDCl$_3$): 1.12 (d, 9H), 1.28 (d, 9H), 1.89 (s, 9H), 2.13 (s, 9H), 2.51-2.60 (m, 3H), 6.14-6.27 (m, 6H), 6.36 (dd, 3H), 7.28-7.31 (m, 6H), 7.40-7.45 (m, 3H).

Figure 38:
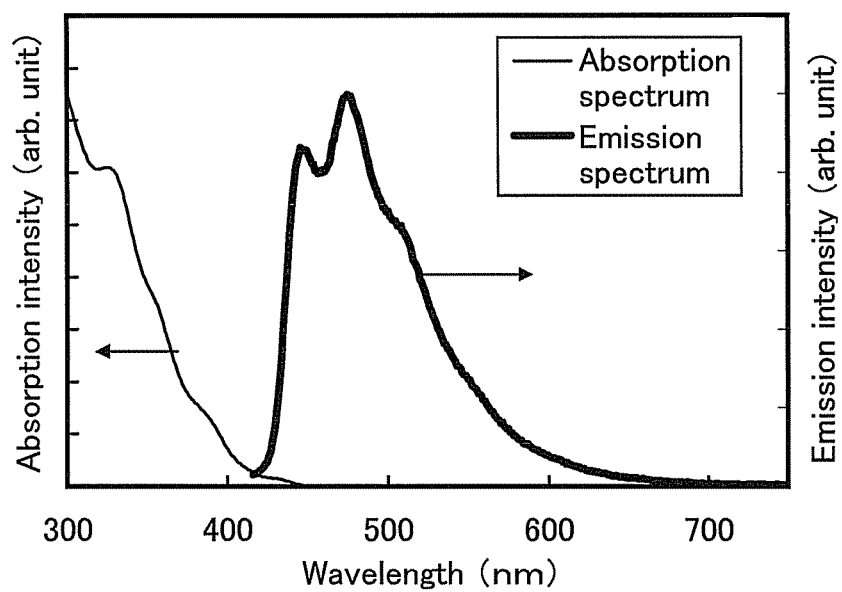
FIG. 38 shows an absorption spectrum and an emission spectrum of [Ir(iPrFptz-dmp)$_3$] in a dichloromethane solution.

Next, an ultraviolet-visible absorption spectrum (hereinafter, simply referred to as an absorption spectrum) and an emission spectrum of [Ir(iPrFptz-dmp)$_3$] in a dichloromethane solution were measured. The absorption spectrum was measured with the use of an ultraviolet-visible light spectrophotometer (V550 type manufactured by Japan Spectroscopy Corporation) in the state where the dichloromethane solution (0.0738 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.0738 mmol/L) was put in a quartz cell at room temperature. FIG. 38 shows measurement results of the absorption spectrum and emission spectrum. The horizontal axis represents wavelength, and the vertical axis represents absorption intensity and emission intensity. In FIG. 38, two solid lines are shown; a thin line

EXAMPLE 13

Synthesis Example 10

In Example 13, a synthesis example of the organometallic complex tris[5-methyl-3-(2-naphthyl)-4-phenyl-4H-1,2,4-triazolato]iridium(III) (abbreviation: [Ir(Mntz)₃]) which is one embodiment of the present invention represented by Structural Formula (138) in Embodiment 1 is specifically described.

Step 1: Synthesis of 2-naphthohydrazide

First, 5.0 g of methyl 2-naphthoate and 20 mL of ethanol were put in a four-neck flask, and stirred. Then, 5 mL of hydrazine monohydrate (NH₂NH₂.H₂O) was added to this mixture, and heated and stirred at 80° C. for 5 hours to be reacted. After the reaction, the solution was added to 100 mL of water, whereby a solid was precipitated. The resulting suspension was subjected to suction filtration to give a solid. This solid was recrystallized from a mixed solvent of chloroform and hexane, so that 4.4 g of 2-naphthohydrazide was prepared as a white solid with a yield of 88%. The synthetic scheme of Step 1 is shown by (a-12).

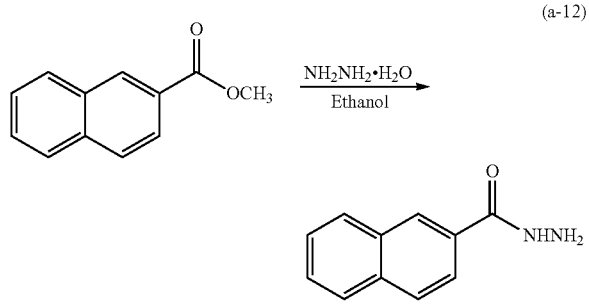

(a-12)

Step 2: Synthesis of 3-methyl-5-(2-naphthyl)-4-phenyl-4H-1,2,4-triazole (abbreviation: HMntz)

Next, 4.0 g of N-[1-(ethylsulfanyl)ethylidene]aniline, 4.1 g of 2-naphthohydrazide that was prepared in Step 1 described above, and 60 mL of 1-butanol were put in a 100 mL three-neck flask, and heated and stirred at 120° C. for 15 hours to be reacted. After the reaction, 1-butanol was distilled off to give a brown oily substance. This oily substance was purified by silica gel column chromatography which uses ethyl acetate as a developing solvent, so that 1.3 g of 3-methyl-5-(2-naphthyl)-4-phenyl-4H-1,2,4-triazole (abbreviation: HMntz) was prepared as a white solid with a yield of 21%. The synthetic scheme of Step 2 is shown by (b-12).

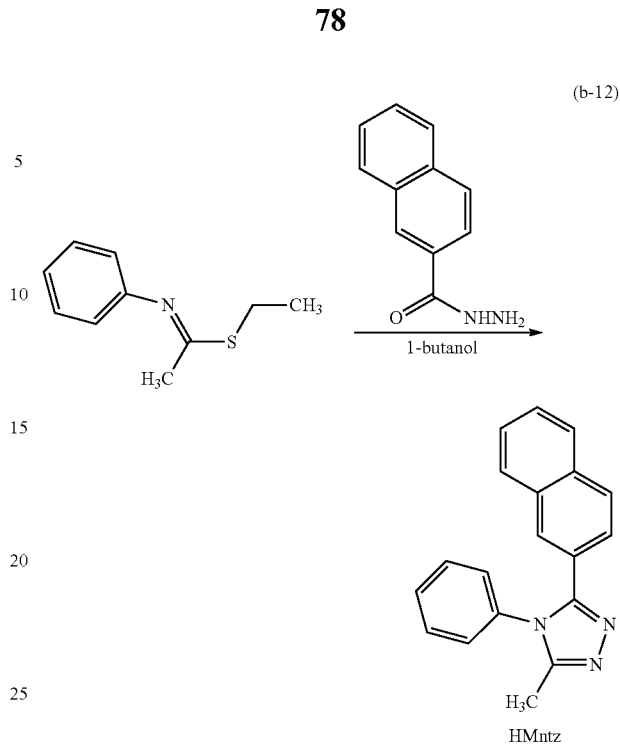

(b-12)

Step 3: Synthesis of tris[5-methyl-3-(2-naphthyl)-4-phenyl-4H-1,2,4-triazolato]iridium(III) (abbreviation [Ir(Mntz)₃])

Next, 1.35 g of the ligand HMntz that was prepared in Step 2 described above, and 0.46 g of tris(acetylacetonate)iridium (III) were put in a reaction container provided with a three-way cock, and the air in the reaction container was replaced with argon. Then, the mixture was heated at 245° C. for 45 hours to be reacted. After the reactant was washed with dichloromethane, it was extracted from an acetone solvent with the use of a Soxhlet extractor. The extract was concentrated and dried to give a residue. The residue was recrystallized from a mixed solvent of dichloromethane and methanol, so that the organometallic complex [Ir(Mntz)₃] which is one embodiment of the present invention was prepared (ocher powder, yield: 9%). The synthetic scheme of Step 3 is shown by (c-12).

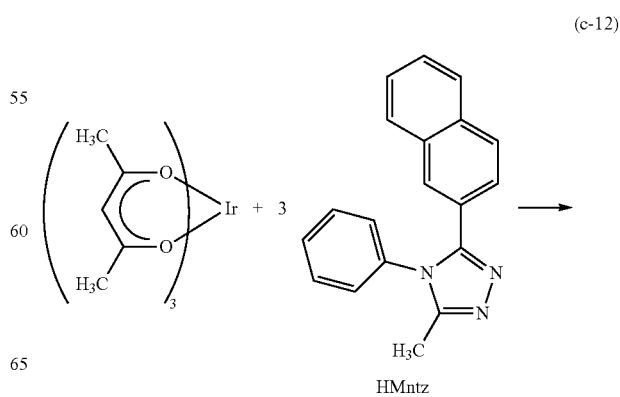

(c-12)

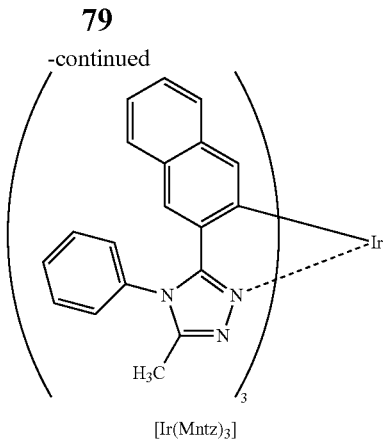

[Ir(Mntz)₃]

Figure 39:
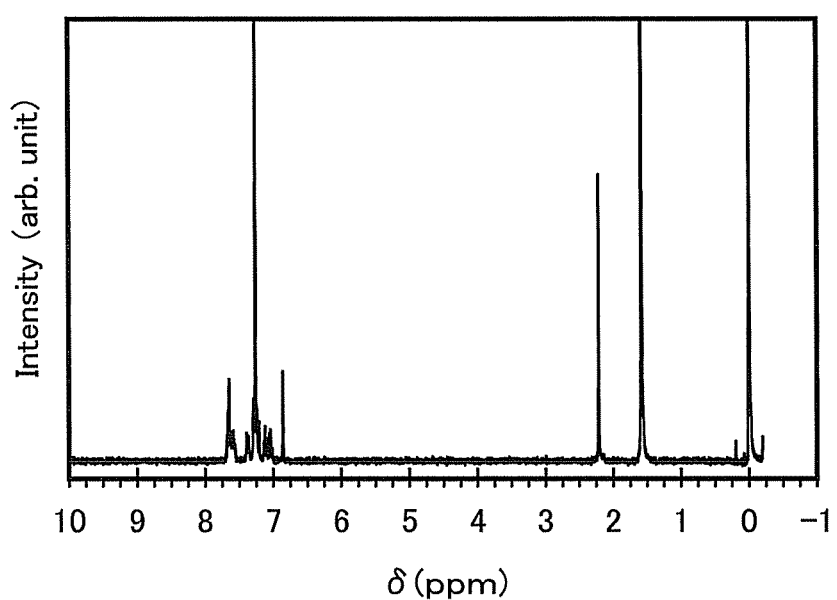
FIG. 39 shows a $^1$H-NMR chart of [Ir(Mntz)$_3$].

An analysis result by nuclear magnetic resonance spectroscopy (¹H-NMR) of the ocher powder prepared in Step 3 described above is shown below. The ¹H-NMR chart is shown in FIG. 39. From the results, it is found that the organometallic complex [Ir(Mntz)₃] which is one embodiment of the present invention represented by Structural Formula (138) was prepared in Synthesis Example 10.

¹H-NMR. δ(CDCl₃): 2.21 (s, 9H), 6.86 (s, 3H), 7.04 (t, 3H), 7.12 (dt, 3H), 7.21-7.29 (m, 9H), 7.38 (d, 3H), 7.58-7.68 (m, 12H).

Figure 40:
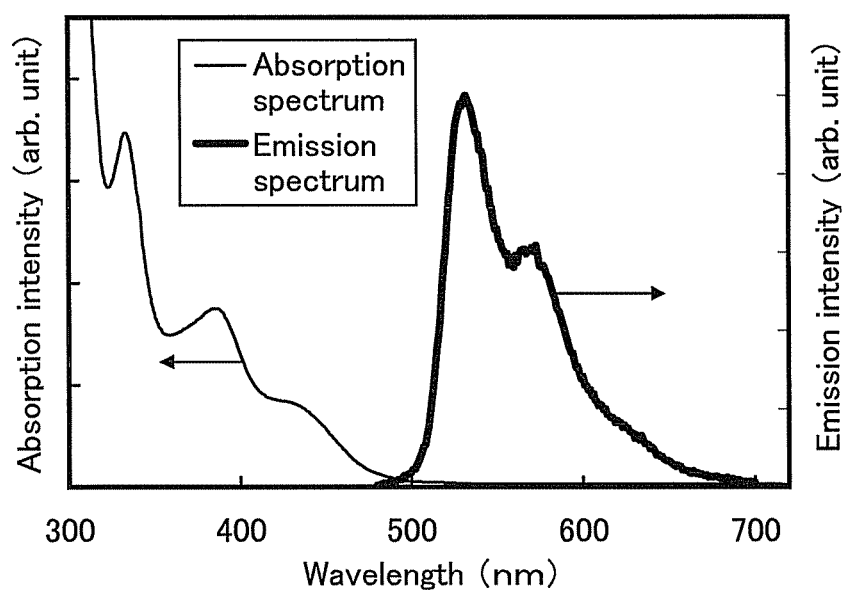
FIG. 40 shows an absorption spectrum and an emission spectrum of [Ir(Mntz)₃] in a dichloromethane solution.

Next, an ultraviolet-visible absorption spectrum (hereinafter, simply referred to as an absorption spectrum) and an emission spectrum of [Ir(Mntz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.0644 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.387 mmol/L) was put in a quartz cell at room temperature. FIG. 40 shows measurement results of the absorption spectrum and emission spectrum. The horizontal axis represents wavelength, and the vertical axis represents absorption intensity and emission intensity. In FIG. 40, two solid lines are shown; a thin line represents the absorption spectrum, and a thick line represents the emission spectrum. Note that the absorption spectrum in FIG. 40 is a result obtained by subtraction of the absorption spectrum of only dichloromethane that was put in a quartz cell from the measured absorption spectrum of the dichloromethane solution (0.0644 mmol/L) in a quartz cell.

As shown in FIG. 40, the organometallic complex [Ir(Mntz)₃] which is one embodiment of the present invention has peaks of emission at 532 nm and 573 nm, and yellow-green light was observed from the dichloromethane solution.

EXAMPLE 14

Synthesis Example 11

In Example 14, a synthesis example of the organometallic complex tris[5-isopropyl-3-(2-naphthyl)-4-phenyl-4H-1,2,4-triazolato]iridium(III) (abbreviation: [Ir(iPrntz)₃]) which is one embodiment of the present invention represented by Structural Formula (150) in Embodiment 1 is specifically described.

Step 1: Synthesis of 3-isopropyl-5-(2-naphthyl)-4-phenyl-4H-1,2,4-triazole (abbreviation: HiPrntz)

First, 5.7 g of N-[1-(ethylsulfanyl)isobutylidene]aniline, 4.4 g of 2-naphthohydrazide, and 40 mL of 1-butanol were put in a 100 mL three-neck flask, and heated and stirred at 120° C. for 20 hours to be reacted. After the reaction, 1-butanol was distilled off to give a brown oily substance. Toluene was added to this oily substance, whereby a solid was precipitated, and then filtrated to give the solid. The resulting solid was recrystallized from toluene, so that 2.7 g of 3-isopropyl-5-(2-naphthyl)-4-phenyl-4H-1,2,4-triazole (abbreviation: HiPrntz) was prepared as a white solid with a yield of 37%. The synthetic scheme of Step 1 is shown by (a-13). As described above, the objective compound of Example 14 has a favorable yield.

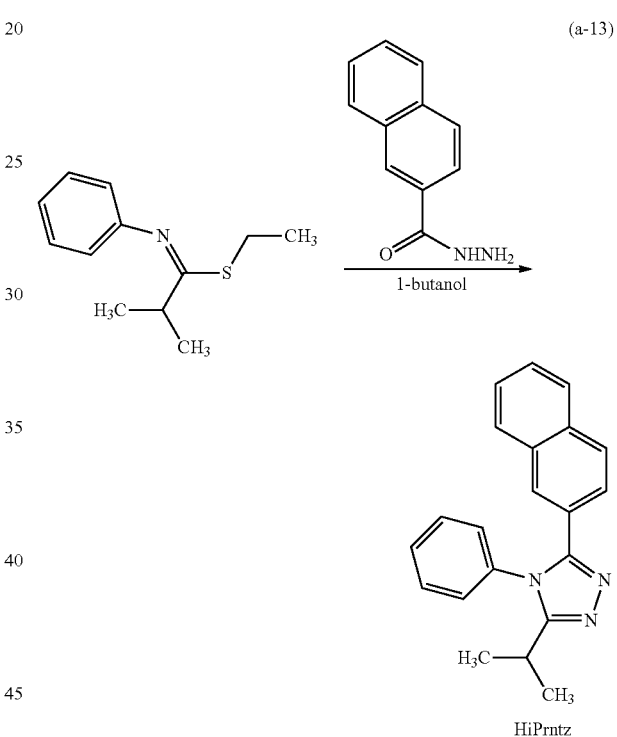

(a-13)

HiPrntz

Step 2: Synthesis of tris[5-isopropyl-3-(2-naphthyl)-4-phenyl-4H-1,2,4-triazolato]iridium(III) (abbreviation [Ir(iPrntz)₃])

Next, 1.56 g of the ligand HiPrntz that was prepared in Step 1 described above, and 0.49 g of tris(acetylacetonate)iridium (III) were put in a reaction container provided with a three-way cock, and the air in the reaction container was replaced with argon. Then, the mixture was heated at 250° C. for 47 hours to be reacted. The reactant was dissolved in dichloromethane, and then filtrated. The resulting filtrate was concentrated and dried, and purified twice by silica gel column chromatography which uses ethyl acetate as a developing solvent, so that the organometallic complex [Ir(iPrntz)₃] which is one embodiment of the present invention was prepared (yellow powder, yield: 23%). The synthetic scheme of Step 2 is shown by (b-13).

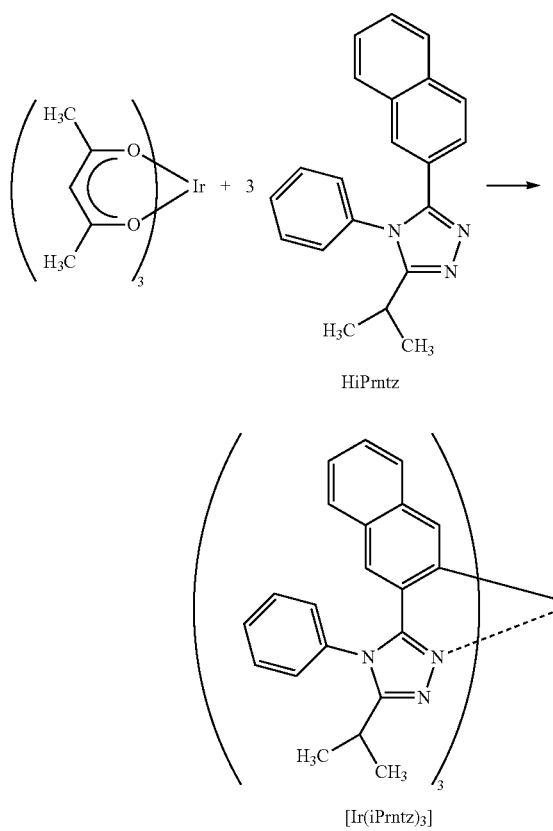

HiPrntz

[Ir(iPrntz)₃]

Figure 41:
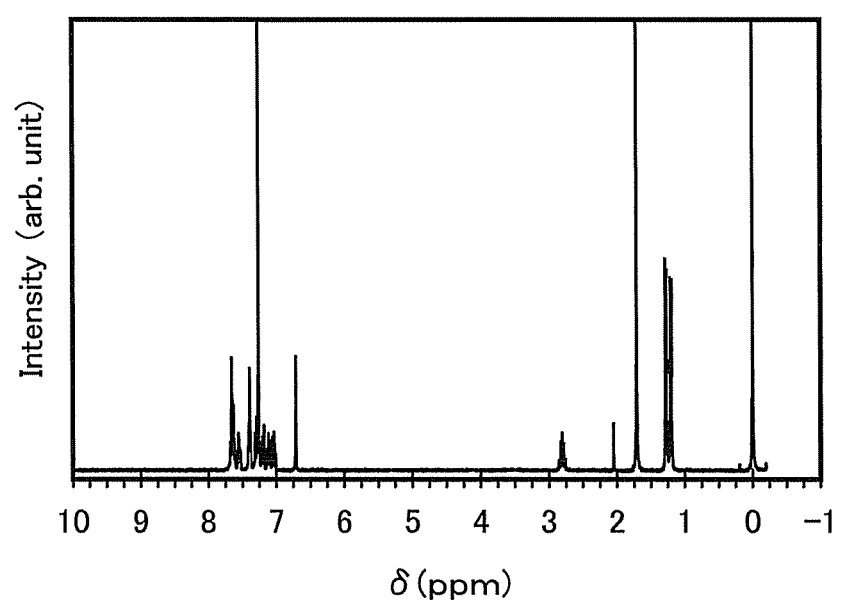
FIG. 41 shows a ¹H-NMR chart of [Ir(iPrntz)₃].

An analysis result by nuclear magnetic resonance spectroscopy (¹H-NMR) of the yellow powder prepared in Step 2 described above is shown below. The ¹H-NMR chart is shown in FIG. 41. From the results, it is found that the organometallic complex [Ir(iPrntz)₃] which is one embodiment of the present invention represented by Structural Formula (150) was prepared in Synthesis Example 11.

¹H-NMR. δ(CDCl₃): 1.20 (d, 9H), 1.28 (d, 9H), 2.81 (sep, 3H), 6.71 (s, 3H), 7.03 (t, 3H), 7.11 (dt, 3H), 7.19 (d, 3H), 7.30 (d, 3H), 7.39 (m, 6H), 7.56 (m, 3H), 7.61-7.68 (m, 9H).

Figure 42:
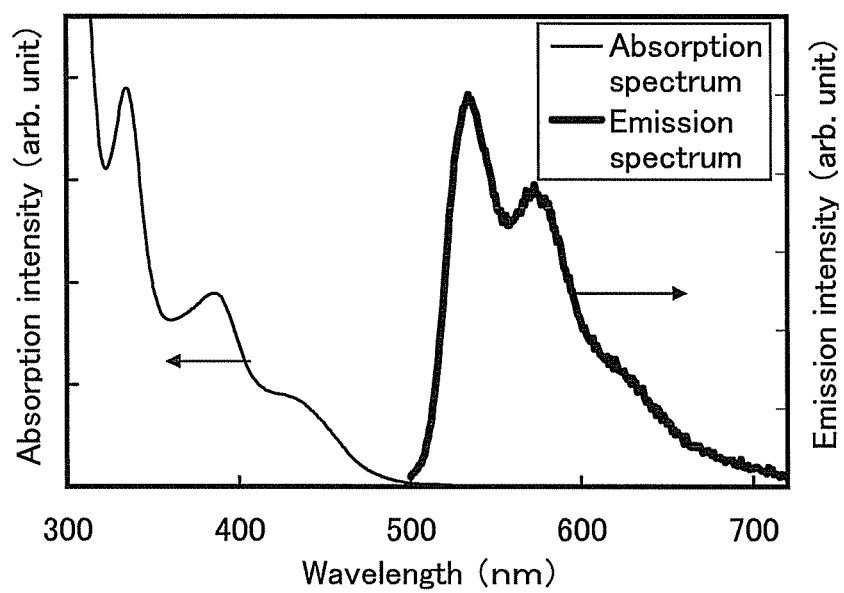
FIG. 42 shows an absorption spectrum and an emission spectrum of [Ir(iPrntz)₃] in a dichloromethane solution.

Next, an ultraviolet-visible absorption spectrum (hereinafter, simply referred to as an absorption spectrum) and an emission spectrum of [Ir(iPrntz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.0874 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.495 mmol/L) was put in a quartz cell at room temperature. FIG. 42 shows measurement results of the absorption spectrum and emission spectrum. The horizontal axis represents wavelength, and the vertical axis represents absorption intensity and emission intensity. In FIG. 42, two solid lines are shown; a thin line represents the absorption spectrum, and a thick line represents the emission spectrum. Note that the absorption spectrum in FIG. 42 is a result obtained by subtraction of the absorption spectrum of only dichloromethane that was put in a quartz cell from the measured absorption spectrum of the dichloromethane solution (0.0874 mmol/L) in a quartz cell.

As shown in FIG. 42, the organometallic complex [Ir(iPrntz)₃] which is one embodiment of the present invention has peaks of emission at 535 nm and 575 nm, and yellow-green light was observed from the dichloromethane solution.

Comparative Example 3

In Comparative Example 3, a synthesis example of tris[4-(2,6-dimethylphenyl)-3-(4-fluorophenyl)-4H-1,2,4-triazolato]iridium(III) (abbreviation: [Ir(Fptz-dmp)₃]) represented by the following structural formula is specifically described.

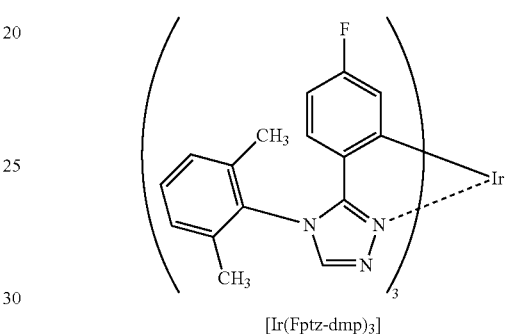

[Ir(Fptz-dmp)₃]

Step 1: Synthesis of N-(2,6-dimethylphenyl)-4-fluorobenzamide

First, 18.7 g of dimethylaniline, 15.6 g of triethylamine, and 150 mL of tetrahydrofuran (THF) were put in a 500 mL three-neck flask, and stirred to be mixed. This mixed solution was cooled in ice, and a mixed solution of 24.6 g of 4-fluorobenzoyl chloride and 50 mL of THF was dripped to be mixed. The temperature of the reaction solution was increased to room temperature, and the solution was stirred at room temperature for 2 hours to be reacted. After the reaction, this mixture was dissolved in chloroform, and washed with water and then a saturated aqueous solution of sodium hydrogen carbonate. After the washing, anhydride magnesium sulfate was added to the resulting organic layer for drying. After the drying, the mixture was subjected to gravity filtration, and the filtrate was concentrated to give a solid. This solid was washed with hexane, so that 38 g of N-(2,6-dimethylphenyl)-4-fluorobenzamide was prepared as a white solid with a yield of 100%. The synthetic scheme of Step 1 is shown by (a-14).

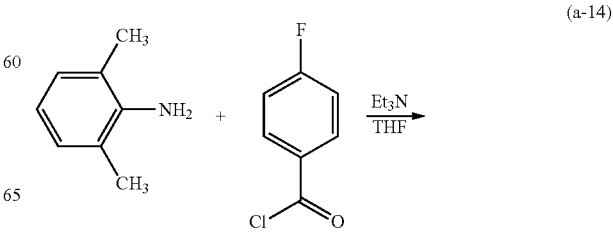

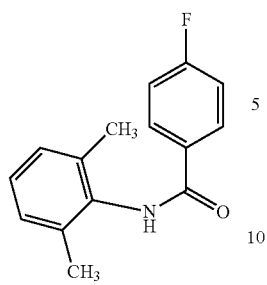

Step 2: Synthesis of N-(2,6-dimethylphenyl)-4-fluorobenzthioamide

Next, 38 g of N-(2,6-dimethylphenyl)-4-fluorobenzamide that was prepared in Step 1 described above and 150 mL of toluene were put in a 500 mL three-neck flask, 30 g of 2,4-bis(4-methoxyphenyl)-1,3,2,4-dithiadiphosphetane-2,4-disulfide (Lawesson's reagent) was added to this mixture, and the mixture was heated and stirred at 130° C. for 3 hours to be reacted. After the reaction, the solution was concentrated, whereby a yellow solid was precipitated. The resulting suspension was subjected to suction filtration, and the resulting solid was washed with toluene, so that 29 g of N-(2,6-dimethylphenyl)-4-fluorobenzthioamide was prepared as a yellow solid with a yield of 72%. The synthetic scheme of Step 2 is shown by (b-14).

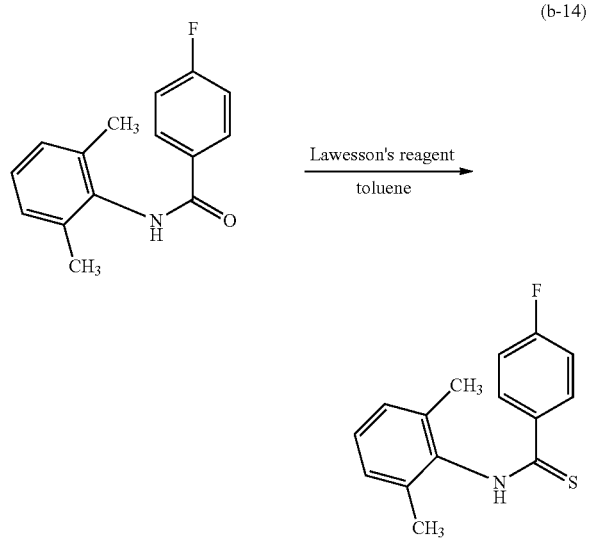

(b-14)

Step 3: Synthesis of N-[(ethylsulfanyl)(4-fluorophenyl)methylidene]-2,6-dimethylaniline Next, 4.0 g of sodium ethoxide and 1.6 g of N-(2,6-dimethylphenyl)-4-fluorobenzthioamide that was prepared in Step 2 described above were put in a 200 mL three-neck flask. Then, 50 mL of ethanol was added to this mixture, and was stirred at room temperature for 1 hour to be reacted. Then, 1.0 mL of iodoethane was added to this mixture, and heated and stirred at 60° C. for 5 hours to be reacted. After the reaction, ethanol was distilled of to give a brown oily substance. This oily substance was dissolved in dichloromethane, and washed with water and then a saturated aqueous solution of sodium hydrogen carbonate. After the washing, anhydrous magnesium sulfate was added to the resulting organic layer for drying. After the drying, the mixture was subjected to gravity filtration, and the resulting filtrate was concentrated, so that 18 g of N-[(ethylsulfanyl)(4-fluorophenyl)methylidene]-2,6-dimethylaniline was prepared with a crude yield of 110%. The synthetic scheme of Step 3 is shown by (c-14).

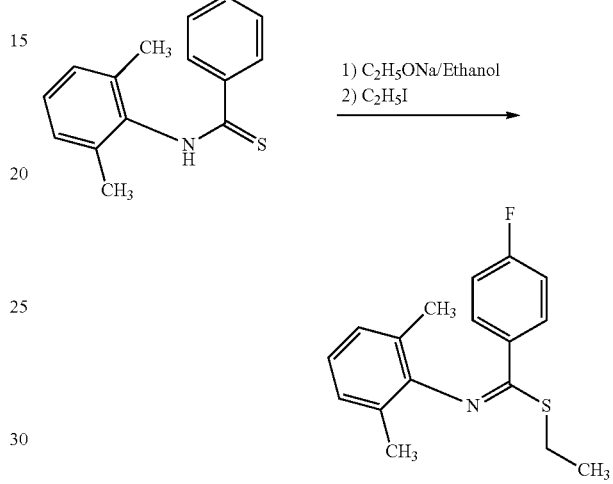

(c-14)

Step 4: Synthesis of 4-(2,6-dimethylphenyl)-3-(4-fluorophenyl)-4H-1,2,4-triazole (abbreviation: HFptz-dmp)

Next, 16 g of ethyl N-[(ethylsulfanyl)(4-fluorophenyl)methylidene]-2,6-dimethylaniline that was prepared in Step 3 described above, 3.5 g of formylhydrazine, and 40 mL of 1-butanol were put in a 200 mL recovery flask, and heated and stirred at 120° C. for 22 hours to be reacted. After the reaction, 1-butanol was distilled of to give a brown oily substance. This oily substance was purified by silica gel column chromatography. As developing solvents, first, toluene was used, and then a mixed solvent of toluene:ethyl acetate=1:1 was used. The resulting fraction was concentrated to give a white solid. Further, the solid was recrystallized from a mixed solvent of ethyl acetate and hexane, so that 3.0 g of 4-(2,6-dimethylphenyl)-3-(4-fluorophenyl)-4H-1,2,4-triazole (abbreviation: HFptz-dmp) was prepared as a white solid with a yield of 20%. The synthetic scheme of Step 4 is shown by (d-14).

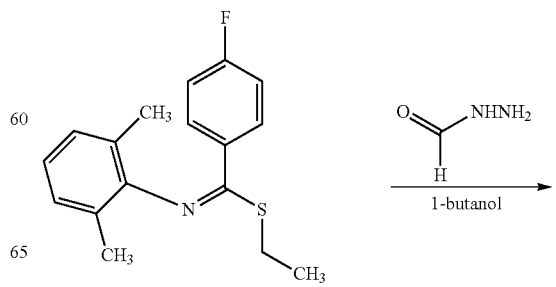

(d-14)

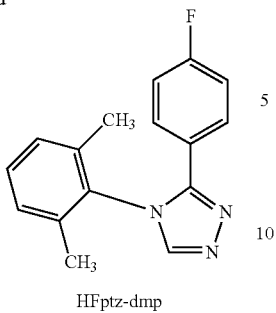

HFptz-dmp

Step 5: Synthesis of tris[4-(2,6-dimethylphenyl)-3-(4-fluorophenyl)-4H-1,2,4-triazolato]iridium(III) (abbreviation: [Ir(Fptz-dmp)₃])

Next, 1.16 g of the ligand HFptz-dmp that was prepared in Step 4 described above, and 0.42 g of tris(acetylacetonate)iridium(III) were put in a reaction container provided with a three-way cock, and the air in the reaction container was replaced with argon. Then, the mixture was heated at 250° C. for 37 hours to be reacted. The reactant was dissolved in dichloromethane, and the solution was filtrated. Although purification of the resulting filtrate was attempted, the objective iridium complex was not prepared. The synthetic scheme of Step 5 is shown by (e-14).

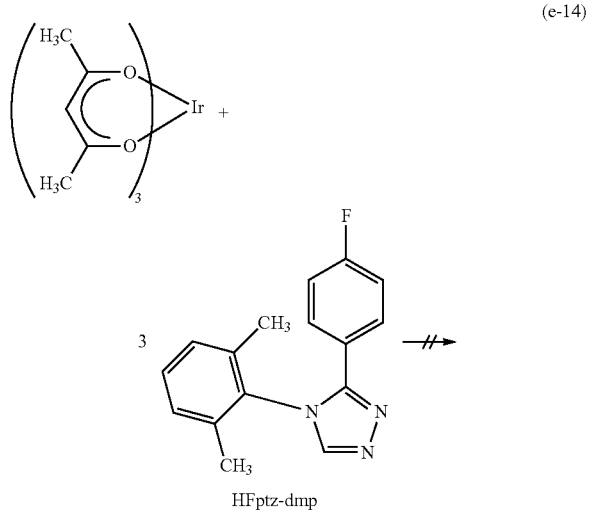

(e-14)

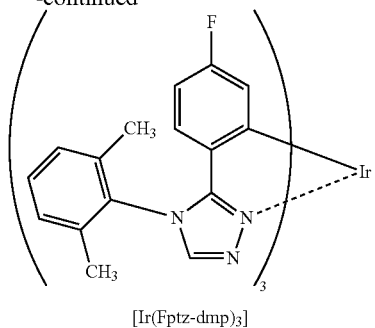

[Ir(Fptz-dmp)₃]

As described in Comparative Example 3, the synthesis of [Ir(Fptz-dmp)₃] was difficult. Thus, it is found that as compared with the organometallic complexes which are described in Synthesis Examples 1 to 11 and each of which is one embodiment of the present invention, a substance where a substituent bonded to the fifth position of a triazole ring is hydrogen has an extremely low yield or cannot be synthesized. That is, it is possible to suppress decomposition reaction in the synthesis of an organometallic complex which is one embodiment of the present invention; therefore, the yield of the synthesis is drastically improved as compared with [Ir(Fptz-dmp)₃].

EXAMPLE 15

Structures, fabrication methods, and measurement results of element characteristics of light-emitting elements each of which includes an organometallic complex which is one embodiment of the present invention are described.

Figure 43:
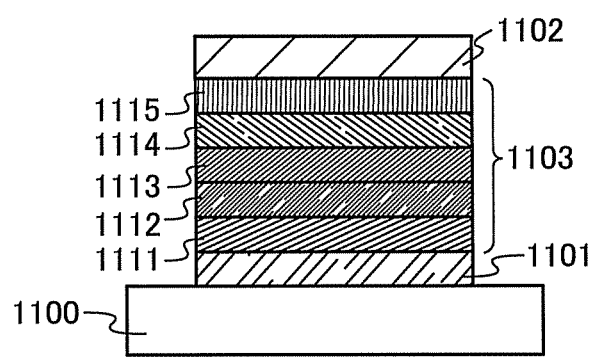
FIG. 43 illustrates a structure of a light-emitting element according to Examples of the present invention.

The element structure of Light-emitting elements 4 to 6 and Light-emitting element 10 which are fabricated in Example 15 is illustrated in FIG. 43. Each of Light-emitting elements 4 to 6 and Light-emitting element 10 includes a substrate 1100, a first electrode 1101 formed thereover, and a second electrode 1102 formed over the first electrode 1101 between which an EL layer 1103 including a stack of a plurality of layers is interposed. The EL layer 1103 of Light-emitting elements 4 to 6 and Light-emitting element 10 of Example 15 has a structure in which a hole-injection layer 1111, a hole-transport layer 1112, a light-emitting layer 1113, an electron-transport layer 1114, and an electron-injection layer 1115 are sequentially stacked.

Detailed structures of the light-emitting elements fabricated are shown in Table 2. Note that the light-emitting layer 1113 is formed using an organometallic complex of one embodiment of the present invention as a light-emitting material in each of Light-emitting elements 4 to 6 and Light-emitting element 10.

TABLE 2

| | First Electrode | Hole-Injection Layer | Hole-transport Layer | Light-emitting Layer | |
|---|---|---|---|---|---|
| Light-emitting Element 4 (101) | ITSO | CBP:MoOx (=2:1) | mCP | mCP: [Ir(Prptz)₃] (=1:0.08) | mDBTBIm-II: [Ir(Prptz)₃] (=1:0.08) |
| | 110 nm | 50 nm | 10 nm | 30 nm | 10 nm |
| Light-emitting Element 5 (102) | ITSO | CBP:MoOx (=2:1) | mCP | mCP: [Ir(iPrptz)₃] (=1:0.08) | mDBTBIm-II: [Ir(iPrptz)₃] (=1:0.08) |
| | 110 nm | 50 nm | 10 nm | 30 nm | 10 nm |
| Light-emitting Element 6 (124) | ITSO | CBP:MoOx (=2:1) | mCP | mCP: [Ir(iPrFptz)₃] (=1:0.08) | mDBTBIm-II: [Ir(iPrFptz)₃] (=1:0.08) |
| | 110 nm | 50 nm | 10 nm | 30 nm | 10 nm |

TABLE 2-continued

| Light-emitting Element 10 (100) | ITSO | CBP:MoOx (=2:1) | mCP | mCP: [Ir(Mptz)$_3$] (=1:0.08) | mDBTBIm-II: [Ir(Mptz)$_3$] (=1:0.08) |
|---|---|---|---|---|---|
| | 110 nm | 50 nm | 10 nm | 30 nm | 10 nm |

| | Electron-transport Layer | Electron-injection Layer | Second Electrode |
|---|---|---|---|
| Light-emitting Element 4 (101) | BPhen 15 nm | LiF 1 nm | Al 200 nm |
| Light-emitting Element 5 (102) | BPhen 15 nm | LiF 1 nm | Al 200 nm |
| Light-emitting Element 6 (124) | BPhen 15 nm | LiF 1 nm | Al 200 nm |
| Light-emitting Element 10 (100) | BPhen 15 nm | LiF 1 nm | Al 200 nm |

Structural formulas of part of the organic compounds used in Example 15 are shown below.

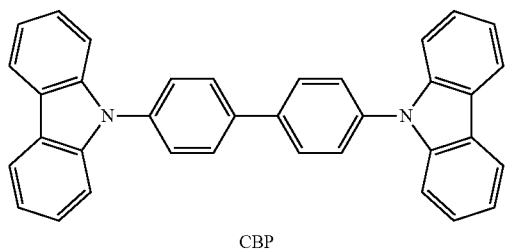

CBP

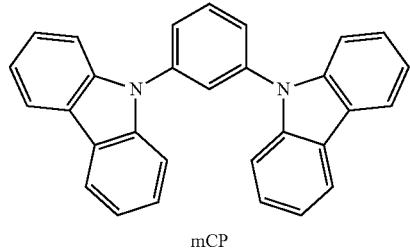

mCP

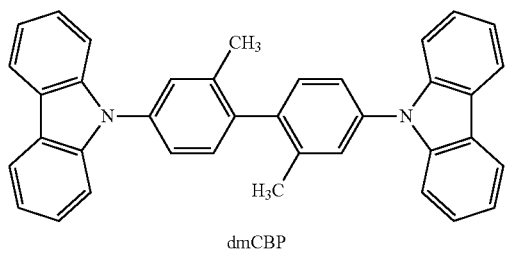

dmCBP

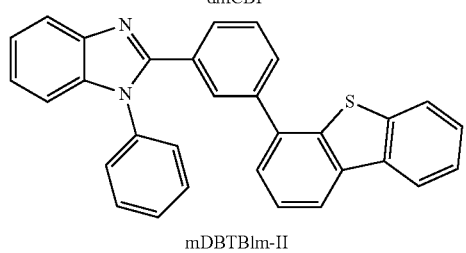

mDBTBIm-II

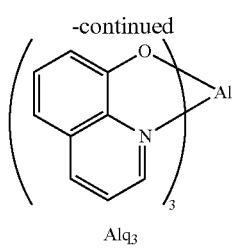

Alq$_3$ (Fabrication of Light-Emitting Element 4)

Next, a method for fabricating Light-emitting element 4 is described. Note that a light-emitting layer of Light-emitting element 4 contains the organometallic complex tris(3,4-diphenyl-5-propyl-4H-1,2,4-triazolato)iridium(III) (abbreviation: [Ir(Prptz)$_3$]), which is one embodiment of the present invention represented by Structural Formula (101) of Embodiment 1, as a light-emitting material.

First, over a glass substrate 1100, indium tin oxide containing silicon oxide (abbreviation: ITSO) was deposited by a sputtering method, so that a first electrode 1101 which functions as an anode was formed. The thickness of the first electrode 1101 was 110 urn and the electrode area was 2 mm×2 mm Next, the glass substrate 1100 over which the first electrode 1101 was formed was fixed to a substrate holder provided in a vacuum evaporation apparatus such that the side on which the first electrode 1101 was formed faced downward, and the pressure was reduced to approximately $10^{-4}$ Pa.

Next, the hole-injection layer 1111 was formed over the first electrode 1101. The hole-injection layer 1111 was formed using a layer containing a composite material of an organic compound and an inorganic compound formed by co-evaporation of 4,4'-di(N-carbazolyl)biphenyl (abbreviation: CBP), and molybdenum(VI) oxide. The thickness of the layer containing a composite material was 50 nm, and the weight ratio of CBP and molybdenum oxide was adjusted to 2:1 (=CBP:molybdenum oxide). Note that the co-evaporation method refers to an evaporation method in which evaporation of a plurality of materials is performed using a plurality of evaporation sources at the same time in one treatment chamber.

Next, the hole-transport layer 1112 was formed over the hole-injection layer 1111. A 10-nm-thick 1,3-bis(N-carbazolyl)benzene (abbreviation: mCP) layer was formed as the hole-transport layer 1112 by an evaporation method using resistance heating.

Next, the light-emitting layer 1113 was formed over the hole-transport layer 1112. The light-emitting layer 1113 was formed with a thickness of 30 nm by co-evaporation of mCP and [Ir(Prptz)$_3$]. The evaporation rate was adjusted so that the weight ratio of mCP and [Ir(Prptz)$_3$] was 1:0.08 (=mCP:[Ir(Prptz)$_3$]).

Next, the electron-transport layer 1114 was formed over the light-emitting layer 1113. A 15-nm-thick bathophenanthroline (abbreviation: BPhen) layer was formed as the electron-transport layer 1114.

Then, the electron-injection layer 1115 was formed over the electron-transport layer 1114. A 1-nm-thick lithium fluoride (LiF) layer was evaporated as the electron-injection layer 1115.

Lastly, the second electrode 1102 was formed over the electron-injection layer 1115. A 200-nm-thick aluminum layer was evaporated as the second electrode 1102; thus, Light-emitting element 4 was fabricated.

Sealing was performed in a glove box under a nitrogen atmosphere so that the resulting Light-emitting element 4 was not exposed to the air, and then operation characteristics of Light-emitting element 4 were measured. Note that the measurement was carried out at room temperature (in an atmosphere kept at 25° C.).

(Fabrication of Light-Emitting Element 5)

Next, a method for fabricating Light-emitting element 5 is described. Note that a light-emitting layer of Light-emitting element 5 contains the organometallic complex tris(5-isopropyl-3,4-diphenyl-4H-1,2,4-triazolato)iridium(III) (abbreviation: [Ir(iPrptz)$_3$]), which is one embodiment of the present invention represented by Structural Formula (102) of Embodiment 1, as a light-emitting material.

Light-emitting element 5 can be formed using the same materials, method, and conditions as Light-emitting element 4 except for a structure of the light-emitting layer 1113. Specifically, the materials and method for forming the first electrode 1101, the hole-injection layer 1111, the hole-transport layer 1112, the electron-transport layer 1114, the electron-injection layer 1115, and the second electrode 1102 may be the same. Thus, for details other than the structure and fabrication method of the light-emitting layer 1113, the above description in (Fabrication of Light-emitting Element 4) can be referred to.

Note that the light-emitting layer 1113 of Light-emitting element 5 was formed with a thickness of 30 nm on the hole-transport layer 1112 by co-evaporation of mCP and [Ir(iPrptz)$_3$]. The evaporation rate was adjusted so that the weight ratio of mCP and [Ir(iPrptz)$_3$] was 1:0.08 (=mCP:[Ir(iPrptz)$_3$]).

Sealing was performed in a glove box under a nitrogen atmosphere so that the resulting Light-emitting element 5 was not exposed to the air, and then operation characteristics of Light-emitting element 5 were measured. Note that the measurement was carried out at room temperature (in an atmosphere kept at 25° C.).

(Fabrication of Light-Emitting Element 6)

Next, a method for fabricating Light-emitting element 6 is described. Note that a light-emitting layer of Light-emitting element 6 contains the organometallic complex tris[3-(4-fluorophenyl)-5-isopropyl-4-phenyl-4H-1,2,4-triazolato]iridium(III) (abbreviation: [Ir(iPrFptz)$_3$]), which is one embodiment of the present invention represented by Structural Formula (124) of Embodiment 1, as a light-emitting material.

Light-emitting element 6 can be formed using the same materials, method, and conditions as Light-emitting element 4 except for a structure of the light-emitting layer 1113. Specifically, the materials and method for forming the first electrode 1101, the hole-injection layer 1111, the hole-transport layer 1112, the electron-transport layer 1114, the electron-injection layer 1115, and the second electrode 1102 may be the same. Thus, for details other than the structure and fabrication method of the light-emitting layer 1113, the above description in (Fabrication of Light-emitting Element 4) can be referred to.

Note that the light-emitting layer 1113 of Light-emitting element 6 was formed with a thickness of 30 nm on the hole-transport layer 1112 by co-evaporation of mCP and [Ir(iPrFptz)$_3$]. The evaporation rate was adjusted so that the weight ratio of mCP and [Ir(iPrFptz)$_3$] was 1:0.08 (=mCP:[Ir(iPrFptz)$_3$]).

Sealing was performed in a glove box under a nitrogen atmosphere so that the resulting Light-emitting element 6 was not exposed to the air, and then operation characteristics of Light-emitting element 6 were measured. Note that the measurement was carried out at room temperature (in an atmosphere kept at 25° C.).

(Fabrication of Light-Emitting Element 10)

Next, a method for fabricating Light-emitting element 10 is described. Note that a light-emitting layer of Light-emitting element 10 contains the organometallic complex tris(5-methyl-3,4-diphenyl-4H-1,2,4-triazolato)iridium(III) (abbreviation: [Ir(Mptz)$_3$]), which is one embodiment of the present invention represented by Structural Formula (100) of Embodiment 1, as a light-emitting material.

Light-emitting element 10 can be formed using the same materials, method, and conditions as Light-emitting element 4 except for a structure of the light-emitting layer 1113. Specifically, the materials and method for forming the first electrode 1101, the hole-injection layer 1111, the hole-transport layer 1112, the electron-transport layer 1114, the electron-injection layer 1115, and the second electrode 1102 may be the same. Thus, for details other than the structure and fabrication method of the light-emitting layer 1113, the above description in (Fabrication of Light-emitting Element 4) can be referred to.

Note that the light-emitting layer 1113 of Light-emitting element 10 was formed with a thickness of 30 nm on the hole-transport layer 1112 by co-evaporation of mCP and [Ir(Mptz)$_3$]. The evaporation rate was adjusted so that the weight ratio of mCP and [Ir(Mptz)$_3$] was 1:0.08 (=mCP:[Ir(Mptz)$_3$]).

Sealing was performed in a glove box under a nitrogen atmosphere so that the resulting Light-emitting element 10 was not exposed to the air, and then operation characteristics of Light-emitting element 10 were measured. Note that the measurement was carried out at room temperature (in an atmosphere kept at 25° C.).

(Evaluation Results)

Figure 44:
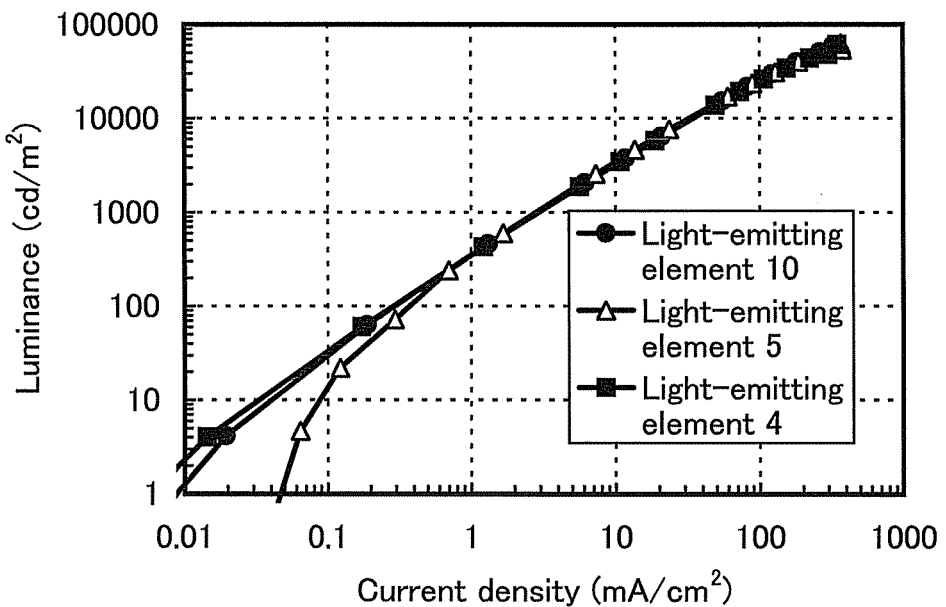
FIG. 44 shows current density vs. luminance characteristics of Light-emitting elements 4, 5, and 10.
Figure 45:
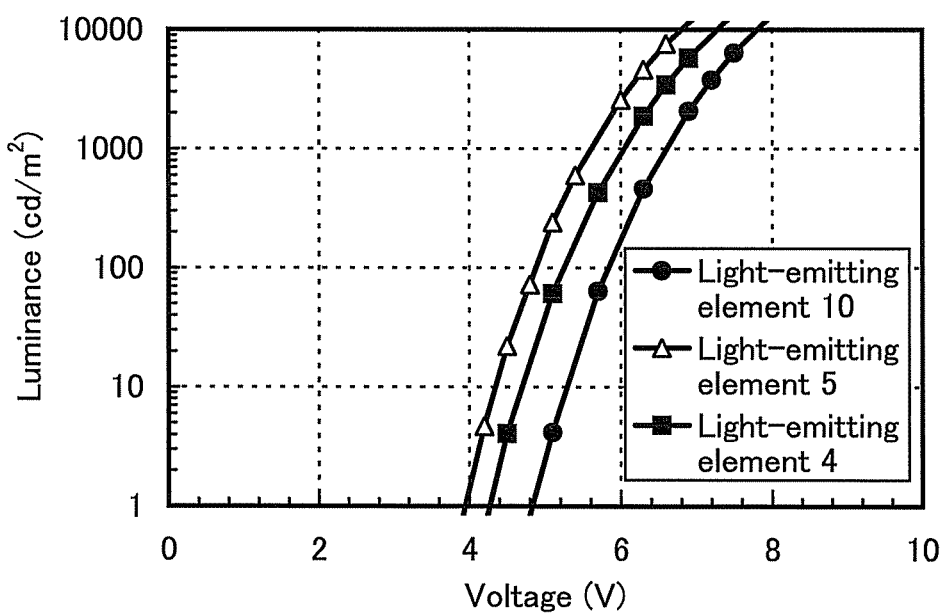
FIG. 45 shows voltage vs. luminance characteristics of Light-emitting elements 4, 5, and 10.
Figure 46:
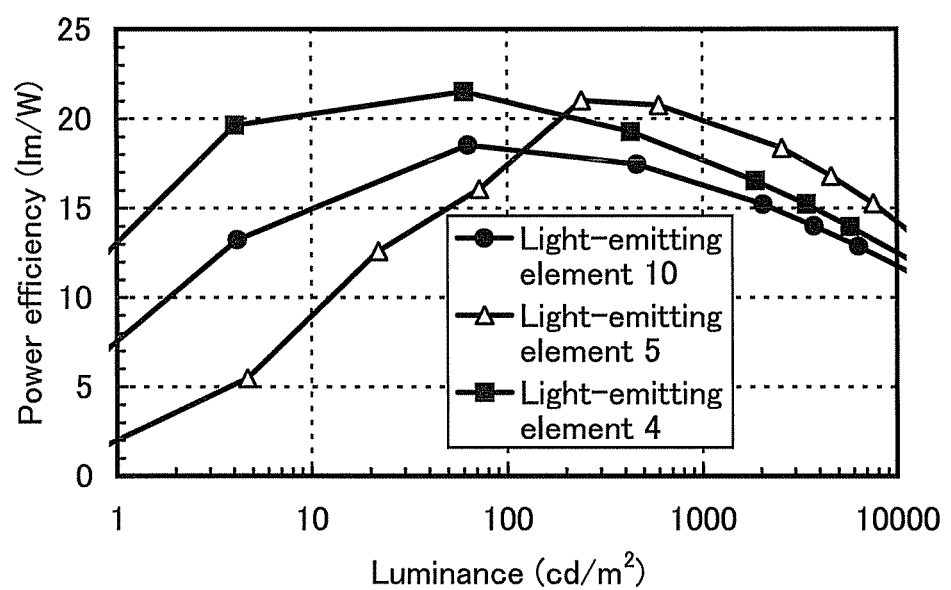
FIG. 46 shows luminance vs. power efficiency characteristics of Light-emitting elements 4, 5, and 10.
Figure 47:
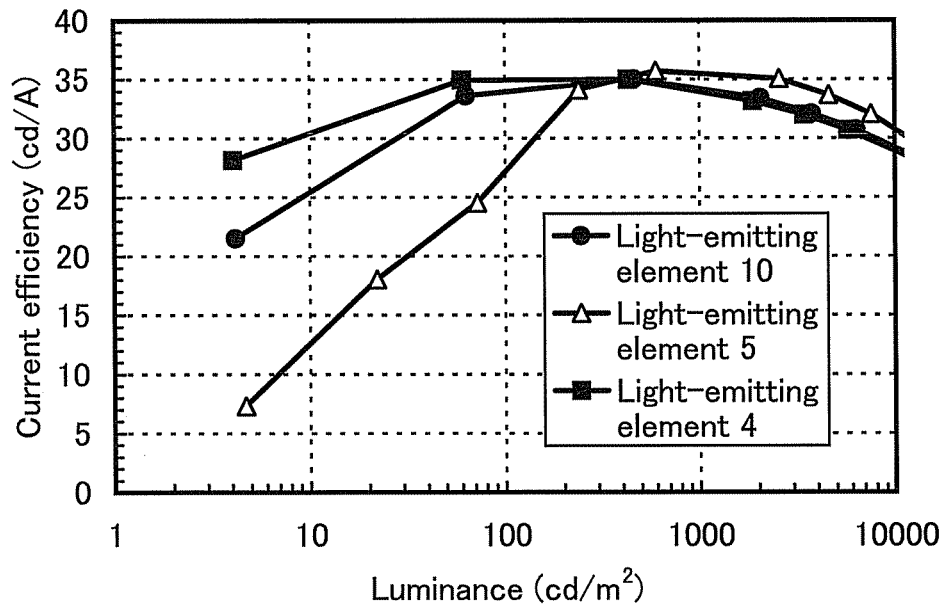
FIG. 47 shows luminance vs. current efficiency characteristics of Light-emitting elements 4, 5, and 10.
Figure 48:
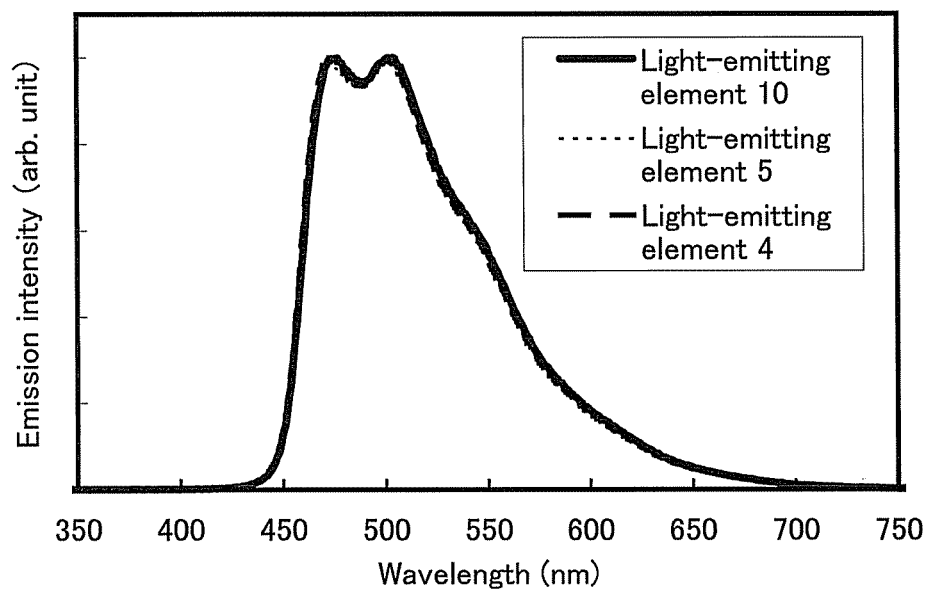
FIG. 48 shows emission spectra of Light-emitting elements 4, 5, and 10.
Figure 49:
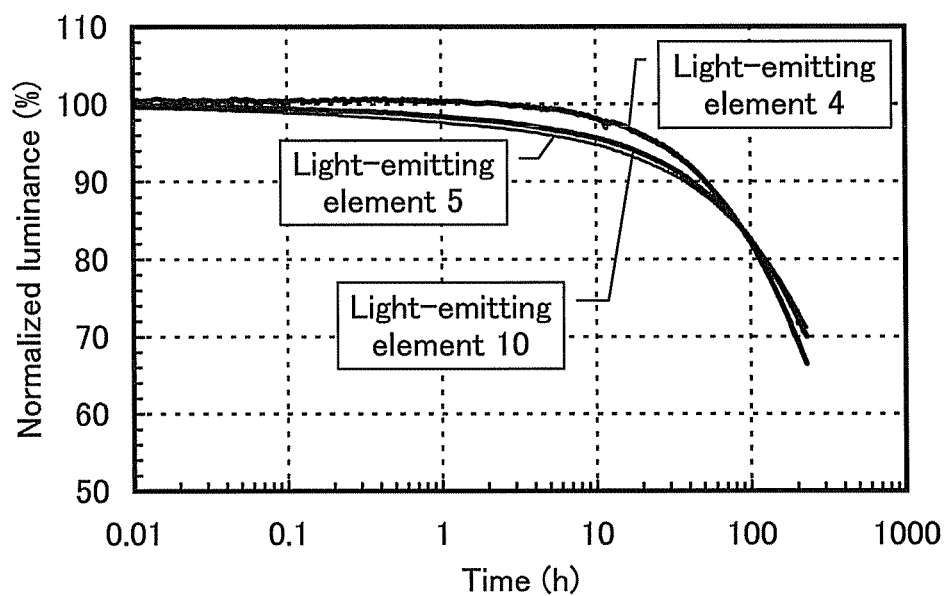
FIG. 49 shows results of continuous lighting tests in which Light-emitting elements 4, 5, and 10 are continuously lit by constant current driving.

FIG. 44 shows current density vs. luminance characteristics of Light-emitting element 4, Light-emitting element 5, and Light-emitting element 10. FIG. 45 shows voltage vs. luminance characteristics thereof. FIG. 46 shows luminance vs. power efficiency characteristics thereof. FIG. 47 shows luminance vs. current efficiency characteristics thereof. In addition, FIG. 48 shows the emission spectra thereof at a current of 0.1 mA, and FIG. 49 shows the time dependence of normalized luminance thereof when the initial luminance was set to approximately 300 cd/m$^2$.

Figure 50:
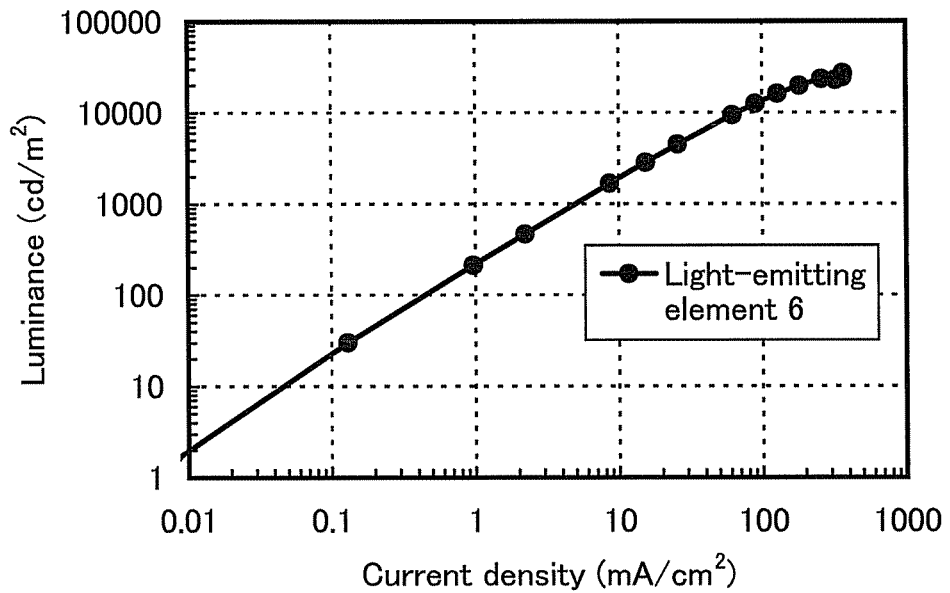
FIG. 50 shows current density vs. luminance characteristics of Light-emitting element 6.
Figure 51:
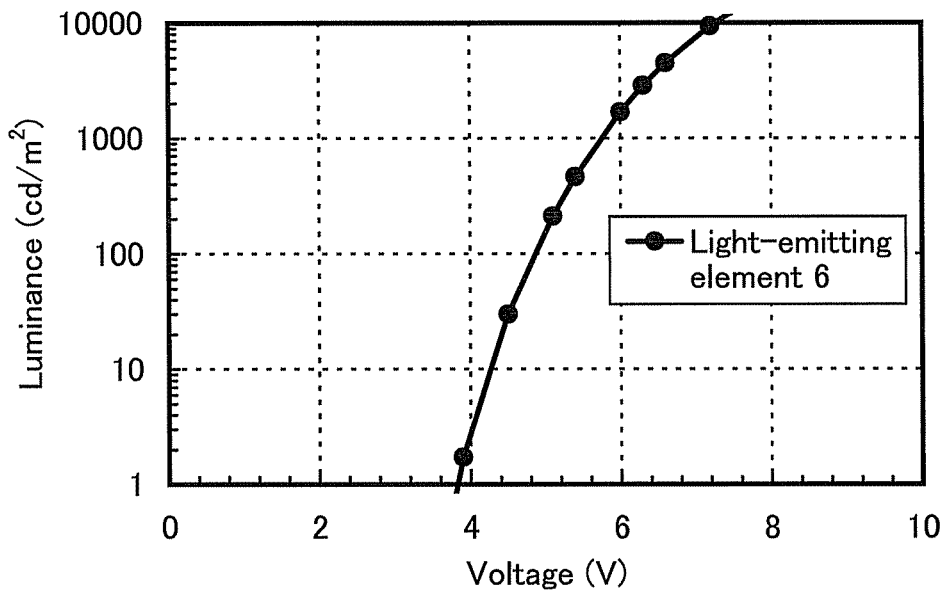
FIG. 51 shows voltage vs. luminance characteristics of Light-emitting element 6.
Figure 52:
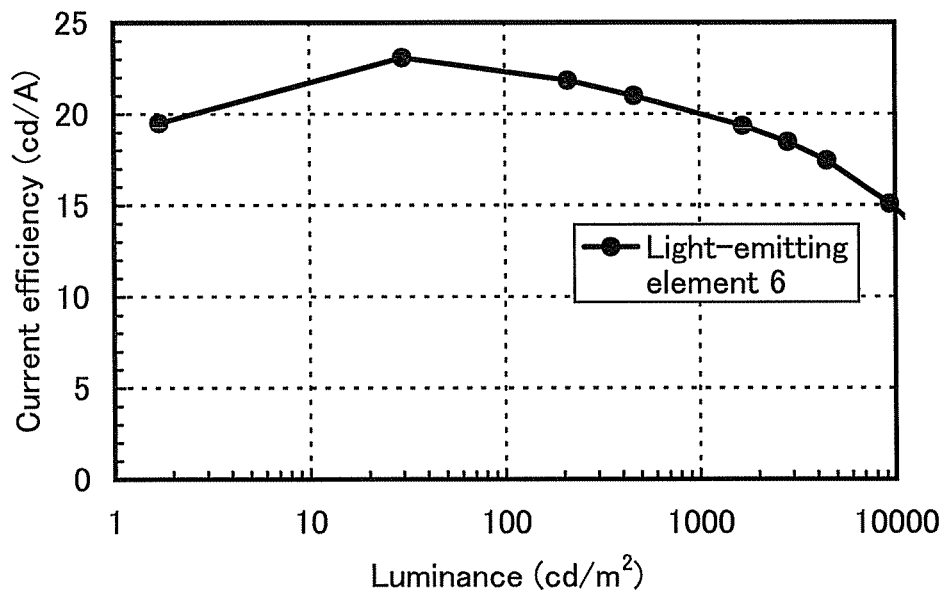
FIG. 52 shows luminance vs. current efficiency characteristics of Light-emitting element 6.
Figure 53:
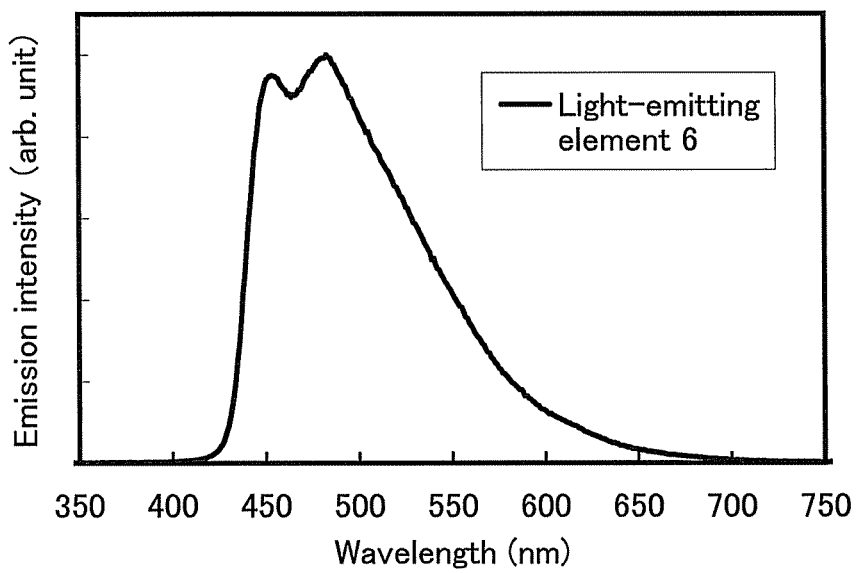
FIG. 53 shows an emission spectrum of Light-emitting element 6.

FIG. 50 shows current density vs. luminance characteristics of Light-emitting element 6. FIG. 51 shows voltage vs. luminance characteristics thereof. FIG. 52 shows luminance vs. current efficiency characteristics thereof. In addition, FIG. 53 shows the emission spectrum thereof at a current of 0.1 mA.

The CIE chromaticity coordinates of Light-emitting element 4 at a luminance of 428 cd/m² are (x=0.22, y=0.40), and blue-green light was emitted. In addition, at a luminance of 428 cd/m², the current efficiency is 35.0 cd/A, the voltage is 5.7 V, and the current density is 1.2 mA/cm². Further, Light-emitting element 4 kept 66% of the initial luminance even after 230 hours, and thus was a long life light-emitting element.

The CIE chromaticity coordinates of Light-emitting element 5 at a luminance of 597 cd/m² are (x=0.22, y=0.40), and blue-green light was emitted. In addition, at a luminance of 597 cd/m², the current efficiency is 35.7 cd/A, the voltage is 5.4 V, and the current density is 1.7 mA/cm². Further, Light-emitting element 5 kept 71% of the initial luminance even after 230 hours, and thus was a long life light-emitting element.

The CIE chromaticity coordinates of Light-emitting element 6 at a luminance of 464 cd/m² are (x=0.19, y=0.28), and blue light was emitted. In addition, at a luminance of 464 cd/m², the current efficiency is 21.0 cd/A, the voltage is 5.4 V, and the current density is 2.2 mA/cm².

The CIE chromaticity coordinates of Light-emitting element 10 at a luminance of 460 cd/m² are (x=0.22, y=0.41), and blue-green light was emitted. In addition, at a luminance of 460 cd/m², the current efficiency is 35.0 cd/A, the voltage is 6.3 V, and the current density is 1.3 mA/cm². Further, Light-emitting element 10 kept 70% of the initial luminance even after 230 hours, and thus was a long life light-emitting element.

These measurement results indicate that Light-emitting element 4 has an extremely high current efficiency. In addition, it is found that Light-emitting element 5 needs a low voltage for obtaining a certain luminance, has low power consumption, and has an extremely high current efficiency. Further, it is found that Light-emitting element 6 needs a low voltage for obtaining a certain luminance, has low power consumption, and has an extremely high current efficiency. It is also found that Light-emitting element 10 has an extremely high current efficiency.

EXAMPLE 16

Structures, fabrication methods, and measurement results of element characteristics of a light-emitting element which includes an organometallic complex which is one embodiment of the present invention are described.

The element structure of Light-emitting element 7 which is fabricated in Example 16 is illustrated in FIG. 43. Light-emitting element 7 includes the substrate 1100, the first electrode 1101 formed thereover, and the second electrode 1102 formed over the first electrode 1101 between which the EL layer 1103 including a stack of a plurality of layers is interposed. The EL layer 1103 of Light-emitting element 7 of Example 16 has a structure in which the hole-injection layer 1111, the hole-transport layer 1112, the light-emitting layer 1113, the electron-transport layer 1114, and the electron-injection layer 1115 are sequentially stacked. Note that the electron-transport layer 1114 has a structure in which a first electron-transport layer, a second electron-transport layer, and a third electron-transport layer are stacked.

Detailed structures of the light-emitting elements fabricated are shown in Table 3. Note that the light-emitting layer 1113 is formed using an organometallic complex of one embodiment of the present invention as a light-emitting material in Light-emitting element 7.

TABLE 3

| | First Electrode | Hole-injection Layer | Hole-transport Layer | Light-emitting Layer |
|---|---|---|---|---|
| Light-emitting Element 7 (125) | ITSO 110 nm | CBP: MoOx (=2:1) 50 nm | dmCBP 10 nm | dmCBP: [Ir(iPrFptz-dmp)₃] (=1:0.08) 30 nm |

| | Electron-transport Layer | | | Electron-injection Layer | Second Electrode |
|---|---|---|---|---|---|
| Light-emitting Element 7 (125) | mDBTBIm-II 10 nm | Alq₃ 10 nm | BPhen 20 nm | LiF 1 nm | Al 200 nm |

(Fabrication of Light-Emitting Element 7)

Next, a method for fabricating Light-emitting element 7 is described. Note that a light-emitting layer of Light-emitting element 7 contains the organometallic complex tris[4-(2,6-dimethylphenyl)-3-(4-fluoro phenyl)-5-isopropyl-4H-1,2,4-triazolato]iridium(III) (abbreviation: [Ir(iPrFptz-dmp)₃]), which is one embodiment of the present invention represented by Structural Formula (125) of Embodiment 1, as a light-emitting material.

First, over the glass substrate 1100, indium tin oxide containing silicon oxide (abbreviation: ITSO) was deposited by a sputtering method, so that the first electrode 1101 which functions as an anode was formed. The thickness of the first electrode 1101 was 110 nm and the electrode area was 2 mm×2 mm.

Next, the glass substrate 1100 over which the first electrode 1101 was formed was fixed to a substrate holder provided in a vacuum evaporation apparatus such that the side on which the first electrode 1101 was formed faced downward, and the pressure was reduced to approximately $10^{-4}$ Pa.

Next, the hole-injection layer 1111 was formed over the first electrode 1101. The hole-injection layer 1111 was formed using a layer containing a composite material of an organic compound and an inorganic compound formed by co-evaporation of 4,4'-di(N-carbazolyl)biphenyl (abbreviation: CBP), and molybdenum(VI) oxide. The thickness of the layer containing a composite material was 50 nm, and the weight ratio of CBP and molybdenum oxide was adjusted to 2:1 (=CBP:molybdenum oxide). Note that the co-evaporation method refers to an evaporation method in which evaporation of a plurality of materials is performed using a plurality of evaporation sources at the same time in one treatment chamber.

Next, the hole-transport layer 1112 was formed over the hole-injection layer 1111. A 10-nm-thick 4,4'-bis(9-carbazol)-2,2'-dimethyl-biphenyl (abbreviation: dmCBP) layer was formed as the hole-transport layer 1112 by an evaporation method using resistance heating.

Next, the light-emitting layer 1113 was formed over the hole-transport layer 1112. The light-emitting layer 1113 was formed with a thickness of 30 nm by co-evaporation of dmCBP and [Ir(iPrFptz-dmp)₃]. The evaporation rate was adjusted so that the weight ratio of din CBP and [Ir(iPrFptz-dmp)₃] was 1:0.08 (=dmCBP: [Ir(iPrFptz-dmp)₃]).

Next, the electron-transport layer 1114 was formed over the light-emitting layer 1113. The electron-transport layer 1114 was formed with three layers: a first electron-transport layer, a second electron-transport layer, and a third electron-transport layer. The first electron-transport layer was formed with a thickness of 10 nm using 2-[3-(dibenzothiophen-4-yl)phenyl]-1-phenyl-1H-benzimidazole (abbreviation: mDBTBIm-II), the second electron-transport layer was formed with a thickness of 10 nm using tris(8-quinolinolato)aluminum (III) (abbreviation: Alq) over the first electron-transport layer, and the third electron-transport layer was formed with a thickness of 20 nm using bathophenanthroline (abbreviation: BPhen) over the second electron-transport layer.

Then, the electron-injection layer 1115 was formed over the electron-transport layer 1114. A 1-nm-thick lithium fluoride (LiF) layer was evaporated as the electron-injection layer 1115.

Lastly, the second electrode 1102 was formed over the electron-injection layer 1115. A 200-nm-thick aluminum layer was evaporated as the second electrode 1102; thus, Light-emitting element 7 was fabricated.

Sealing was performed in a glove box under a nitrogen atmosphere so that the resulting Light-emitting element 7 was not exposed to the air, and then operation characteristics of Light-emitting element 7 were measured. Note that the measurement was carried out at room temperature (in an atmosphere kept at 25° C.).

(Evaluation Results)

Figure 54:
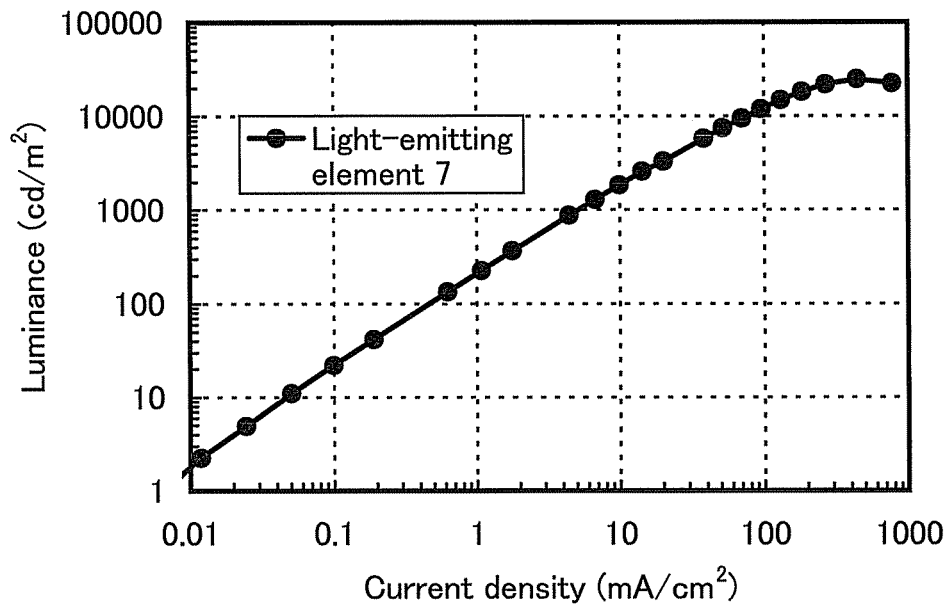
FIG. 54 shows current density vs. luminance characteristics of Light-emitting element 7.
Figure 55:
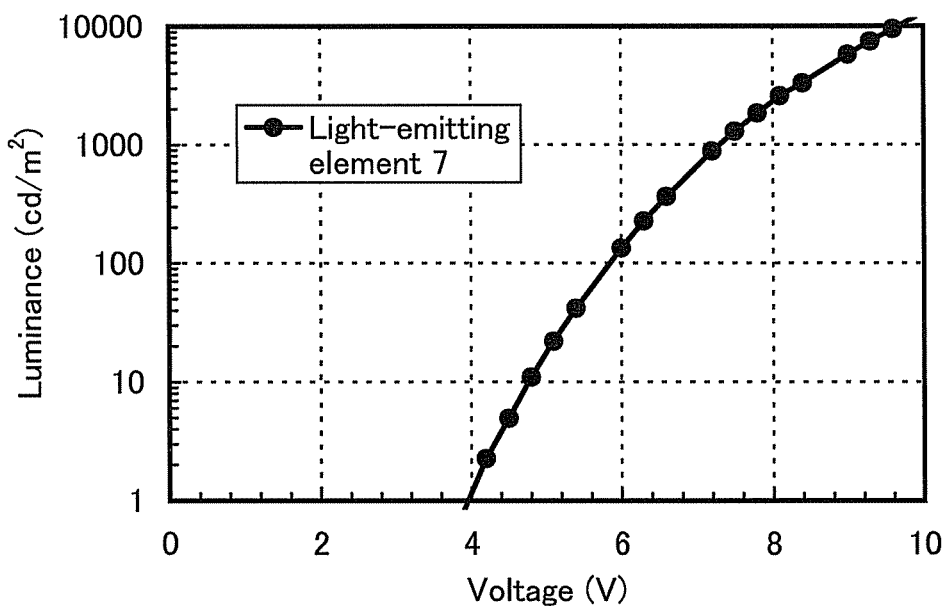
FIG. 55 shows voltage vs. luminance characteristics of Light-emitting element 7.
Figure 56:
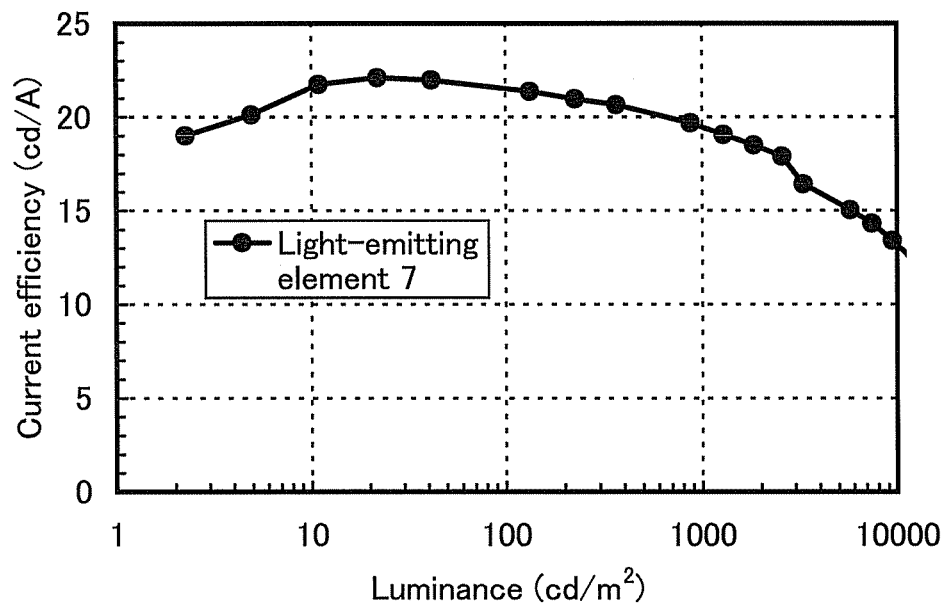
FIG. 56 shows luminance vs. current efficiency characteristics of Light-emitting element 7.
Figure 57:
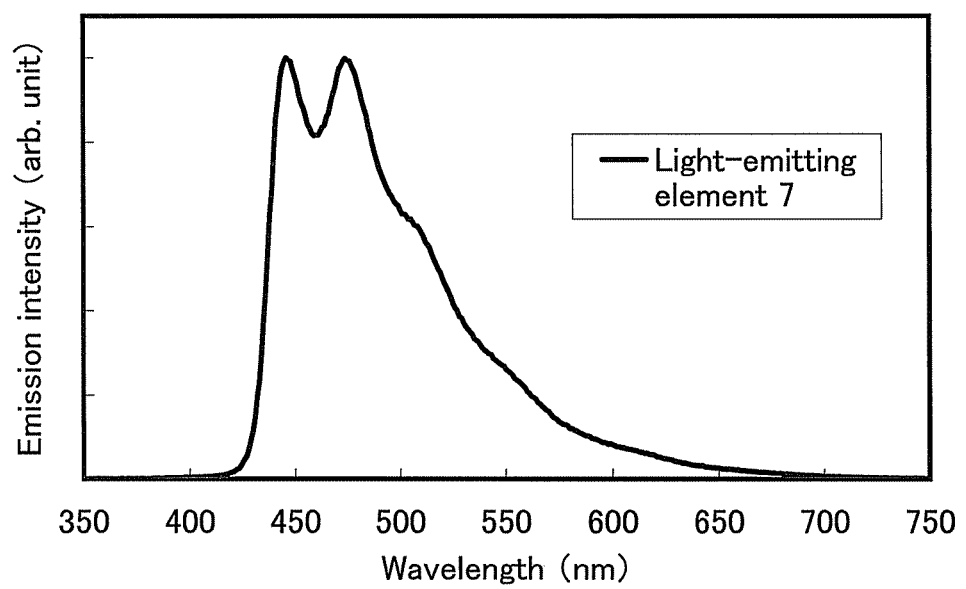
FIG. 57 shows an emission spectrum of Light-emitting element 7.

Next, FIG. 54 shows current density vs. luminance characteristics of Light-emitting element 7. FIG. 55 shows voltage vs. luminance characteristics thereof. FIG. 56 shows luminance vs. current efficiency characteristics thereof. In addition, FIG. 57 shows the emission spectrum thereof at a current of 0.1 mA.

The CIE chromaticity coordinates of Light-emitting element 7 at a luminance of 876 cd/m² are (x=0.18, y=0.22), and blue light with extremely high color purity was emitted. In addition, at a luminance of 876 cd/m², the current efficiency is 19.7 cd/A, the voltage is 7.2 V, and the current density is 4.45 mA/cm².

These measurement results indicate that Light-emitting element 7 emits blue light with extremely high color purity and has an extremely high current efficiency.

EXAMPLE 17

Structures, fabrication methods, and measurement results of element characteristics of light-emitting elements each of which includes an organometallic complex which is one embodiment of the present invention are described.

The element structure of Light-emitting elements 8 and 9 which are fabricated in Example 17 is illustrated in FIG. 43. Each of Light-emitting elements 8 and 9 includes the substrate 1100, the first electrode 1101 formed thereover, and the second electrode 1102 formed over the first electrode 1101 between which the EL layer 1103 including a stack of a plurality of layers is interposed. The EL layer 1103 of Light-emitting elements 8 and 9 of Example 17 has a structure in which the hole-injection layer 1111, the hole-transport layer 1112, the light-emitting layer 1113, the electron-transport layer 1114, and the electron-injection layer 1115 are sequentially stacked. Note that the light-emitting layer 1113 has a structure in which a first light-emitting layer and a second light-emitting layer are stacked, and the electron-transport layer 1114 has a structure in which the first electron-transport layer and the second electron-transport layer are stacked.

Detailed structures of the light-emitting elements fabricated are shown in Table 4. Note that the light-emitting layer 1113 is formed using an organometallic complex of one embodiment of the present invention as a light-emitting material in each of Light-emitting elements 8 and 9.

TABLE 4

| | First Electrode | Hole-injection Layer | Hole-transport Layer | Light-emitting Layer | |
|---|---|---|---|---|---|
| Light-emitting Element 8 (138) | ITSO | BPAFLP: MoOx (=2:1) | BPAFLP | DBTBIm-II: PCBA1BP: [Ir(Mntz)$_3$] (=1:0.25:0.08) | DBTBIm-II: [Ir(Mntz)$_3$] (=1:0.08) |
| | 110 nm | 50 nm | 10 nm | 20 nm | 20 nm |
| Light-emitting Element 9 (150) | ITSO | BPAFLP: MoOx (=2:1) | BPAFLP | DBTBIm-II: PCBA1BP: [Ir(iPrntz)$_3$] (=1:0.25:0.08) | DBTBIm-II: [Ir(iPrntz)$_3$] (=1:0.08) |
| | 110 nm | 50 nm | 10 nm | 20 nm | 10 nm |

| | Electron-transport Layer | | Electron-injection Layer | Second Electrode |
|---|---|---|---|---|
| Light-emitting Element 8 (138) | DBTBIm-II 15 nm | BPhen 15 nm | LiF 1 nm | Al 200 nm |
| Light-emitting Element 9 (150) | DBTBIm-II 10 nm | BPhen 15 nm | LiF 1 nm | Al 200 nm |

Structural formulas of part of the organic compounds used in Example 17 are shown below.

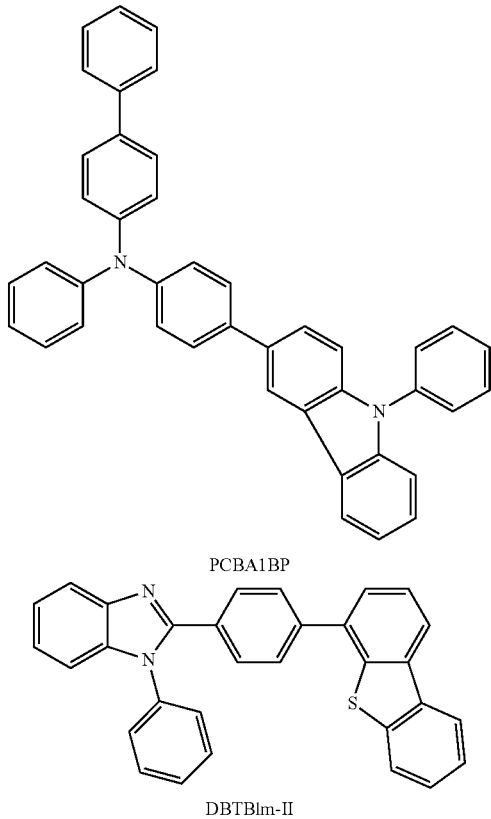

PCBA1BP

DBTBIm-II (Fabrication of Light-Emitting Element 8)

Next, a method for fabricating Light-emitting element 8 is described. Note that a light-emitting layer of Light-emitting element 8 contains the organometallic complex tris[5-methyl-3-(2-naphthyl)-4-phenyl-4H-1,2,4-triazolato]iridium (III) (abbreviation: [Ir(Mntz)$_3$]), which is one embodiment of the present invention represented by Structural Formula (138) of Embodiment 1, as a light-emitting material.

First, over the glass substrate 1100, indium tin oxide containing silicon oxide (abbreviation: ITSO) was deposited by a sputtering method, so that the first electrode 1101 which functions as an anode was formed. The thickness of the first electrode 1101 was 110 nm and the electrode area was 2 mm×2 mm.

Next, the glass substrate 1100 over which the first electrode 1101 was formed was fixed to a substrate holder provided in a vacuum evaporation apparatus such that the side on which the first electrode 1101 was formed faced downward, and the pressure was reduced to approximately $10^{-4}$ Pa.

Next, the hole-injection layer 1111 was formed over the first electrode 1101. The hole-injection layer 1111 was formed using a layer containing a composite material of an organic compound and an inorganic compound formed by co-evaporation of BPAFLP and molybdenum(VI) oxide. The thickness of the layer containing a composite material was 50 nm, and the weight ratio of BPAFLP and molybdenum oxide was adjusted to 2:1 (=BPAFLP:molybdenum oxide). Note that the co-evaporation method refers to an evaporation method in which evaporation of a plurality of materials is performed using a plurality of evaporation sources at the same time in one treatment chamber.

Next, the hole-transport layer 1112 was formed over the hole-injection layer 1111. A 10-nm-thick BPAFLP layer was formed as the hole-transport layer 1112 by an evaporation method using resistance heating.

Next, the light-emitting layer 1113 was formed over the hole-transport layer 1112. The light-emitting layer 1113 was formed with the first light-emitting layer and the second light-emitting layer. Note that the first light-emitting layer was formed with a thickness of 20 nm by co-evaporation of 2-[4-(dibenzothiophene-4-yl)phenyl]-1-phenyl-1H-benzoimidazol (abbreviation: 4-phenyl-4'-(9-phenyl-9H-carbazol-3-yl) triphenylamine (abbreviation: PCBA1BP), and [Ir(Mntz)$_3$]. The evaporation rate was adjusted so that the weight ratio of DBTBIm-II, PCBA1BP, and [Ir(Mntz)$_3$] was 1:0.25:0.08 (=DBTBIm-II:PCBA1BP:[Ir(Mntz)$_3$]).

The second light-emitting layer was formed over the first light-emitting layer with a thickness of 20 nm by co-evaporation of DBTBIm-II and [Ir(Mntz)$_3$]. The evaporation rate was adjusted so that the weight ratio of DBTBIm-II and [Ir(Mntz)$_3$] was 1:0.08 (=DBTBIm-II:[Ir(Mntz)$_3$]).

Next, the electron-transport layer 1114 was formed over the light-emitting layer 1113. The electron-transport layer 1114 was formed with the first electron-transport layer and the second electron-transport layer. The first electron-transport layer was formed with a thickness of 15 nm using DBTBIm-II, and the second electron-transport layer was formed with a thickness of 15 nm using bathophenanthroline (abbreviation: BPhen) over the first electron-transport layer.

Then, the electron-injection layer 1115 was formed over the electron-transport layer 1114. A 1-nm-thick lithium fluoride (LiF) layer was evaporated as the electron-injection layer 1115.

Lastly, the second electrode 1102 was formed over the electron-injection layer 1115. A 200-nm-thick aluminum layer was evaporated as the second electrode 1102; thus, Light-emitting element 8 was fabricated.

Sealing was performed in a glove box under a nitrogen atmosphere so that the resulting Light-emitting element 8 was not exposed to the air, and then operation characteristics of Light-emitting element 8 were measured. Note that the measurement was carried out at room temperature (in an atmosphere kept at 25° C.).

(Fabrication of Light-Emitting Element 9)

Next, a method for fabricating Light-emitting element 9 is described. Note that a light-emitting layer of Light-emitting element 9 contains the organometallic complex tris[5-isopropyl-3-(2-naphthyl)-4-phenyl-4H-1,2,4-triazolato]iridium (III) (abbreviation: [Ir(iPrntz)$_3$]), which is one embodiment of the present invention represented by Structural Formula (150) of Embodiment 1, as a light-emitting material.

Light-emitting element 9 can be formed using the same materials, method, and conditions as Light-emitting element 8 except for a structure of the light-emitting layer 1113. Specifically, the materials and method for forming the first electrode 1101, the hole-injection layer 1111, the hole-transport layer 1112, the electron-transport layer 1114, the electron-injection layer 1115, and the second electrode 1102 may be the same. Thus, for details other than the structure and fabrication method of the light-emitting layer 1113, the above description in (Fabrication of Light-emitting Element 8) can be referred to.

Note that the light-emitting layer 1113 of Light-emitting element 9 was formed with the first light-emitting layer and the second light-emitting layer. The first light-emitting layer was formed over the hole-transport layer 1112 with a thickness of nm by co-evaporation of 2-[4-(dibenzothiophene-4-yl)phenyl]-1-phenyl-1H-benzoimidazol (abbreviation: DBT- BIm-II), 4-phenyl-4'-(9-phenyl-9H-carbazol-3-yl)triphenylamine (abbreviation: PCBA1BP), and [Ir(iPrntz)₃]. The evaporation rate was adjusted so that the weight ratio of DBTBIm-II, PCBA1BP, and [Ir(iPrntz)₃] was 1:0.25:0.08 (=DBTBIm-II:PCBA1BP:[Ir(iPrntz)₃]).

The second light-emitting layer was formed over the first light-emitting layer with a thickness of 10 nm by co-evaporation of DBTBIm-II and [Ir(iPrntz)₃]. The evaporation rate was adjusted so that the weight ratio of DBTBIm-II and [Ir(iPrntz)₃] was 1:0.08 (=DBTBIm-II:[Ir(iPrntz)₃]).

Sealing was performed in a glove box under a nitrogen atmosphere so that the resulting Light-emitting element 9 was not exposed to the air, and then operation characteristics of Light-emitting element 9 were measured. Note that the measurement was carried out at room temperature (in an atmosphere kept at 25° C.).

(Evaluation Results)

Figure 58:
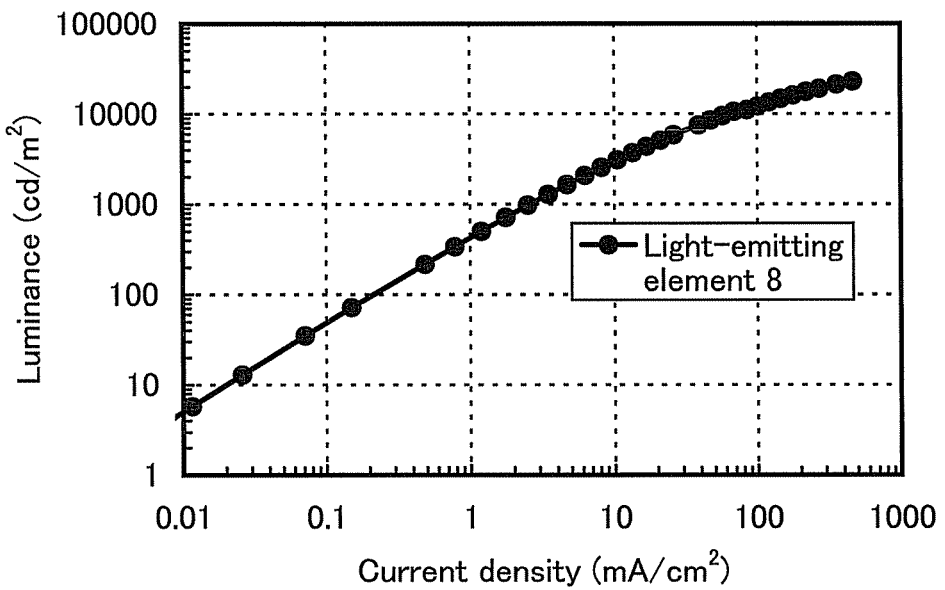
FIG. 58 shows current density vs. luminance characteristics of Light-emitting element 8.
Figure 59:
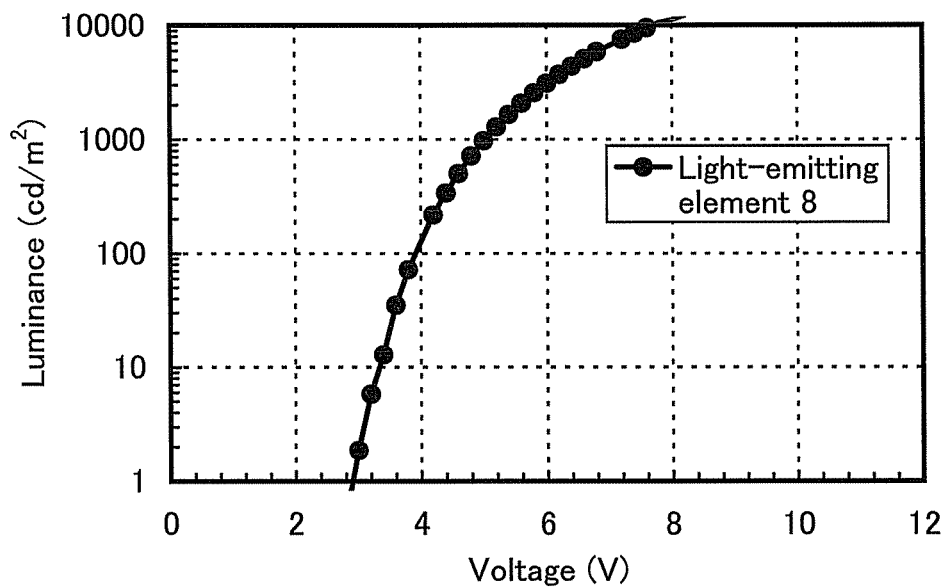
FIG. 59 shows voltage vs. luminance characteristics of Light-emitting element 8.
Figure 60:
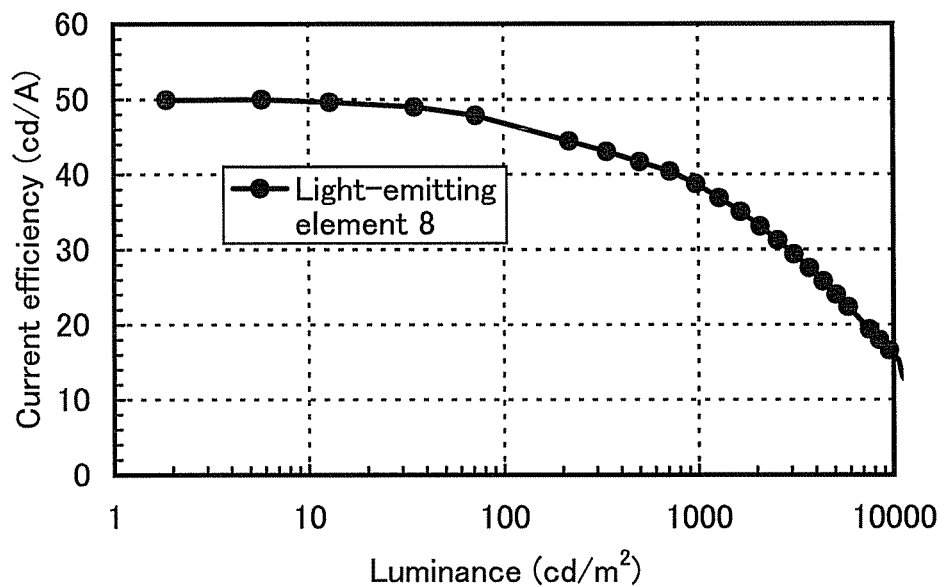
FIG. 60 shows luminance vs. current efficiency characteristics of Light-emitting element 8.
Figure 61:
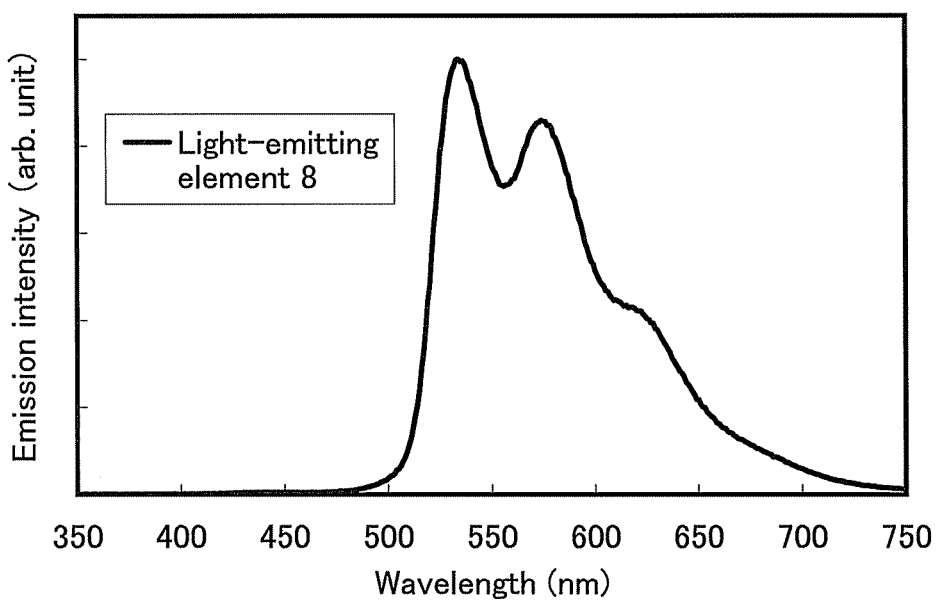
FIG. 61 shows an emission spectrum of Light-emitting element 8.

FIG. 58 shows current density vs. luminance characteristics of Light-emitting element 8. FIG. 59 shows voltage vs. luminance characteristics thereof. FIG. 60 shows luminance vs. current efficiency characteristics thereof. In addition, FIG. 61 shows the emission spectrum thereof at a current of 0.1 mA.

The CIE chromaticity coordinates of Light-emitting element 8 at a luminance of 972 cd/m² are (x=0.43, y=0.55), and yellow-green light was emitted. In addition, at a luminance of 972 cd/m², the current efficiency is 38.7 cd/A, the voltage is 5.0 V, and the current density is 2.5 mA/cm².

These measurement results indicate that Light-emitting element 8 has an extremely high current efficiency.

Figure 62:
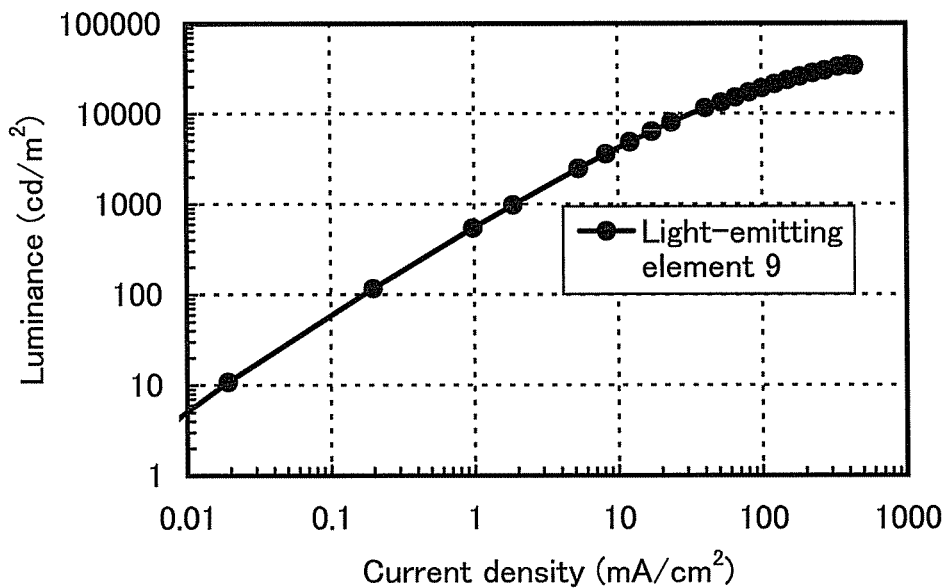
FIG. 62 shows current density vs. luminance characteristics of Light-emitting element 9.
Figure 63:
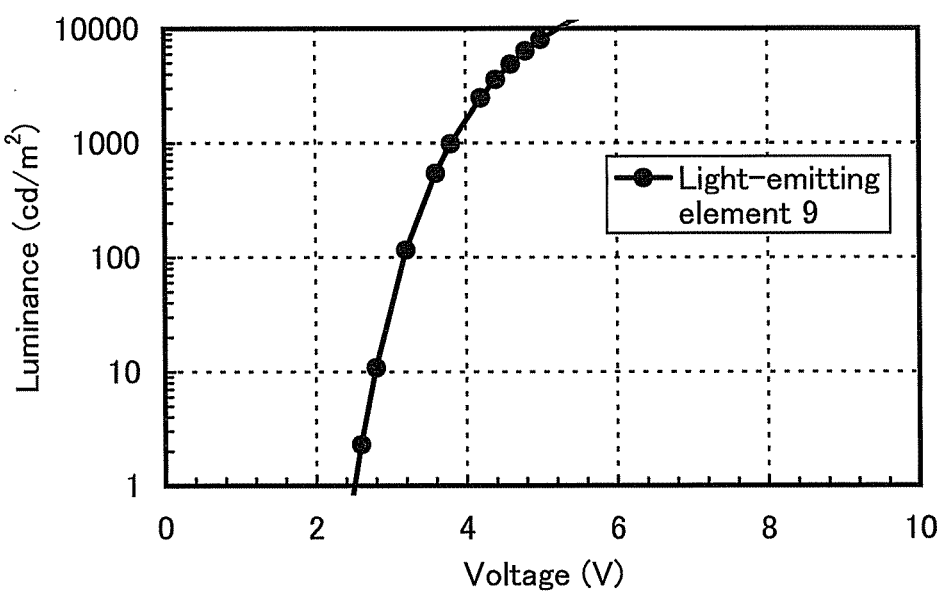
FIG. 63 shows voltage vs. luminance characteristics of Light-emitting element 9.
Figure 64:
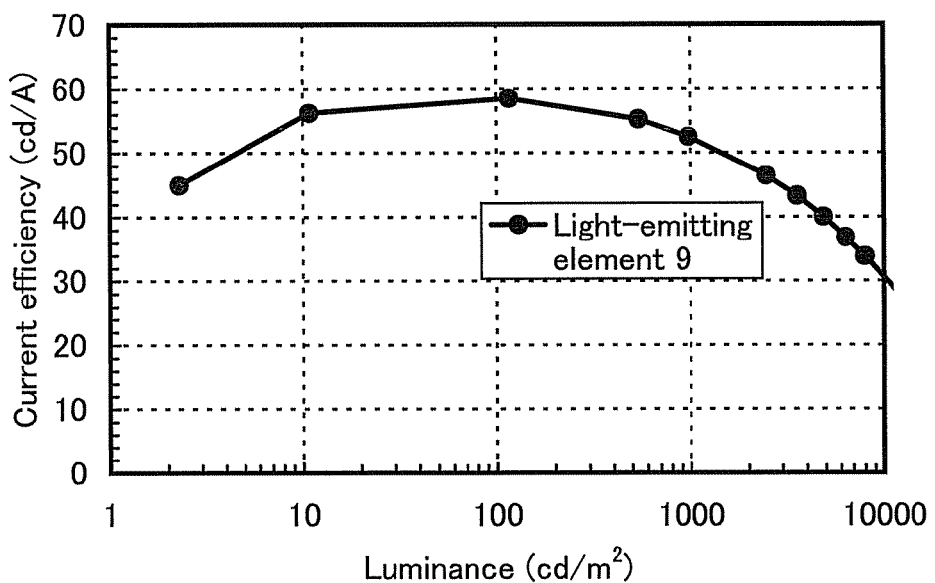
FIG. 64 shows luminance vs. current efficiency characteristics of Light-emitting element 9.
Figure 65:
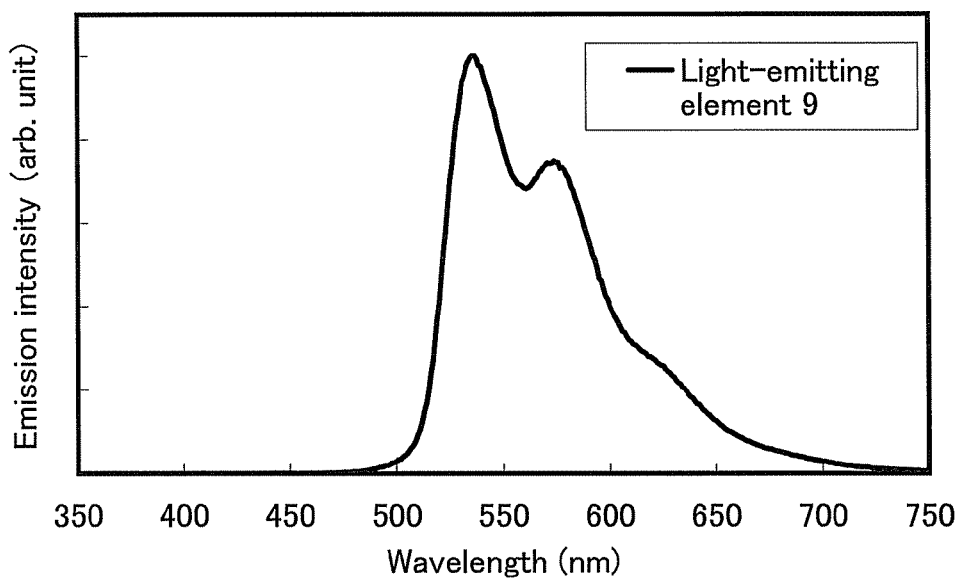
FIG. 65 shows an emission spectrum of Light-emitting element 9.

Next, FIG. 62 shows current density vs. luminance characteristics of Light-emitting element 9. FIG. 63 shows voltage vs. luminance characteristics thereof. FIG. 64 shows luminance vs. current efficiency characteristics thereof. In addition, FIG. 65 shows the emission spectrum thereof at a current of 0.1 mA.

The CIE chromaticity coordinates of Light-emitting element 9 at a luminance of 980 cd/m² are (x=0.42, y=0.57), and yellow-green light was emitted. In addition, at a luminance of 980 cd/m², the current efficiency is 52.5 cd/A, the voltage is 3.8 V, and the current density is 1.87 mA/cm².

These measurement results indicate that Light-emitting element 9 needs a low voltage for obtaining a certain luminance, has low power consumption, and has an extremely high current efficiency.

EXAMPLE 18

Synthesis Example 12

In Example 18, a synthesis example of the organometallic complex tris(3-phenyl-4,5-dipropyl-4H-1,2,4-triazolato)iridium(III) (abbreviation: [Ir(Prptz-Pr)₃]) which is one embodiment of the present invention represented by Structural Formula (146) in Embodiment 1 is specifically described.

Step 1: Synthesis of N-propylbenzamide

First, 10 g of propylamine, 26 g of triethylamine, and 200 mL of tetrahydrofuran (THF) were put in a 500 mL three-neck flask, and stirred. This mixed solution was cooled in ice, and a mixed solution of 24 g of benzoyl chloride and 50 mL of THF was dripped, and then, the temperature was increased to room temperature and the mixture was stirred for 2 hours. After the stirring, chloroform was added to this mixture, the mixture was washed with water and then a saturated aqueous solution of sodium hydrogen carbonate, and anhydrate magnesium sulfate was added for drying. The mixture after the drying was subjected to gravity filtration, and the filtrate was concentrated to give a solid. This solid was washed with hexane, so that 25 g of N-propylbenzamide was prepared as a white solid with a yield of 92%. The synthetic scheme of Step 1 is shown by (a-15).

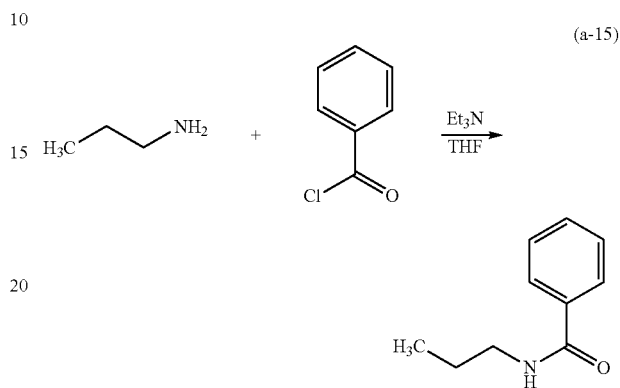

Step 2: Synthesis of N-propylbenzthioamide

Next, 15 g of N-propylbenzamide that was prepared in Step 1 described above, 19 g of 2,4-bis(4-methoxyphenyl)-1,3,2,4-dithiadiphosphetane-2,4-disulfide (Lawesson's reagent), and 100 mL of toluene were put in a 300 mL three-neck flask, and the mixture was heated and refluxed at 120° C. for 5 hours to be reacted. Toluene was distilled off from the reaction solution to give a yellow oily substance. This oily substance was purified by silica gel column chromatography. Toluene was used as a developing solvent. A fraction that showed one spot by thin-layer chromatography (TLC) from the resulting fraction was concentrated, so that 5.8 g of N-propylbenzthioamide was prepared as a yellow oily substance. Further, the other fraction was concentrated to give a mixture of a solid and an oily substance. This mixture was dissolved in ethanol and the solution was subjected to suction filtration to remove insoluble matter. The resulting filtrate was concentrated, so that 10.8 g of N-propylbenzthioamide was prepared as a yellow oily substance. The total yield was 100%. The synthetic scheme of Step 2 is shown by (b-15).

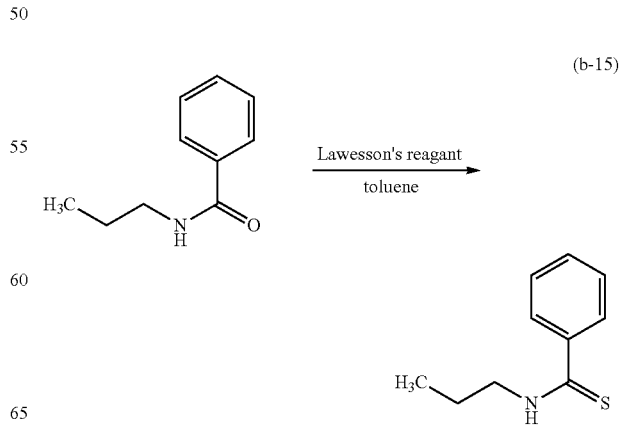

Step 3: Synthesis of N-[(ethylsulfanyl)phenylmethylidene]propylamine

Next, 2.3 g of sodium ethoxide and 5.8 g of N-propylbenzthioamide that was prepared in Step 2 described above were put in a 200 mL recovery flask, 50 mL of ethanol was added, and the mixture was stirred at room temperature for 1 hour. After the stirring, 3.0 mL of iodoethane was added to this mixture, and heated and stirred at 60° C. for 5 hours. After the stirring, ethanol was distilled off to give a brown oily substance. This oily substance was dissolved in dichloromethane, and washed with water and then a saturated aqueous solution of sodium hydrogen carbonate. After the washing, anhydrous magnesium sulfate was added to the resulting organic layer for drying. This mixture was subjected to gravity filtration, and the resulting filtrate was concentrated, so that 5.9 g of N-[(ethylsulfanyl)phenylmethylidene]propylamine was prepared as an orange oily substance with a yield of 88%. The synthetic scheme of Step 3 is shown by (c-15).

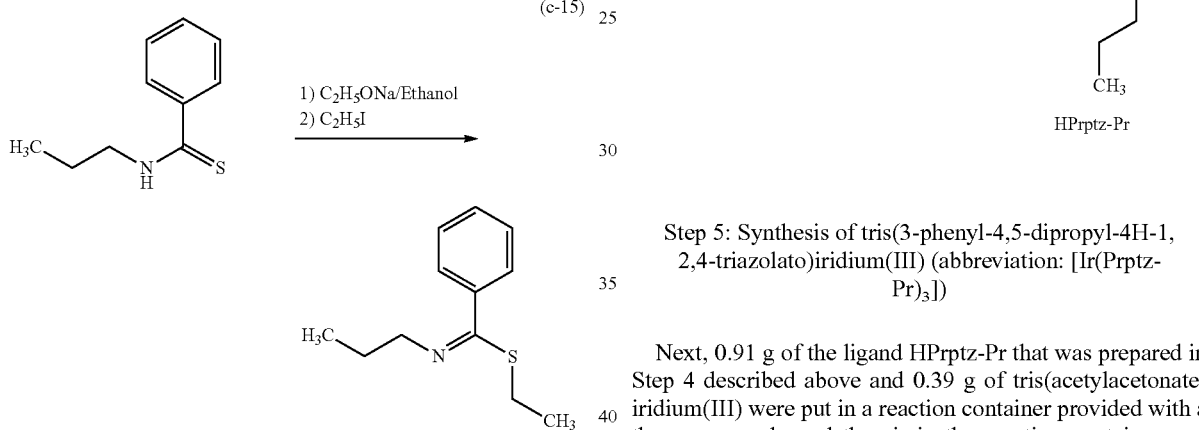

(c-15)

Step 4: Synthesis of 3-phenyl-4,5-dipropyl-4-phenyl-4H-1,2,4-triazole (abbreviation: HPrptz-Pr)

Next, 2.6 g of methyl butanoate and 0.83 mL of hydrazine monohydrate were put in a 100 mL round-bottomed flask, and the air in the flask was replaced with argon. This reaction container was subjected to irradiation with a microwave (2.45 GHz, 100 W) with use of a microwaves synthesis system (Discover, produced by CEM Corporation) to be heated to 90° C. for 1 hour, and the mixture was reacted. Next, 5.9 g of N-[(ethylsulfanyl)phenylmethylidene]propylamine that was prepared in Step 3 described above and 20 mL of 1-butanol were put into this reaction solution, and heated and refluxed at 130° C. for 10 hours. After the reflux, 1-butanol was distilled off to give a residue. This residue was washed with a small amount of ethyl acetate, and subjected to suction filtration. The resulting filtrate was purified by silica gel column chromatography. Ethyl acetate was used as a developing solvent. The resulting fraction was concentrated, so that 3-phenyl-4,5-dipropyl-4-phenyl-4H-1,2,4-triazole (abbreviation: HPrptz-Pr) was prepared (a yellow oily substance, yield: 35%). The synthetic scheme of Step 4 is shown by (d-15).

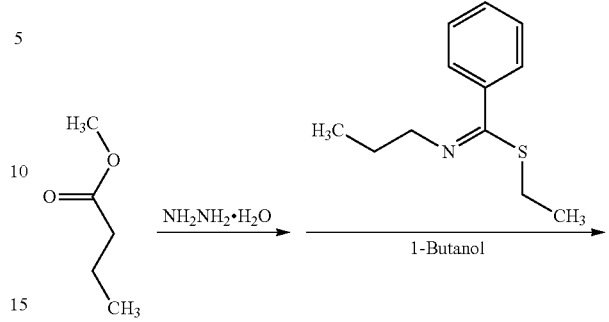

(d-15)

Step 5: Synthesis of tris(3-phenyl-4,5-dipropyl-4H-1,2,4-triazolato)iridium(III) (abbreviation: [Ir(Prptz-Pr)$_3$])

Next, 0.91 g of the ligand HPrptz-Pr that was prepared in Step 4 described above and 0.39 g of tris(acetylacetonate)iridium(III) were put in a reaction container provided with a three-way cock, and the air in the reaction container was replaced with argon. Then, the mixture was heated at 200° C. for 41 hours to be reacted. The reactant was dissolved in dichloromethane, and this solution was filtrated through an filter aid in which Celite and silica gel is stacked. The solvent of the resulting filtrate was distilled off and purification was conducted by silica gel column chromatography which uses chloroform:ethyl acetate=20:1 (v/v) as a developing solvent. The solvent of the resulting fraction was distilled off, so that the organometallic complex [Ir(iPrFptz)$_3$] which is one embodiment of the present invention was prepared (light yellow powder, yield: 6%). The synthetic scheme of Step 5 is shown by (e-15).

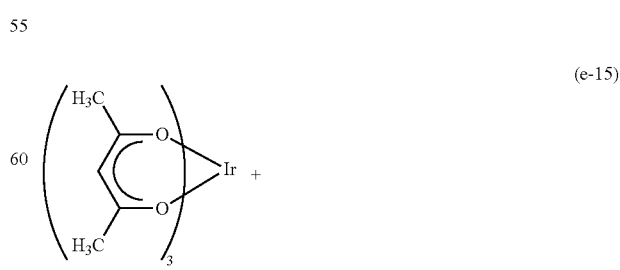

(e-15)

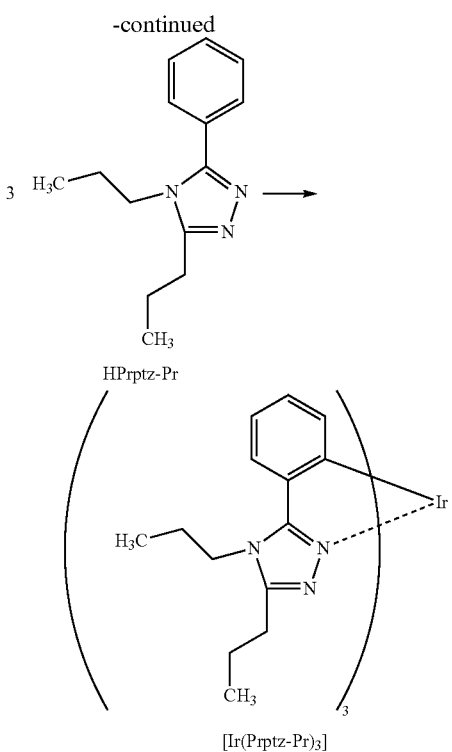

[Ir(Prptz-Pr)₃]

An analysis result by nuclear magnetic resonance spectroscopy (¹H-NMR) of the light yellow powder prepared in Step 5 described above is shown below. From the results, it is found that the organometallic complex [Ir(Prptz-Pr)₃] which is one embodiment of the present invention represented by Structural Formula (146) was prepared in Synthesis Example 12.

¹H-NMR. δ(CDCl₃): 0.98 (t, 9H), 1.05 (t, 9H), 1.78-1.98 (m, 12H), 2.75 (t, 6H), 4.05 (t, 6H), 7.26-7.38 (m, 9H), 8.06 (d, 3H).

EXAMPLE 19

Synthesis Example 13

In Example 19, a synthesis example of the organometallic complex tris[3-(5-biphenyl)-5-isopropyl-4-phenyl-4H-1,2,4-triazolato]iridium(III) (abbreviation: [Ir(iPr5btz)₃]) which is one embodiment of the present invention represented by Structural Formula (149) in Embodiment 1 is specifically described.

Step 1: Synthesis of 3-phenylethyl benzoate

First, 7.98 g of phenylboronic acid, 15 g of 3-bromoethyl benzoate, 0.265 g of tri(ortho-tolyl)phosphine, 200 mL of toluene, 30 mL of ethanol, and 65 mL of 2.0M aqueous solution of potassium carbonate were put in a 500 mL three-neck flask, and the air in the flask was replaced with nitrogen. Then, 0.147 g of palladium(II) acetate (Pd(OAc)₂) was added to this mixed solution, and heated and stirred at 80° C. for 5 hours. After a certain time, an aqueous layer of this mixture was extracted with toluene. The extract and the organic layer were combined, washed with a saturated aqueous solution of sodium hydrogen carbonate and then saturated saline. Anhydrate magnesium sulfate was added to the organic layer for drying, and the resulting mixture was subjected to gravity filtration to give a filtrate. This filtrate was concentrated to give an oily substance. The given oily substance was purified using silica gel column chromatography. As developing solvents, first, hexane was used, and then a mixed solvent of hexane:ethyl acetate=9:1 was used. The resulting fraction was concentrated, so that 3-phenylethyl benzoate was prepared (a colorless oily substance, yield: 88%). The synthetic scheme of Step 1 is shown by (a-16).

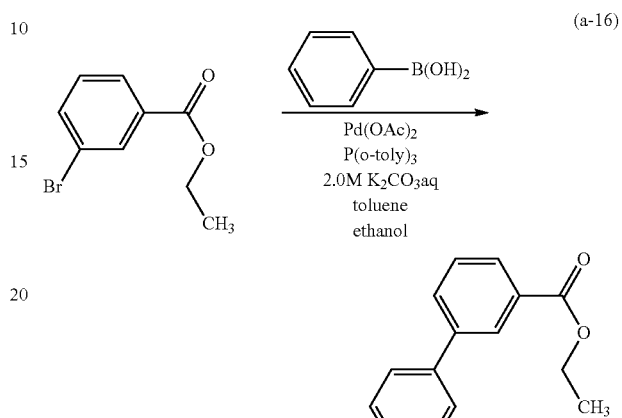

(a-16)

Step 2: Synthesis of biphenyl-3-carboxylic Acid Hydrazide

Next, 13.1 g of 3-phenylethyl benzoate that was prepared in Step 1 described above and 80 mL of ethanol were put in a 200 mL three-neck flask. Then, 15 mL of hydrazine monohydrate was added to this mixed solution, and heated and stirred at 80° C. for 5 hours. After a predetermined time, the reaction solution was cooled to room temperature, whereby a solid was precipitated. The resulting mixture was added to 200 mL of water and subjected to suction filtration to give a solid. This solid was washed with hexane, so that biphenyl-3-carboxylic acid hydrazide was prepared (a white solid, yield: 91%). The synthetic scheme of Step 2 is shown by (b-16).

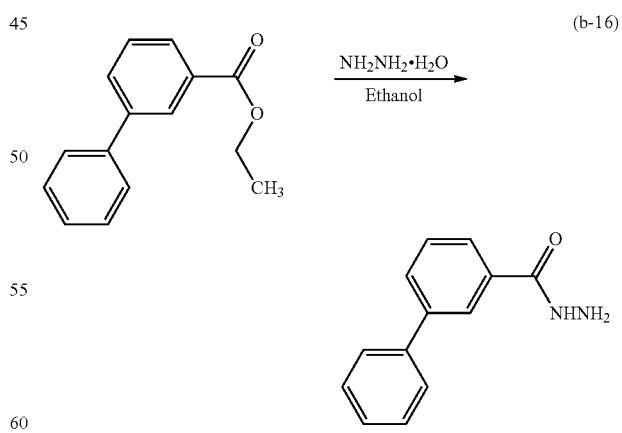

(b-16)

Step 3: Synthesis of 3-(3-biphenyl)-5-isopropyl-4-phenyl-4H-1,2,4-triazole (abbreviation: HiPr5btz)

Next, 5.0 g of N-[1-(ethylsulfanyl)isobutylidene]aniline, 4.60 g of biphenyl-3-carboxylic acid hydrazide that was prepared in Step 2 described above, and 30 mL of 1-butanol, were put in a 100 mL three-neck flask, and heated and stirred at 130° C. for 15 hours. After the stirring, the reaction solution was concentrated to give a solid. This solid was purified by silica gel column chromatography. Ethyl acetate was used as a developing solvent. The resulting fraction was concentrated to give an oily substance. This oily substance was recrystallized from a mixed solvent of ethanol and hexane, so that 3-(3-biphenyl)-5-isopropyl-4-phenyl-4H-1,2,4-triazole (abbreviation: HiPr5btz) was prepared (a white solid, yield: 19%). The synthetic scheme of Step 3 is shown by (c-16).

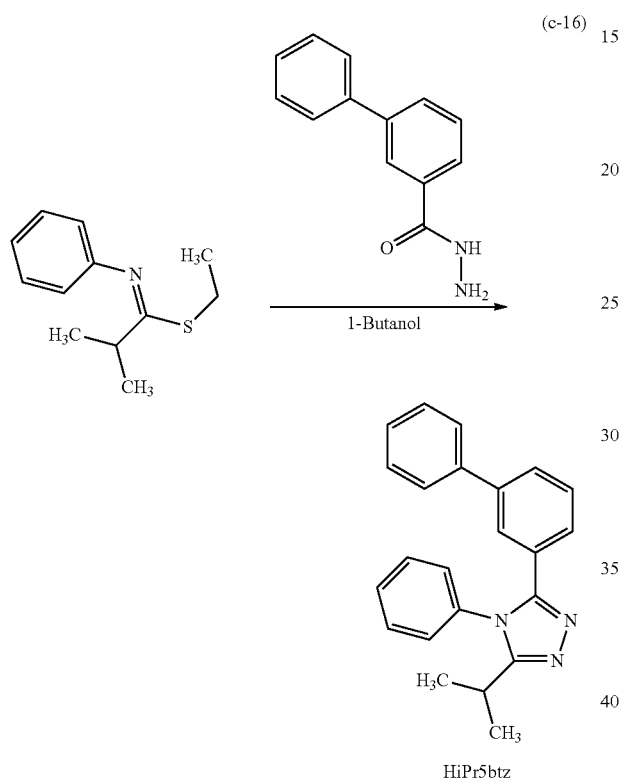

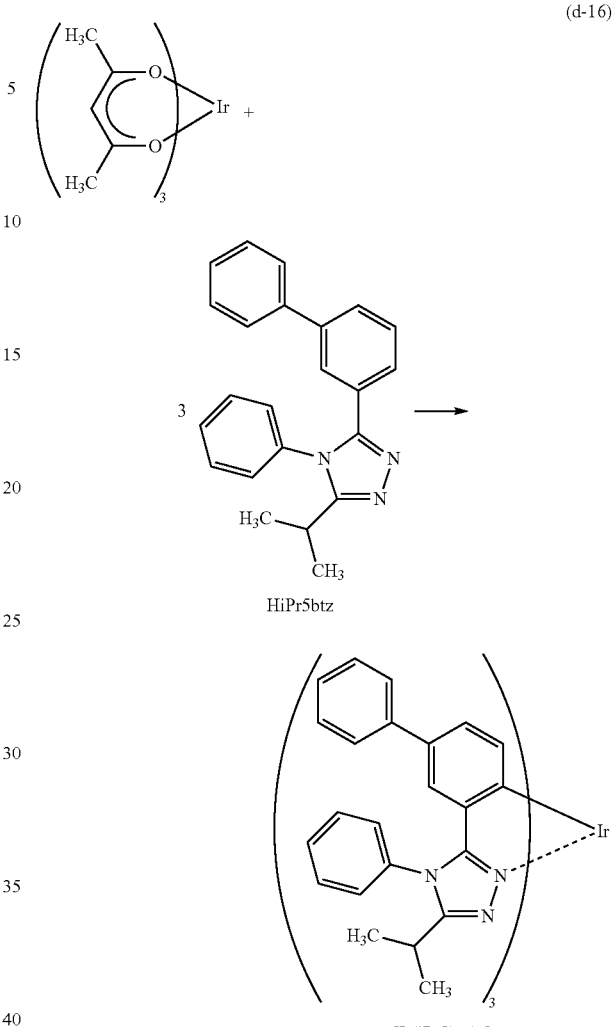

Step 4: Synthesis of tris[3-(5-biphenyl)-5-isopropyl-4-phenyl-4H-1,2,4-triazolato]iridium(III) (abbreviation: [Ir(iPr5btz)₃])

Next, 1.41 g of the ligand HiPr5btz that was prepared in Step 3 described above, and 0.41 g of tris(acetylacetonate)iridium(III) were put in a reaction container provided with a three-way cock, and the air in the reaction container was replaced with argon. First, the mixture was heated at 220° C. for 49 hours, and then heated at 250° C. for 20 hours to be reacted. The resulting reaction mixture was dissolved in dichloromethane and purified by silica gel column chromatography. A mixed solvent of dichloromethane:ethyl acetate=5:1 was used as a developing solvent. The resulting fraction was concentrated to give a solid. This solid was recrystallized from a mixed solvent of ethyl acetate and hexane, so that the organometallic complex [Ir(iPr5btz)₃] which is one embodiment of the present invention was prepared (yellow powder, yield: 8%). The synthetic scheme of Step 4 is shown by (d-16).

Figure 66:
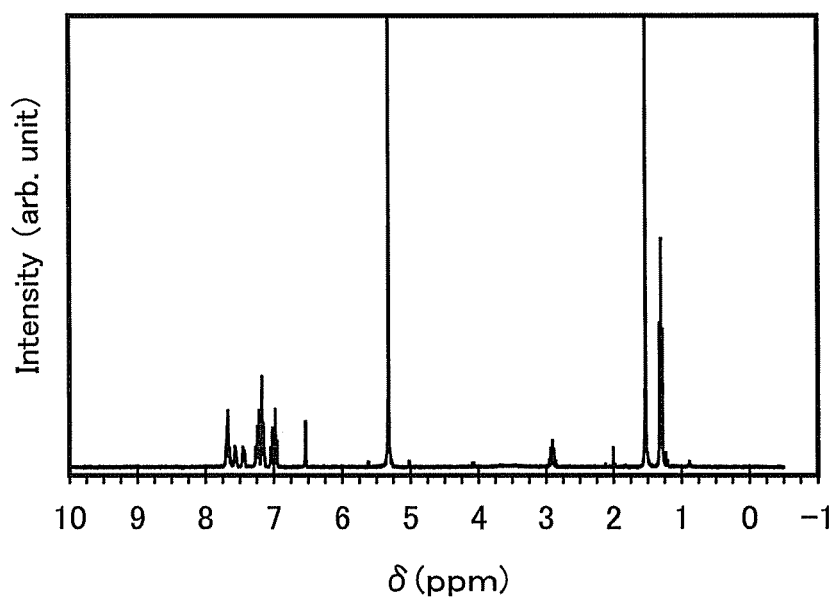
FIG. 66 shows a ¹H-NMR chart of [Ir(iPr5btz)₃].

An analysis result by nuclear magnetic resonance spectroscopy (¹H-NMR) of the yellow powder prepared in Step 4 described above is shown below. The ¹H-NMR chart is shown in FIG. 66. From the results, it is found that the organometallic complex [Ir(iPr5btz)₃] which is one embodiment of the present invention represented by Structural Formula (149) was prepared in Synthesis Example 13.

¹H-NMR. δ(CD₂Cl₂): 1.27-1.32 (m, 18H), 2.93 (sep, 3H), 6.53 (d, 3H), 6.95-7.05 (m, 6H), 7.13-7.27 (m, 15H), 7.43-7.46 (m, 3H), 7.54-7.56 (m, 3H), 7.57-7.70 (m, 9H).

Figure 67:
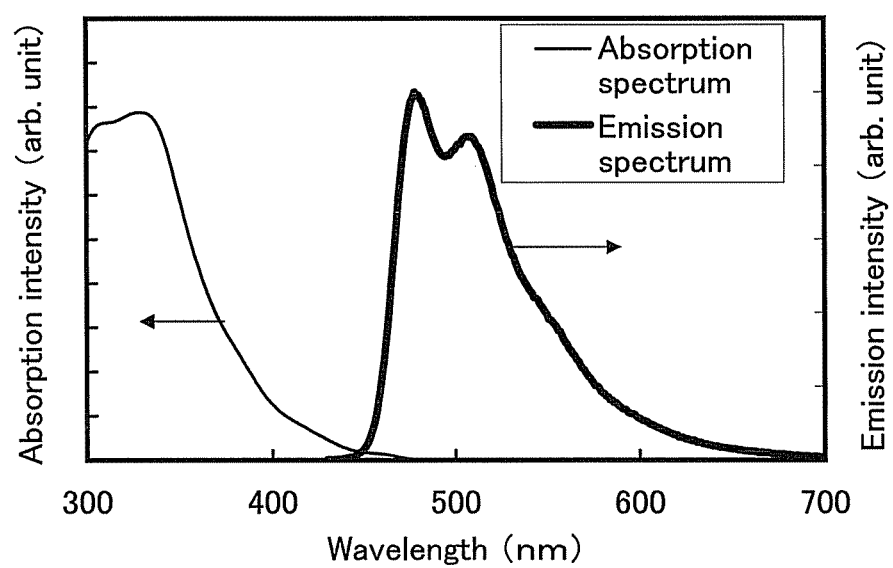
FIG. 67 shows an absorption spectrum and an emission spectrum of [Ir(iPr5btz)₃] in a dichloromethane solution.

Next, an ultraviolet-visible absorption spectrum (hereinafter, simply referred to as an absorption spectrum) and an emission spectrum of [Ir(iPr5btz)₃] in a dichloromethane solution were measured. The absorption spectrum was measured with the use of an ultraviolet-visible light spectrophotometer (V550 type manufactured by Japan Spectroscopy Corporation) in the state where the dichloromethane solution (0.041 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.082 mmol/L) was put in a quartz cell at room temperature. FIG. 67 shows measurement results of the absorption spectrum and emission spectrum. The horizontal axis represents wavelength and the vertical axis represents absorption intensity and emission intensity. In FIG. 67, two solid lines are shown; a thin line represents the absorption spectrum, and a thick line represents the emission spectrum. Note that the absorption spectrum in FIG. 67 is a result obtained by subtraction of the absorption spectrum of only dichloromethane that was put in a quartz cell from the measured absorption spectrum of the dichloromethane solution (0.041 mmol/L) in a quartz cell.

As shown in FIG. 67, the organometallic complex [Ir(iPr5btz)$_3$] which is one embodiment of the present invention has a peak of emission at 500 nm, and green light was observed from the dichloromethane solution.

EXAMPLE 20

Synthesis Example 14

In Example 20, a synthesis example of the organometallic complex tris[3-(5-biphenyl)-5-isopropyl-4-(2,6-dimethylphenyl)-4H-1,2,4-triazolato]iridium(III) (abbreviation: [Ir(iPr5btz-dmp)$_3$]) which is one embodiment of the present invention represented by Structural Formula (152) in Embodiment 1 is specifically described.

Step 1: Synthesis of
N-(2,6-dimethylphenyl)-3-bromobenzamide

First, 13.8 g of 2,6-dimethylaniline, 17.3 g of triethylamine, and 150 mL of tetrahydrofuran (THF) were put in a 500 mL three-neck flask, and stirred. This mixed solution was cooled in ice, and a mixed solution of 25 g of 3-bromobenzoyl chloride and 30 mL of THF was dripped through a dropping funnel, and then, the temperature was increased to room temperature and the mixture was stirred for 24 hours. After the stirring, chloroform was added to this mixture, the mixture was washed with water and then saturated saline, and anhydrate magnesium sulfate was added for drying. The mixture after the drying was subjected to gravity filtration, and the filtrate was concentrated to give a solid. This solid was washed with hexane, so that N-(2,6-dimethylphenyl)-3-bromobenzamide was prepared as a white solid with a yield of 53%. The synthetic scheme of Step 1 is shown by (a-17).

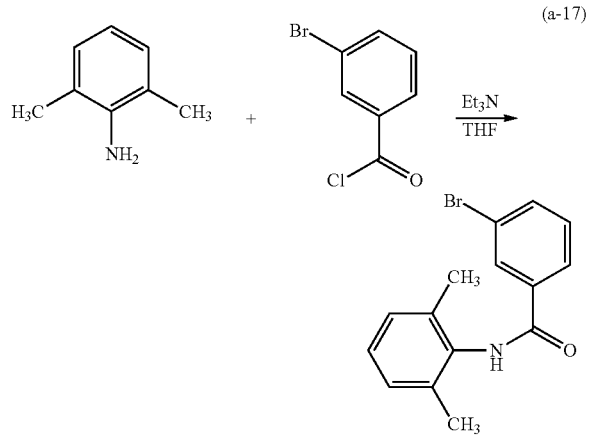

Step 2: Synthesis of
N-(2,6-dimethylphenyl)-3-bromobenzthioamide

Next, 13.8 g of N-(2,6-dimethylphenyl)-3-bromobenzamide that was prepared in Step 1 described above, 19 g of 2,4-bis(4-methoxyphenyl)-1,3,2,4-dithiadiphosphetane-2,4-disulfide (Lawesson's reagent), and 100 mL of toluene were put in a 300 mL three-neck flask, and the mixture was heated and refluxed at 110° C. for 3.5 hours to be reacted. Toluene was distilled off from the reaction solution to give a yellow oily substance. This oily substance was purified by silica gel column chromatography. As a developing solvent, toluene:hexane=4:1 (v/v) was used. The resulting fraction was concentrated to give a solid. This solid was washed with a mixed solvent of toluene and hexane, so that N-(2,6-dimethylphenyl)-3-bromobenzthioamide was prepared as a yellow solid with a yield of 86%. The synthetic scheme of Step 2 is shown by (b-17).

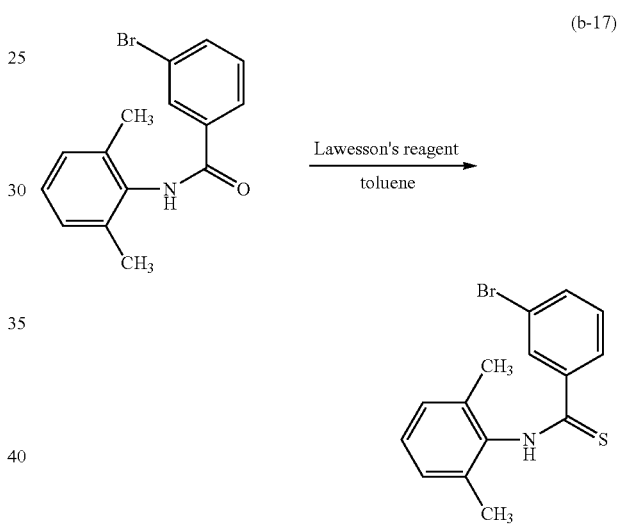

Step 3: Synthesis of N-[(3-bromophenyl)(ethylsulfanyl)methylidene]-2,6-dimethylaniline Next, 2.66 g of sodium ethoxide and 12.5 g of N-(2,6-dimethylphenyl)-3-bromobenzthioamide that was prepared in Step 2 described above were put in a 200 mL recovery flask, 30 mL of ethanol was added, and the mixture was stirred at room temperature for 1 hour. After the stirring, 5 mL of iodoethane was added to this mixture, and further stirred at 60° C. for 10 hours. After the stirring, ethanol was distilled off to give a residue. This residue was dissolved in dichloromethane, and washed with water and then a saturated aqueous solution of sodium hydrogen carbonate, and further with saturated saline, and anhydrate magnesium sulfate was added for drying. This mixture was subjected to gravity filtration, and the resulting filtrate was concentrated, so that N-[(3-bromophenyl)(ethylsulfanyl)methylidene]-2,6-dimethylaniline was prepared as a brown oily substance with a yield of 85%. The synthetic scheme of Step 3 is shown by (c-17).

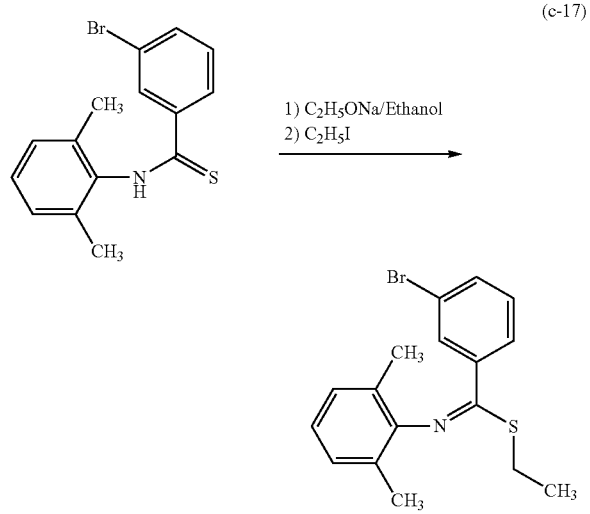

(c-17)

Step 4: Synthesis of 3-(3-bromophenyl)-5-isopropyl-4-(2,6-dimethylphenyl)-4H-1,2,4-triazole Next, 11.6 g of N-[(3-bromophenyl)(ethylsulfanyl)methylidene]-2,6-dimethylaniline that was prepared in Step 3 described above and 50 mL of 1-butanol were put in a 100 mL three-neck flask, and stirred. Further, 2.72 g of isobutyric acid hydrazide was added to this mixed solution, and heated and refluxed at 130° C. for 14 hours. After that, 1.36 g of isobutyric acid hydrazide was further added, and heated and refluxed at 130° C. for 12.5 hours. After the reflux, 1-butanol was distilled off to give a residue. This residue was purified by silica gel column chromatography. Ethyl acetate was used as a developing solvent. The resulting fraction was condensed to give a solid. This solid was recrystallized from a mixed solvent of ethyl acetate and hexane, so that 3-(3-bromophenyl)-5-isopropyl-4-(2,6-dimethylphenyl)-4H-1,2,4-triazole was prepared (white powder, yield: 16%). The synthetic scheme of Step 4 is shown by (d-17).

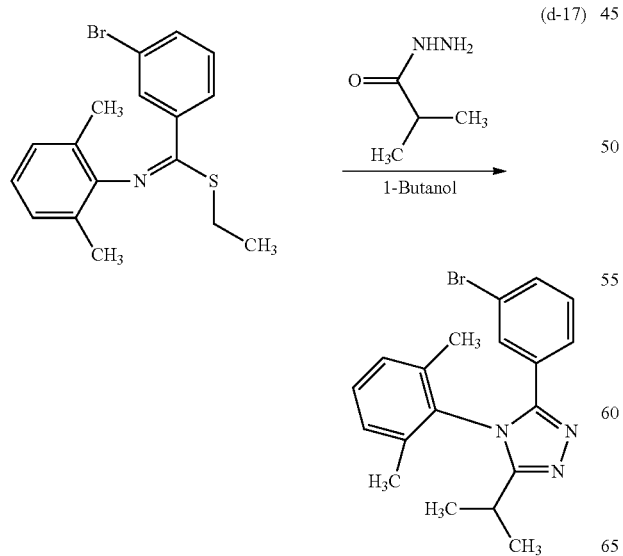

(d-17)

Step 5: Synthesis of 3-(3-biphenyl)-5-isopropyl-4-(2,6-dimethylphenyl)-4H-1,2,4-triazole (abbreviation: HiPr5btz-dmp)

Next, 1.97 g of 3-(3-bromophenyl)-5-isopropyl-4-(2,6-dimethylphenyl)-4H-1,2,4-triazole that was prepared in Step 4 described above, 0.650 g of phenylboronic acid, 0.048 g of tri(ortho-tolyl)phosphine, 15 mL of toluene, 3 mL of ethanol, and 5.3 mL of 2.0M aqueous solution of potassium carbonate were put in a 100 mL three-neck flask, and the air in the flask was replaced with nitrogen. Then, 0.012 g of palladium(II) acetate was added to this mixed solution, and heated and stirred at 80° C. for 6 hours to be reacted. After the reaction, this mixture was separated to an organic layer and an aqueous layer, and the aqueous layer was extracted with toluene. The extract and the previously resulting organic layer were combined, and washed with a saturated aqueous solution of sodium hydrogen carbonate and then with saturated saline, and anhydrate magnesium sulfate was added for drying. After the drying, the resulting mixture was subjected to gravity filtration to give a filtrate. This filtrate was concentrated to give an oily substance. The given oily substance was purified by silica gel column chromatography. As a developing solvent, hexane:ethyl acetate=1:1 (v/v) was used. The resulting fraction was concentrated, so that 3-(3-biphenyl)-5-isopropyl-4-(2,6-dimethyl-phenyl)-4H-1,2,4-triazole (abbreviation: HiPr5btz-dmp) was prepared (white powder, yield: 85%). The synthetic scheme of Step 5 is shown by (e-17).

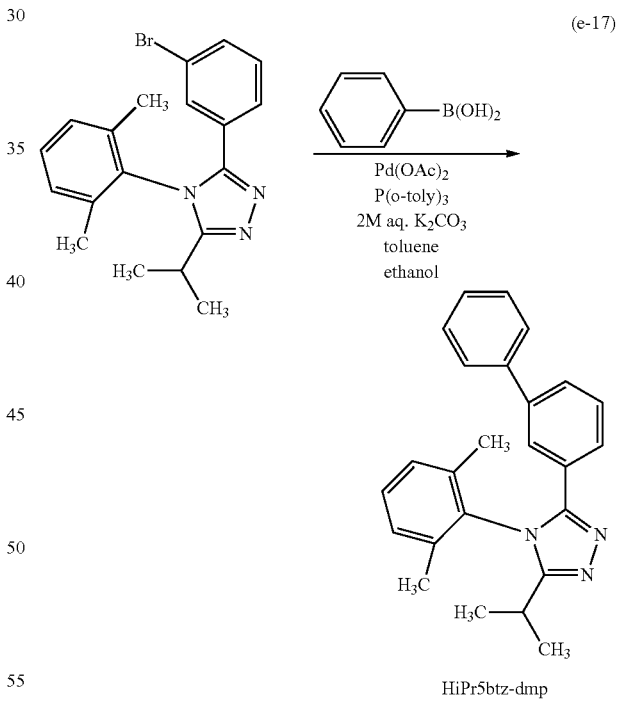

(e-17)

Step 6: Synthesis of tris[3-(5-biphenyl)-5-isopropyl-4-(2,6-dimethylphenyl)-4H-1,2,4-triazolato]iridium (III) (abbreviation: [Ir(iPr5btz-dmp)₃])

Further, 0.55 g of the ligand HiPr5btz-dmp that was prepared in Step 5 described above and 0.15 g of tris(acetylacetonate)iridium(III) were put in a reaction container provided with a three-way cock, and the air in the reaction container was replaced with argon. Then, the mixture was heated at 250° C. for 43.5 hours to be reacted. The reactant was dissolved in dichloromethane, and purified by silica gel column chromatography which uses dichloromethane:ethyl acetate=10:1 (v/v) as a developing solvent. The solvent of the resulting fraction was distilled off and the resulting solid was washed with a mixed solvent of ethyl acetate and hexane. Then, recrystallization was carried out with a mixed solvent of ethanol and hexane, so that the organometallic complex [Ir(iPr5btz-dmp)$_3$] which is one embodiment of the present invention was prepared (yellow powder, yield: 0.2%). The synthetic scheme of Step 6 is shown by (f-17).

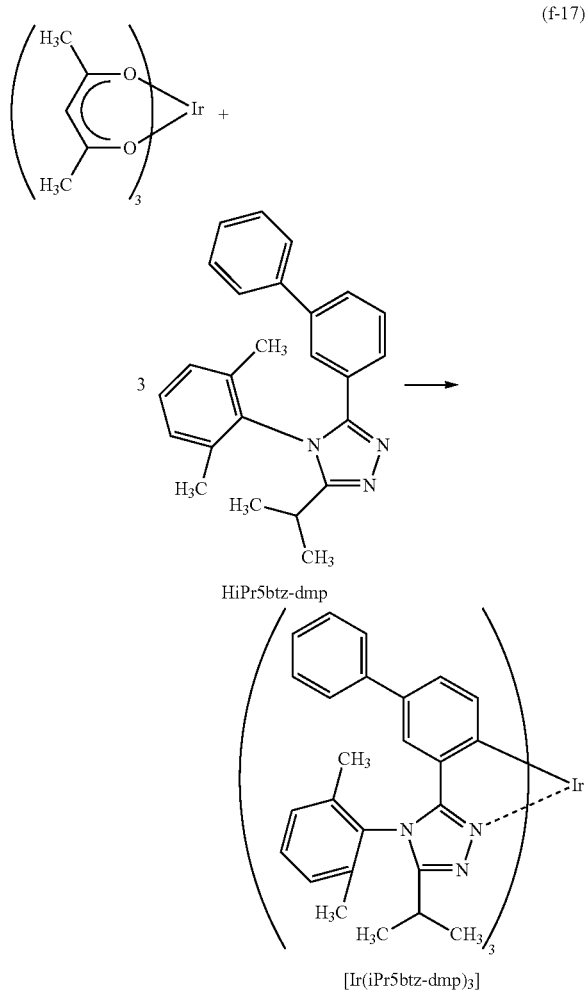

Figure 68:
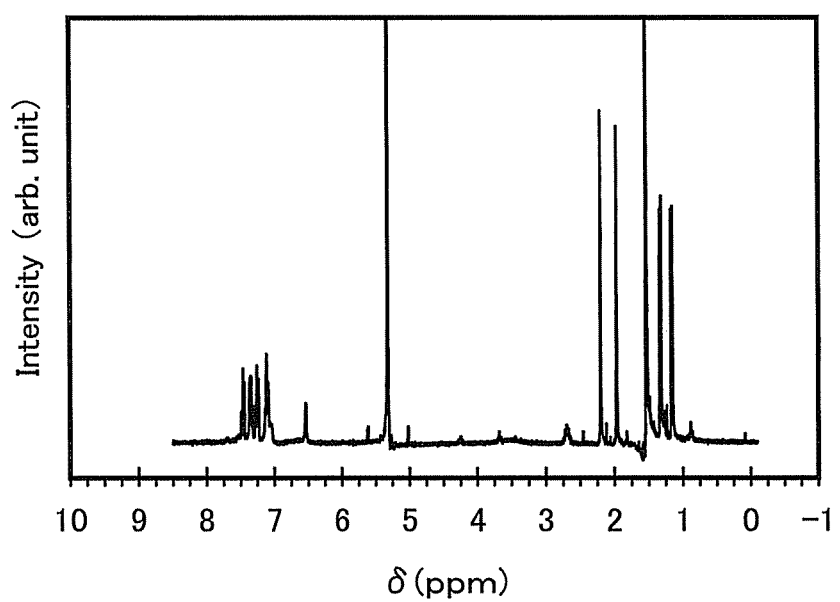
FIG. 68 shows a ¹H-NMR chart of [Ir(iPr5btz-dmp)₃].

An analysis result by nuclear magnetic resonance spectroscopy ($^1$H-NMR) of the yellow powder prepared in Step 6 described above is shown below. The $^1$H-NMR chart is shown in FIG. 68. From the results, it is found that the organometallic complex [Ir(iPr5btz-dmp)$_3$] which is one embodiment of the present invention represented by Structural Formula (152) was prepared in Synthesis Example 14.

$^1$H-NMR. δ(CDCl$_3$): 1.16 (d, 9H), 1.33 (d, 9H), 1.97 (s, 9H), 2.20 (s, 9H), 2.67-2.74 (m, 3H), 6.54 (s, 3H), 7.04-7.11 (m, 12H), 7.23-7.37 (m, 15H), 7.46 (t, 3H).

Figure 69:
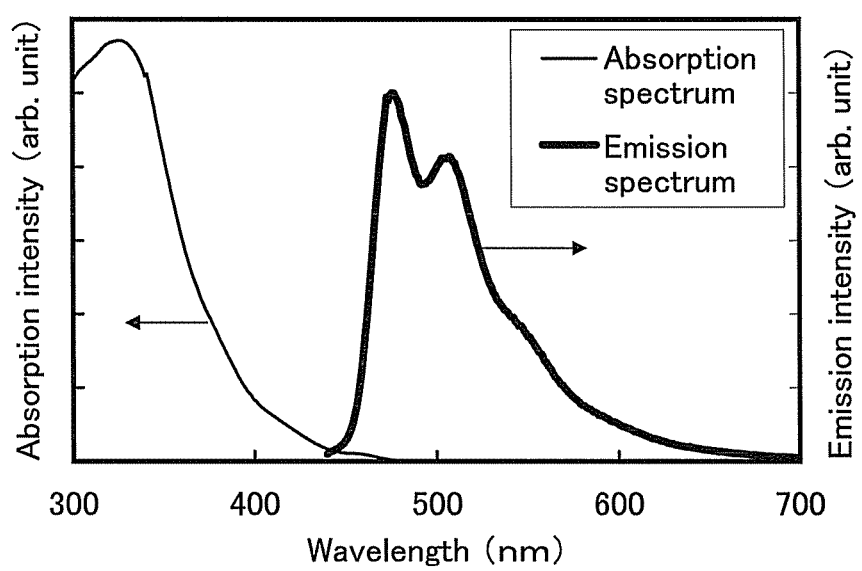
FIG. 69 shows an absorption spectrum and an emission spectrum of [Ir(iPr5btz-dmp)₃] in a dichloromethane solution.

Next, an ultraviolet-visible absorption spectrum (hereinafter, simply referred to as an absorption spectrum) and an emission spectrum of [Ir(iPr5btz-dmp)$_3$] in a dichloromethane solution were measured. The absorption spectrum was measured with the use of an ultraviolet-visible light spectrophotometer (V550 type manufactured by Japan Spectroscopy Corporation) in the state where the dichloromethane solution (0.059 mmol/L) was put in a quartz cell at room temperature. The emission spectrum was measured with the use of a fluorescence spectrophotometer (FS920 manufactured by Hamamatsu Photonics Corporation) in the state where the degassed dichloromethane solution (0.059 mmol/L) was put in a quartz cell at room temperature. FIG. 69 shows measurement results of the absorption spectrum and emission spectrum. The horizontal axis represents wavelength and the vertical axis represents absorption intensity and emission intensity. In FIG. 69, two solid lines are shown; a thin line represents the absorption spectrum, and a thick line represents the emission spectrum. Note that the absorption spectrum in FIG. 69 is a result obtained by subtraction of the absorption spectrum of only dichloromethane that was put in a quartz cell from the measured absorption spectrum of the dichloromethane solution (0.059 mmol/L) in a quartz cell.

As shown in FIG. 69, the organometallic complex [Ir(iPr5btz-dmp)$_3$] which is one embodiment of the present invention has peaks of emission at 477 tun and 509 nm, and green light was observed from the dichloromethane solution.

EXAMPLE 21

Structures, fabrication methods, and measurement results of element characteristics of a light-emitting element which includes an organometallic complex which is one embodiment of the present invention are described.

The element structure of Light-emitting element 11 which is fabricated in Example 21 is illustrated in FIG. 43. Light-emitting element 11 includes the substrate 1100, the first electrode 1101 formed thereover, and the second electrode 1102 formed over the first electrode 1101 between which the EL layer 1103 including a stack of a plurality of layers is interposed. The EL layer 1103 of Light-emitting element 11 of Example 21 has a structure in which the hole-injection layer 1111, the hole-transport layer 1112, the light-emitting layer 1113, the electron-transport layer 1114, and the electron-injection layer 1115 are sequentially stacked. Note that the light-emitting layer 1113 has a structure in which a first light-emitting layer and a second light-emitting layer are stacked.

Detailed structures of the light-emitting element manufactured are shown in Table 5. Note that the light-emitting layer 1113 is formed using an organometallic complex of one embodiment of the present invention as a light-emitting material in Light-emitting element 11.

TABLE 5

| | First Electrode | Hole-injection Layer | Hole-transport Layer | Light-emitting Layer | |
|---|---|---|---|---|---|
| Light-emitting Element 11 (149) | ITSO 110 nm | CBP: MoOx (=2:1) 50 nm | mCP 10 nm | mCP: [Ir(iPr5btz)$_3$] (=1:0.08) 30 nm | mDBTBIm-II: [Ir(iPr5btz)$_3$] (=1:0.08) 10 nm |

| | Electron-transport Layer | Electron-injection Layer | Second Electrode |
|---|---|---|---|
| Light-emitting Element 11 (149) | BPhen 15 nm | LiF 1 nm | Al 200 nm |

(Fabrication of Light-Emitting Element 11)

Next, a method for manufacturing Light-emitting element 11 is described. Note that a light-emitting layer of Light-emitting element 11 contains the organometallic complex tris[3-(5-biphenyl)-5-isopropyl-4-phenyl-4H-1,2,4-triazolato]iridium(III) (abbreviation: [Ir(iPr5btz)$_3$]), which is one embodiment of the present invention represented by Structural Formula (149) of Embodiment 1, as a light-emitting material.

First, over the glass substrate 1100, indium tin oxide containing silicon oxide (abbreviation: ITSO) was deposited by a sputtering method, so that the first electrode 1101 which functions as an anode was formed. The thickness of the first electrode 1101 was 110 nm and the electrode area was 2 mm×2 mm.

Next, the glass substrate 1100 over which the first electrode 1101 was formed was fixed to a substrate holder provided in a vacuum evaporation apparatus such that the side on which the first electrode 1101 was formed faced downward, and the pressure was reduced to approximately $10^{-4}$ Pa.

Next, the hole-injection layer 1111 was formed over the first electrode 1101. The hole-injection layer 1111 was formed using a layer containing a composite material of an organic compound and an inorganic compound formed by co-evaporation of 4,4'-di(N-carbazolyl)biphenyl (abbreviation: CBP), and molybdenum(VI) oxide. The thickness of the layer containing a composite material was 50 nm, and the weight ratio of CBP and molybdenum oxide was adjusted to 2:1 (=CBP:molybdenum oxide).

Next, the hole-transport layer 1112 was formed over the hole-injection layer 1111. A 10-nm-thick 1,3-bis(N-carbazolyl)benzene (abbreviation: mCP) layer was formed as the hole-transport layer 1112 by an evaporation method using resistance heating.

Next, the light-emitting layer 1113 was formed over the hole-transport layer 1112. The light-emitting layer 1113 was formed in such a manner that a 30-nm-thick film is formed by co-evaporation of mCP and [Ir(iPr5btz)$_3$] and a 10-nm-thick film by co-evaporation of 2-[3-(dibenzothiophene-4-yl)phenyl]-1-phenyl-1H-benzimidazol (abbreviation: mDBTBIm-II) and [Ir(iPr5btz)$_3$]. The evaporation rate was adjusted so that the weight ratio of mCP and [Ir(iPr5btz)$_3$] was 1:0.08 (=mCP:[Ir(iPr5btz)$_3$]). The evaporation rate was adjusted so that the weight ratio of mDBTBIm-II and [Ir(iPr5btz)$_3$] was 1:0.08 (=mDBTBIm-II:[Ir(iPr5btz)$_3$]).

Next, the electron-transport layer 1114 was formed over the light-emitting layer 1113. A 20-nm-thick bathophenanthroline (abbreviation: BPhen) layer was formed as the electron-transport layer 1114 by an evaporation method using resistance heating.

Then, the electron-injection layer 1115 was formed over the electron-transport layer 1114. A 1-nm-thick lithium fluoride (LiF) layer was evaporated as the electron-injection layer 1115.

Lastly, the second electrode 1102 was formed over the electron-injection layer 1115. A 200-nm-thick aluminum layer was evaporated as the second electrode 1102; thus, Light-emitting element 11 was fabricated.

Sealing was performed in a glove box under a nitrogen atmosphere so that the resulting Light-emitting element 11 was not exposed to the atmosphere, and then operation characteristics of this light-emitting element were measured. Note that the measurement was carried out at room temperature (in an atmosphere kept at 25° C.).

(Evaluation Results)

Figure 70:
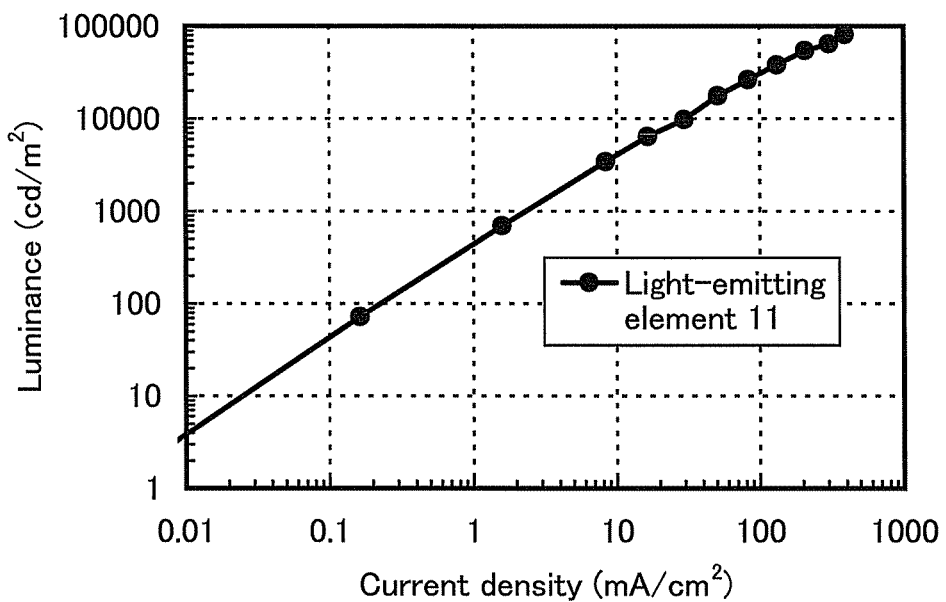
FIG. 70 shows current density vs. luminance characteristics of Light-emitting element 11.
Figure 71:
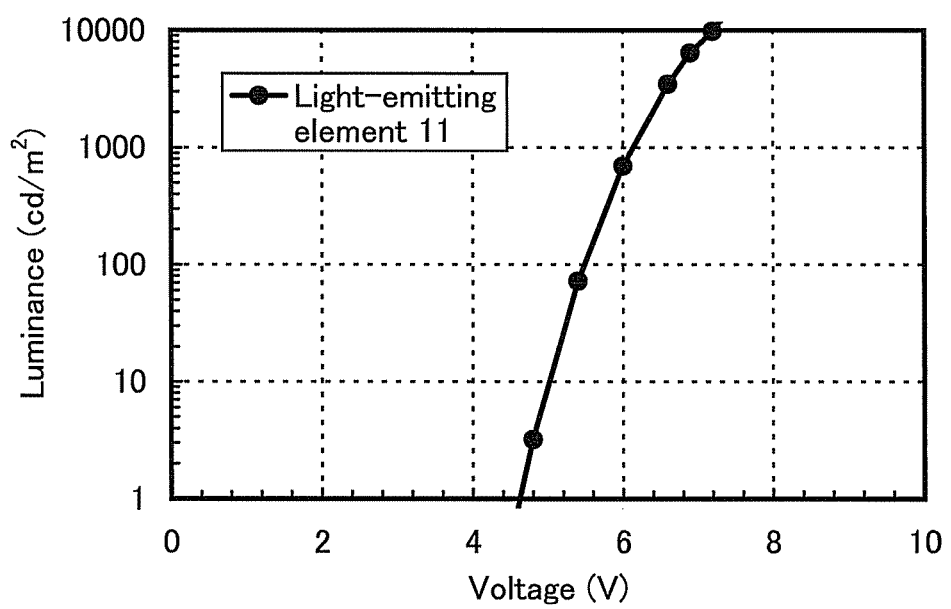
FIG. 71 shows voltage vs. luminance characteristics of Light-emitting element 11.
Figure 72:
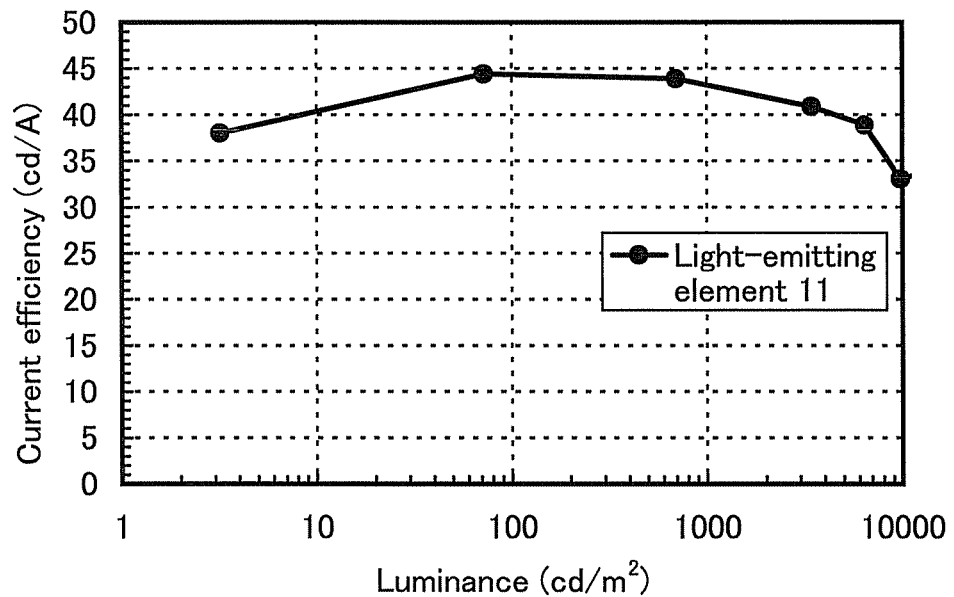
FIG. 72 shows luminance vs. current efficiency characteristics of Light-emitting element 11.
Figure 73:
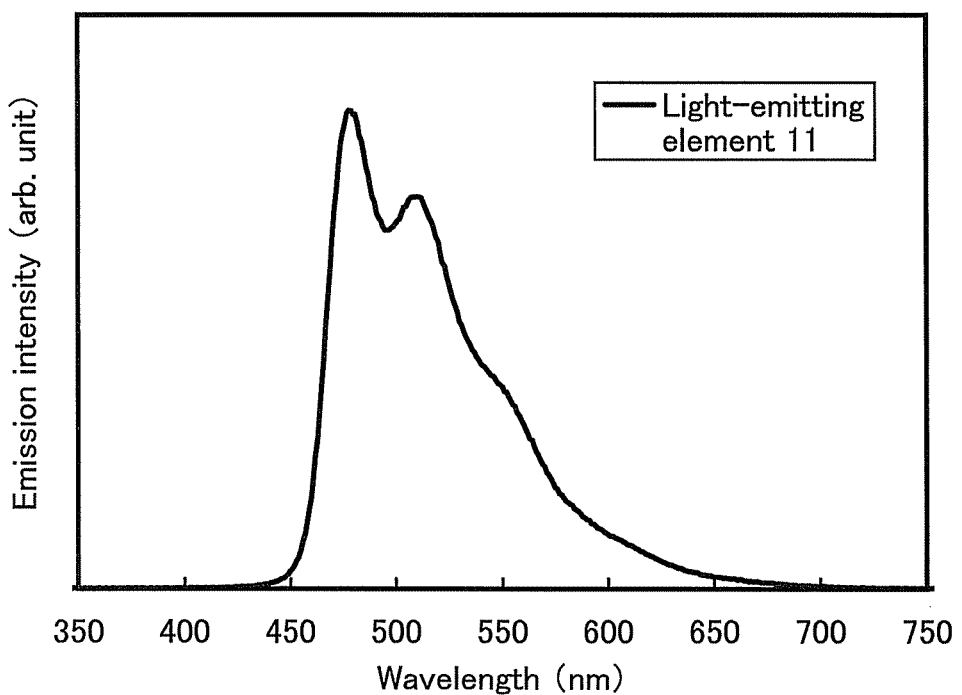
FIG. 73 shows an emission spectrum of Light-emitting element 11.

Next, FIG. 70 shows current density vs. luminance characteristics of Light-emitting element 11. FIG. 71 shows voltage vs. luminance characteristics thereof FIG. 72 shows luminance vs. current efficiency characteristics thereof. FIG. 73 shows the emission spectrum thereof at a current of 0.1 mA.

The CIE chromaticity coordinates of Light-emitting element 11 at a luminance of 696 cd/m$^2$ are (x=0.22, y=0.45). In addition, at a luminance of 696 cd/m$^2$, the current efficiency is 43.9 cd/A, the voltage is 6.0 V, and the current density is 1.58 mA/cm$^2$.

These measurement results indicate that Light-emitting element 11 has an extremely high current efficiency.

This application is based on Japanese Patent Application serial no. 2009-252168 filed with Japan Patent Office on Nov. 2, 2009, and Japanese Patent Application serial no. 2010-169870 filed with Japan Patent Office on Jul. 28, 2010, the entire contents of which are hereby incorporated by reference.

The invention claimed is:

1. An organometallic complex comprising a structure represented by General Formula (G1):

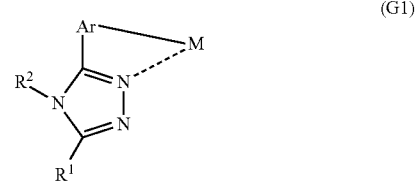

(G1)

wherein:
R$^1$ represents any of a substituted or unsubstituted cycloalkyl group having 5 to 8 carbon atoms, and a substituted or unsubstituted aralkyl group having 7 to 10 carbon atoms;
R$^2$ represents any of an alkyl group having 1 to 6 carbon atoms, a substituted or unsubstituted cycloalkyl group having 5 to 8 carbon atoms, and a substituted or unsubstituted aryl group having 6 to 12 carbon atoms;
Ar represents a substituted or unsubstituted arylene group having 6 to 13 carbon atoms; and
M represents a Group 9 element or a Group 10 element.

2. The organometallic complex according to claim 1, wherein the organometallic complex comprises a structure represented by General Formula (G3):

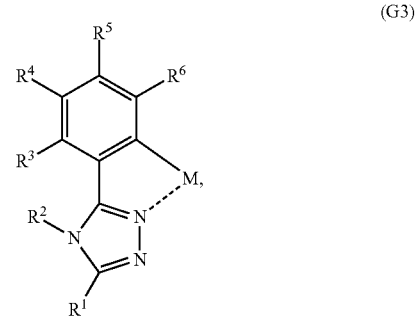

(G3)

and
wherein:
R$^3$ to R$^6$ individually represent any of hydrogen, an alkyl group having 1 to 6 carbon atoms, a cycloalkyl group having 5 to 8 carbon atoms, an alkoxy group having 1 to 4 carbon atoms, an aryloxy group having 6 to 12 carbon atoms, an alkylthio group having 1 to 4 carbon atoms, an arylthio group having 6 to 12 carbon atoms, an alkylamino group having 1 to 4 carbon atoms, a monoarylamino or diarylamino group having 6 to 24 carbon atoms, a cyano group, a halogen group, a haloalkyl group having 1 to 4 carbon atoms, and an aryl group having 6 to 12 carbon atoms.

3. The organometallic complex according to claim 1, wherein the organometallic complex comprises a structure represented by General Formula (G5):

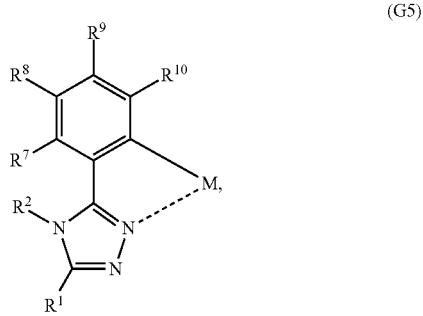

(G5)

and
wherein:
$R^7$ to $R^{10}$ individually represent hydrogen or an electron-withdrawing group.

4. The organometallic complex according to claim 3, wherein the electron-withdrawing group is a cyano group, a fluoro group, a trifluoromethyl group, a phenyl group substituted by a fluoro group, or a phenyl group substituted by a trifluoromethyl group.

5. The organometallic complex according to claim 1, wherein the organometallic complex comprises a structure represented by General Formula (G7):

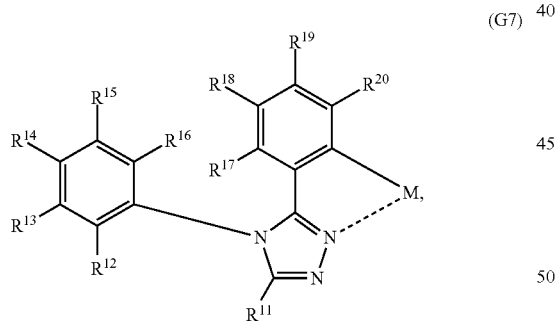

(G7)

and
wherein:
$R^{11}$ represents a cycloalkyl group having 5 to 8 carbon atoms;
$R^{12}$ to $R^{16}$ individually represent any of hydrogen, an alkyl group having 1 to 6 carbon atoms, a cycloalkyl group having 5 to 8 carbon atoms, and a phenyl group; and
$R^{17}$ to $R^{20}$ individually represent hydrogen or an electron-withdrawing group.

6. The organometallic complex according to claim 5, wherein the electron-withdrawing group is a cyano group, a fluoro group, a trifluoromethyl group, a phenyl group substituted by a fluoro group, or a phenyl group substituted by a trifluoromethyl group.

7. The organometallic complex according to claim 5, wherein each of $R^{12}$ to $R^{16}$ is hydrogen.

8. A light-emitting element comprising the organometallic complex according to claim 1 between a pair of electrodes.

9. A display device comprising a pixel portion, wherein the pixel portion comprises the light-emitting element according to claim 8.

10. An electronic device comprising a display portion, wherein the display portion comprises the light-emitting element according to claim 8.

11. A lighting device comprising the light-emitting element according to claim 8.

12. A light-emitting element comprising;
a first light-emitting unit and a second light-emitting unit between a pair of electrodes,
wherein the first light-emitting unit contains the organometallic complex according to claim 1, and
wherein the second light-emitting unit contains a light-emitting material that emits light with a longer wavelength than the organometallic complex.

13. A light-emitting element comprising;
a first light-emitting unit, a second light-emitting unit, and a third light-emitting unit between a pair of electrodes,
wherein the first light-emitting unit contains the organometallic complex according to claim 1,
wherein the second light-emitting unit contains a first light-emitting material that emits light with a longer wavelength than the organometallic complex, and
wherein the third light-emitting unit contains a second light-emitting material that emits light with a longer wavelength than the organometallic complex and a shorter wavelength than the first light-emitting material.

14. An organometallic complex represented by General Formula (G2):

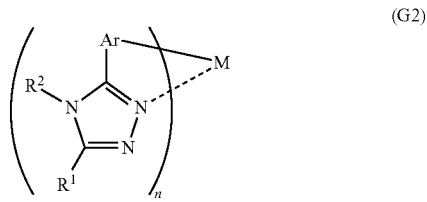

(G2)

wherein:
$R^1$ represents any of a substituted or unsubstituted cycloalkyl group having 5 to 8 carbon atoms, and a substituted or unsubstituted aralkyl group having 7 to 10 carbon atoms;
$R^2$ represents any of an alkyl group having 1 to 6 carbon atoms, a substituted or unsubstituted cycloalkyl group having 5 to 8 carbon atoms, and a substituted or unsubstituted aryl group having 6 to 12 carbon atoms;
Ar represents a substituted or unsubstituted arylene group having 6 to 13 carbon atoms;
M represents a Group 9 element or a Group 10 element; and
n=3 when M is a Group 9 element, and n=2 when M is a Group 10 element.

15. The organometallic complex according to claim 14, wherein the organometallic complex is represented by General Formula (G4):

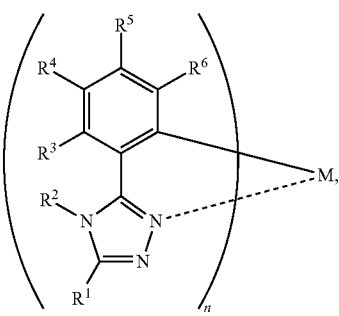

(G4)

and
wherein:
R³ to R⁶ individually represent any of hydrogen, an alkyl group having 1 to 6 carbon atoms, a cycloalkyl group having 5 to 8 carbon atoms, an alkoxy group having 1 to 4 carbon atoms, an aryloxy group having 6 to 12 carbon atoms, an alkylthio group having 1 to 4 carbon atoms, an arylthio group having 6 to 12 carbon atoms, an alkylamino group having 1 to 4 carbon atoms, a monoarylamino or diarylamino group having 6 to 24 carbon atoms, a cyano group, a halogen group, a haloalkyl group having 1 to 4 carbon atoms, and an aryl group having 6 to 12 carbon atoms.

16. The organometallic complex according to claim 14, wherein the organometallic complex is represented by General Formula (G6):

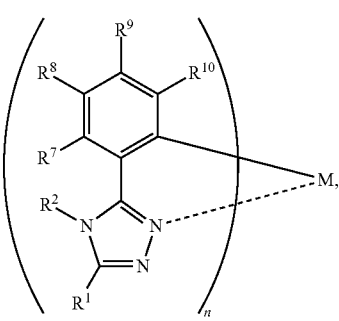

(G6)

and
wherein:
R⁷ to R¹⁰ individually represent hydrogen or an electron-withdrawing group.

17. The organometallic complex according to claim 14, wherein the organometallic complex is represented by General Formula (G8):

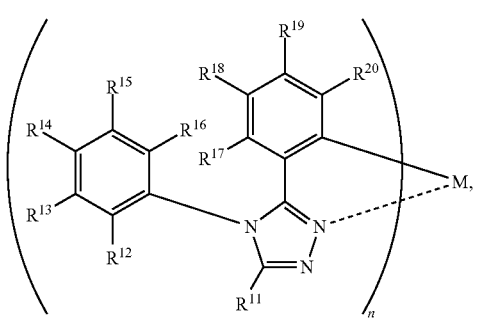

(G8)

and
wherein:
R¹¹ represents a cycloalkyl group having 5 to 8 carbon atoms;
R¹² to R¹⁶ individually represent any of hydrogen, an alkyl group having 1 to 6 carbon atoms, a cycloalkyl group having 5 to 8 carbon atoms, and a phenyl group; and
R¹⁷ to R²⁰ individually represent hydrogen or an electron-withdrawing group.

18. The organometallic complex according to claim 17, wherein the electron-withdrawing group is a cyano group, a fluoro group, a trifluoromethyl group, a phenyl group substituted by a fluoro group, or a phenyl group substituted by a trifluoromethyl group.

19. The organometallic complex according to claim 17, wherein each of R¹² to R¹⁶ is hydrogen.

20. The organometallic complex according to claim 16, wherein the electron-withdrawing group is a cyano group, a fluoro group, a trifluoromethyl group, a phenyl group substituted by a fluoro group, or a phenyl group substituted by a trifluoromethyl group.

21. A light-emitting element comprising the organometallic complex according to claim 14 between a pair of electrodes.

22. A display device comprising a pixel portion, wherein the pixel portion comprises the light-emitting element according to claim 21.

23. An electronic device comprising a display portion, wherein the display portion comprises the light-emitting element according to claim 21.

24. A lighting device comprising the light-emitting element according to claim 21.

25. A light-emitting element comprising;
a first light-emitting unit and a second light-emitting unit between a pair of electrodes,
wherein the first light-emitting unit contains the organometallic complex according to claim 14, and
wherein the second light-emitting unit contains a light-emitting material that emits light with a longer wavelength than the organometallic complex.

26. A light-emitting element comprising;
a first light-emitting unit, a second light-emitting unit, and a third light-emitting unit between a pair of electrodes,
wherein the first light-emitting unit contains the organometallic complex according to claim 14,
wherein the second light-emitting unit contains a first light-emitting material that emits light with a longer wavelength than the organometallic complex, and
wherein the third light-emitting unit contains a second light-emitting material that emits light with a longer wavelength than the organometallic complex and a shorter wavelength than the first light-emitting material.

* * * * *